US011679250B2

(12) United States Patent
Alexander et al.

(10) Patent No.: US 11,679,250 B2
(45) Date of Patent: Jun. 20, 2023

(54) REMOVABLE MECHANICAL CIRCULATORY SUPPORT FOR SHORT TERM USE

(71) Applicants: Theodosios Alexander, Venice, FL (US); Martin T. Rothman, Bodega Bay, CA (US)

(72) Inventors: Theodosios Alexander, Venice, FL (US); Martin T. Rothman, Bodega Bay, CA (US)

(*) Notice: Subject to any disclaimer, the term of this patent is extended or adjusted under 35 U.S.C. 154(b) by 0 days.

(21) Appl. No.: 16/914,019

(22) Filed: Jun. 26, 2020

(65) Prior Publication Data

US 2020/0405926 A1 Dec. 31, 2020

Related U.S. Application Data

(60) Provisional application No. 62/868,265, filed on Jun. 28, 2019, provisional application No. 62/991,410, filed on Mar. 18, 2020.

(51) Int. Cl.
*A61M 60/804* (2021.01)
*A61M 60/422* (2021.01)
(Continued)

(52) U.S. Cl.
CPC .......... *A61M 60/422* (2021.01); *A61M 60/13* (2021.01); *A61M 60/139* (2021.01);
(Continued)

(58) Field of Classification Search
CPC ............... A61F 2/82; A61F 2230/001; A61M 2205/0266; A61M 60/135; A61M 60/139; A61M 60/148; A61M 60/205; A61M 60/237; A61M 60/414; A61M 60/422; A61M 60/804; A61M 60/806; A61M 60/81; A61M 60/808; A61M 60/812
See application file for complete search history.

(56) References Cited

U.S. PATENT DOCUMENTS 3,174,851 A 3/1965 Buchler et al.
5,267,940 A 12/1993 Moulder
(Continued)

FOREIGN PATENT DOCUMENTS

CN 113413122 9/2021
EP 3519008 8/2019
(Continued)

OTHER PUBLICATIONS

Extended European Search Report for EP 18809622.6 dated Apr. 14, 2021 in 18 pages.
(Continued)

*Primary Examiner* — Jon Eric C Morales
(74) *Attorney, Agent, or Firm* — Knobbe, Martens, Olson & Bear, LLP

(57) ABSTRACT

A temporary, removable mechanical circulatory support heart-assist device has at least two propellers or impellers. Each propeller or impeller has a number of blades arranged around an axis of rotation. The blades are configured to pump blood. The two propellers or impellers rotate in opposite directions from each other. The device can be configured to be implanted and removed with minimally invasive surgery.

20 Claims, 96 Drawing Sheets

(51) Int. Cl.
*A61M 60/139* (2021.01)
*A61M 60/148* (2021.01)
*A61M 60/216* (2021.01)
*A61M 60/221* (2021.01)
*A61M 60/569* (2021.01)
*A61M 60/585* (2021.01)
*A61M 60/808* (2021.01)
*A61M 60/82* (2021.01)
*A61M 60/824* (2021.01)
*A61M 60/857* (2021.01)
*A61M 60/88* (2021.01)
*A61M 60/13* (2021.01)
*A61M 60/419* (2021.01)

(52) U.S. Cl.
CPC ........ *A61M 60/148* (2021.01); *A61M 60/216* (2021.01); *A61M 60/221* (2021.01); *A61M 60/569* (2021.01); *A61M 60/585* (2021.01); *A61M 60/808* (2021.01); *A61M 60/82* (2021.01); *A61M 60/824* (2021.01); *A61M 60/857* (2021.01); *A61M 60/88* (2021.01); *A61M 60/419* (2021.01); *A61M 2205/0266* (2013.01)

(56) References Cited

U.S. PATENT DOCUMENTS

| | | |
|---|---|---|
| 6,171,078 B1 | 1/2001 | Schob |
| 6,375,458 B1 | 4/2002 | Moorleghem et al. |
| 6,575,717 B2 | 6/2003 | Ozaki et al. |
| 6,716,157 B2 | 4/2004 | Goldowsky |
| 7,240,677 B2 | 7/2007 | Fox |
| 7,841,976 B2 | 11/2010 | McBride et al. |
| 7,976,271 B2 | 7/2011 | Larose et al. |
| 8,177,703 B2 | 5/2012 | Smith et al. |
| 8,449,443 B2 | 5/2013 | Rodefeld et al. |
| 8,684,904 B2 | 4/2014 | Campbell et al. |
| 8,690,749 B1 | 4/2014 | Nunez |
| 8,727,959 B2 | 5/2014 | Reitan et al. |
| 8,992,163 B2 | 3/2015 | McBride et al. |
| 9,211,368 B2 | 12/2015 | Wampler |
| 9,308,302 B2 | 4/2016 | Zeng |
| 9,327,067 B2 | 5/2016 | Zeng et al. |
| 9,358,329 B2 | 6/2016 | Fitzgerald et al. |
| 9,364,592 B2 | 6/2016 | McBride et al. |
| 9,364,593 B2 | 6/2016 | McBride et al. |
| 9,394,612 B2 | 7/2016 | Bayer et al. |
| 9,638,202 B2 | 5/2017 | Ozaki et al. |
| 9,717,833 B2 | 8/2017 | McBride et al. |
| 9,737,651 B2 | 8/2017 | Wampler |
| 9,872,948 B2 | 1/2018 | Siess |
| 9,913,937 B2 | 3/2018 | Schwammenthal et al. |
| 9,962,258 B2 | 5/2018 | Seguin et al. |
| 10,027,114 B2 | 7/2018 | Potharaju et al. |
| 10,039,874 B2 | 8/2018 | Schwammenthal et al. |
| 10,179,197 B2 | 1/2019 | Kaiser et al. |
| 10,215,187 B2 | 2/2019 | McBride et al. |
| 10,219,901 B2 | 3/2019 | Seguin et al. |
| 10,285,686 B2 | 5/2019 | Gammie et al. |
| 10,299,918 B2 | 5/2019 | Tuval |
| 10,350,341 B2 | 7/2019 | Throckmorton et al. |
| 10,363,350 B2 | 7/2019 | Schwammenthal et al. |
| 10,478,540 B2 | 11/2019 | Scheckel et al. |
| 10,478,542 B2 | 11/2019 | Jahangir |
| 10,500,323 B2 | 12/2019 | Heuring et al. |
| 10,583,231 B2 | 3/2020 | Schwammenthal et al. |
| 10,667,821 B2 | 6/2020 | Dehdashtian et al. |
| 10,695,114 B2 | 6/2020 | Fox |
| 10,722,631 B2 | 7/2020 | Salahieh et al. |
| 10,792,413 B2 | 10/2020 | Dann et al. |
| 10,808,704 B2 | 10/2020 | Siess et al. |
| 10,842,921 B2 | 11/2020 | Siess et al. |
| 10,856,979 B2 | 12/2020 | Tuval et al. |
| 10,857,274 B2 | 12/2020 | Alexander et al. |
| 10,864,309 B2 | 12/2020 | McBride et al. |
| 10,864,310 B2 | 12/2020 | Schwammenthal et al. |
| 10,881,770 B2 | 1/2021 | Tuval et al. |
| 10,893,927 B2 | 1/2021 | Sohn |
| 10,898,320 B2 | 1/2021 | Spence et al. |
| 10,898,625 B2 | 1/2021 | Toellner et al. |
| 10,905,808 B2 | 2/2021 | Tuval et al. |
| 10,907,646 B2 | 2/2021 | Bredenbreuker et al. |
| 10,918,773 B2 | 2/2021 | Guo et al. |
| 10,918,774 B2 | 2/2021 | Stanfield et al. |
| 10,960,116 B2 | 3/2021 | Campbell et al. |
| 10,980,927 B2 | 4/2021 | Pfeffer et al. |
| 10,993,805 B2 | 5/2021 | Staubinger et al. |
| 10,993,824 B2 | 5/2021 | Longo |
| 10,994,120 B2 | 5/2021 | Tuval et al. |
| 11,020,582 B2 | 6/2021 | Cambronne et al. |
| 11,020,584 B2 | 6/2021 | Siess et al. |
| 11,033,275 B2 | 6/2021 | Franano et al. |
| 11,033,390 B2 | 6/2021 | Krivoruchko |
| 11,033,727 B2 | 6/2021 | Tuval et al. |
| 11,033,729 B2 | 6/2021 | Scheckel et al. |
| 11,039,917 B2 | 6/2021 | Bruchman et al. |
| 11,045,316 B2 | 6/2021 | Zhang |
| 11,045,317 B2 | 6/2021 | Nguyen et al. |
| 11,045,338 B2 | 6/2021 | Boyle et al. |
| 11,045,638 B2 | 6/2021 | Keenan et al. |
| 11,051,833 B2 | 7/2021 | Martin et al. |
| 11,051,959 B2 | 7/2021 | Bar et al. |
| 11,058,536 B2 | 7/2021 | Huber |
| 11,058,539 B2 | 7/2021 | Dixon et al. |
| 11,058,563 B2 | 7/2021 | Van Langenhove |
| 11,058,564 B2 | 7/2021 | Carpenter et al. |
| 11,058,565 B2 | 7/2021 | Laramy et al. |
| 11,058,853 B2 | 7/2021 | Rosenberg et al. |
| 11,058,865 B2 | 7/2021 | Fitzgerald et al. |
| 11,060,382 B2 | 7/2021 | Sherman |
| 11,065,007 B2 | 7/2021 | Demeritt |
| 11,065,028 B2 | 7/2021 | Farhangnia et al. |
| 11,065,029 B2 | 7/2021 | Mcmahon et al. |
| 11,065,114 B2 | 7/2021 | Raanani et al. |
| 11,065,115 B2 | 7/2021 | Benichou et al. |
| 11,065,117 B2 | 7/2021 | Zeng |
| 11,065,138 B2 | 7/2021 | Schreck et al. |
| 11,065,140 B2 | 7/2021 | Mcweeney et al. |
| 11,065,141 B2 | 7/2021 | Wood et al. |
| 11,071,533 B2 | 7/2021 | Rothstein et al. |
| 11,072,201 B2 | 7/2021 | Nicastri et al. |
| 11,116,959 B2 | 9/2021 | Alexander et al. |
| 11,179,557 B2 | 11/2021 | Georges et al. |
| 11,524,153 B2 | 12/2022 | Alexander et al. |
| 2002/0094281 A1 | 7/2002 | Khanvilkar et al. |
| 2003/0228214 A1 | 12/2003 | McBride |
| 2003/0233143 A1 | 12/2003 | Gharib et al. |
| 2004/0106974 A1 | 6/2004 | Greenberg et al. |
| 2006/0245959 A1 | 11/2006 | Larose et al. |
| 2008/0058146 A1 | 3/2008 | Pizzichil et al. |
| 2008/0300447 A1 | 12/2008 | Lu et al. |
| 2009/0326508 A1 | 12/2009 | Braun et al. |
| 2010/0076247 A1 | 3/2010 | Zilbershlag et al. |
| 2011/0021994 A1 | 1/2011 | Anderson et al. |
| 2011/0034874 A1 | 2/2011 | Reitan et al. |
| 2011/0091515 A1 | 4/2011 | Zilberman et al. |
| 2011/0152600 A1 | 6/2011 | Scott et al. |
| 2011/0200451 A1 | 8/2011 | Lehmann et al. |
| 2011/0238172 A1 | 9/2011 | Akdis |
| 2011/0239693 A1 | 10/2011 | Fujisaku et al. |
| 2011/0257462 A1 | 10/2011 | Rodefeld et al. |
| 2012/0253103 A1 | 10/2012 | Robert |
| 2012/0277520 A1 | 11/2012 | Duncan |
| 2012/0310036 A1 | 12/2012 | Peters et al. |
| 2013/0030240 A1 | 1/2013 | Schima et al. |
| 2013/0281762 A1 | 10/2013 | Mi-Vad |
| 2014/0051908 A1 | 2/2014 | Hridaya |
| 2014/0275726 A1 | 9/2014 | Zeng |
| 2015/0152878 A1 | 6/2015 | McBride et al. |
| 2015/0297813 A1 | 10/2015 | Korakianitis et al. |
| 2015/0335309 A1 | 11/2015 | Stigall et al. |
| 2016/0089482 A1 | 3/2016 | Siegenthaler |

(56) References Cited

U.S. PATENT DOCUMENTS

| | | | |
|---|---|---|---|
| 2016/0271309 | A1 | 9/2016 | Throckmorten et al. |
| 2017/0056169 | A1 | 3/2017 | Johnson et al. |
| 2017/0274128 | A1 | 9/2017 | Tamburino et al. |
| 2017/0340788 | A1 | 11/2017 | Korakianitis et al. |
| 2018/0169313 | A1 | 6/2018 | Schwammenthal et al. |
| 2019/0269840 | A1 | 9/2019 | Tuval et al. |
| 2019/0321529 | A1* | 10/2019 | Korakianitis ....... A61M 60/857 |
| 2020/0015987 | A1 | 1/2020 | Einav et al. |
| 2020/0237981 | A1 | 7/2020 | Tuval et al. |
| 2021/0077687 | A1 | 3/2021 | Leonhardt |
| 2021/0154463 | A1 | 5/2021 | Alexander et al. |
| 2021/0162196 | A1 | 6/2021 | Georges et al. |
| 2021/0260358 | A1 | 8/2021 | Alexander et al. |
| 2021/0260360 | A1 | 8/2021 | Georges et al. |
| 2022/0040470 | A1 | 2/2022 | Alexander et al. |
| 2022/0296852 | A1 | 9/2022 | Georges |
| 2022/0323744 | A1 | 10/2022 | Georges et al. |
| 2023/0056440 | A1 | 2/2023 | Georges et al. |

FOREIGN PATENT DOCUMENTS

| | | |
|---|---|---|
| EP | 3630218 | 4/2020 |
| JP | H07-207390 | 8/1995 |
| JP | 2017-515607 | 6/2017 |
| WO | WO 2006/020942 | 2/2006 |
| WO | WO 2014/036317 | 3/2014 |
| WO | WO 2015/177793 | 11/2015 |
| WO | WO 2016/097976 | 6/2016 |
| WO | WO 2016/185473 | 11/2016 |
| WO | WO 2018/067410 | 4/2018 |
| WO | WO 2018/096531 | 5/2018 |
| WO | WO 2018/209191 | 11/2018 |
| WO | WO 2018/223060 | 12/2018 |
| WO | WO 2019/195480 | 10/2019 |
| WO | PCT/US2020/039978 | 6/2020 |
| WO | WO 2020/264417 | 12/2020 |
| WO | WO 2021/127503 | 6/2021 |
| WO | WO 2021/152013 | 8/2021 |

OTHER PUBLICATIONS

Extended European Search Report for EP 19780961.9 dated Nov. 26, 2021 in 8 pages.
U.S. Appl. No. 16/338,961, filed Apr. 2, 2019, Korakianitis et al.
U.S. Appl. No. 15/720,592, filed Sep. 29, 2017, Korakianitis et al.
U.S. Appl. No. 16/914,019, filed Jun. 26, 2020, Korakianitis et al.
Search Report and Written Opinion for PCT/US2017/054573 dated Dec. 15, 2017 in 14 pages.
Extended European Search Report for EP 17858942.0 dated Jul. 23, 2020 in 14 pages.
Partial Supplementary European Search Report for EP 17858942.0 dated Apr. 22, 2020 in 18 pages.
Search Report and Written Opinion for PCT/US2018/035694 dated Nov. 5, 2018 in 12 pages.
Search Report and Written Opinion for PCT/US2019/025667 dated Jul. 29, 2019 in 19 pages.
Search Report and Written Opinion for PCT/US2020/039978 dated Nov. 20, 2020 in 25 pages.
Invitation to Pay Additional Fees for PCT/US20/39978 dated Sep. 15, 2020.
Partial Supplementary European Search Report for EP 18809622.6 dated Jan. 12, 2021 in 22 pages.
Hosseinipour, M., et al. (2017). Rotary mechanical circulatory support systems. Journal of Rehabilitation and Assistive Technologies Engineering, 2017, vol. 4: 1-24. https://doi.org/10.1177/2055668317725994.
Mieghem et al. (2018). Design and principle of operation of the HeartMate PHP (percutaneous heart pump). EuroIntervention 2018,13,1662-1666 published online Dec. 2016. DOI: 10.4244/EIJ-D-15-00467.
Miller, L., et al. (2019). Use of Ventricular Assist Devices and Heart Transplantation for Advanced Heart Failure. Circulation Research, 2019;124:1658-1678. DOI: 10.1161/CIRCRESAHA.119.313574.
Siess, T., et al. (2001). From a Lab Type to a Product: A Retrospective View on Impella's Assist Technology. Artificial Organs, 2001, 25(5):414-421.
Yancy CW, Jessup M, Bozkurt B, et al. 2013 ACCF/AHA guideline for the management of heart failure: a report of the American College of Cardiology Foundation/American Heart Association Task Force on practice guidelines. Circulation. Oct. 15, 2013;128(16):e240-327, also published in J Am Coll Cardiol Oct. 15, 2013;62(16):e147full-text.
Lund LH, Edwards LB, Kucheryavaya AY, Dipchand AI, Benden C, Christie JD, Dobbels F, Kirk R, Rahmel AO, Yusen RD, Stehlik J, International Society for Heart and Lung Transplantation. The Registry of the International Society for Heart and Lung Transplantation: Thirtieth Official Adult Heart Transplant Report—2013; focus theme: age. Journal of Heart and Lung Transplantation Oct. 2013; 32(10):951-964.
Lund, L.H., Edwards, L.B., Dipchand, A.I., Goldfarb, S., Kucheryavaya, A.Y., Lewey, B.J., Meiser, B., Rossano, J.W., Yusen, R.D., Stehlik, J. The Registry of the International Society for Heart and Lung Transplantation: Thirty-third Adult Heart Transplantation Report—2016; Focus Theme: Primary Diagnostic Indications for Transplant vol. 35, Issue 10, Oct. 1, 2016, pp. 1158-1169.
Fonarow GC, Abraham WT, Albert N, Gattis W, Gheorghiade M, Greenberg B, O'Connor CM, She L, Yancy CW, Young JB. Organized program to initiate lifesaving treatment in hospitalized patients with heart failure (OPTIMIZE-HF): rationale and design American Heart Journal. vol. 148, Issue 1, Jul. 2004, pp. 43-51 https://doi.org/10.1016/j.ahj.2004.03.004.
Gheorghiade M, Zannad F, Sopko G, Klein L, Pina IL, Konstam MA, et al. Acute heart failure syndromes: current state and framework for future research. Circulation 2005;112(25): 3958-68.
Rangaswami et al. Cardiorenal Syndrome: Classification, Pathophysiology, Diagnosis, and Treatment Strategies: A Scientific Statement from the American Heart Association. Circulation. 2019;139:e840-e878.
Benjamin et al. Heart Disease and Stroke Statistics—2017 Update: A Report From the American Heart Association. Circulation. 2017. (Part 1 of 5).
Benjamin et al. Heart Disease and Stroke Statistics—2017 Update: A Report From the American Heart Association. Circulation. 2017. (Part 2 of 5).
Benjamin et al. Heart Disease and Stroke Statistics—2017 Update: A Report From the American Heart Association. Circulation. 2017. (Part 3 of 5).
Benjamin et al. Heart Disease and Stroke Statistics—2017 Update: A Report From the American Heart Association. Circulation. 2017. (Part 4 of 5).
Benjamin et al. Heart Disease and Stroke Statistics—2017 Update: A Report From the American Heart Association. Circulation. 2017. (Part 5 of 5).
Gheorghiade M. et al., Rehospitalization for heart failure: problems and perspectives. JACC vol. 61, No. 4, 2013:391-403.
Optimization of Axial Pump Characteristic Dimensions and Induced Hemolysis for Mechanical Circulatory Support Devices. Korakianitis T., Rezaienia M.A., Paul G., Avital E., Rothman M., and Mozafari S. (2018) ASAIO Journal Nov./Dec. 2018;64(6):727-734. DOI: 10.1097/MAT.0000000000000719.
In Vitro Cardiovascular System Emulator (Bioreactor) for the Simulation of Normal and Diseased Conditions With and Without Mechanical Circulatory Support Ruiz P., Rezaienia M.A., Rahideh A., Keeble T.R., Rothman M.T., and Korakianitis T. Artificial Organs, vol. 37, No. 6, 2013, pp. 549-560, doi:10.1111/aor.12109.
In-vitro investigation of cerebral-perfusion effects of a rotary blood pump installed in the descending aorta Rezaienia M.A., Paul G., Avital E., Rahideh A., Rothman M.T., and Korakianitis T. Journal of Biomechanics, vol. 49, p. 1865-1872, 2016. http://dx.doi.org/10.1016/j.jbiomech.2016.04.027.
In-vitro investigation of the hemodynamic responses of the cerebral, coronary and renal circulations with a rotary blood pump installed in the descending aorta Rezaienia M.A., Paul G., Avital E.J.,

(56) References Cited

OTHER PUBLICATIONS

Mozafari S., Rothman M., and Korakianitis T. Medical Engineering and Physics, vol. 40, pp. 2-10, 2017. http://dx.doi.org/10.1016/j.medengphy.2016.11.006.

Chang B. Y, Keller S. P., Bhavsar S. S., Josephy N. and Edelman E. R. Mechanical circulatory support device-heart hysteretic interaction can predict left ventricular end diastolic pressure Sci Transl Med. Feb. 28, 2018; 10(430) 2018 doi:10.1126/scitranslmed.aao2980.

Initial tests with a new cardiac assist device. Reitan O., Ohlin H., Peterzen B., Granfeldt H., Steen S., and Emanuelsson H. Asaio Journal vol. 45, 317-321, 1999.

Hydrodynamic Properties of a New Percutaneous Intra-aortic Axial Flow Pump. Reitan O., Sternby J., and Ohlin H. Asaio Journal vol. 46, 323-329, May-Jun. 2000.

Hemodynamic Effects of a New Percutaneous Circulatory Support Device in a Left Ventricular Failure Model Reitan O., Steen S., and Ohlin H. Asaio Journal Nov.-Dec. 2003, vol. 49, No. 6, 731-736. DOI: 10.1097/01.MAT.0000093964.33468.CA.

An Expandable Percutaneous Catheter Pump for Left Ventricular Support—Proof of Concept Thomas Schmitz-Rode, Jürgen Graf, Joachim G. Pfeffer, Frank Buss, Christoph Brücker, Rolf W. Günther Journal of the American College of Cardiology. Vol. 45, No. 11, 2005 doi:10.1016/j.jacc.2005.02.071.

Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).

Throckmorton et al., (2012) Uniquely shaped cardiovascular stents enhance the pressure generation of intravascular blood pumps. The Journal of Thoracic and Cardiovascular Surgery, Sep. 2012, pp. 704-709, vol. 133, No. 3. doi: 10.1016/j.jtcvs.2011.12.061.

Throckmorton et al. (2012) Controlled Pitch-Adjustment of Impeller Blades for an Intravascular Blood Pump ASAIO Journal, 2012 DOI: 10.1097/MAT.0b013e31825d018e.

Search Report and Written Opinion for PCT/US2022/49853 dated Mar. 27, 2023 in 21 pages.

Office Action for IN 202017047035 dated Sep. 23, 2022.

Invitation to Pay Additional Fees for PCT/US22/49850 dated Feb. 2, 2023.

Fernandez et al., Understanding the Shape-Memory Alloys Used in Orthodonics, 2011.

Search Report and Written Opinion for PCT/US2022/49853 dated Feb. 23, 2023 in 27 pages.

Office Action for JP2021-503705 dated Mar. 6, 2023.

\* cited by examiner

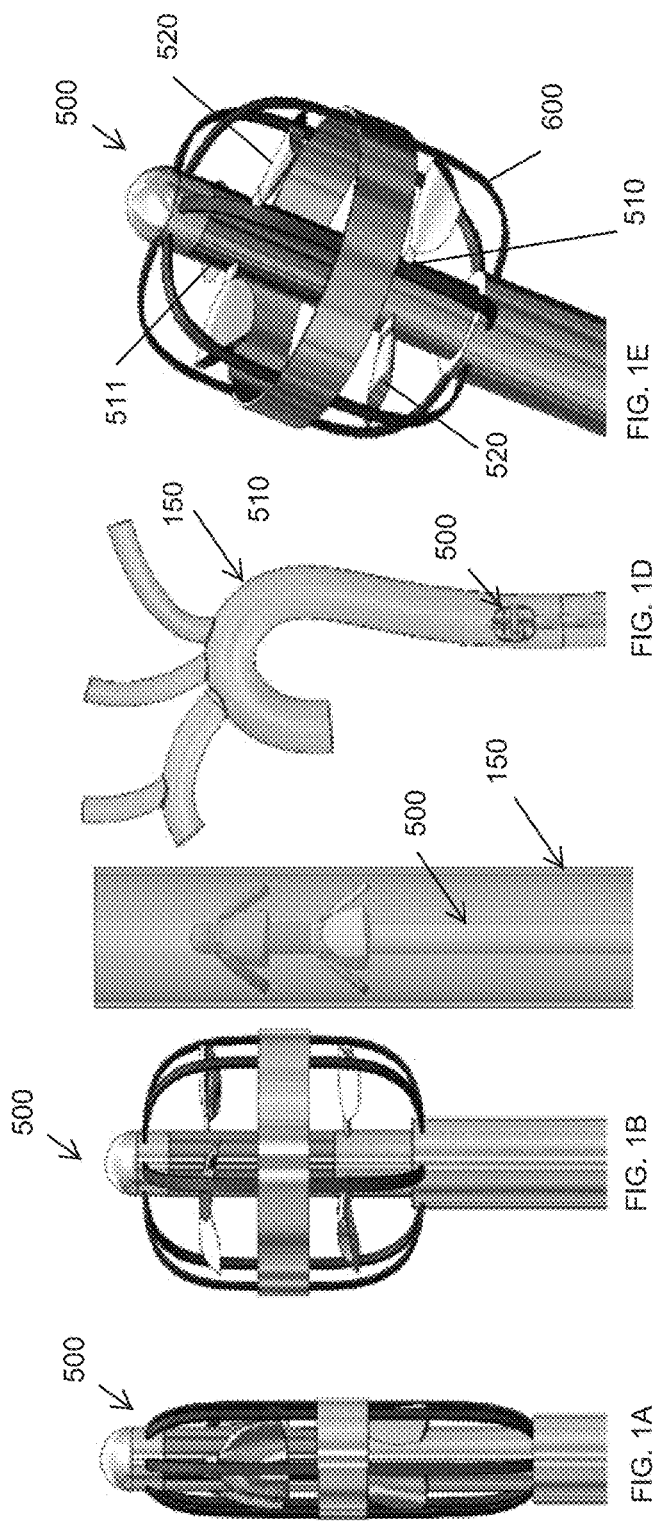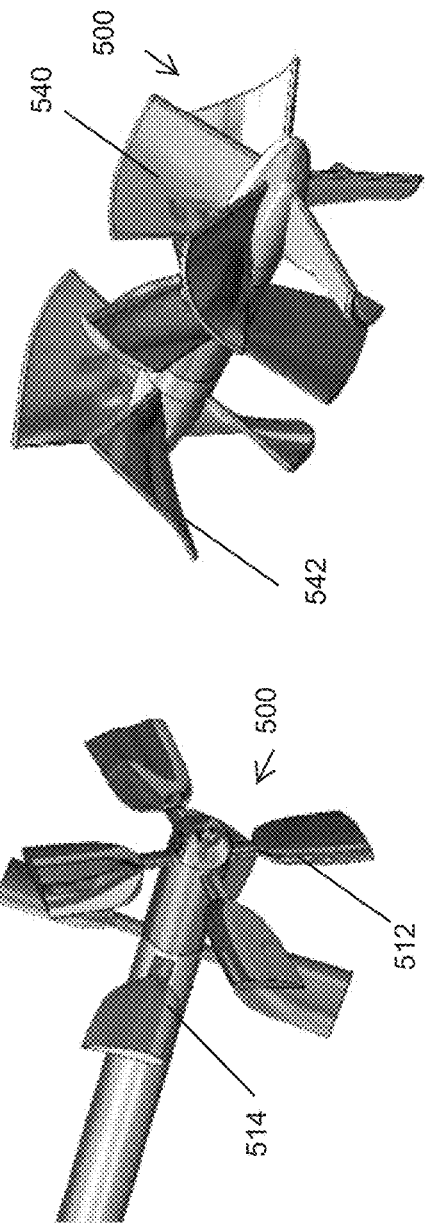

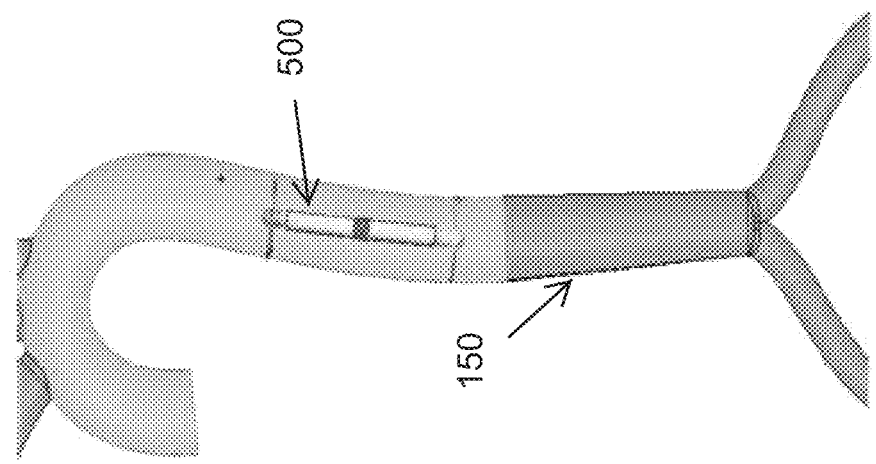
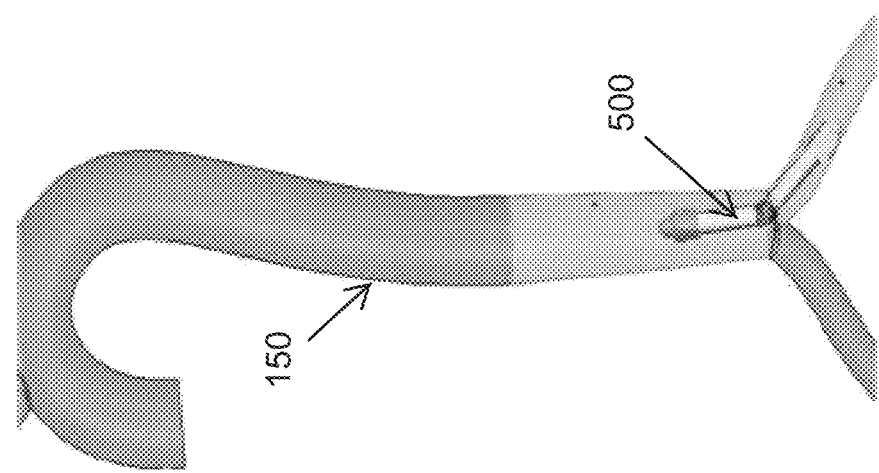
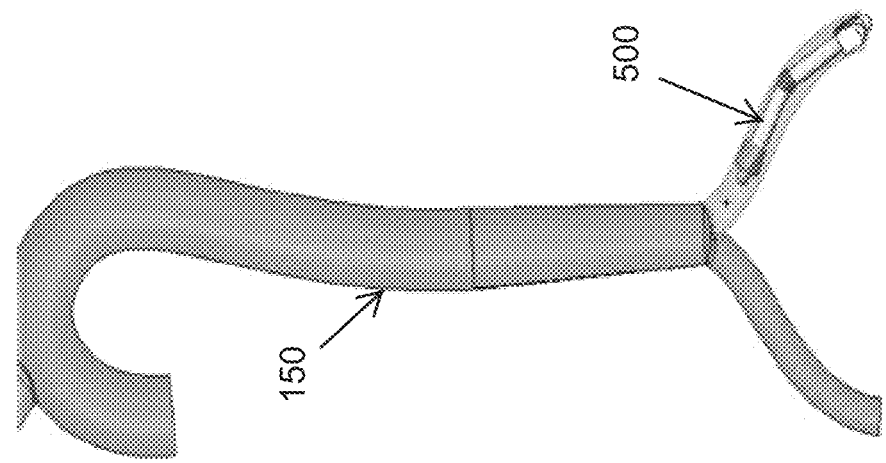

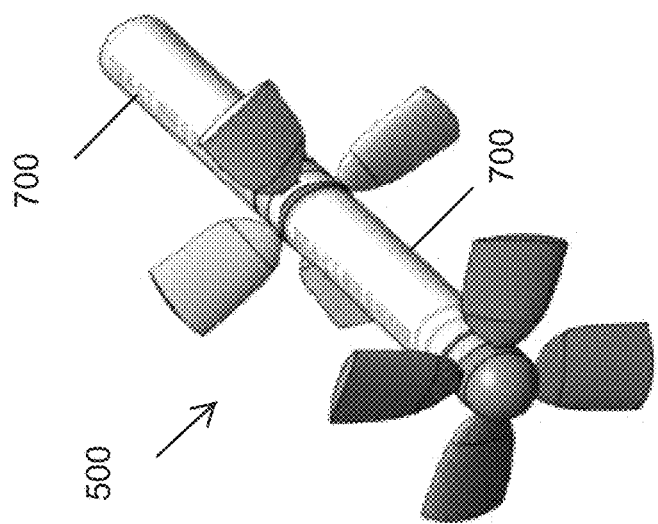
FIG. 5C
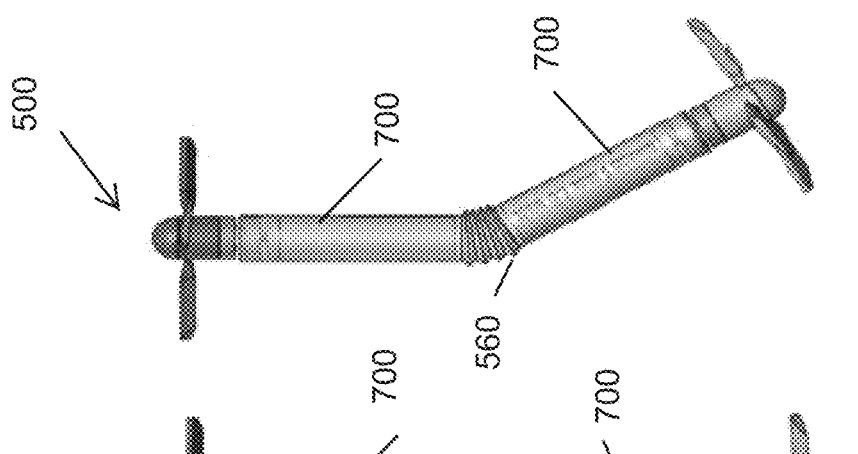
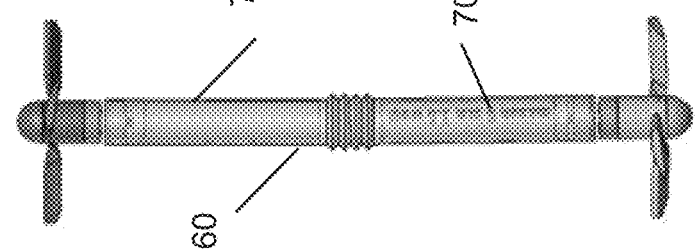
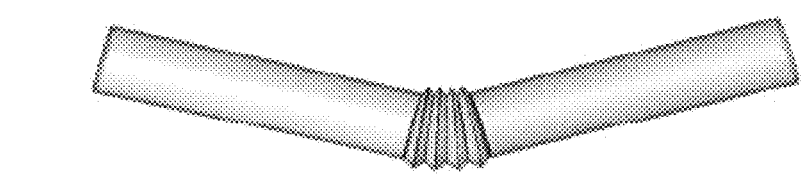
FIG. 5B
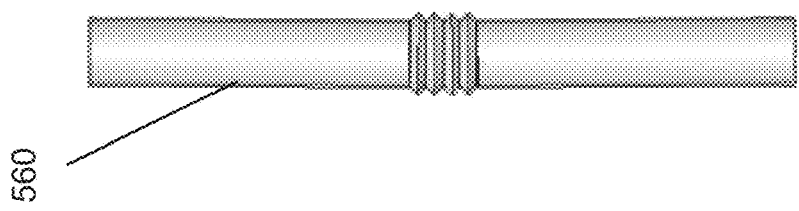
FIG. 5A

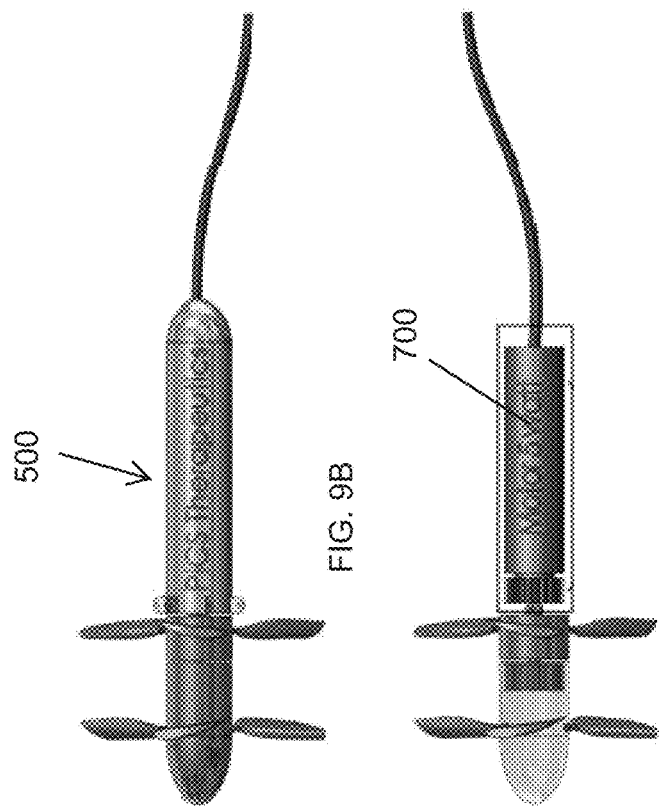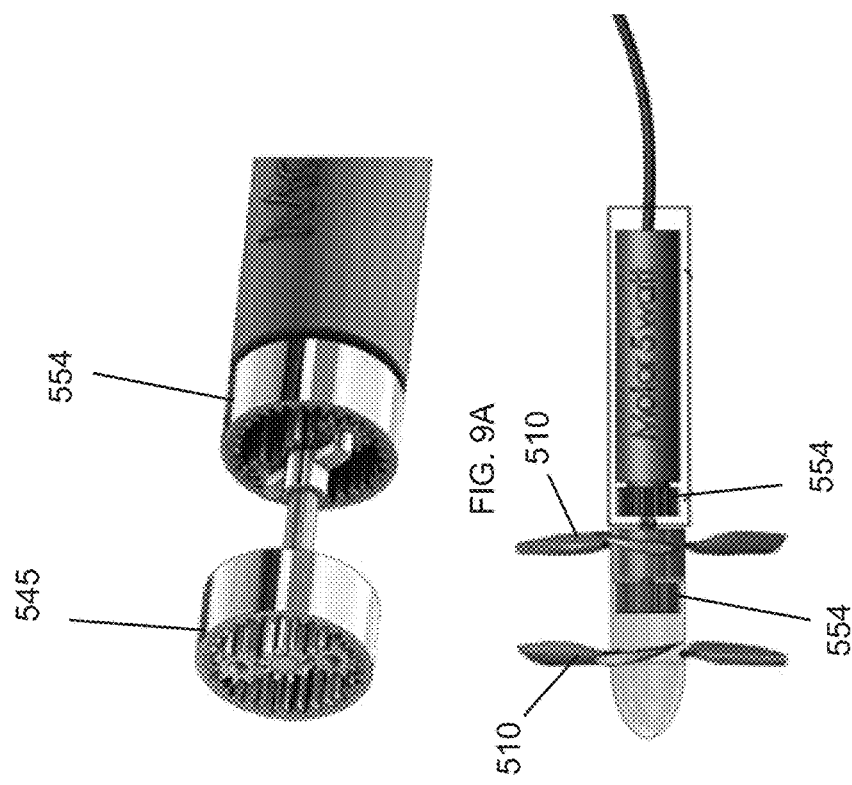

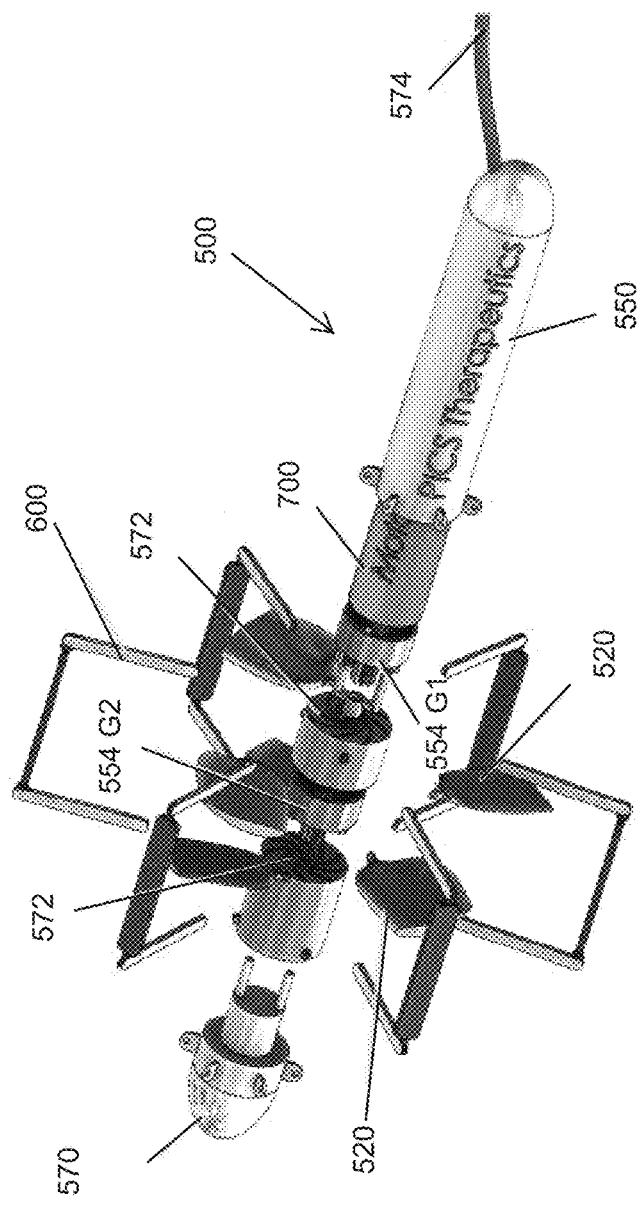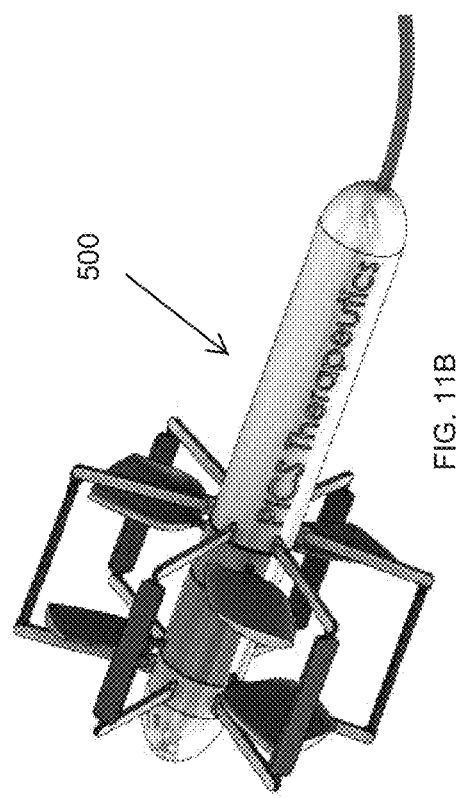

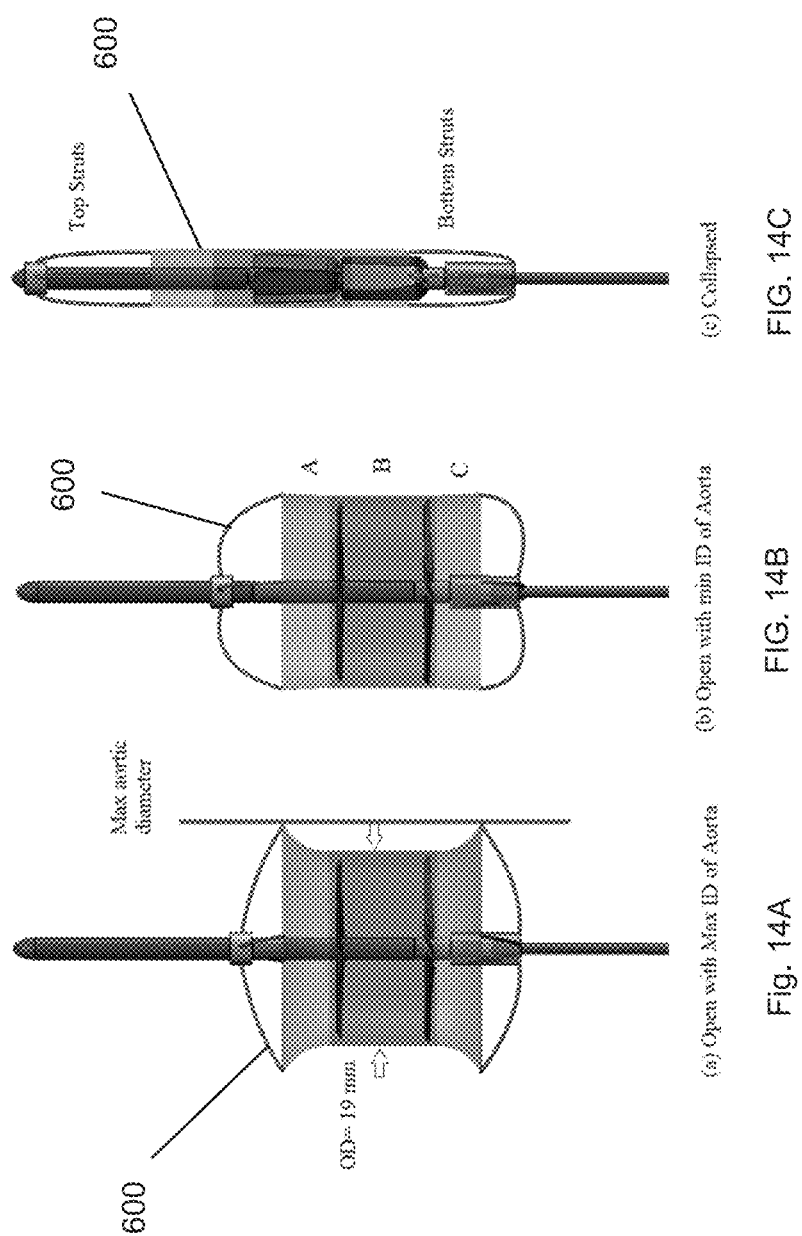

(a) Collapsed (b) Fully Open

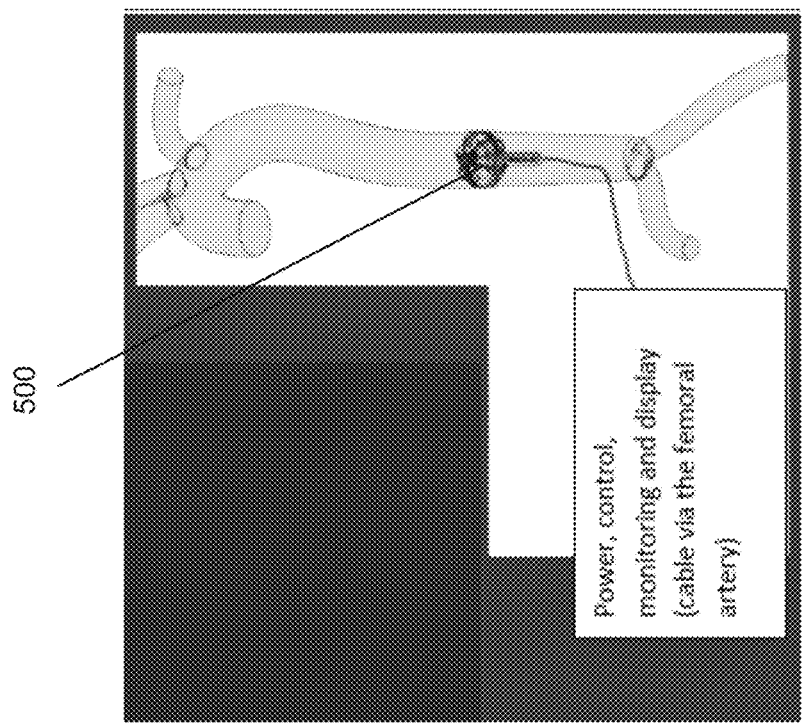
FIG. 16C
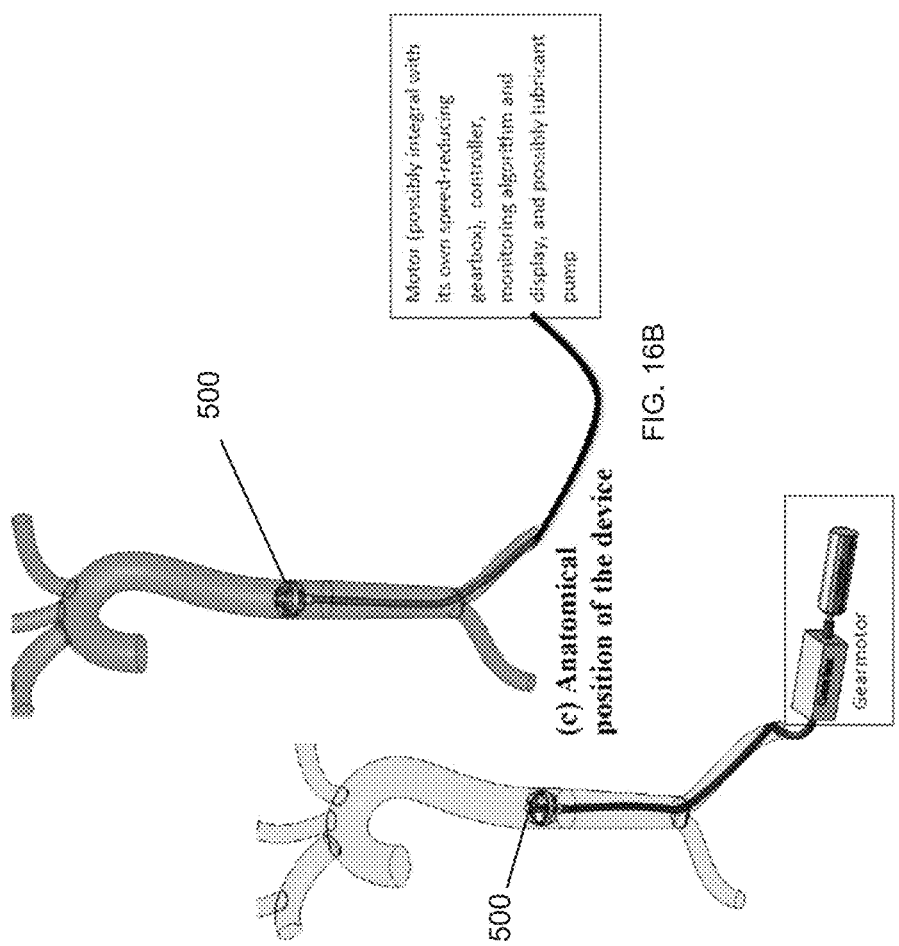
FIG. 16A
FIG. 16B

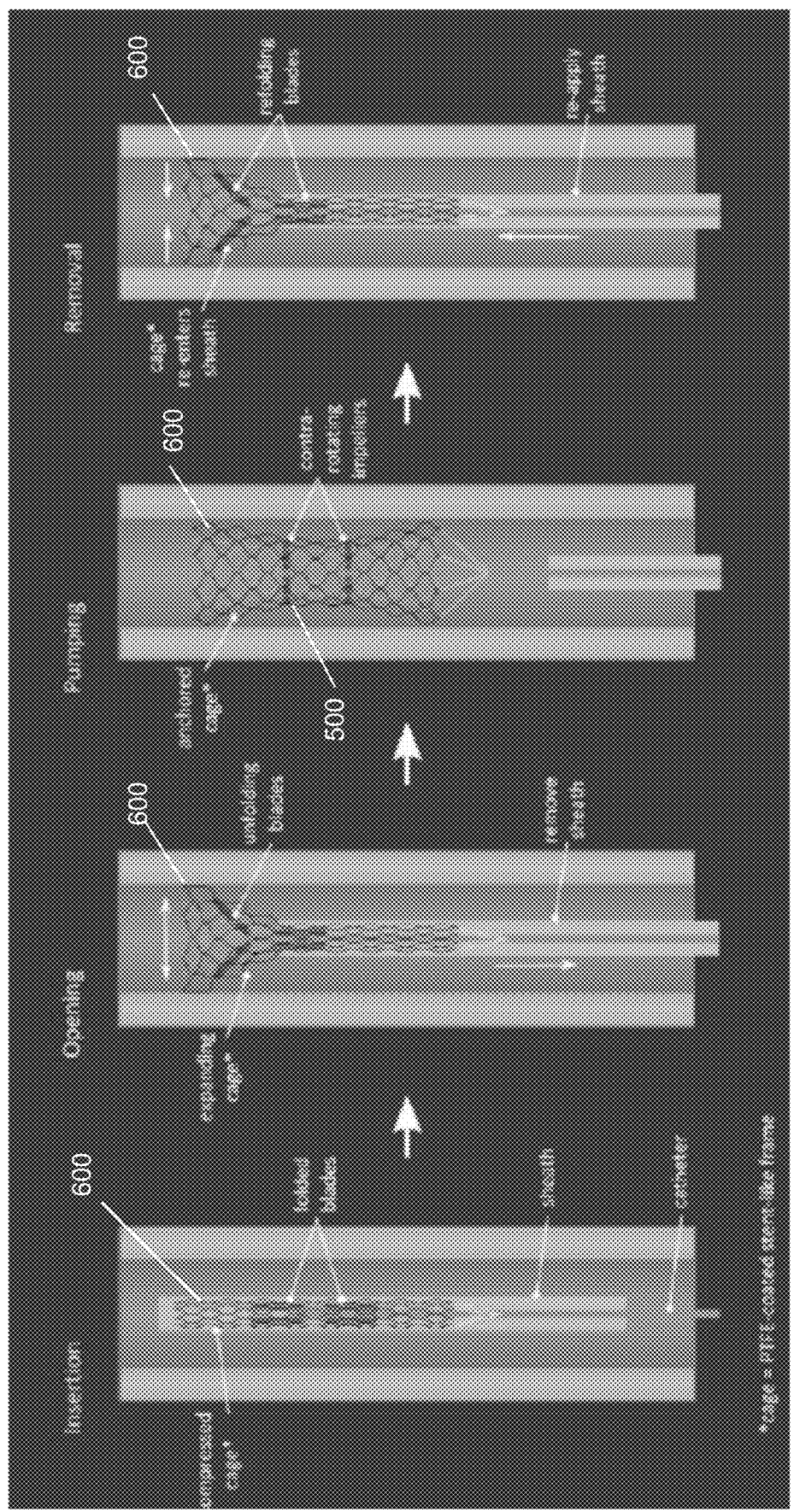

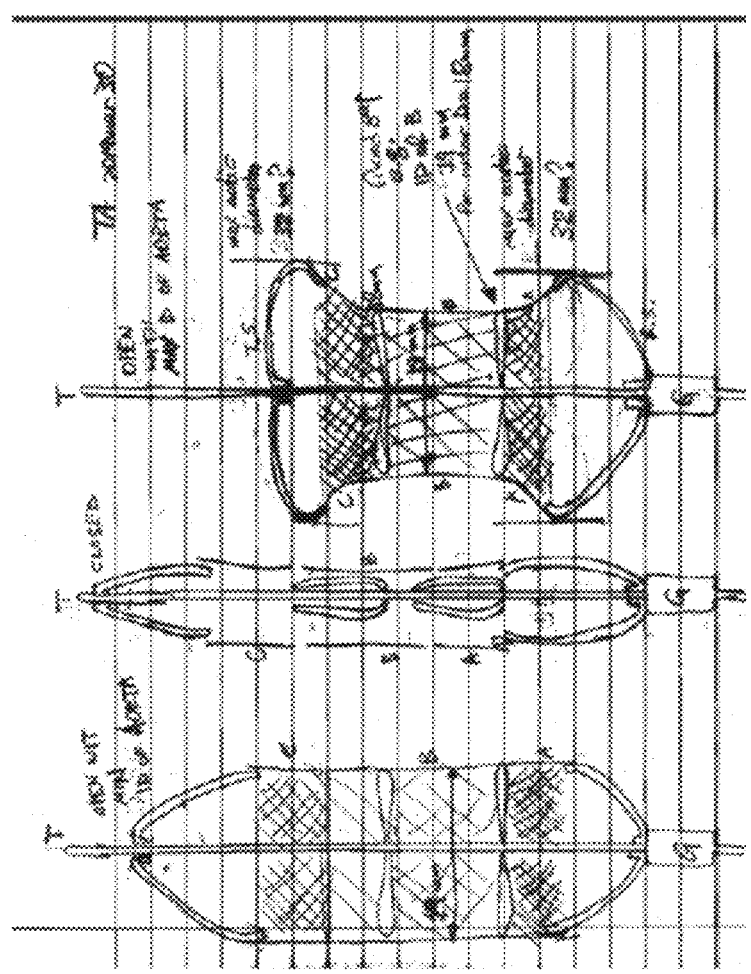

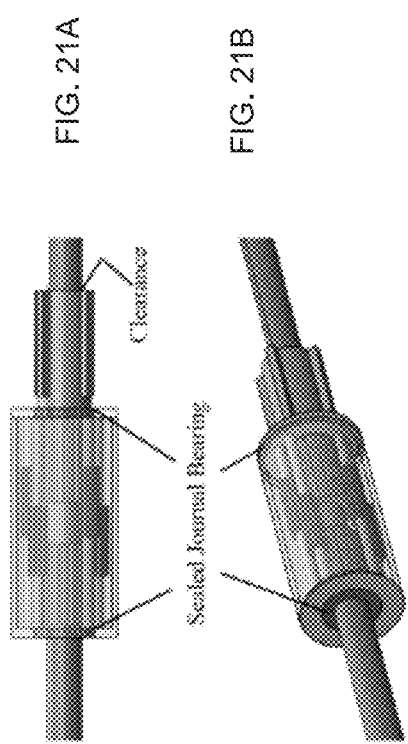
FIG. 21A
FIG. 21B
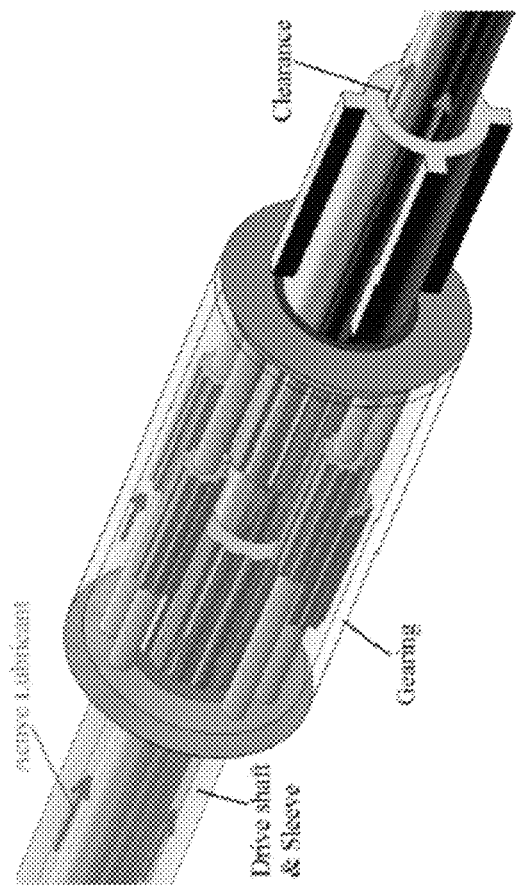
FIG. 21C

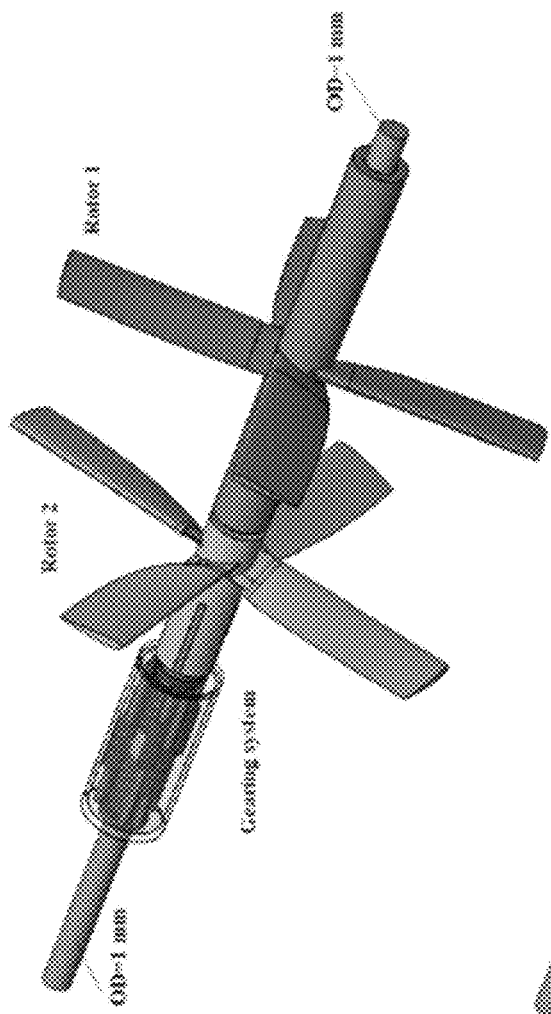
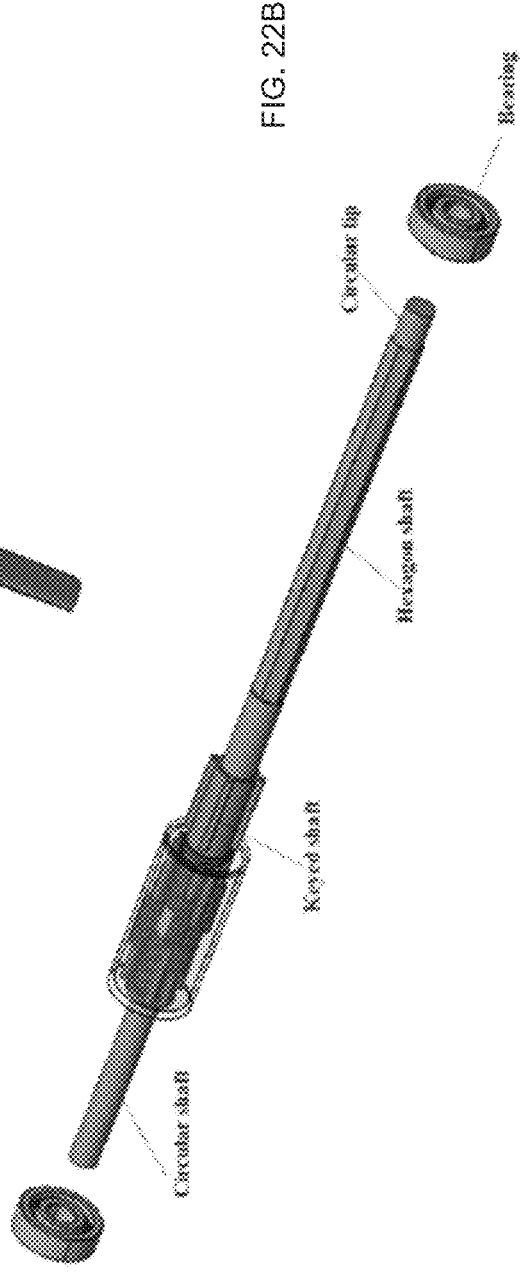
FIG. 22A
FIG. 22B

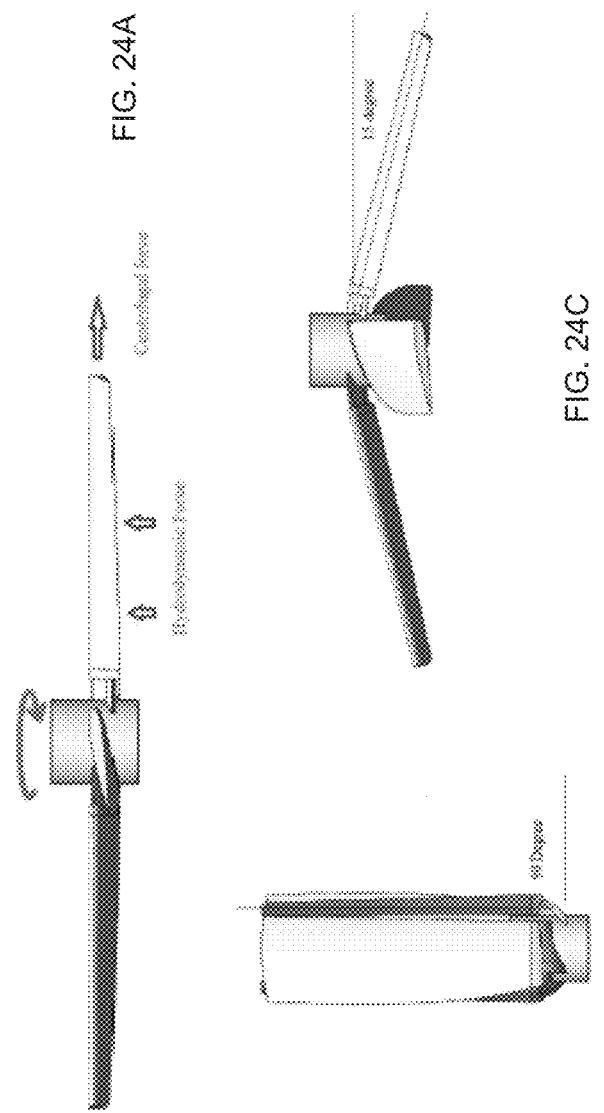

Folded Downwards

Folded Upwards

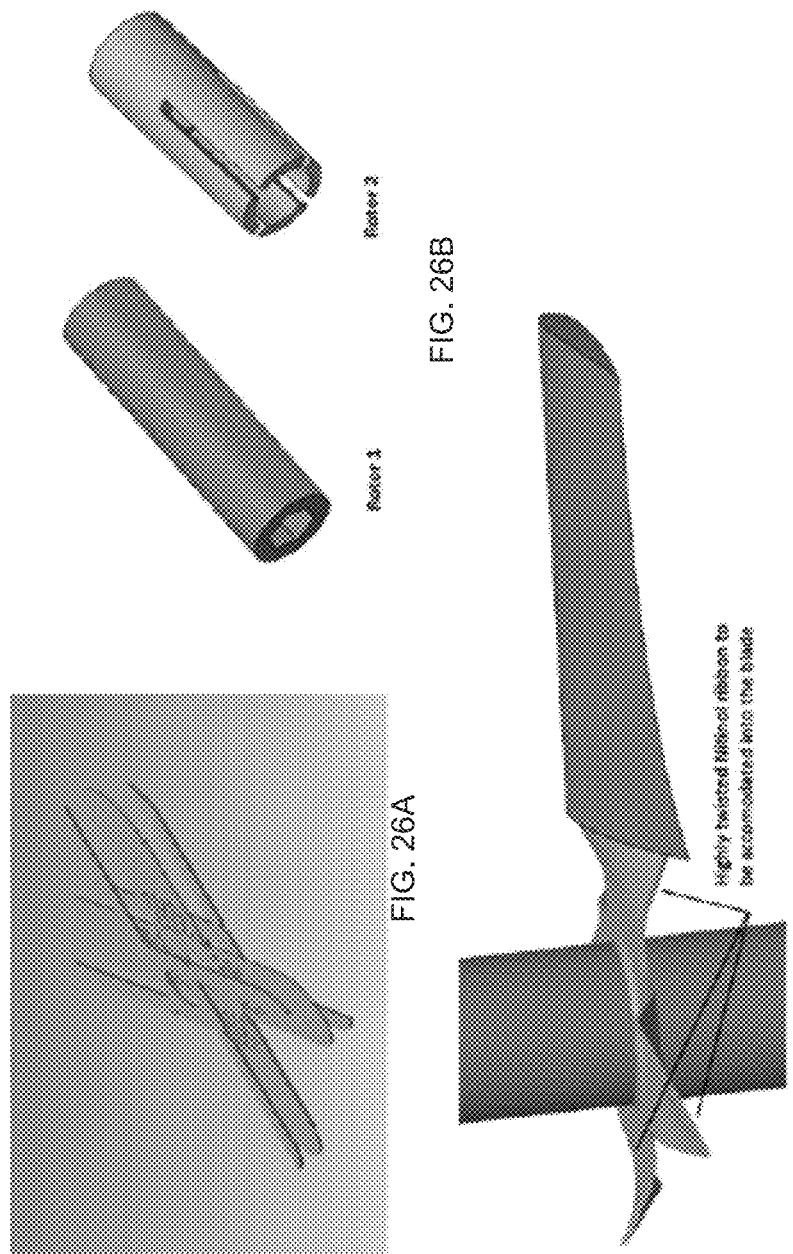

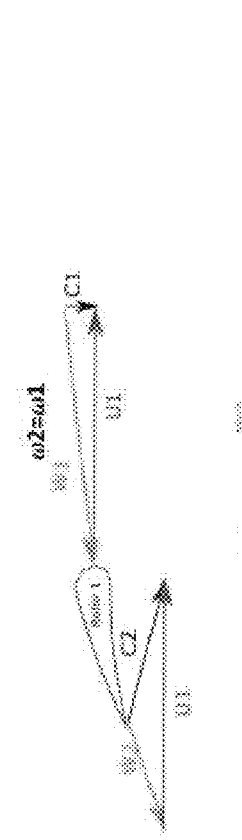
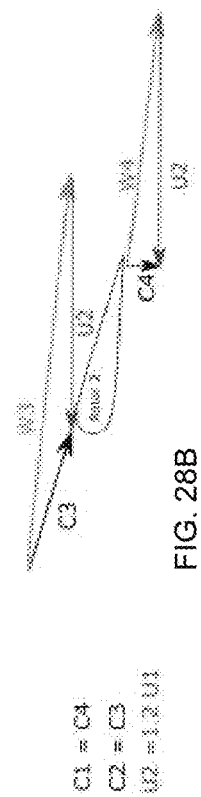
FIG. 28A
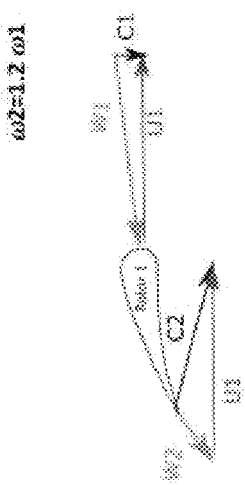
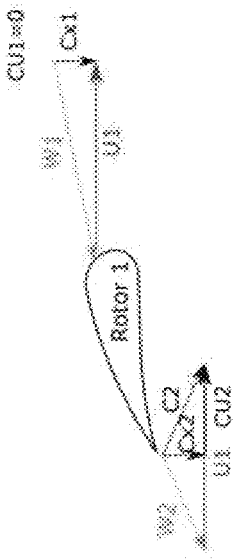
FIG. 28B
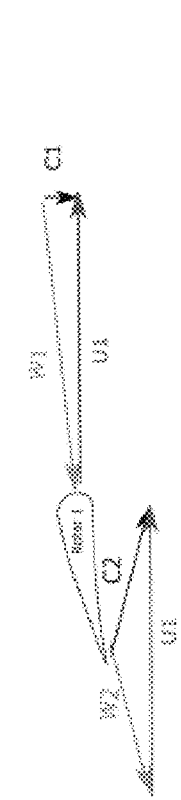
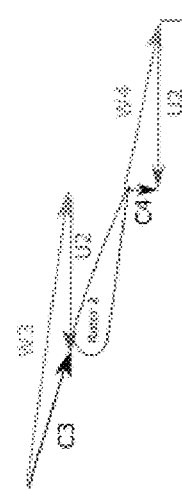
FIG. 28C
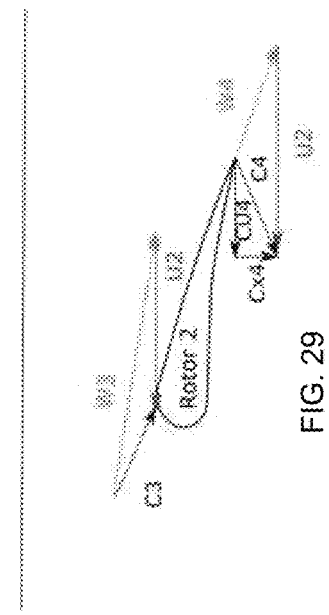
FIG. 29

| Example of vortex flow pattern | |
|---|---|
| Radius (mm) | Turns in 30 cm |
| At tip (20) | 2.4 |
| Near Tip (18) | 2.2 |
| Near Mean (10) | 0.82 |
| Near Hub (4) | 0.25 |

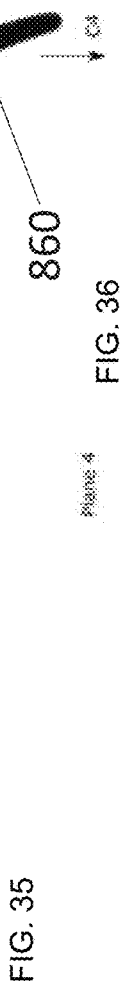
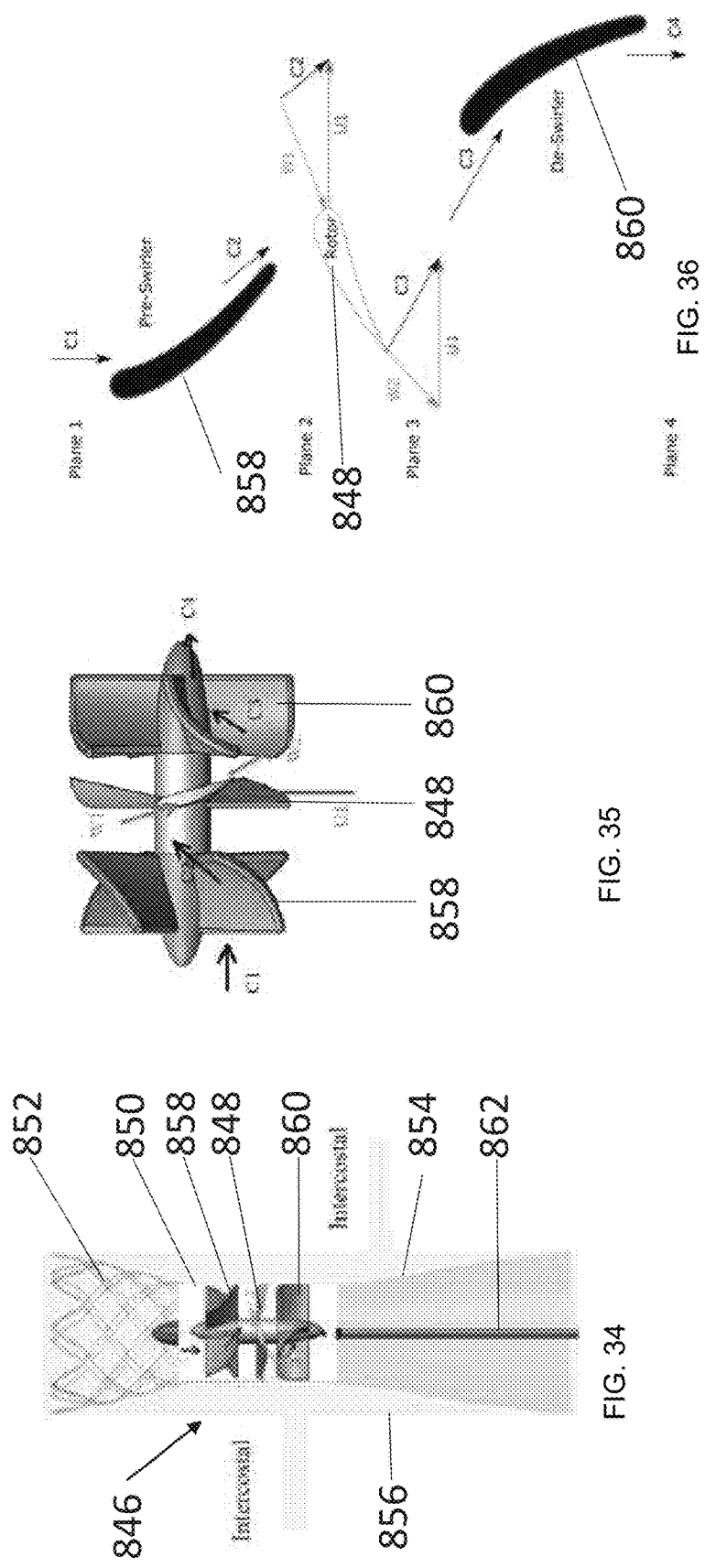
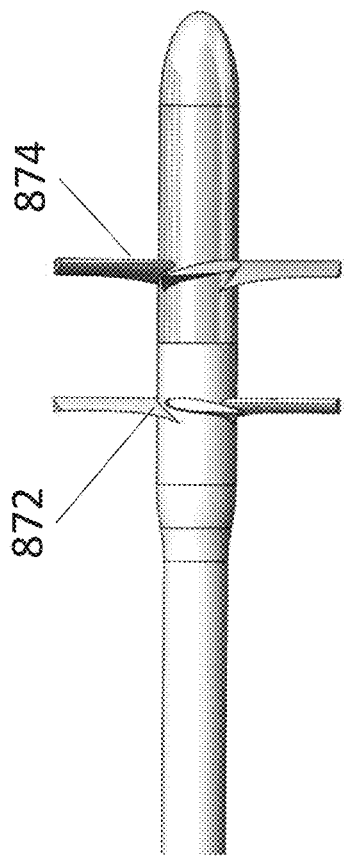
FIG. 36
FIG. 35
FIG. 37
FIG. 34

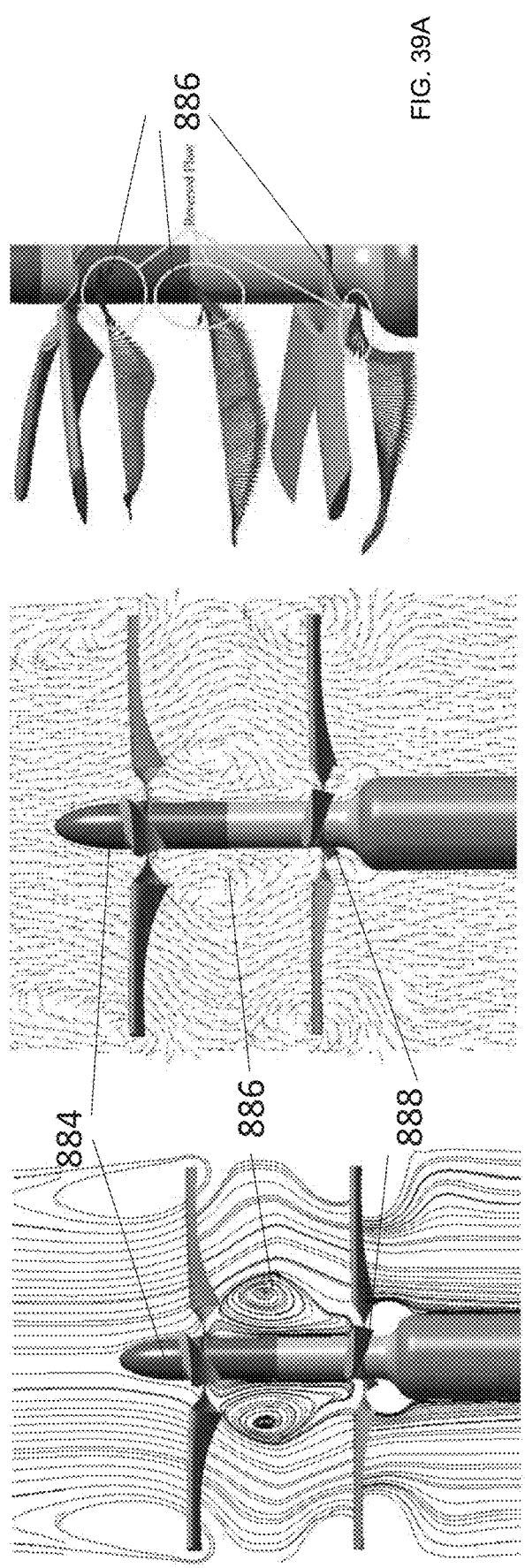
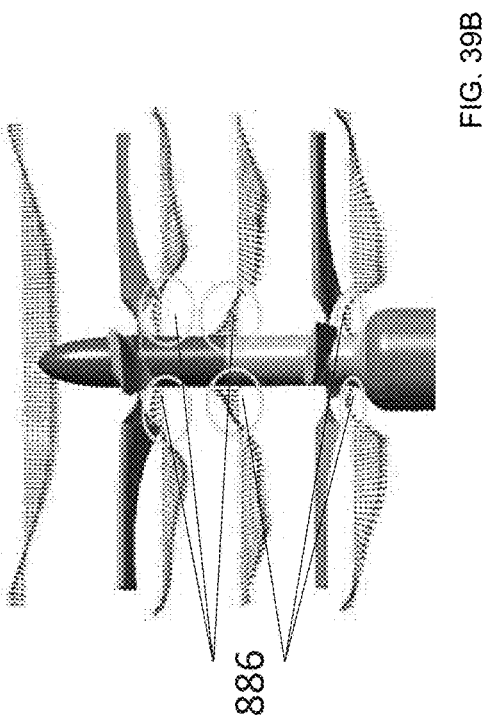
FIG. 38A
FIG. 38B
FIG. 39A
FIG. 39B

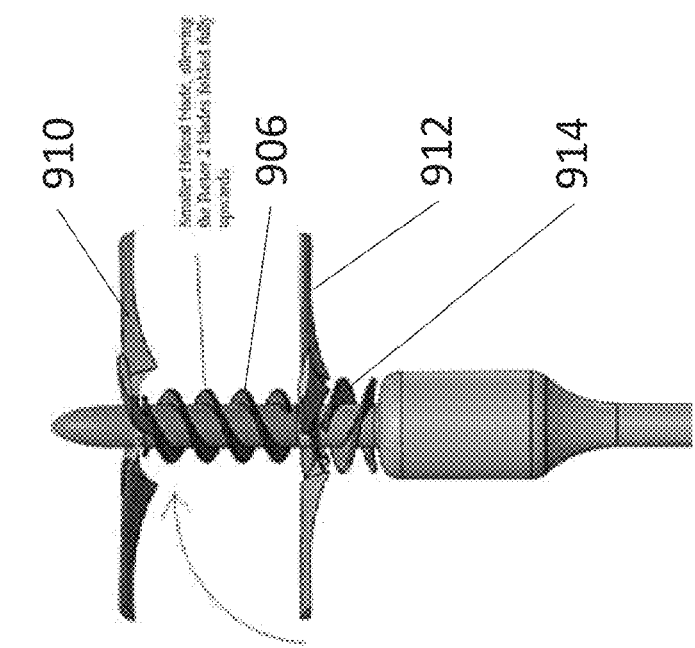
FIG. 45
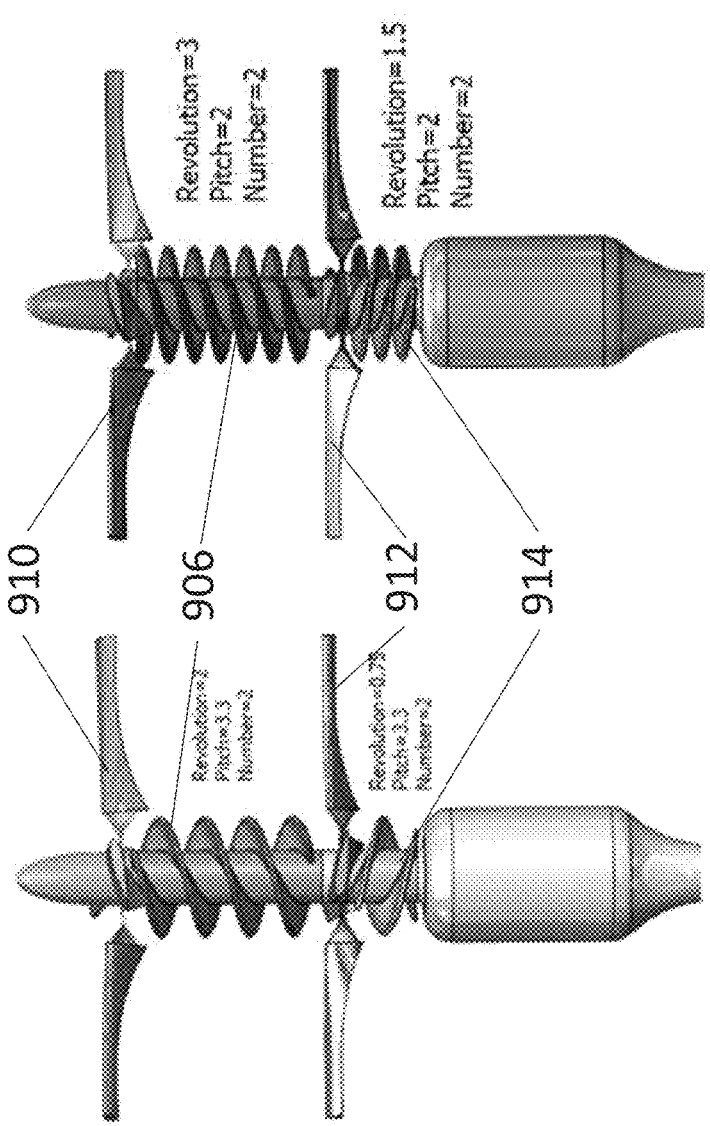
FIG. 44B
FIG. 44A

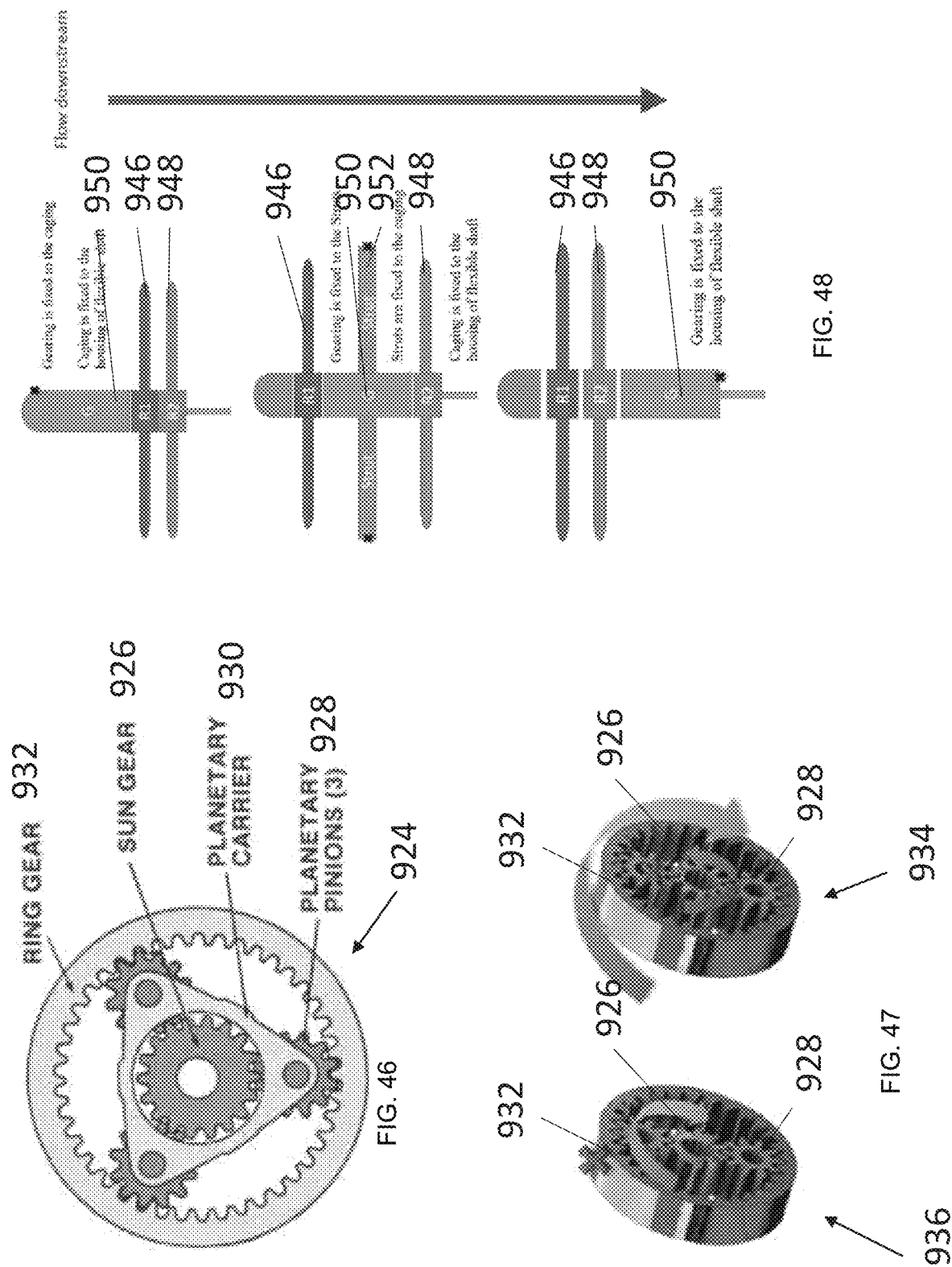

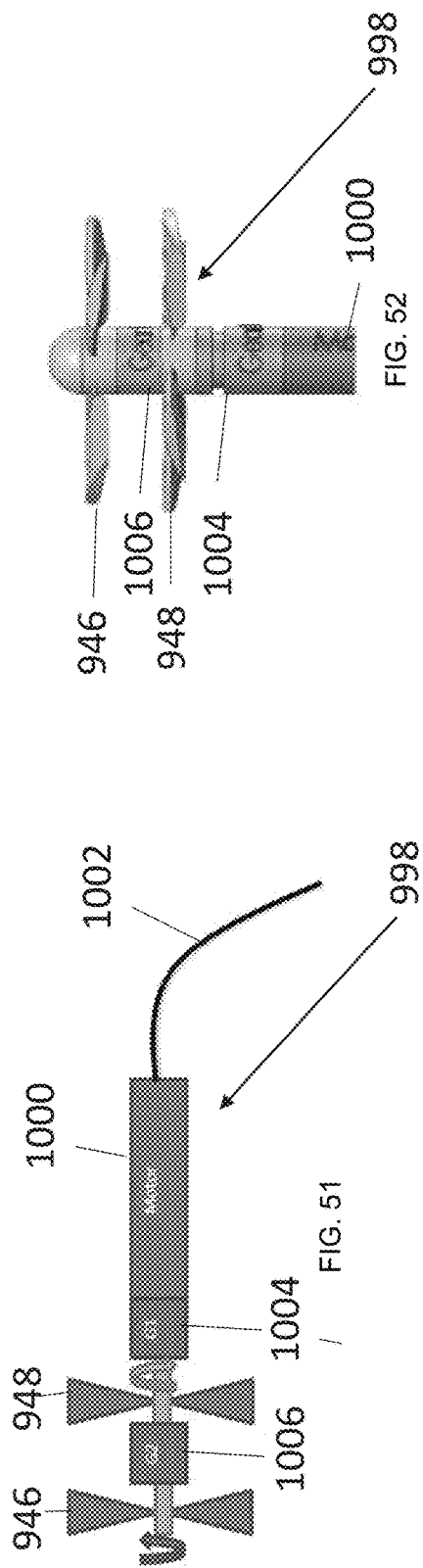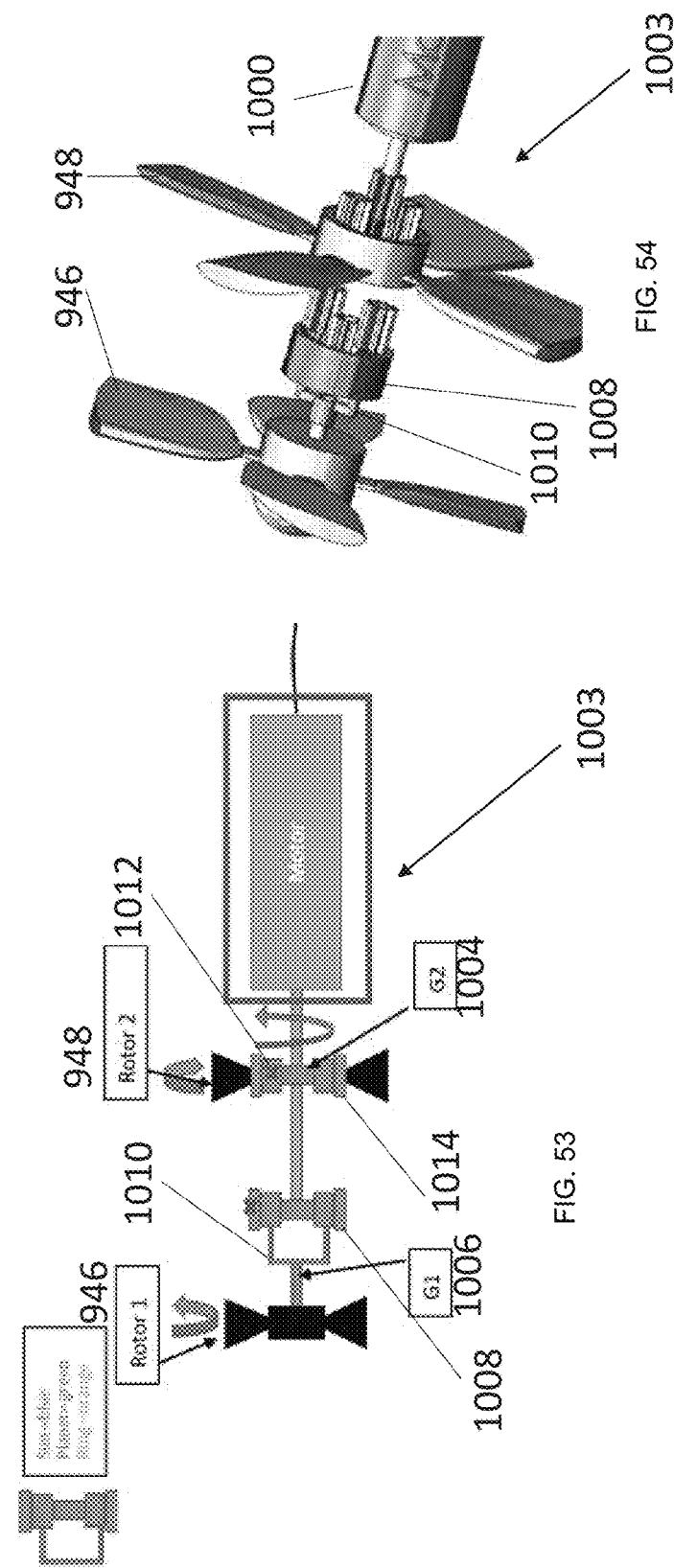

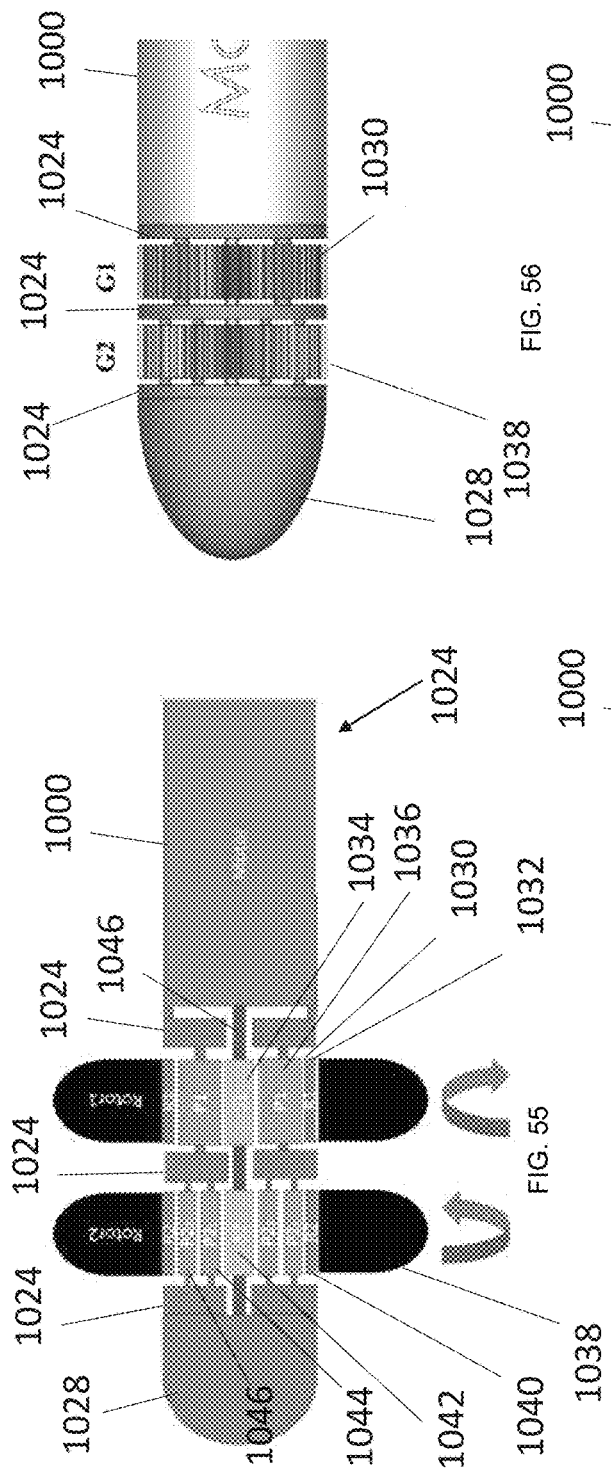
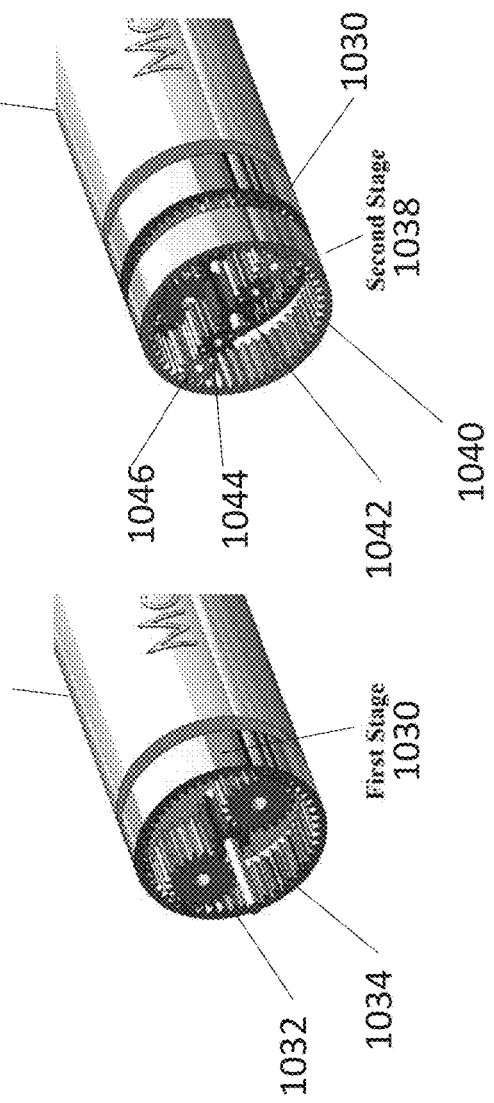
FIG. 56
FIG. 55
FIG. 57A
FIG. 57B

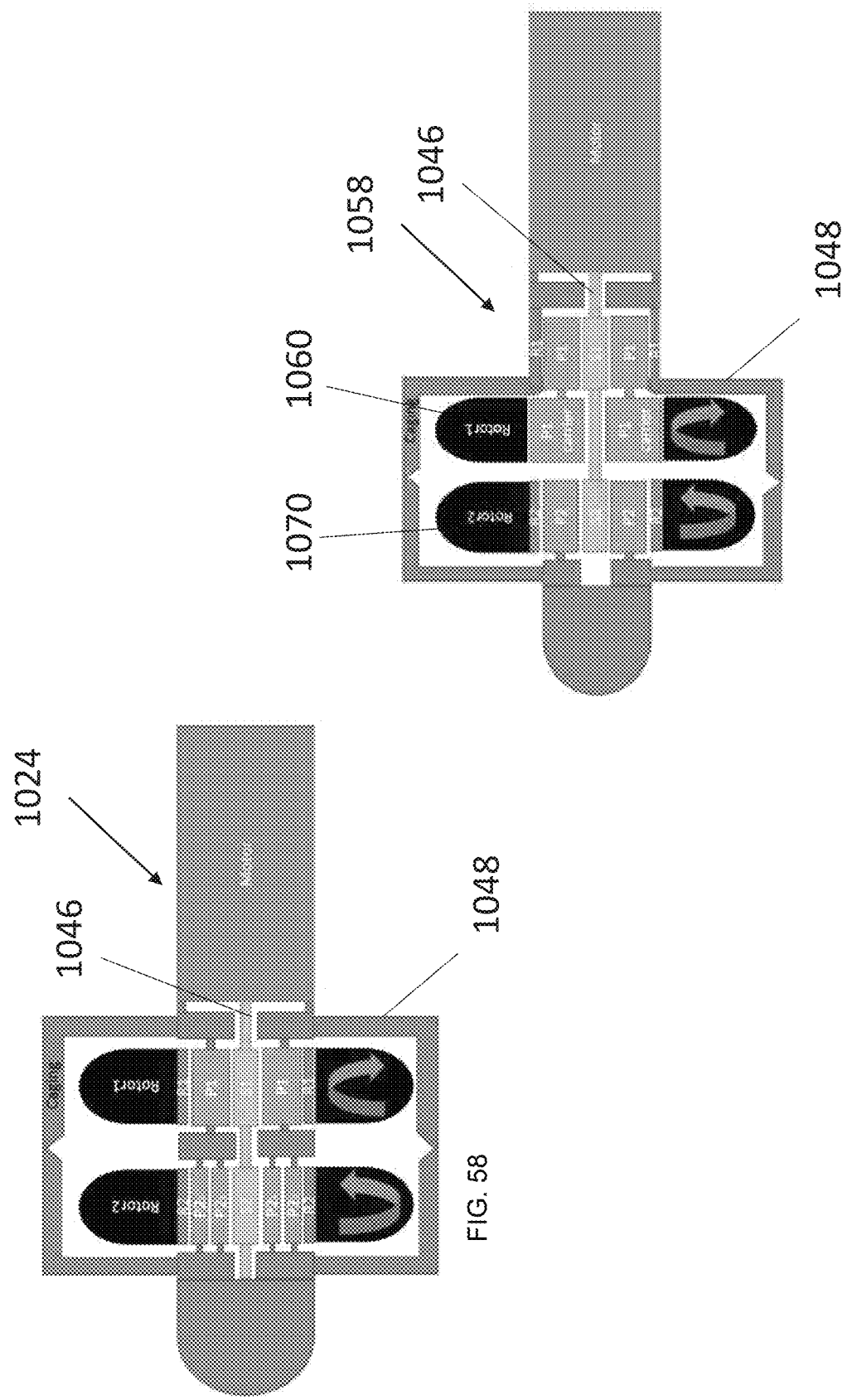

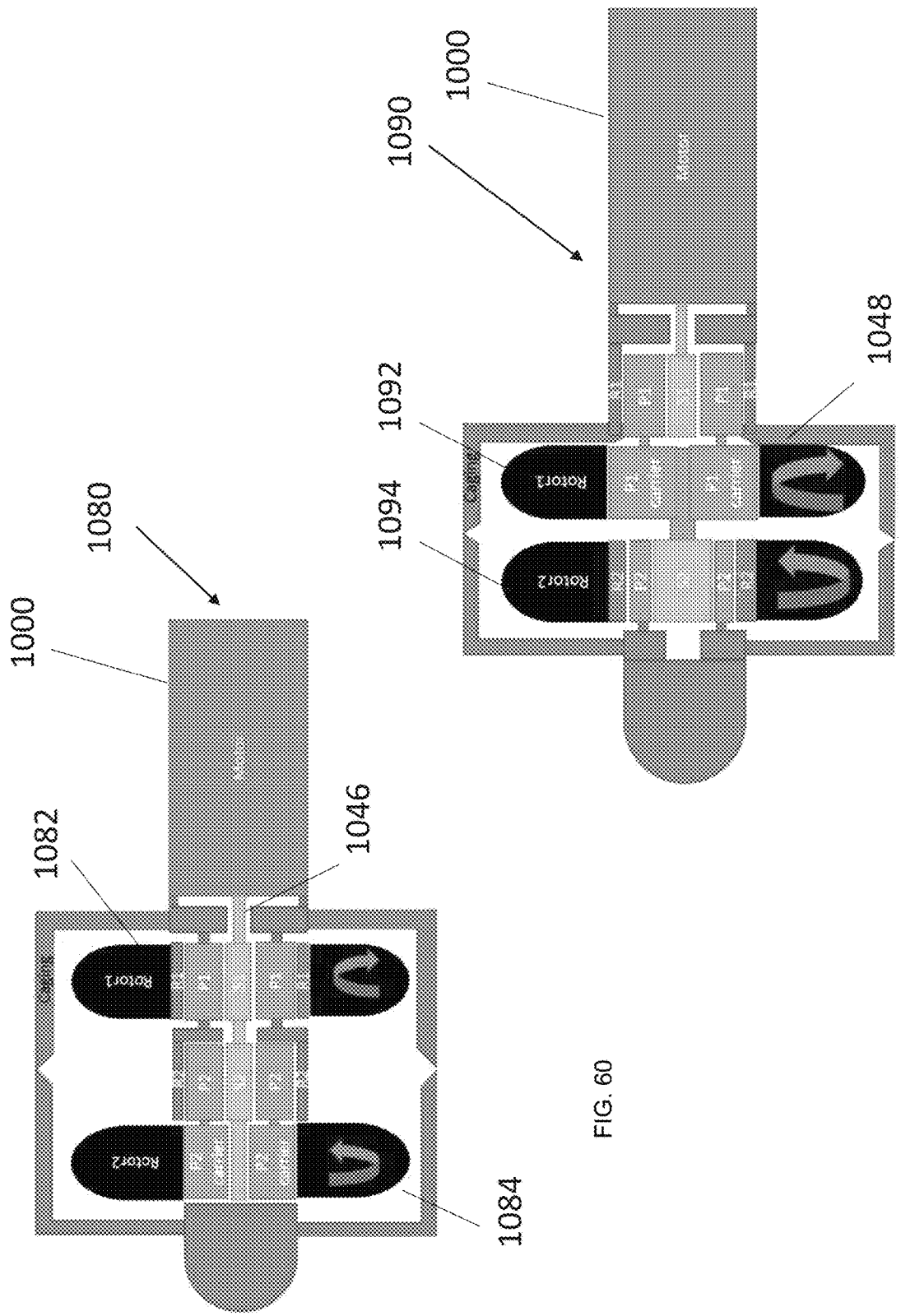

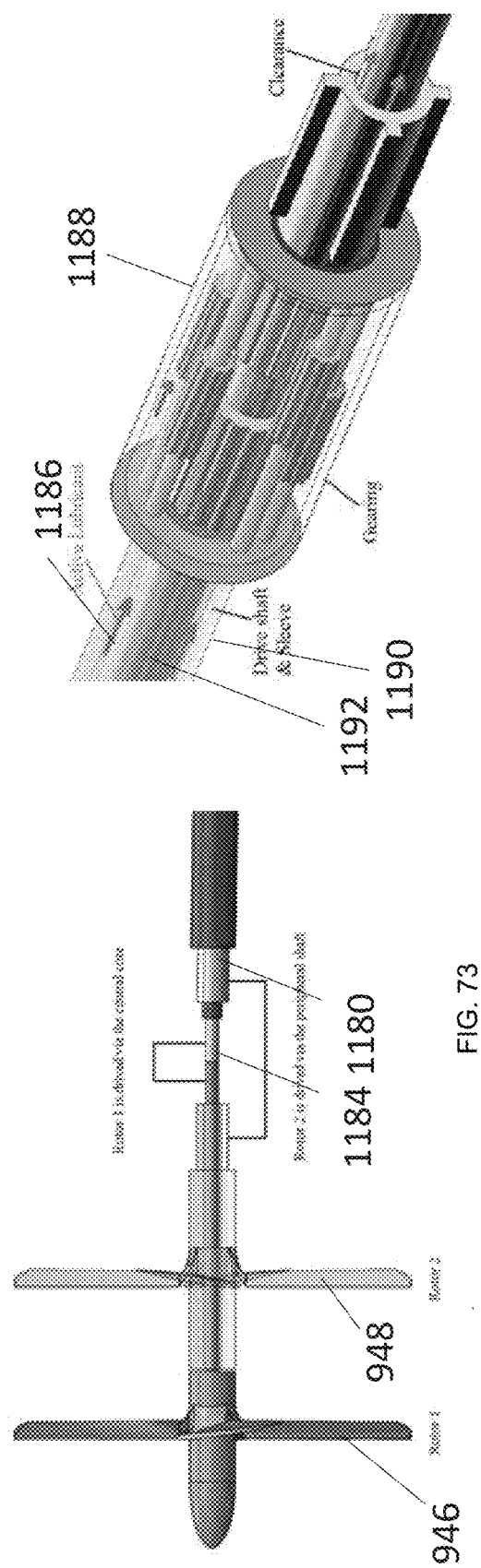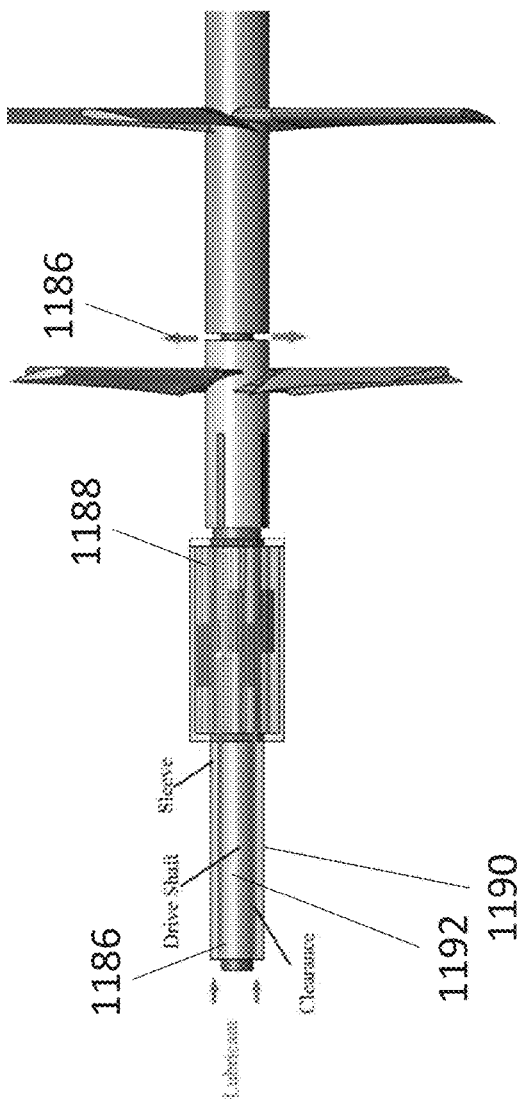
FIG. 73
FIG. 74
FIG. 75

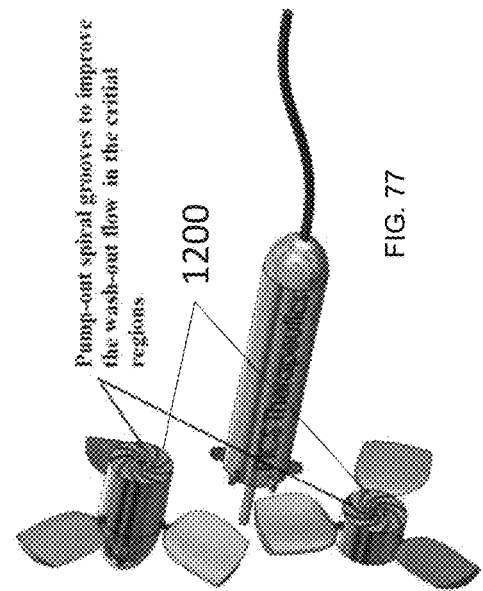
FIG. 77
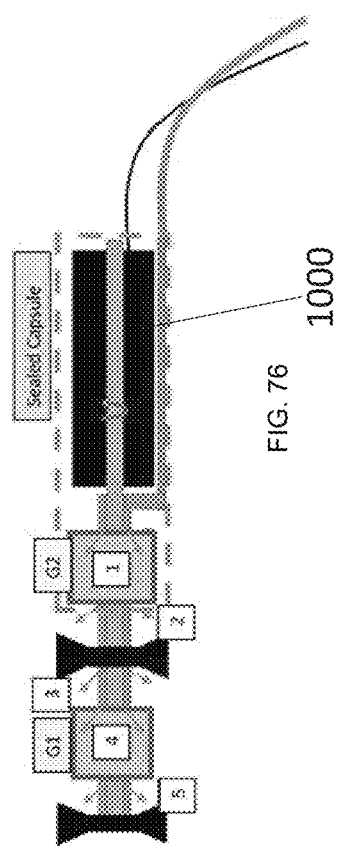
FIG. 76
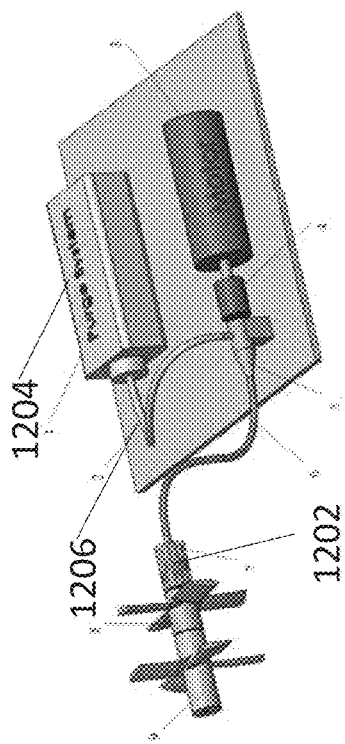
FIG. 78
FIG. 79

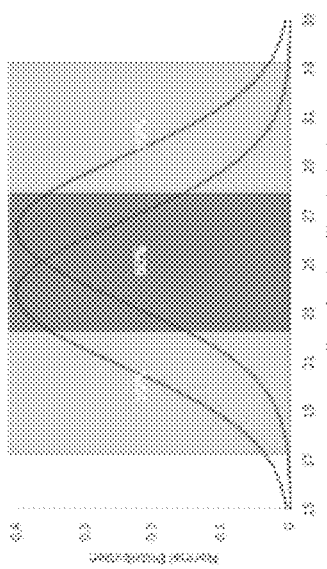
FIG. 80
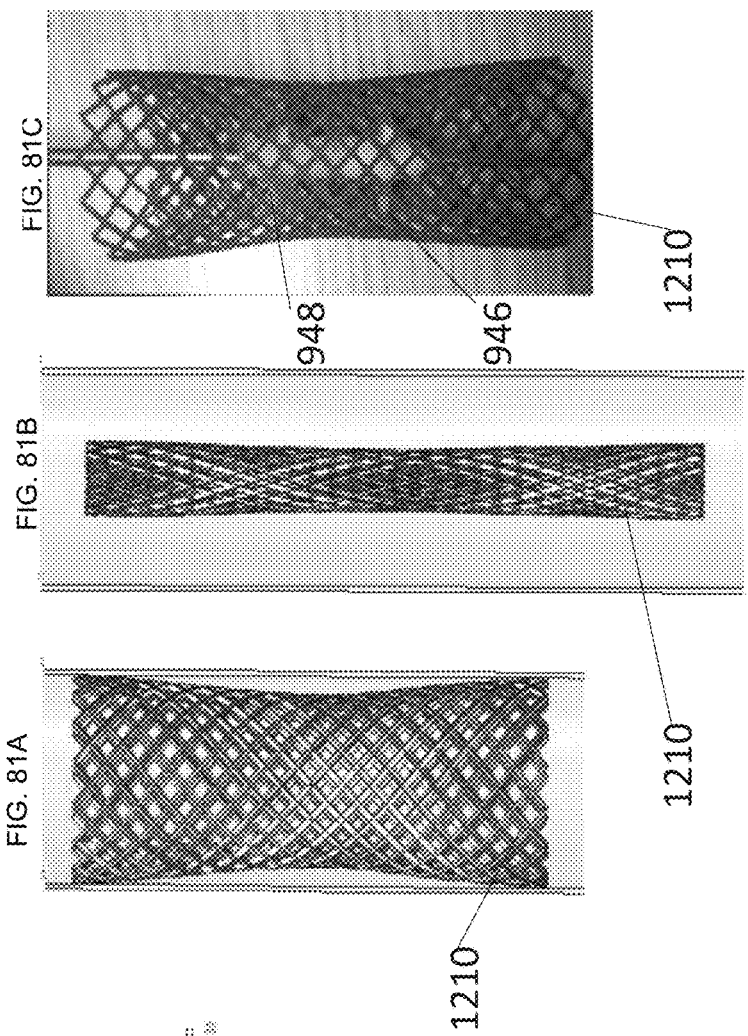

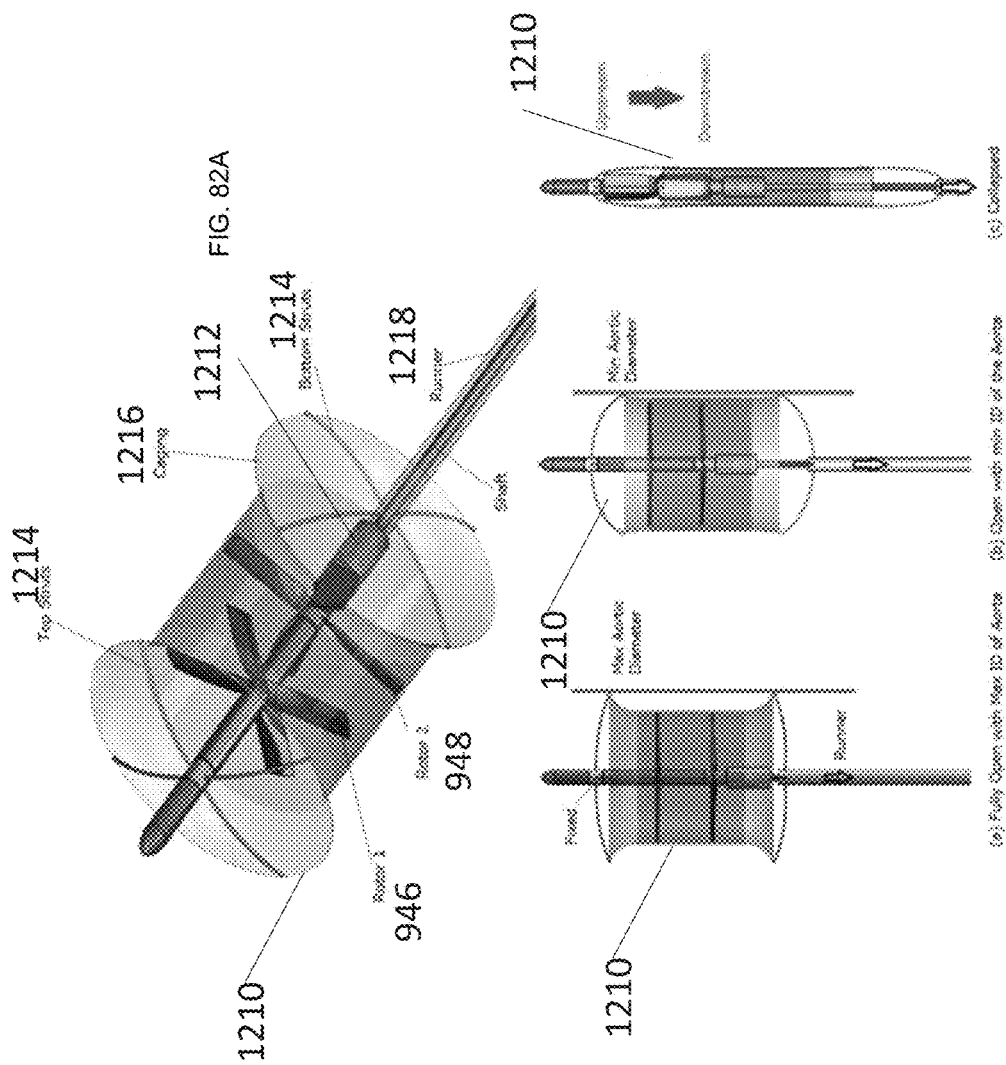

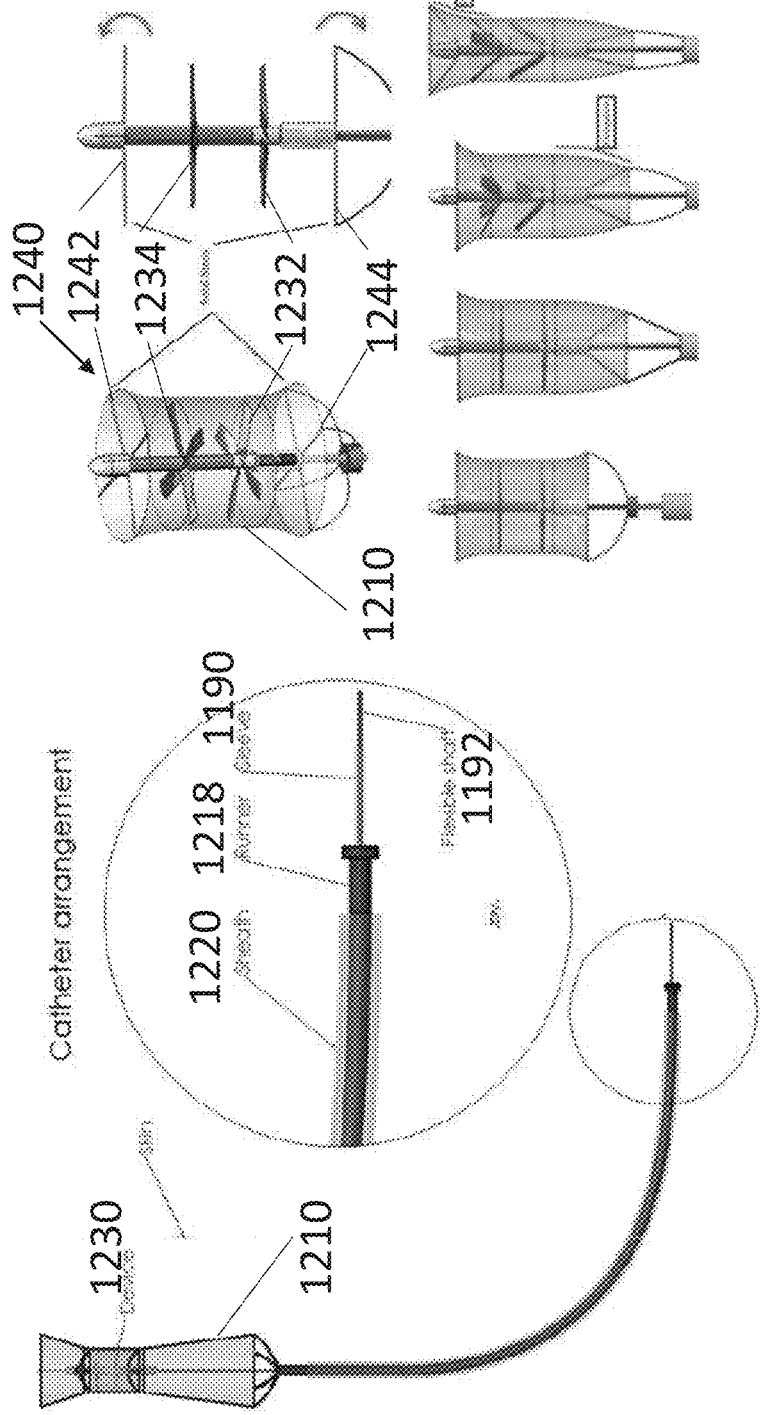
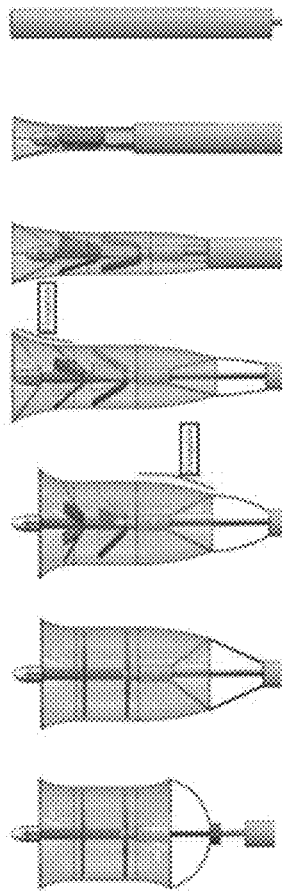
FIG. 85
FIG. 84

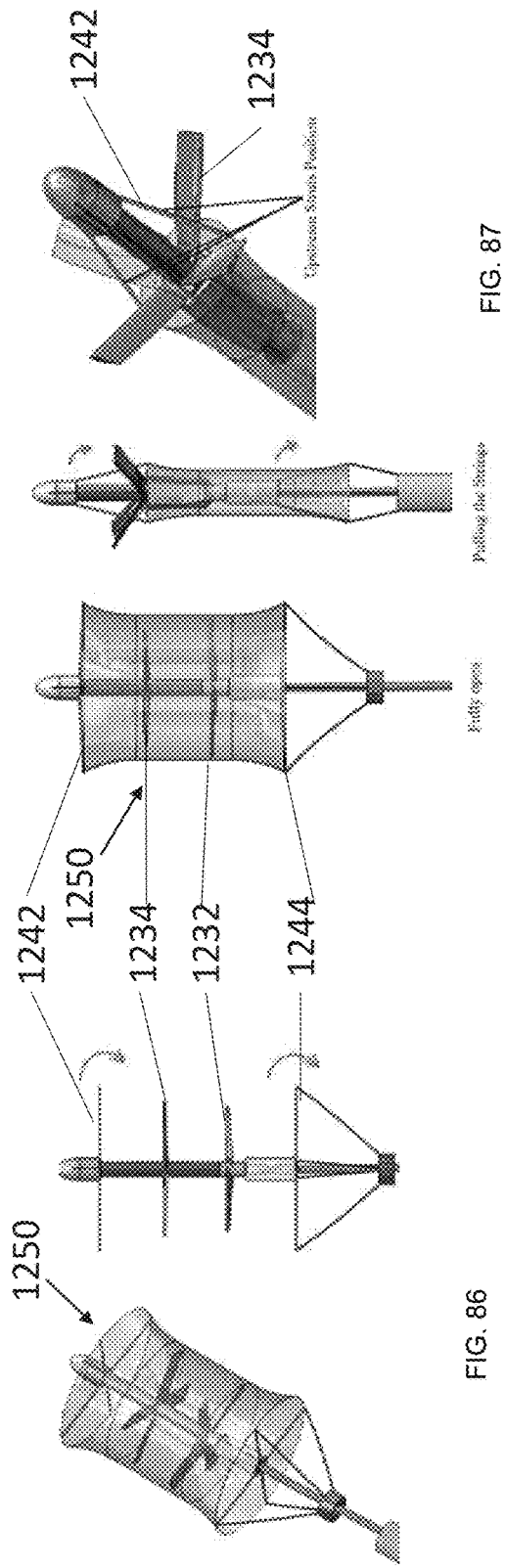
FIG. 86
FIG. 87
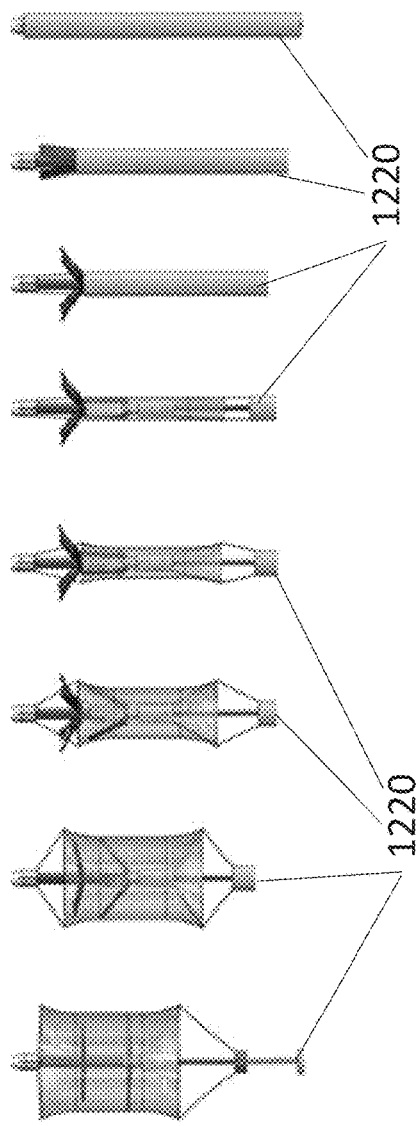
FIG. 88

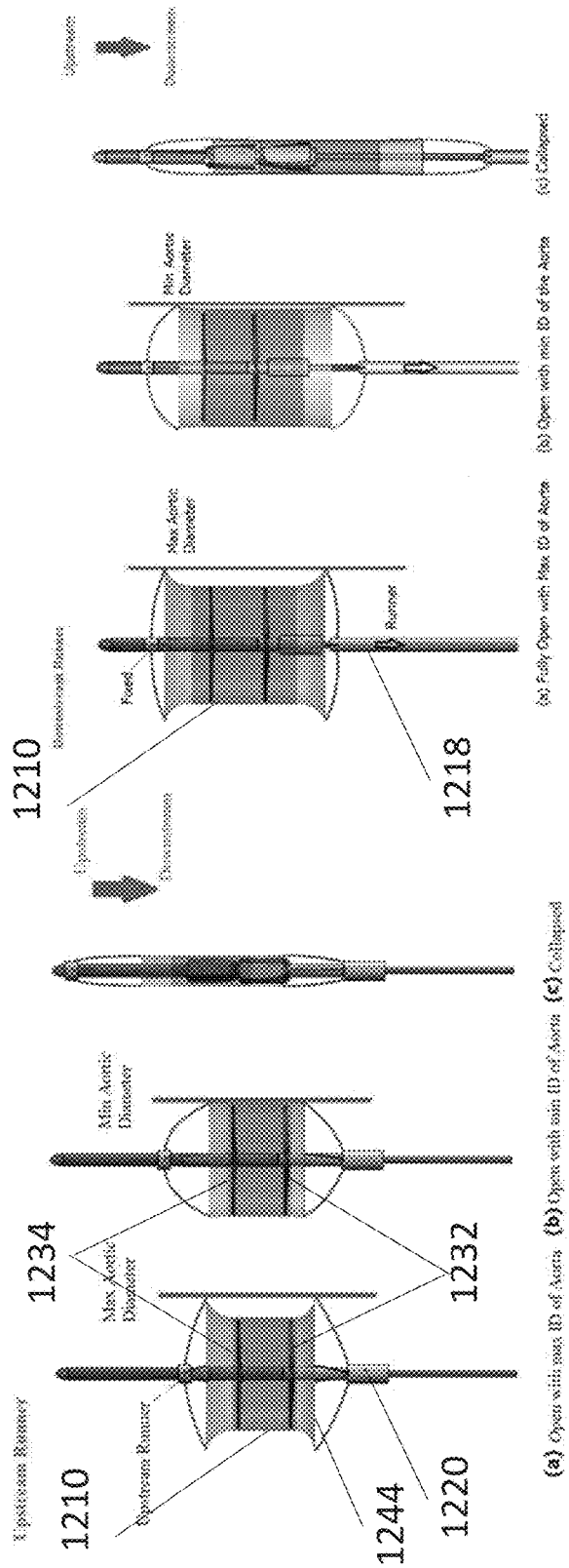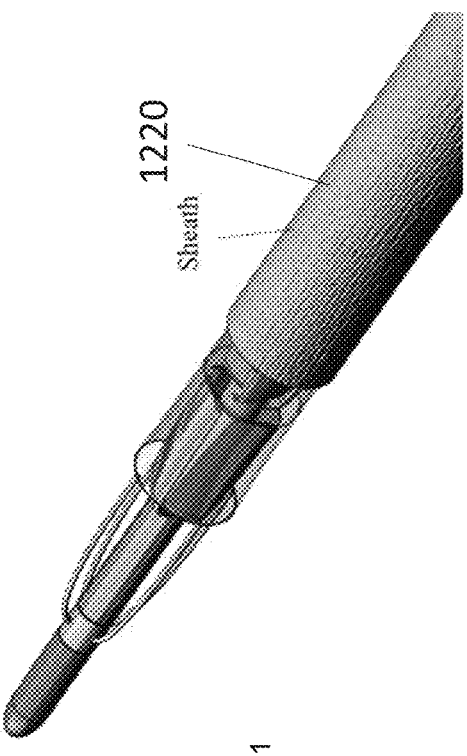
FIG. 89
FIG. 90
FIG. 91

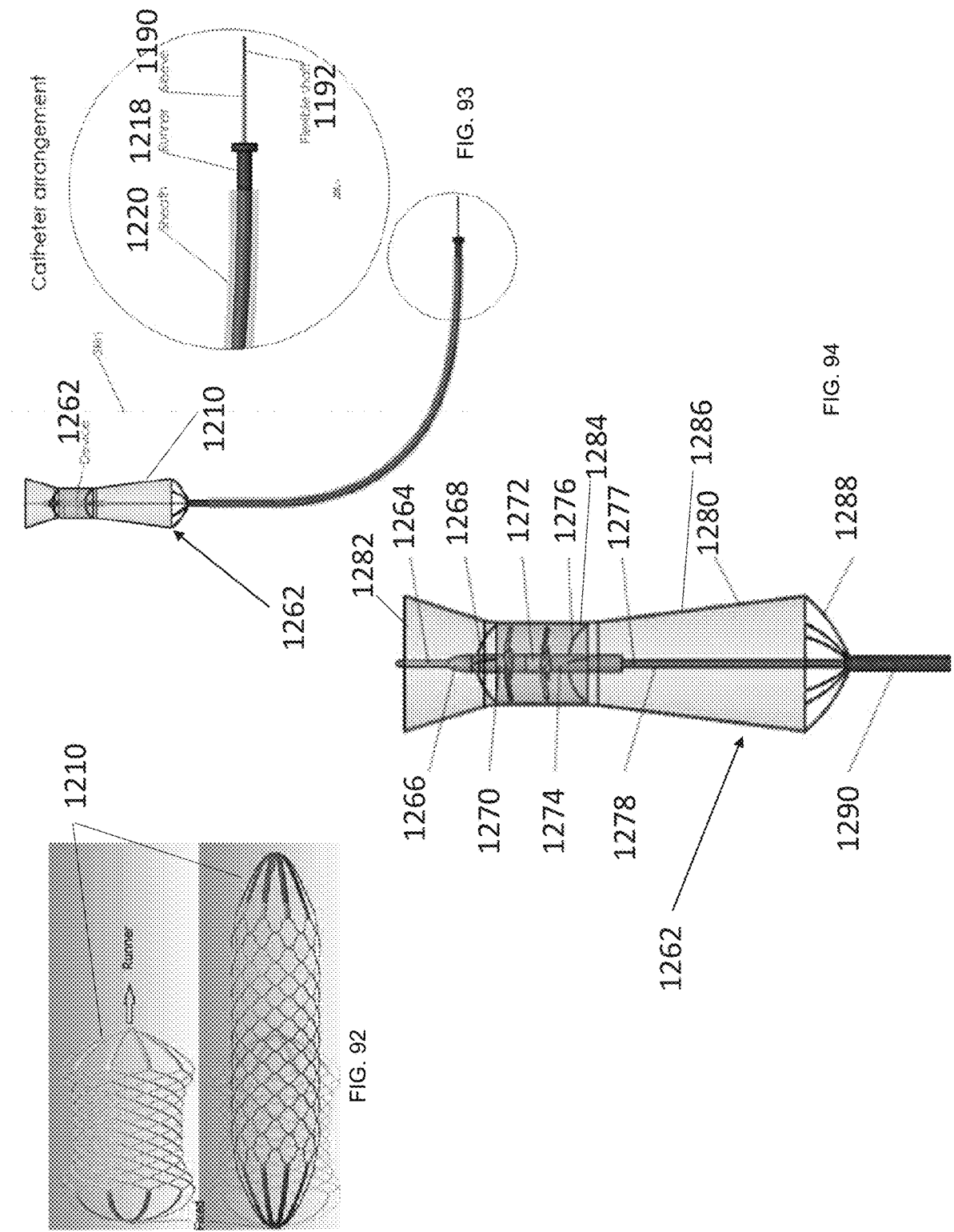

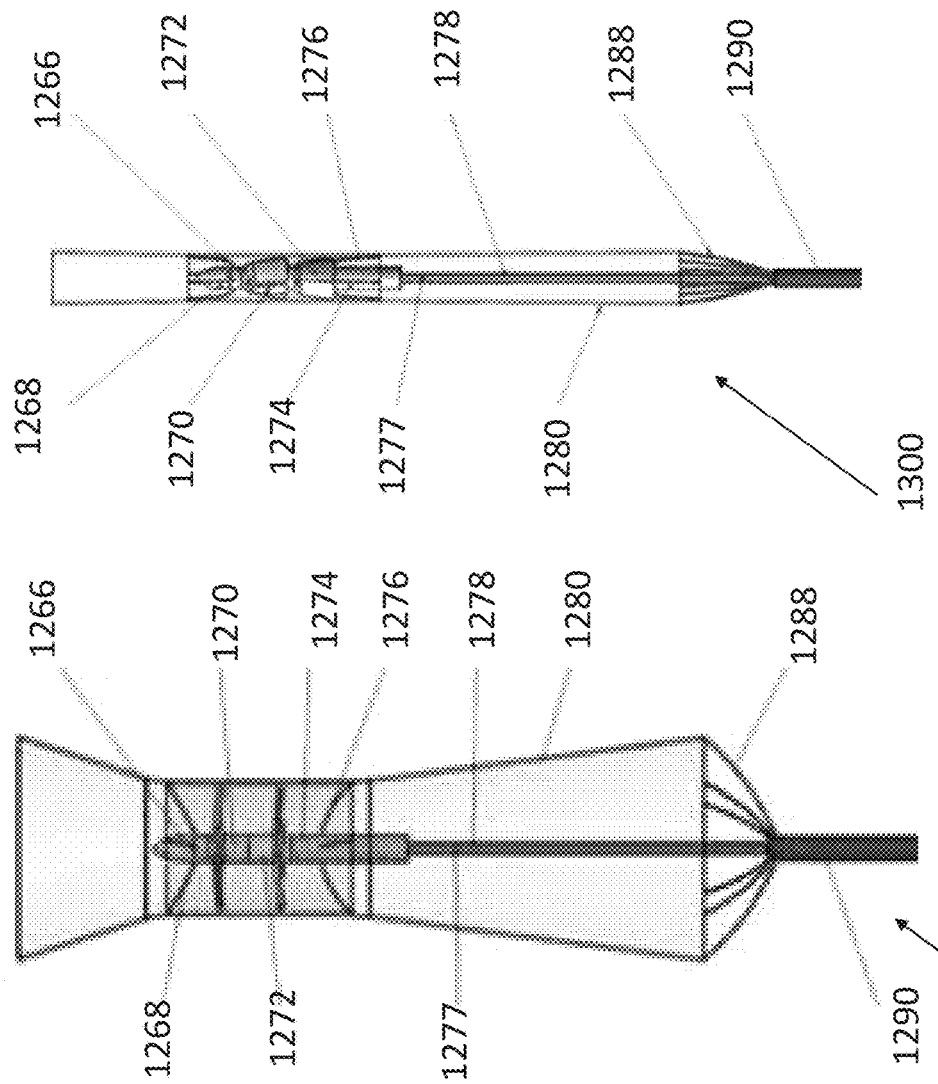

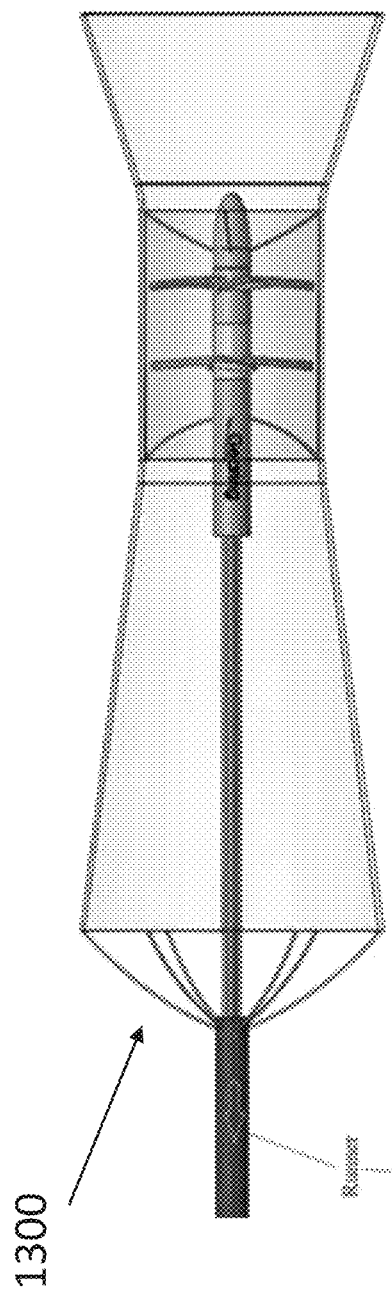
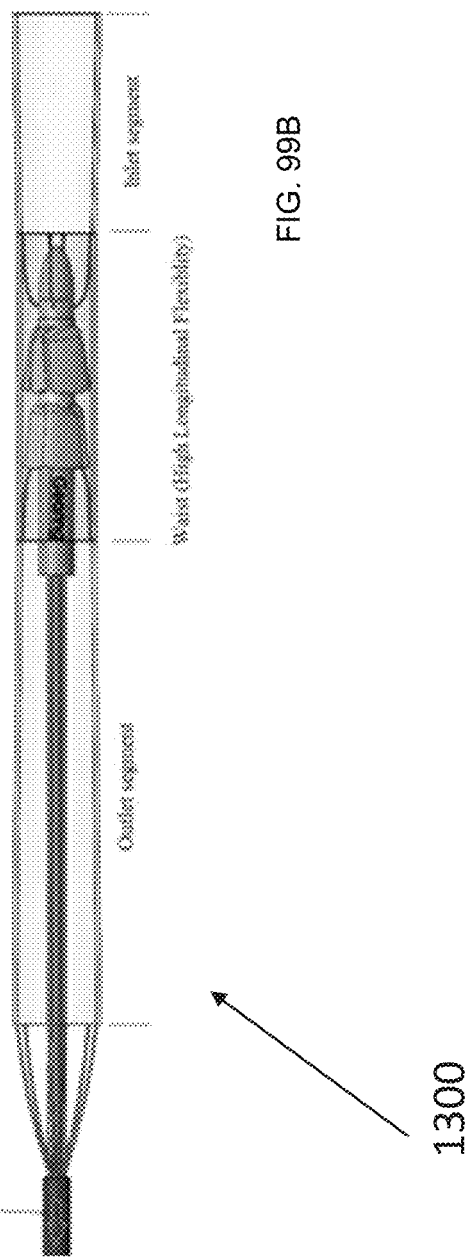
FIG. 99A
FIG. 99B

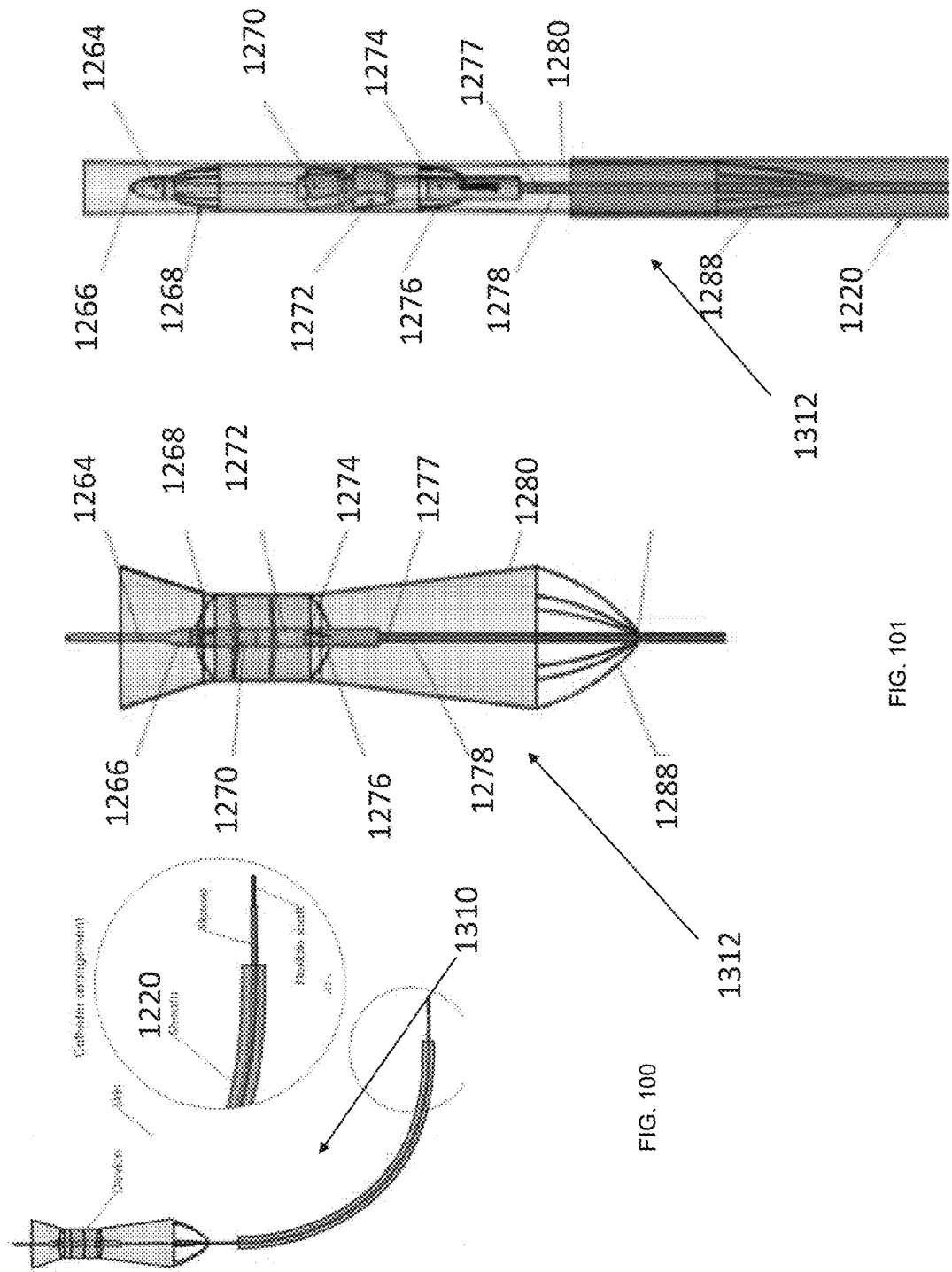

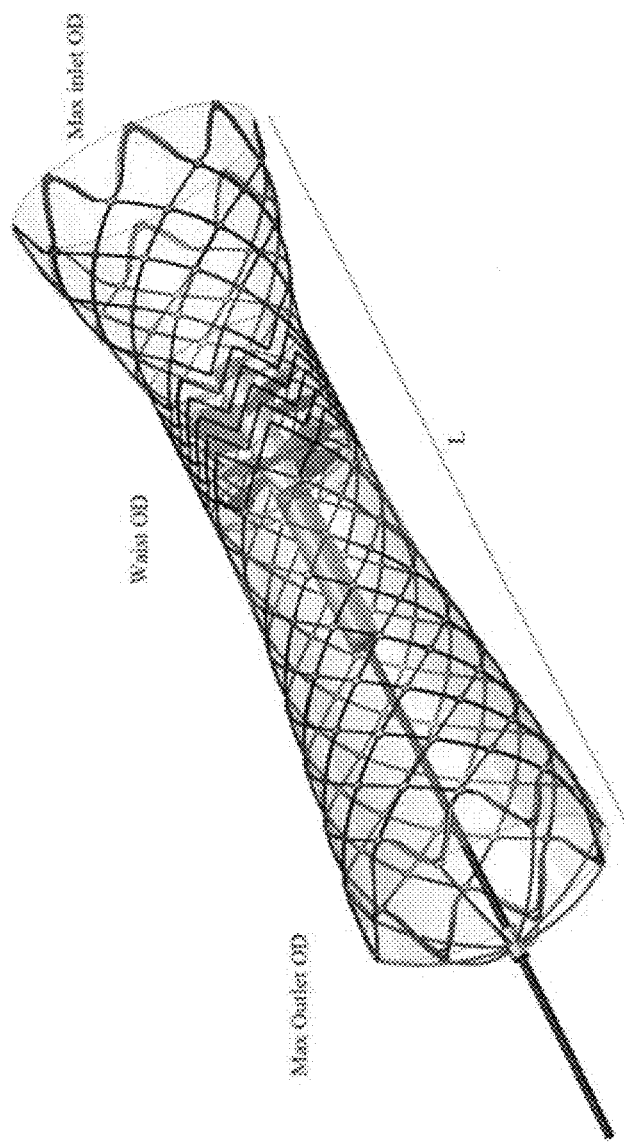
FIG. 104
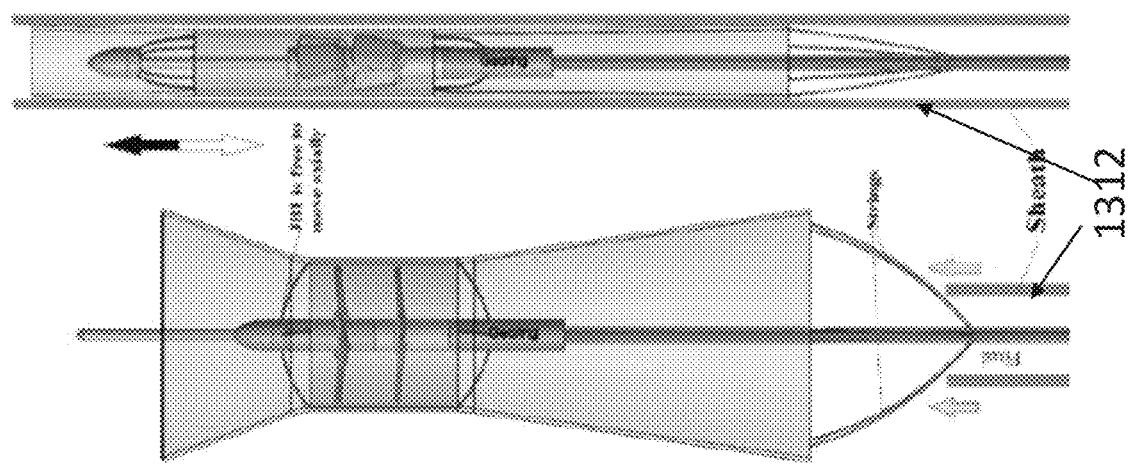
FIG. 103A
FIG. 103B

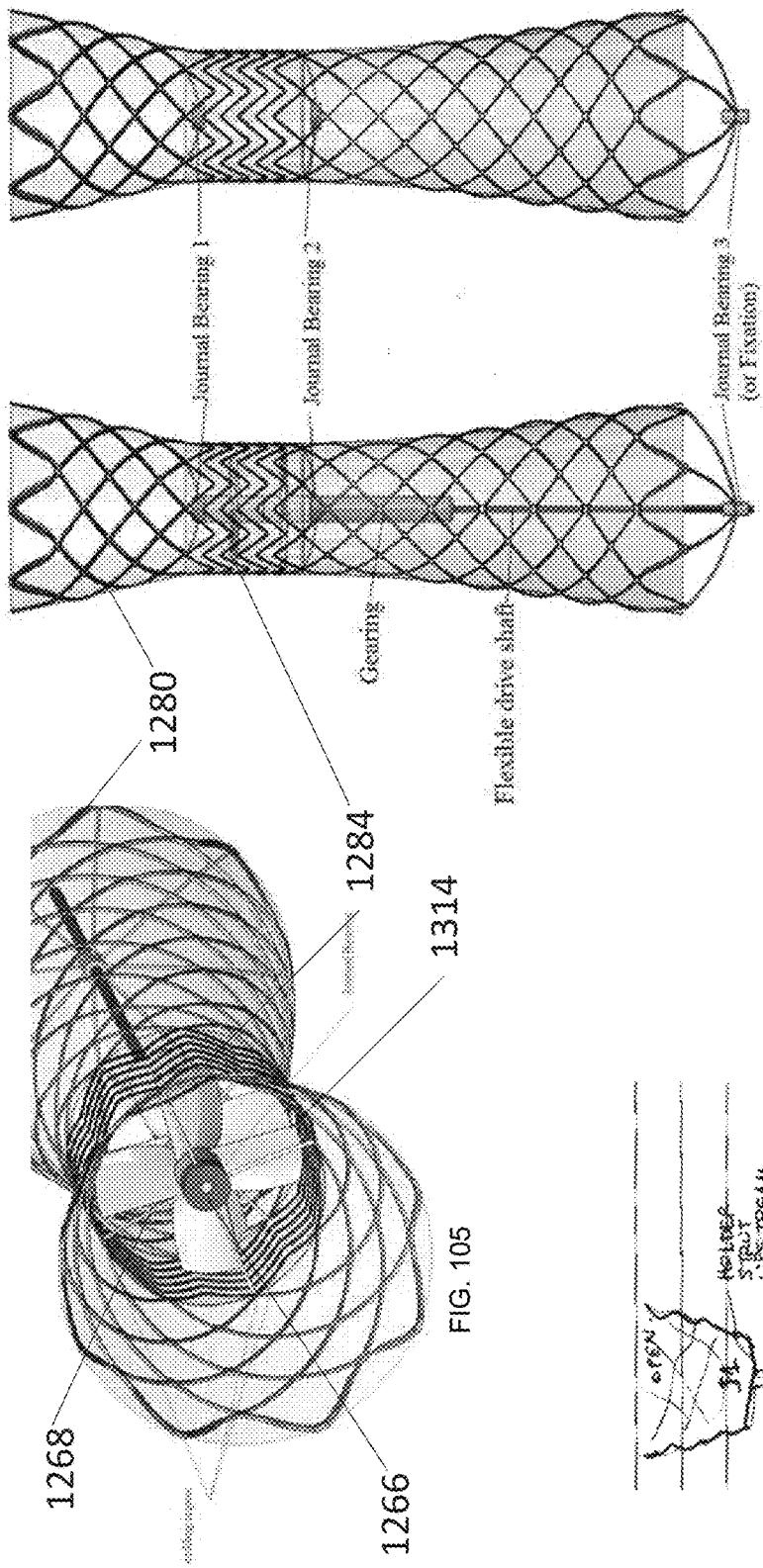
FIG. 105
FIG. 106
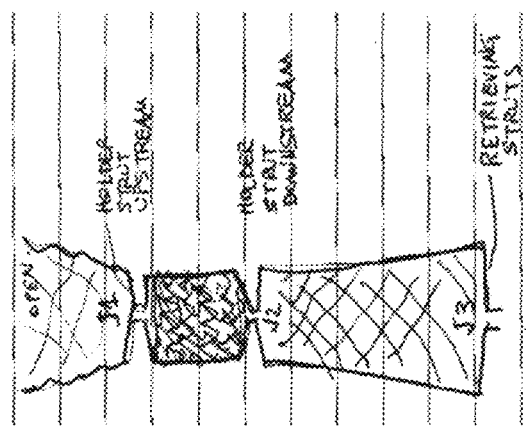
FIG. 107

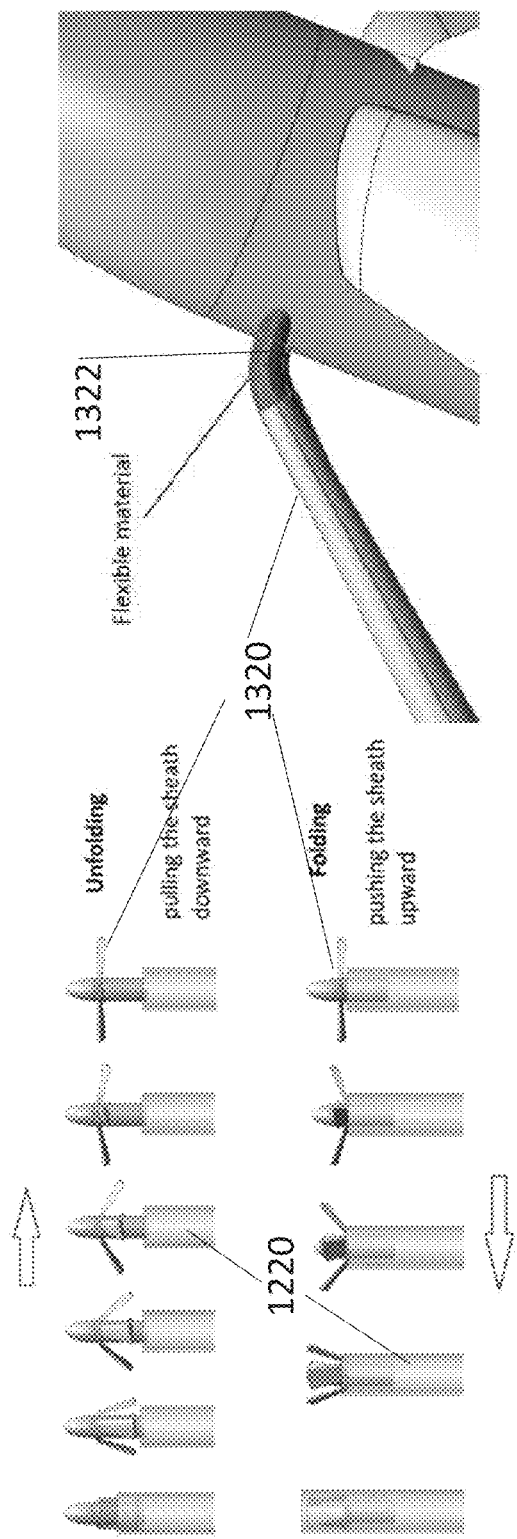
FIG. 109
FIG. 108
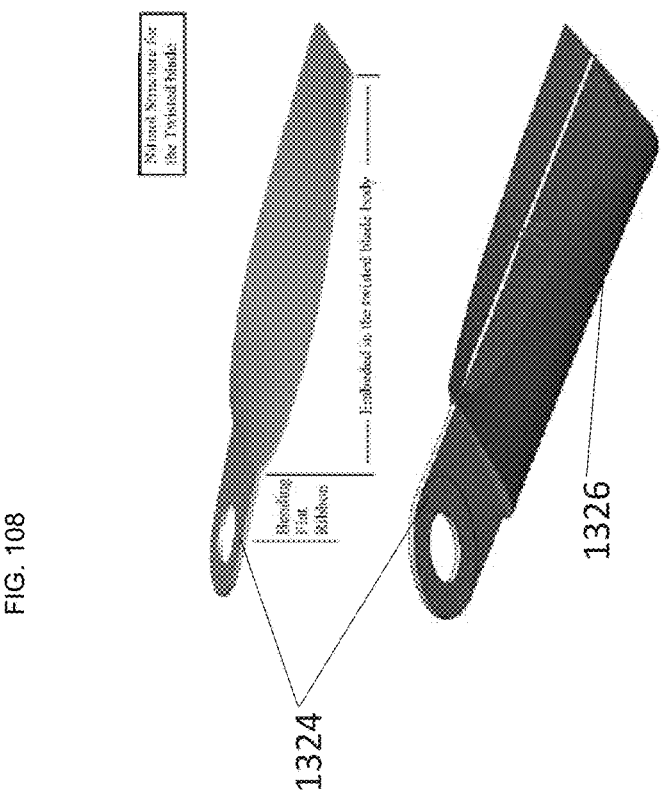
FIG. 110

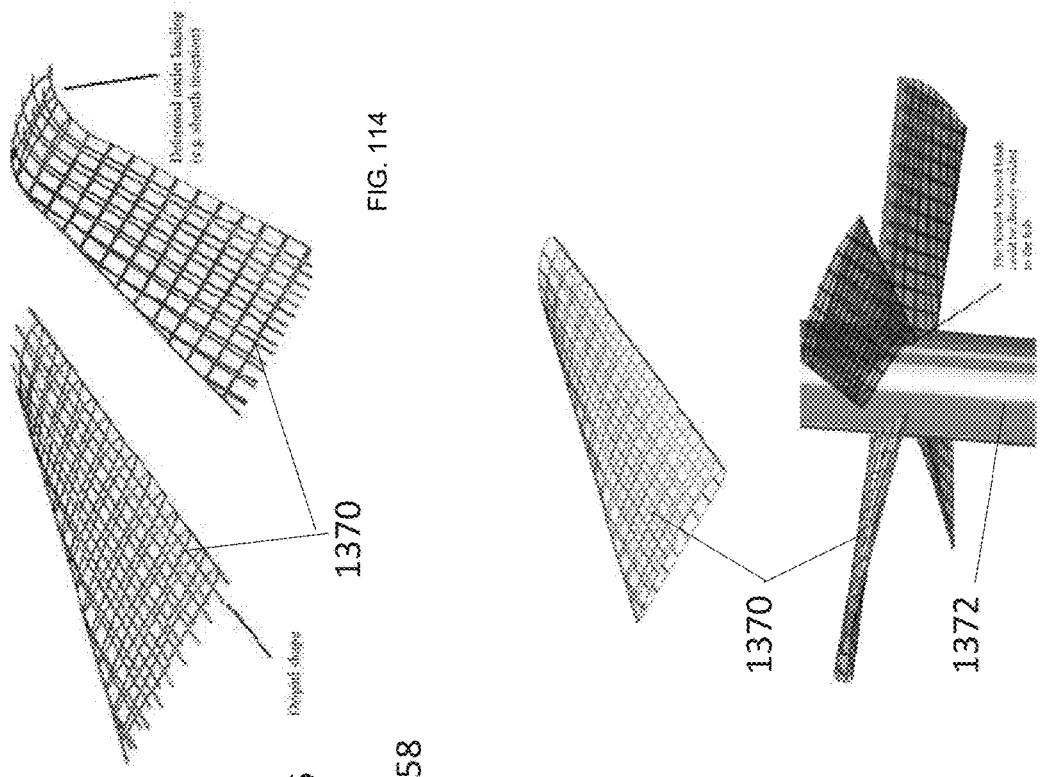
FIG. 114
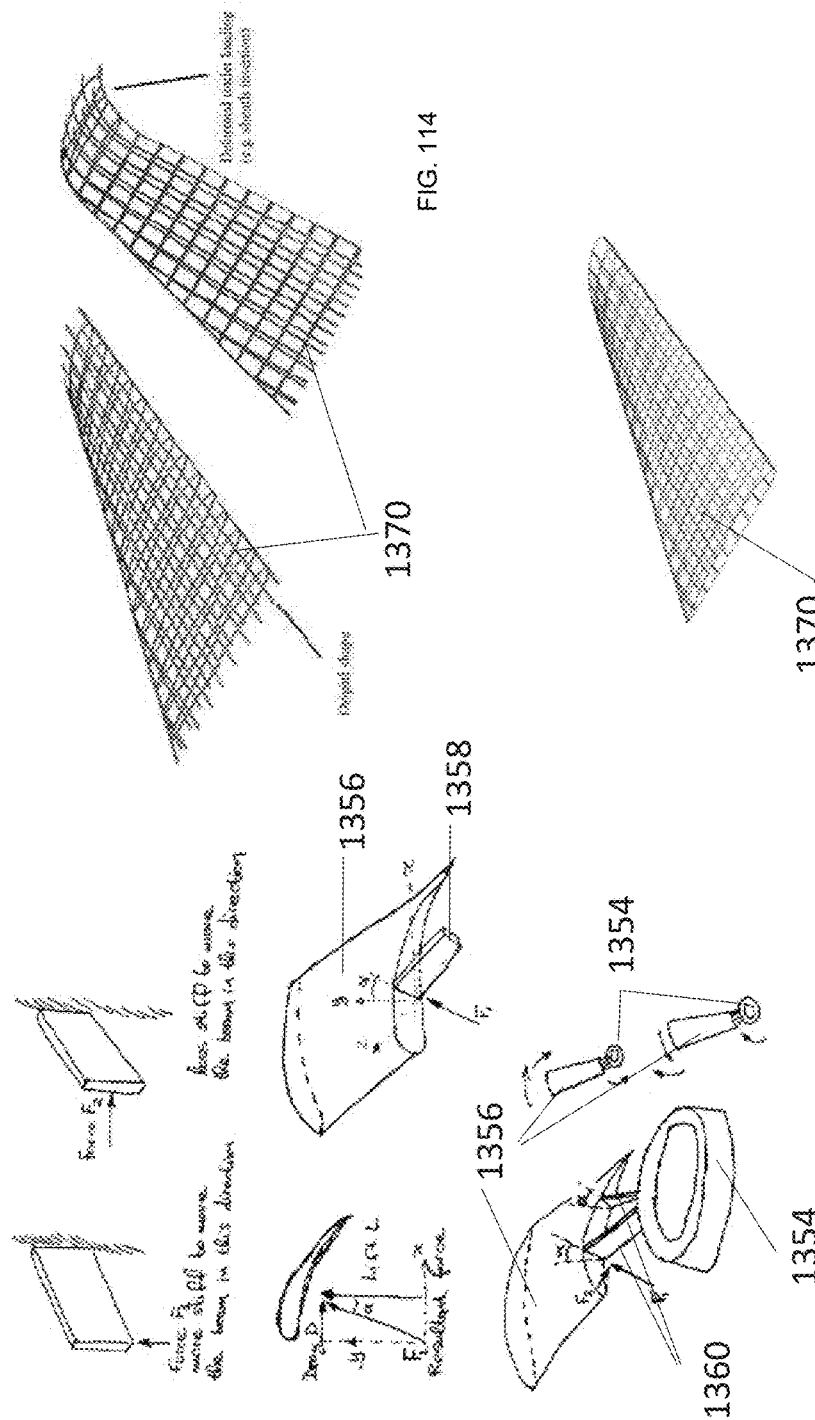
FIG. 115
FIG. 113

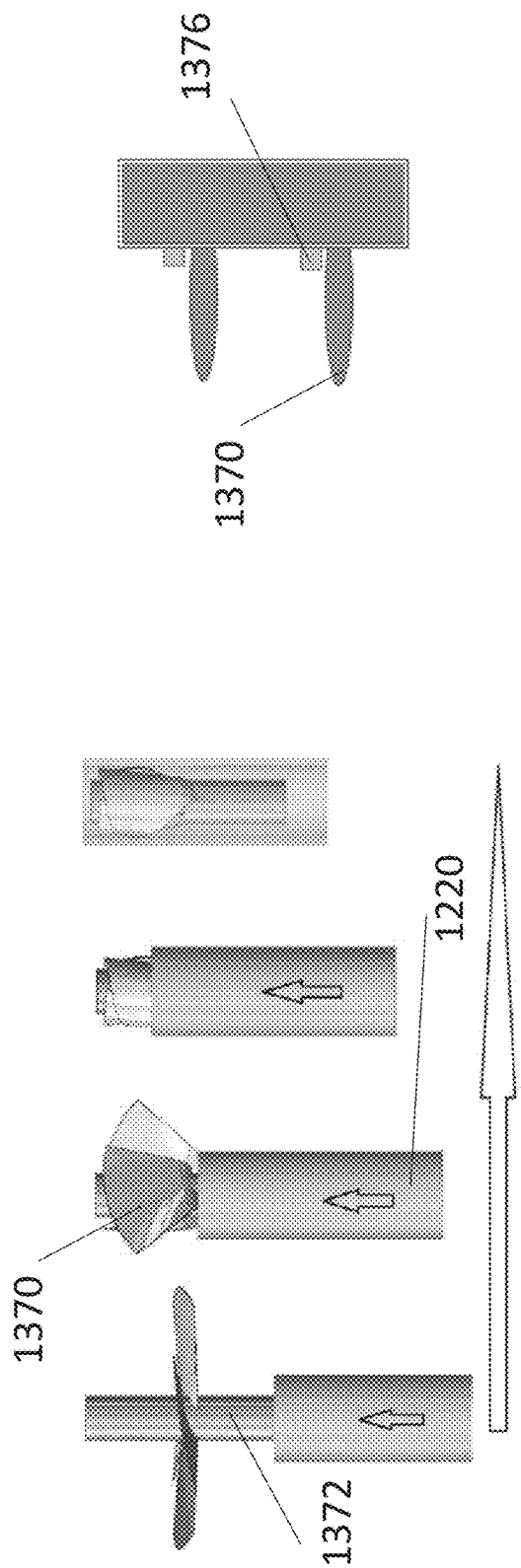
FIG. 116
FIG. 118
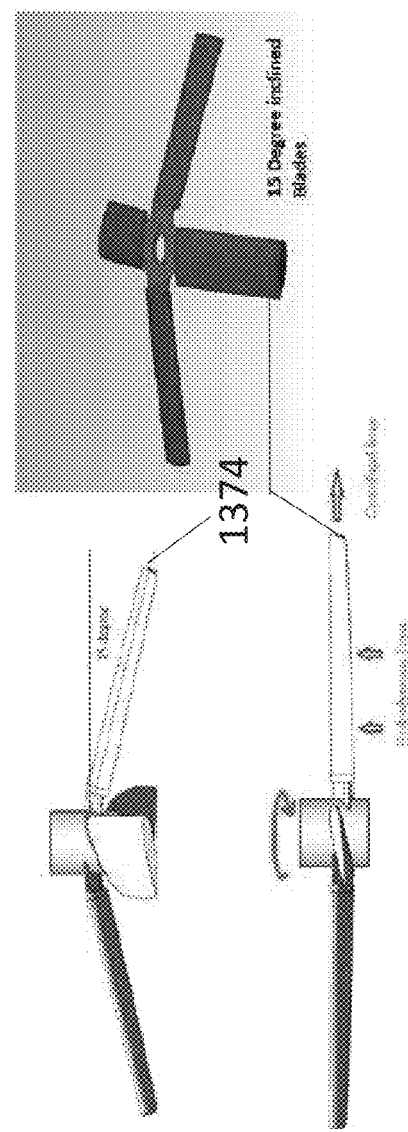
FIG. 117

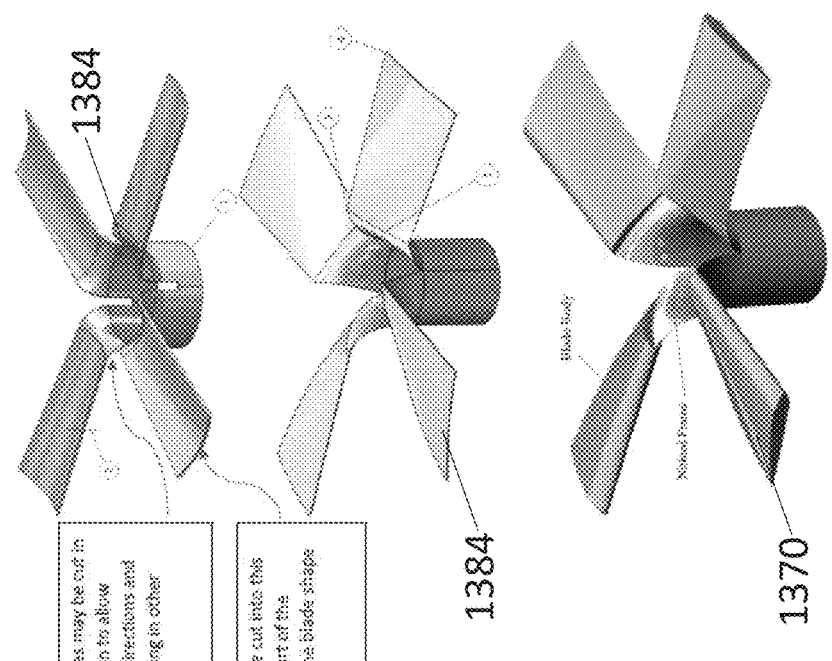
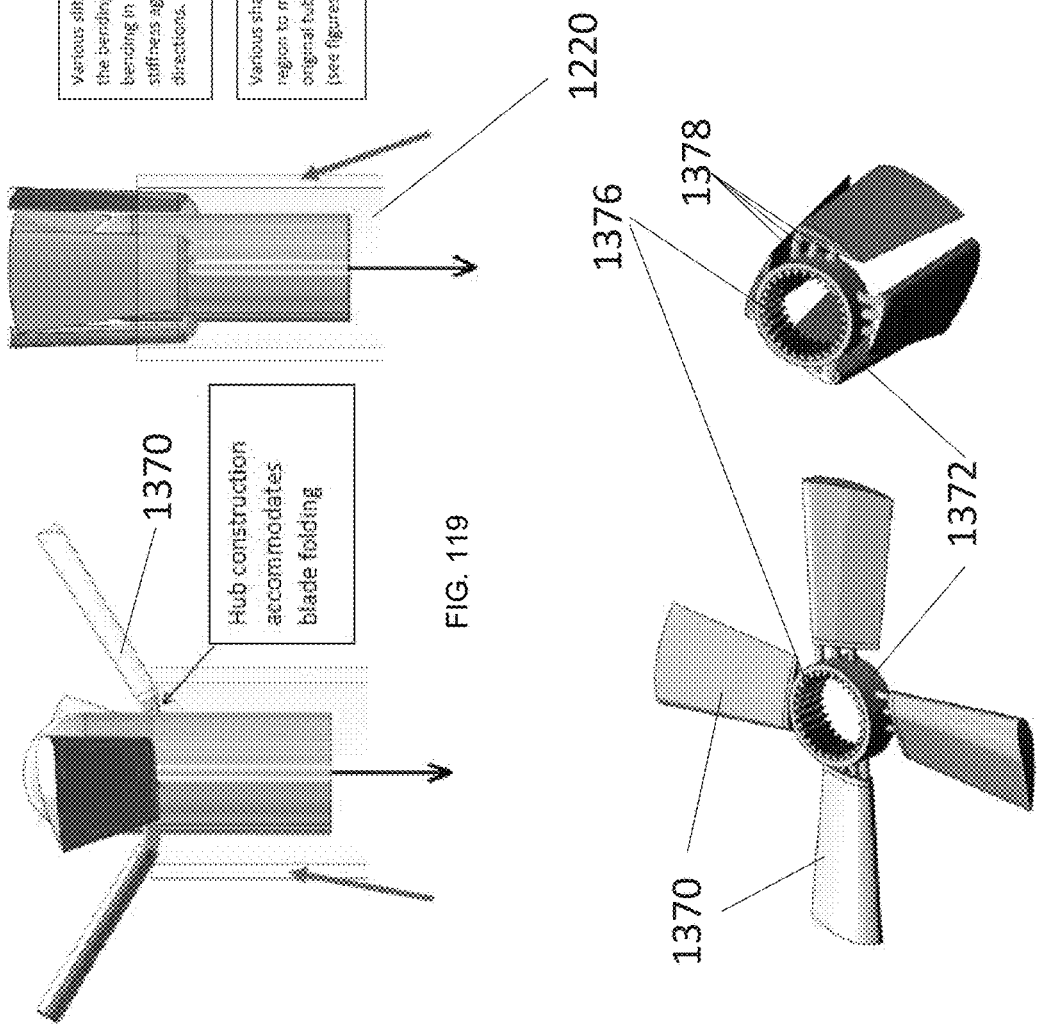
FIG. 119
FIG. 120
FIG. 121

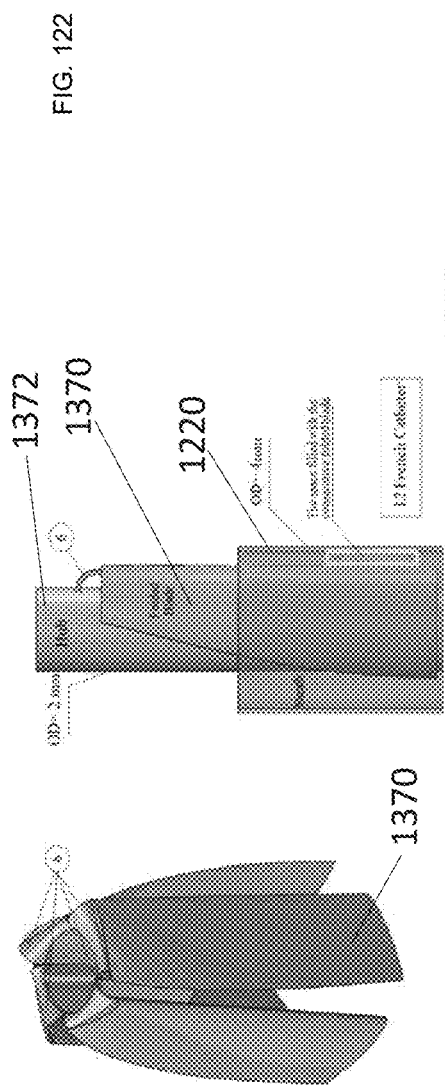
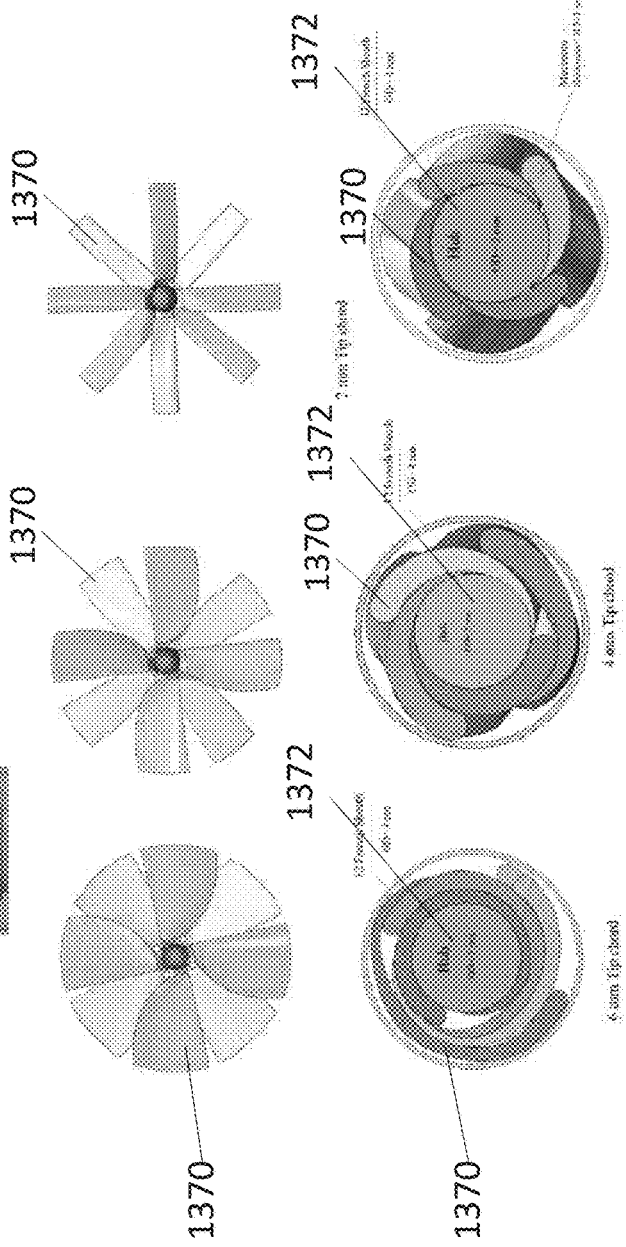
FIG. 122
FIG. 123A
FIG. 123B
FIG. 123C

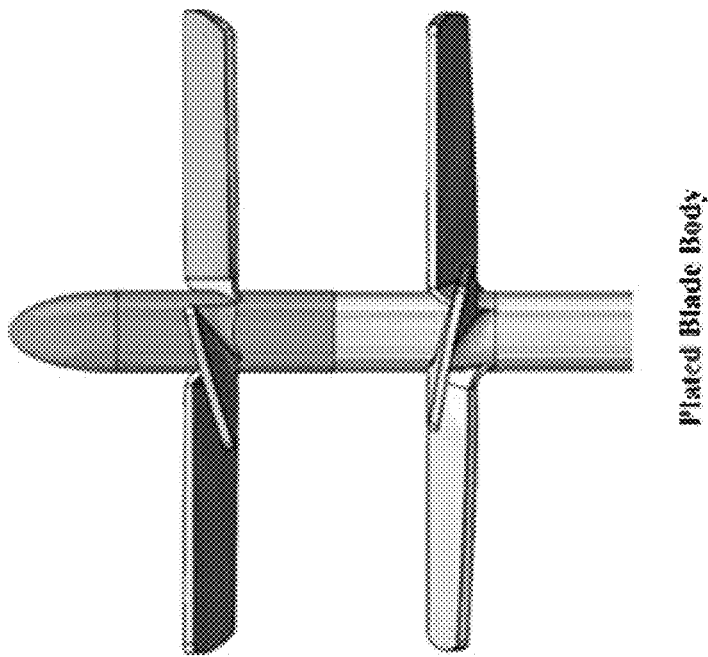
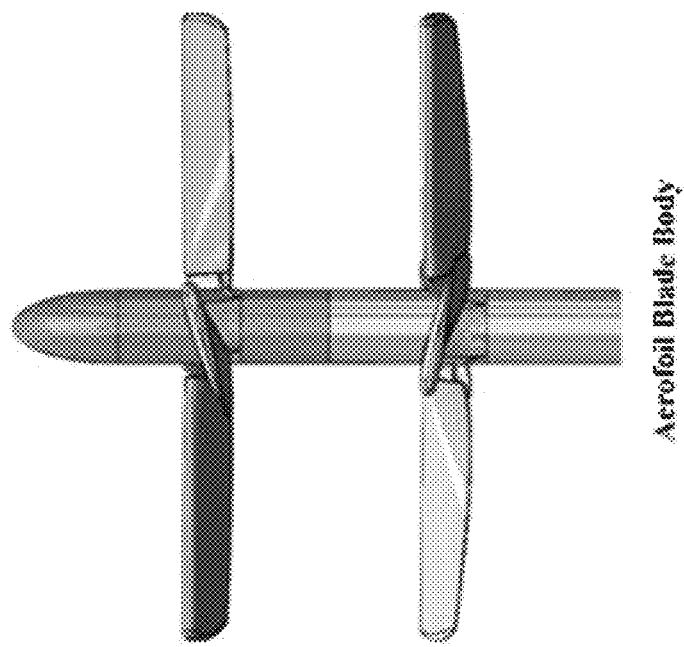
FIG. 126B

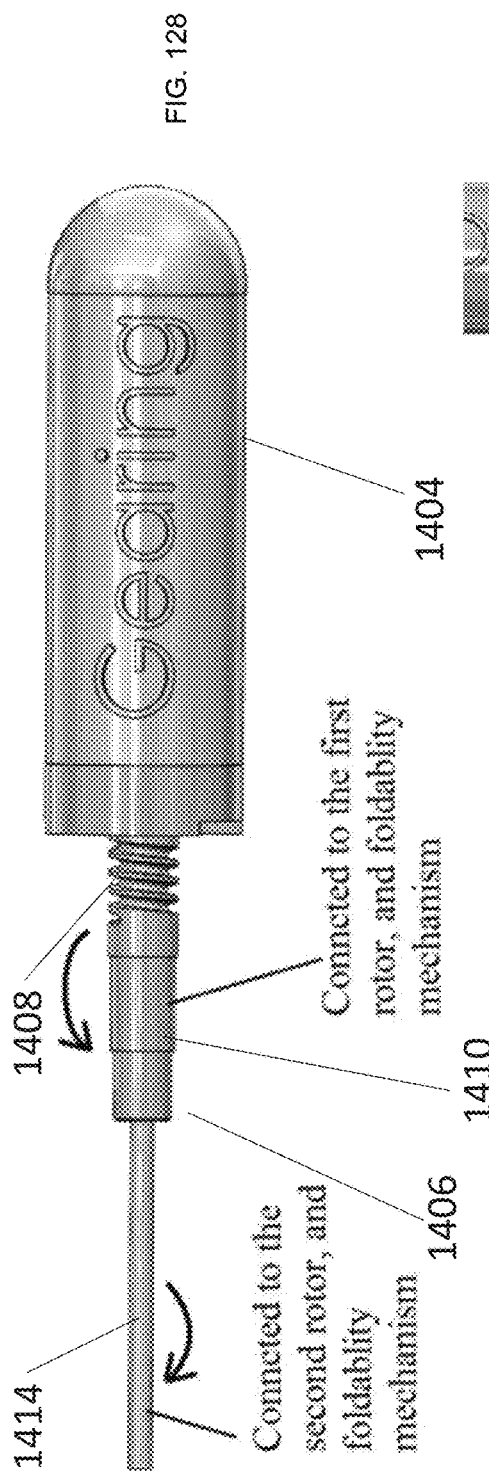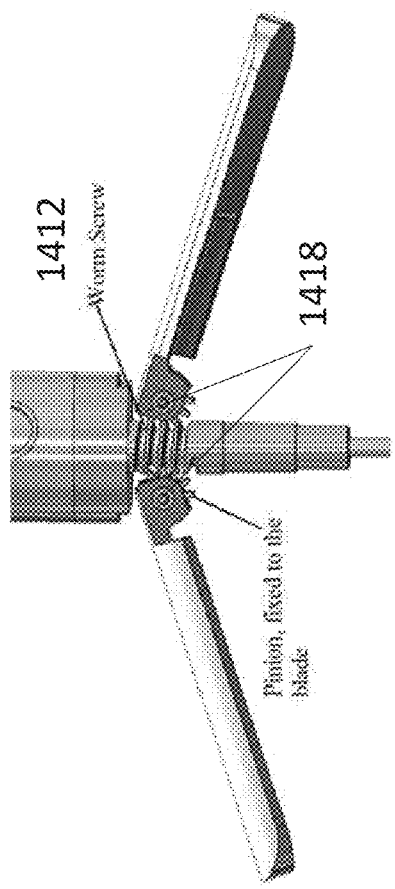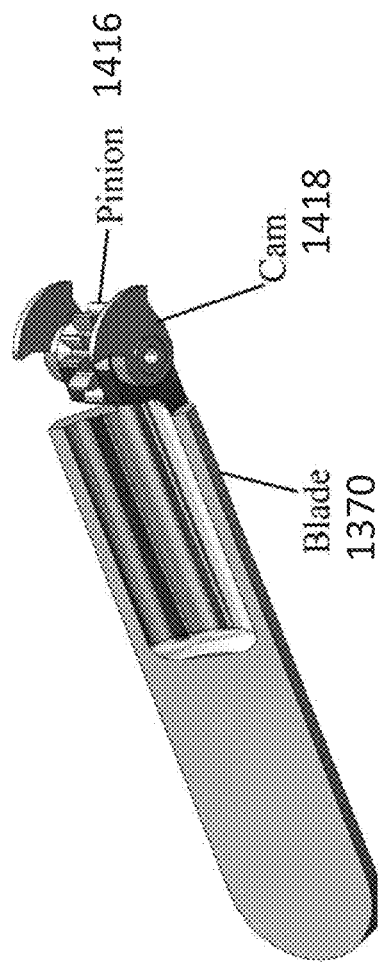

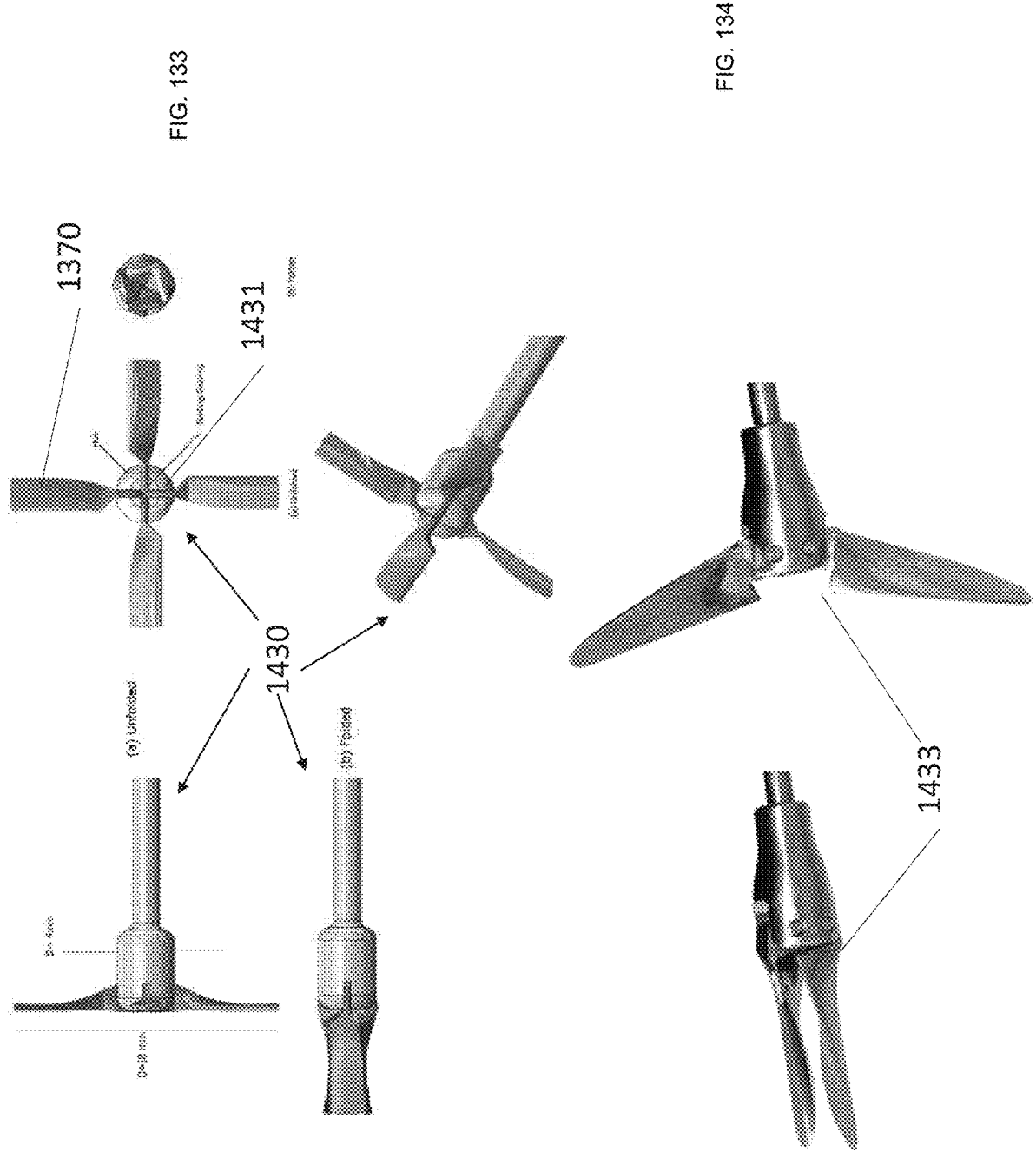

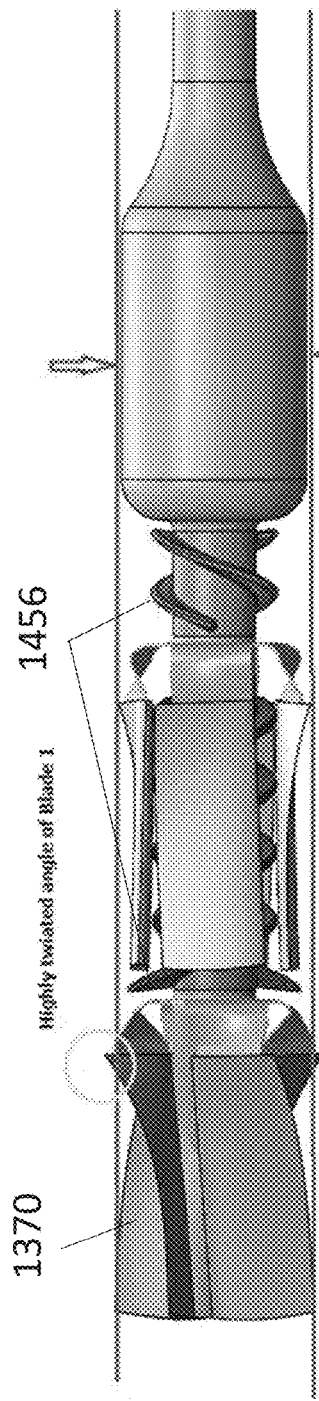
FIG. 143
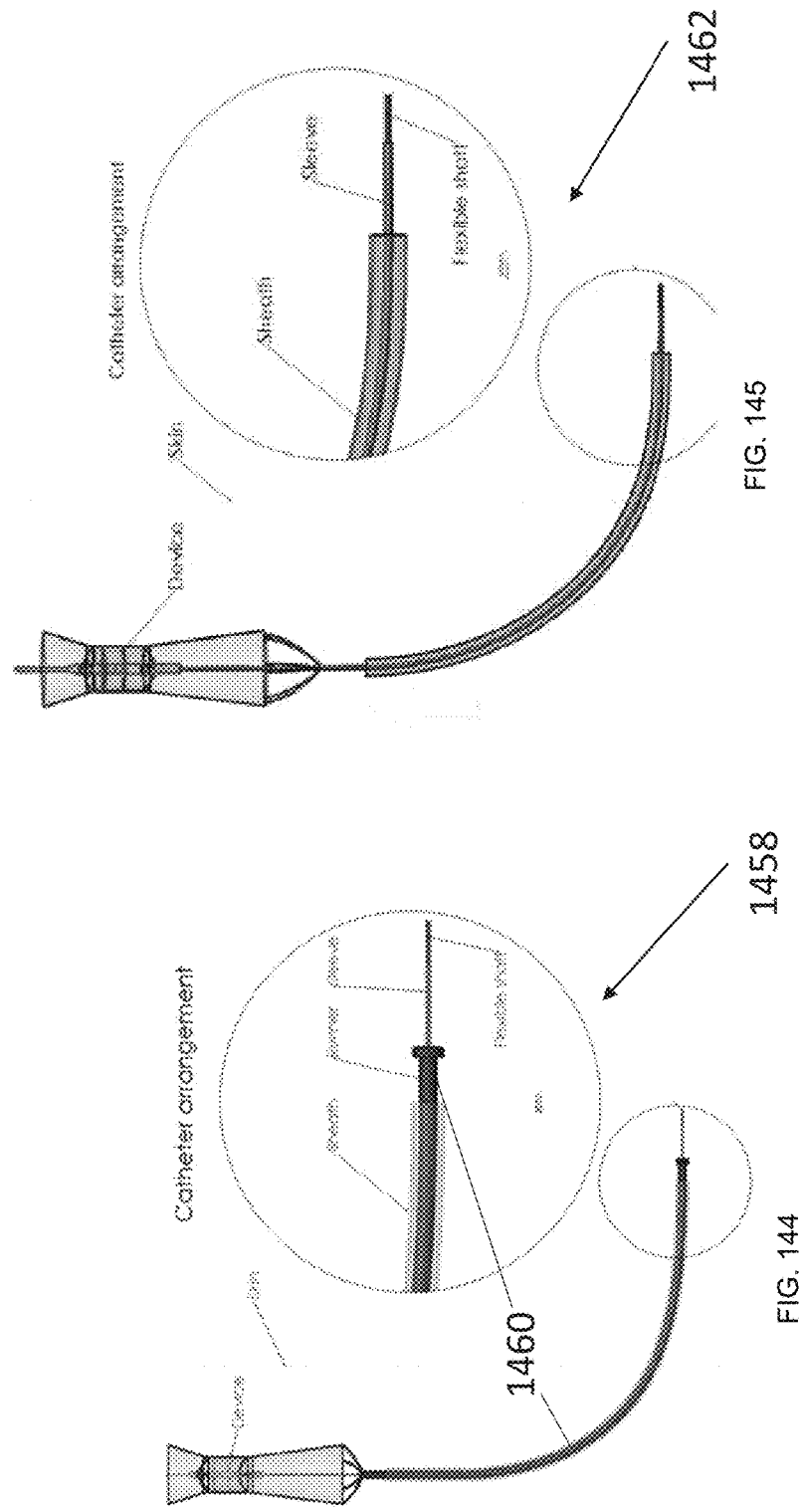
FIG. 145
FIG. 144

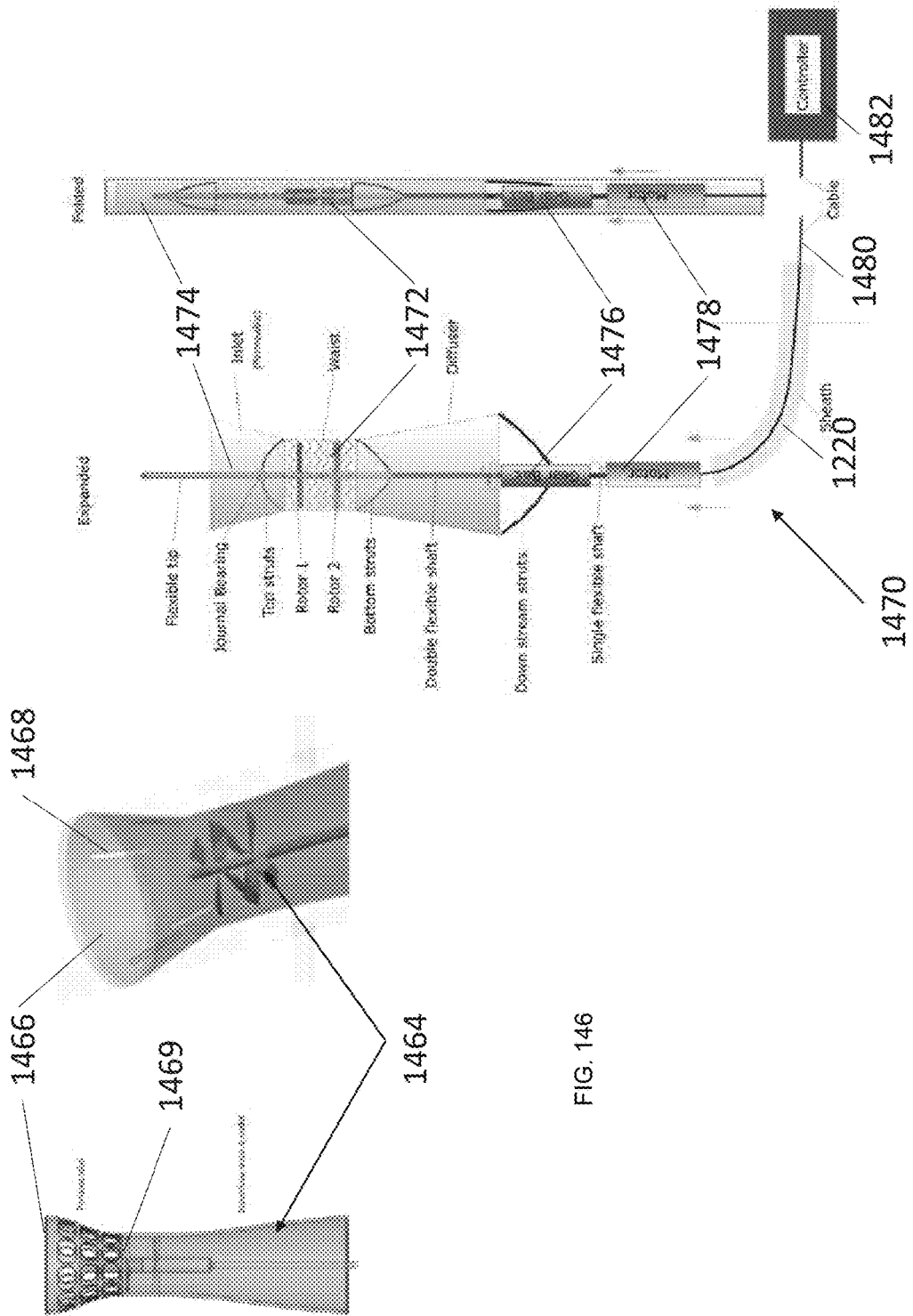

REMOVABLE MECHANICAL CIRCULATORY SUPPORT FOR SHORT TERM USE

INCORPORATION BY REFERENCE

This application claims priority benefit of U.S. Provisional Patent Application No. 62/868,265 filed Jun. 28, 2019, and U.S. Provisional Patent Application No. 62/991,410, filed Mar. 18, 2020, each of which is incorporated herein by reference in its entirety for all purposes. Any and all applications related thereto by way of priority thereto or therefrom are hereby incorporated by reference in their entirety. Systems and methods as disclosed herein can include any combination of features disclosed, for example, in PCT Pub. Nos. PCT/US2018/035694 filed Jun. 1, 2018, PCT/US2017/054573 filed Sep. 29, 2017, and PCT/US2019/025667 filed Apr. 3, 2019, and which are hereby incorporated by reference in their entireties.

BACKGROUND

Field

Some embodiments of the present invention relate to a mechanical circulatory support (MCS), otherwise known as a mechanical circulatory support device (MCSD), for assisting or replacing native heart function in cases of congestive heart failure (CHF). Some embodiments also relate to percutaneously implantable cardiovascular support (PICS) and percutaneously implantable temporary mechanical circulatory support device (TAD).

Patients with CHF usually have a low cardiac output state as the native heart functions (pumps) poorly. This in turn leads to poor organ perfusion and the symptoms of heart failure including fatigue, breathlessness and feeling generally unwell. In heart failure the kidneys also suffer with poor perfusion and their function often deteriorates considerably (a condition called "the cardio-renal syndrome"). Poor kidney function means that patients feel more unwell, and important drugs have to be withdrawn as they can further adversely affect kidney function.

CHF is common and is a significant health care burden. It is graded from stage I-IV in severity. Once diagnosed a patient has 4-5 years of progression from stage I to IV and death. Stage IV patients are breathless at rest, candidates for heart transplantation, and medication is considered palliative. Congestive heart failure (CHF) is the main cause of mortality for men and women alike in the western world, affecting about 2% of the population. In the USA alone there are 5.7 million patients suffering from CHF and costs to treat this exceed $37.2 billion/year. In the Western world current supply of donor hearts only meets about 12% of demand. This percentage is higher than the actual number because most potential recipients are not included in the calculation; they are considered not suitable for a transplant because of co-morbidities or lack of a matched donor. This shortfall has resulted in the development of MCS devices as a transplant alternative. MCS devices are expensive and require invasive cardiac surgery (sternotomy or thoracotomy). Implantation carries a significant risk. Not all candidates are suitable for MCS because of co-morbidities.

Most permanent MCS devices assist the ventricle and are attached to it in use. These are called Ventricular Assist Devices (VADs), and are designed to drive a flow of blood that is in parallel with flow within the native heart, between the ventricle and the aorta. In other words, they are designed as left (or right) ventricular assist devices (LVADs or RVADs), pumping devices that directly unload the respective ventricle. Such "in-parallel" configurations involve the device and heart sharing, and therefore competing, for inlet flow, which can disrupt normal functioning of the heart. Regeneration of heart muscle may be impeded and the heart is not able to pump to its best capacity. The inlet of most of these VADs is anastomosed to the apex of the left ventricle of the heart, and therefore their installation requires major sternotomy or thoracotomy and cardiopulmonary bypass (CPB), i.e. stopping of the heart during a prolonged surgical operation, for permanent installation. Survival rates of patients on VADs have been poor.

Due to inefficiencies, existing MCS/VAD devices typically require significantly more input power than is necessary from a theoretical point of view purely to impart the desired momentum to the blood. The excess power is used to overcome the losses. The portion of the power that is used to overcome flow losses is imparted as unnecessary damage to the blood, leading to increased levels of hemolysis and/or thrombus formation that would be avoided with devices having higher fluid dynamic efficiency.

VADs entered clinical use as displacement (or pulsatile flow) devices, which mimic the native left ventricle by providing pulsatile flow taking over the function of the patient's own left ventricle. Most widely used displacement, pulsatile, devices have been extracorporeal devices such as the BVS® 5000 VAD of Abiomed, Inc. (Danvers, Mass., USA) and the Thoratec VAD of Thoratec Corporation (Pleasanton, Calif., USA), and intracorporeal devices such as the Novacor® LVA System of WorldHeart, Inc. (Oakland, Calif., USA), the HeartMate IP and VE/XVE of Thoratec Corporation. Although the large external pneumatic consoles of the first-generation displacement VADs have been replaced by implantable electric systems with a portable controller and power source, the serious problems of device weight (e.g., approximately 1.5 kg for the HeartMate XVE), size, noise, driveline infection and thromboembolism persist. Consequently, newer displacement devices are totally implantable, such as the LionHeart™ VAD of Arrow International, Inc. (Reading, Pa., USA), and the Novacor® LVA System of WorldHeart, Inc. (Oakland, Calif., USA).

Rotary (or continuous flow) devices (second-generation VADs) have been developed to overcome the shortcomings of pulsatile devices. Initial concerns with their pulseless flow are now overcome, provided that the patient's native system still provides some pulsatility, and they have their own relative advantages (e.g., fewer moving parts, lower power required, absence of bioprosthetic valves) and disadvantages (e.g., complex control, high afterload and low preload sensitivity, and hemolysis and thrombosis from unnatural flow patterns). Examples of axial rotary pumps (which operate at 10,000-20,000 rpm) are the DeBakey VAD® of MicroMed Cardiovascular, Inc. (Houston, Tex., USA), the FlowMaker® of Jarvik Heart, Inc. (New York, N.Y., USA), formerly known as Jarvik 2000, the HeartMate II of Thoratec Corporation (Pleasanton, Calif., USA), and the Impella Recover® system of Impella CardioSystems AG (Aachen, Germany) intended for short-term circulatory support for up to seven days. These existing devices attempt to provide total flow and pressure capacity, forcing the pump to operate in inefficient flow regimes. Another example of pumps include the HeartMate III of Thoratec Corporation.

Centrifugal or radial flow blood pumps are generally somewhat larger than axial flow devices and provide non-pulsatile flow, but the rotational speeds are generally much slower (2,000-10,000 rpm) than axial flow blood pumps.

While axial flow blood pumps are the smallest VAD, they are higher speed lower pressure rise devices, while centrifugal VADs are better suited to take over heart function and to provide total pressure rise and flow (about 120 mmHg and 5 L/min). Examples are the Gyro C1E3 of Kyocera Corporation (Kyoto, Japan) which evolved into the NEDO PI-601 pump (animal studies).

Third-generation VADs are those that have replaced the mechanical bearings of second generation ones with hydrodynamic or magnetic-suspension bearings. Examples of axial flow VADS are: the INCOR® LVAD of Berlin Heart AG (Berlin, Germany); the MicroVad currently under development at Helmholtz-Institute for Biomedical Engineering (Aachen, Germany); and the MagneVAD I and II of Gold Medical Technologies, Inc. (Valhalla, N.Y., USA). Examples of centrifugal flow VADs are: the HVAD of HeartWare Ltd (Sydney, NSW, Australia); the EVAHEART™ of Evaheart Medical USA, Inc. (Pittsburgh, Pa., USA); the VentrAssist LVAD of Ventracor Ltd (Chatswood, NSW, Australia); the CorAide™ LVAD of Arrow International (Reading, Pa., USA); the DuraHeart of Terumo Heart, Inc. (Ann Arbor, Mich., USA); the HeartQuest VAD of WorldHeart, Inc. (Oakland, Calif., USA); the HeartMate III of Thoratec Corporation (Pleasanton, Calif., USA); and the MiTiHeart™ LVAD of Mohawk Innovative Technology, Inc. (Albany, N.Y., USA). All the above devices require major sternotomy or otherwise invasive surgery and CPB.

SUMMARY

It is an object of the invention to provide a device that can be installed with less risk to the patient, which reduces disruption to normal functioning of the heart and/or which minimizes damage to the blood.

In some embodiments, a mechanical circulatory support heart-assist device is provided. The mechanical circulatory support heart-assist device may be configured to be implanted and removed with minimally invasive surgery. The mechanical circulatory support heart-assist device may be a pump, where the pump comprises two impellers rotating in opposite directions.

In some embodiments, the pump is placed in the vasculature in order to assist with perfusion. In some embodiments, the pump is placed to hold in the open position one of the four heart valves in order to assist with perfusion. In some embodiments, contra-rotation of impellers is achieved with a gearbox placed near the pump head. In some embodiments, the gearbox has two concentric output shafts driving the impellers in opposite directions, and one input shaft connected via a flexible shaft to an electric motor or gearmotor. In some embodiments, the electric motor or gearmotor is intracorporeal. In some embodiments, the electric motor or gearmotor is extracorporeal. In some embodiments, the upstream impeller is driven by an epicyclic-type gearbox, the downstream impeller is driven in the opposite direction to the upstream impeller by a second epicyclic-type gearbox, and the suns of both epicyclic gearboxes are driven by sun gears connected via an input shaft to an electric motor. In some embodiments, the electric motor or gearmotor is intracorporeal. In some embodiments, the electric motor or gearmotor is extracorporeal. In some embodiments, the blades of the impellers rotating in opposite directions have flexible connections to the impeller hubs to accommodate insertion and removal with folded blades, and operation with unfolded blades. In some embodiments, the blades of the impellers rotating in opposite directions have mechanical connections to the impeller hubs to accommodate insertion and removal with folded blades in a catheter, and operation with unfolded blades. In some embodiments, the mechanical folding mechanism for the blades is like an umbrella, with a runner and a stretcher. In some embodiments, the mechanical folding mechanism for the blades is with a screw and cam like in marine folding propellers. In some embodiments a catheter is inserted to collapse the frame the blades into the catheter.

In some embodiments, one size fits small and large patients. In some embodiments, the impellers are folded in a housing, such as a cage, e.g., an hourglass-shaped cage forming an inlet upstream of the first rotor accelerating the axial component of flow velocity and a flow diffuser downstream of the second rotor decelerating the axial component of flow velocity. In some embodiments, the cage diameter between the inlet and the diffuser is constant and designed to make one size of rotor diameters fit anatomically different larger inside diameters of the blood vessel. In some embodiments, the housing, e.g., cage, e.g., hourglass is made of memory alloy covered with a biocompatible material preventing blood flow through the biocompatible material. In some embodiments, the waist section has a constant diameter sized to accommodate an impeller of fixed diameter and thus a fixed gap between blade tips and inner diameter of waist section. In some embodiments, where the gap between the impeller and diameter of the waist is fixed, and chosen to minimize blood trauma by friction in the blood while minimizing backflow across the impellers form the high pressure region to the low pressure region of the pump. In some embodiments, the pump rotors are axially secured by connecting members (e.g., struts) to a surrounding cage. In some embodiments, the cage is secured to the perimeter of the surrounding blood vessel, so that the cage protects the inside perimeter of the blood vessel.

In some embodiments, the frame, e.g., hourglass frame can advantageously reduce contact with the vessel wall. As referred to herein, a housing, stent, or frame may be referred to as an hourglass; however, other shapes are contemplated and as such any embodiment herein can include housing, stents, or frames that are not necessarily hourglass shaped. In some embodiments, the hourglass frame can include a distal point of contact. In some embodiments, the hourglass frame can include a proximal point of contact. The point of contact can be circumferential ring of contact. The one or more points of contact can center the frame. The one or more points of contact can anchor the frame. The one or more points of contact can be atraumatic. The one or more points of contact can allow a substantial length of the device to be away from the vessel wall. The one or more points of contact can minimize contact with the vessel wall. The one or more points of contact can expand to contact the vessel wall regarding of the diameter of the vessel wall. The one or more points of contact can exert a force on the vessel wall while the impellers rotate. The one or more points of contact can maintain their position against the vessel wall while the impellers rotate. The frame, e.g., hourglass frame can be easily expandable. The frame, e.g., hourglass frame can be easily collapsible. The hourglass frame can be collapsible by a proximal and/or distal motion of the proximal and/or distal hub. The hourglass frame can include a constant diameter waist. The constant diameter waist can be selected based on the blade length. The hourglass frame can expand to various diameters while maintaining the constant diameter waist.

In some embodiments, a mechanical circulatory support heart-assist device is provided. The mechanical circulatory support heart-assist device may be a pump which comprises impellers rotating in opposite directions. In some embodiments, the inlet to the pump is anastomosed to a chamber of the heart, and the outlet of the pump is anastomosed to the vascular system. In some embodiments the inlet and outlet of the support, e.g., hourglass support are attached to a blood vessel.

In some embodiments, a mechanical circulatory support heart-assist device includes two contra-rotating impellers. In some embodiments, two contra-rotating impellers result in maximum efficiency. In some embodiments, two contra-rotating impellers result in minimum rotor rpm. In some embodiments, two contra-rotating impellers result in minimum hemolysis. In some embodiments, two contra-rotating impellers in VAD and MCSD minimize rpm. In some embodiments, two contra-rotating impellers in VAD and MCSD maximize efficiency. In some embodiments, two contra-rotating impellers in VAD and MCSD minimize hemolysis. In some embodiments, the downstream rotor reduces the swirling flow imparted by the upstream rotor in order to achieve near-axial downstream flow velocity. In some embodiments, reducing the swirling flow emulates the blood flow in healthy conditions of about one clockwise flow rotation downstream from aortic arch to renal arteries. In some embodiments, reducing the swirling flow maximizes pumping efficiency. In some embodiments, reducing the swirling flow reduces impeller rpm. In some embodiments, reducing the swirling flow reduces friction and turbulence from swirling flow downstream of the pump. In some embodiments, the downstream rotor reduces the swirling flow imparted by the upstream rotor in order to achieve near-axial downstream flow velocity, thus emulating the blood flow in healthy conditions of about 1 to about 3 clockwise flow rotation downstream from aortic arch to renal arteries, while maximizing pumping efficiency, reducing impeller rpm, and reducing friction and turbulence from swirling flow downstream of the pump. In some embodiments, the structures of the struts locating the hourglass cage axially may be shaped to open into 3D blades directing the flow in the desired direction. In some embodiments, the device may include pre-swirler and de-swirler struts to optimize flow angles and turbomachinery efficiency. In some embodiments, the device may include one or more pre-swirlers. In some embodiments, the device may include one or more de-swirlers. The pre-swirlers and/or de-swirlers can impart any desired flow characteristics. The one or more pre-swirlers can impart characteristics to the flow before the flow encounters an impeller. The one or more de-swirlers can impart characteristics to the flow after the flow encounters an impeller. In some embodiment, a single impeller is utilized with a pre-swirler. In some embodiment, a single impeller is utilized with a de-swirler. In some embodiment, a single impeller is utilized with a pre-swirler and/or de-swirler as an alternative to two-contra-rotating impellers.

In some embodiments, a mechanical circulatory support heart-assist device may include a simpler stator-rotor-stator configuration. The mechanical circulatory support heart-assist device may include one rotating impeller with upstream pre-swirler and downstream de-swirler stationary vanes. In some embodiments, the upstream pre-swirler and downstream de-swirler stationary vane may also be the support structures of the hub of the turbomachine to the cage around the rotor. In some embodiments, the struts may open in blade shapes.

In some embodiments, a mechanical circulatory support heart-assist device may include an hourglass cage. The hourglass cage may be implanted first alone and separately from the impeller device. In some embodiments, the impeller device may be a stent cage. In some embodiments, the impeller device may have a balloon or space occupying feature configured to ensure the central lumen matches the diameter of the impeller, and that there is not excessive gap between tip of impeller blades and wall of vessel/or wall of stent tube or cage configuration. In some embodiments, if the stent cage is delivered independently, the impeller device may have pre-swirlers and post-swirlers that are self-expanding or mechanically expanded disks. In some embodiments, the pre-swirlers and post-swirlers may be configured centralize the impeller and prevent collision with vessel wall. In some embodiments, the pre-swirlers and post-swirlers may be collapsible when removal is required. In some embodiments, the support/housing and turbomachine are collapsed into a catheter together.

In some embodiments, coupling of turbomachine to motor may be via shaft or via magnetic coupling. In some embodiments, bearings at proximal and distal end may be hydrodynamic or magnetic or self-lubricating using circulating blood. In some embodiments, with use of intra-corporeal motor(s) in turbomachine hub(s), the electric cables may be installed around the perimeter of the cage, or along the hub of the device.

In some embodiments, biocompatible lubricant may be pumped through the motor and/or gearbox or gearboxes. In some embodiments, the lubricant may be diffused in the blood stream. In some embodiments, the lubricant may be returned outside the body. In some embodiments, spiral grooves may be used between rotating and stationary elements in the pump head to remove stagnant blood flow between rotating and stationary components. In some embodiments, the gearbox is configured with a single input shaft. In some embodiment, the gearbox is configured with two output contra-rotating shafts. In some embodiments, the impellers rotate in the same direction. In some embodiments, the impellers rotate in opposite directions. In some embodiments, the gearbox can achieve contra-rotation.

According to an aspect of the invention, there is provided a mechanical circulatory support, comprising: a body portion defining an internal lumen; an inlet port in fluid communication with the lumen; an outlet port in fluid communication with the lumen; and a pump for driving fluid flow from the inlet port towards the outlet port, wherein: the inlet port is arranged to provide a connection, or is in a state of connection, into the aorta of a human body.

This arrangement does not require any connections to be made directly to the heart and can be installed using minimally invasive surgery, greatly reducing the risks associated with installation relative to arrangements that need to be connected directly to the heart. There is no need to perform a cardiopulmonary bypass for example. The reduced installation risk makes the device more suitable for treatment of earlier stage CHF than existing MCS/VAD devices, for example early stage IV CHF. In some embodiments, the device may be suitable for treating stage III or stage IV CHF. The device may be particularly suited to treat late stage III CHF or early stage IV CHF.

The outlet port may be connected to a downstream position in the aorta so as to be connected in series with the native heart. This type of connection is less disruptive to the normal functioning of the heart than systems which work in parallel with the heart and may help to promote regeneration of the heart muscle. Additionally or alternatively, by allowing the native heart to pump to its best capacity the additional pumping power required by the support may be reduced.

In an embodiment, the series connection is implemented by connecting the support in parallel with a small section of the descending aorta. In an alternative embodiment, the descending aorta is interrupted so that all of the blood flow passes through the support.

In other embodiments, the outlet port is connected at other positions in the vasculature, for example in the ascending aorta. In an embodiment, the support comprises one outlet port in the descending aorta and one outlet port in the ascending aorta. In this way, a proportion of the outflow is provided to the ascending aorta to support coronary flow more directly. In an embodiment, the inlet port is connected to one or more other strategic locations such as the ascending aorta, and the outlet port(s) connected as previously described into the descending aorta, the ascending aorta, or both. The descending aorta outlet has additional advantages for renal, splanchnic, and other organ perfusion without affecting brain flow.

In an embodiment, the pump is a centrifugal pump. The inventors have discovered that such pumps can provide particularly effective impetus to the circulating blood. In particular, unnecessary blood shear and fluid-dynamic diffusion (the effect of pressure rise as flow decelerates along the device passage) and turbulence can be minimized, which in turn minimizes the imposed shear stress to blood cells, thus minimizing blood cell lysis (haemolysis) and thrombus formation. The improved pumping efficiency reduces power requirements, enabling the power supply to be made smaller and more comfortable to carry. In addition, the pump itself can be made more compact. In an alternative embodiment, the pump is a mixed flow pump (e.g. a pump having characteristics intermediate between a centrifugal pump and an axial pump). In a still further embodiment, the pump is a helical pump. In a still further embodiment, the pump is an axial pump.

In an embodiment, the pump is configured to provide a continuous, rather than pulsatile flow. The inventors have realized that it is not necessary for the pump to mimic the pulsatile flow imparted by the native heart, particularly when installed so as to work in series with the heart. The pump can thus interact more smoothly with the blood flow, further minimizing damage to the blood. Additionally, the efficiency of a continuous pump can be optimized further than a pulsatile pump. Acceleration and deceleration of the blood is reduced, which reduces the stresses that need to be applied to the blood as well as the needed power input to the pump. In alternative embodiments the pump is configured to provide a pulsatile flow (synchronous or asynchronous or different fixed phase or variable phase with the heart).

In an embodiment, the support comprises a power receiving member that is configured to receive power for driving the pump transcutaneously, for example by electromagnetic induction. Alternatively or additionally, power can be supplied percutaneously.

According to an aspect of the invention, there is provided a mechanical circulatory support, comprising: a pump configured to be installed, or in a state of installation, in a human body and configured to operate in series with the native heart; and a device for electromagnetically driving the pump that is configured to be mounted to the body. Thus, a support is provided that is suitable for "permanent" installation (e.g. so that the patient can leave the hospital with the support installed and operational) and which provides a pumping action that is in series, rather than in parallel, with the native heart.

MCSs which generate full physiological pressure rises (about 120 mmHg), such as VADs in-parallel with the heart, may impart tremendous damage to the blood (e.g., hemolysis), especially in later stages of CHF. MCSs which are installed in-series with the heart (i.e. the left ventricle) may exploit the existing pressure rise of the native heart and provide an additive pressure rise. Disclosed herein are embodiments of MCSs configured for in-series installation in the aorta, particularly the descending aorta. Installation within the descending aorta advantageously is conducive to installation via minimally invasive surgery (e.g., percutaneous installation or thoracoscopy), which produces better outcomes (e.g., reduced morbidity) and shorter recovery periods for patients, especially those suffering CHF. Additionally, minimally invasive surgical procedures may generally be performed at district hospitals by vascular surgeons, unlike the sternoscopy procedures that are generally necessary for installation of VADs, which usually must be performed by cardiothoracic surgeons in critical care units. Installation within the descending aorta is further advantageous because the MCS intercept location is downstream of the cerebral blood flow, fed by the carotid arteries, reducing the risk of cerebral thromboembolism or stroke. Any blood damaged by an MCS installed in the descending aorta is pumped to the renal inflow arteries and remaining systemic and pulmonary perfusion system prior to reaching the cerebral blood flow. MCSs which are installed in the descending aorta must be careful not to establish such a large pressure rise that upstream blood perfusion to the cerebral blood flow is not suppressed, or stolen, by the suction of the MCS.

MCSs may be designed with operating conditions specifically configured for particular stages of CHF. For instance, a MCS designed for late stage II or early stage III CHF may provide a 20-50 mmHg pressure rise, while a MCS designed for late stage III or early stage IV CHF may provide a 40-80 mmHg pressure rise, to better supplant the failing heart. The reduced pressure requirements of MCSs that are installed in-series with the heart may effectively reduce the load on the heart (afterload reduction) by lowering the resistance to blood flow, which can advantageously provide the heart increased potential for regeneration of diseased tissue. MCSs with less than full physiological pressure rises generally will require less power and will be smaller and lighter weight than MCSs such as VADs which generate larger pressure rises. MCSs installed in series may be configured to maintain the physiological flow rate of a healthy individual of about 5 L/min. The MCSs may pump blood at a continuous flow, while the native heart may maintain pulsatility in total perfusion. In alternative embodiments, the MCS may provide a pulsatile flow. Such pulsatile flow may be established, for example, by axially oscillating the impeller within the MCS casing. Devices may be configured to address Acute Cardiogenic Shock (CGS), Percutaneous Coronary Intervention (PCI), acute decompensated heart failure (ADHF), Cardio Renal Syndrome (CRS), and/or temporary relief of the native heart in early or late stages of congestive heart failure. Other uses of the devices are contemplated.

Turbomachines operate efficiently over only a very narrow regime of pressure rise, flow rate and rotational speed specifications, all of which translate into a narrow regime of optimal angles of attack (angle of incoming flow) to turbomachinery airfoils. Therefore, a turbomachine configured, for example, to generate a 120 mmHg pressure rise, such as a VAD designed for in-parallel implantation with the left ventricle, will operate substantially less efficient if instead installed in the descending aorta and operated at a much lower pressure differential (e.g., 70 mm Hg). For instance, operating a turbomachine below its configured pressure differential will: operate at a much different than as-designed pressure rise, flow rate, and rotational speed; operate away from the as-designed optimal condition for angles of attack to turbomachine blades; will not work efficiently; and will create unnecessary blood shear, turbulence, stall and losses. These deviations from optimal as-designed operating conditions will increase blood trauma and reduce device efficiency and efficacy for use in this location.

Disclosed herein are embodiments of MCS devices and systems along with methods of installing and/or using MCS devices to treat CHF. In various embodiments, the MCS is a centrifugal pump, comprising an impeller suspended in a casing, an inlet introducing blood flow from the native vasculature to the impeller in an axial direction, and a diffuser with an entrance positioned along the circumference of the impeller and an outlet returning blood flow to the native vasculature. The impeller may be magnetically suspended in a contactless manner within the casing and rotated using an electromagnetic motor. An external controller implanted within the body may provide power to the MCS and control the electrical operations. The MCS may be powered by internal and/or external batteries. The internal batteries may be recharged and/or power may be delivered from external batteries through transcutaneous or percutaneous energy transfer systems. In various embodiments, the MCS is specifically suited for late stage III and/or early stage IV CHF and generates pressures rises between about 40 to about 80 mmHg and maintains a flow rate of approximately 5 L/min.

In some embodiments, a mechanical circulatory support for assisting the heart support comprises a casing comprising a main body, an inlet configured to introduce blood flow from an upstream portion of a human aorta into the main body, and an outlet configured to return the blood flow from the main body to a downstream portion of the human aorta. The support further comprises an impeller positioned within an internal volume of the main body of the casing so as to receive blood flow from the inlet, the direction of the received blood flow defining a longitudinal axis, wherein the impeller comprises a plurality of blades for pumping blood, the blades being arranged around the longitudinal axis so as to define an outer circumference. The impeller is configured to rotate around the longitudinal axis to pump the blood in a centrifugal manner toward the outer circumference. The support further comprises a diffuser integral with or joined to the casing, the diffuser configured to receive blood outflow from the impeller and direct the blood flow to the outlet. The diffuser is at least partially open to the internal volume of the main body of the casing along at least a portion of the outer circumference of the impeller.

The impeller may be a shrouded impeller. The shrouded impeller may comprise a blade passage chamber, an upper portion forming a ceiling to the blade passage chamber, and a lower portion forming a floor to the blade passage chamber. The upper portion may have an upper channel extending along the longitudinal axis from a top of the impeller to the blade passage chamber. The lower portion may have a lower channel extending along the longitudinal axis from the bottom of the impeller to the blade passage chamber. The blades may extend from an inner circumference around the longitudinal axis to the outer circumference, the blades extending axially between the floor and the ceiling of the blade passage chamber to join the upper portion and the lower portion together.

The casing may further comprise a projection extending from the bottom of the casing into the lower channel. The casing may be configured to allow blood to flow from the outer circumference of the blades along secondary flow paths between an internal surface of the casing and the lower portion of the impeller, and between the projection and an internal surface of the lower channel back to the blade passage chamber so as to prevent blood stagnation.

The impeller may be an unshrouded impeller.

The impeller may be magnetically suspended in an axial direction within the casing by a combination of axial-suspension permanent magnets coupled to a top half and a bottom half of the casing and permanent magnets coupled to a top half and a bottom half of the impeller. The axial-suspension permanent magnets coupled to the top half of the casing may be axially spaced apart from the permanent magnets coupled to the top half of the impeller. The axial-suspension permanent magnets coupled to the bottom half of the casing may be axially spaced apart from the permanent magnets coupled to the bottom half of the impeller. The impeller may be magnetically suspended in a radial direction within the casing by a radial-suspension permanent magnet coupled to the casing near the permanent magnet in the top half of the impeller and by a radial-suspension permanent magnet coupled to the casing near the permanent magnet in the bottom half of the impeller. However, some embodiments may include impellers that do not include magnets, and are not magnetically suspended.

The impeller may be configured to be radially stabilized by an eccentric hydrodynamic journal bearing force between the impeller and the casing.

The impeller may be configured to be radially stabilized by at least two electromagnets positioned on opposite sides of each of the radial suspension permanent magnets, wherein the force of each of the electromagnets is driven according to impeller positioning information attained from eddy current sensors coupled to the casing.

At least one of the electromagnets coupled to the upper half of the casing may be axially displaced from the permanent magnet coupled to the upper half of the impeller and at least one of the electromagnets coupled to the lower half of the casing may be axially displaced from the permanent magnet coupled to the lower half of the impeller. The position of the impeller may be configured to be oscillated in the axial direction to create a pulsatile flow by pulsatile phases of current applied to the electromagnets. However, some embodiments do not include any electromagnets, or magnets at all.

The support may further comprise a motor for electromagnetically (or purely mechanically in some cases) rotating the impeller around the axial direction. The motor may comprise a stator within the casing comprising a plurality of electromagnets and a rotor within the impeller comprising a plurality of permanent drive magnets, the rotor configured to be positioned concentrically within the stator.

The support may be configured to create a vortex in an outflow of blood exiting the outlet to emulate the naturally-occurring vortex in the native aorta of a healthy human heart.

The support may be configured to create a pressure rise in the introduced blood flow between about 5 mmHg and about 40 mmHg. The support may be configured to maintain a blood flow rate of about 5 L/min.

The support may be configured to be installed in-series with a portion of the descending aorta of a human aorta.

The inlet may be configured to redirect the blood flow 90 degrees before it enters the main body, such that the inlet and the outlet are parallel with each other.

The blood flow may be redirected toward an axial direction prior to reaching the outlet, such that the outlet is substantially collinear with the inlet.

The diffuser may wrap around the casing in a spiral configuration to facilitate the formation of a vortex in the outflow which emulates the naturally-occurring vortex in the native aorta of a healthy human heart.

The support may further comprise a splitter vane positioned within at least a portion of the diffuser which rotates with respect to a circumference of the diffuser to facilitate the formation of a vortex in the outflow which emulates the naturally-occurring vortex in the native aorta of a healthy human heart.

The support may further comprise a splitter vane positioned within at least a portion of a volute of the outlet which rotates with respect to a circumference of the volute to facilitate the formation of a vortex in the outflow which emulates the naturally-occurring vortex in the native aorta of a healthy human heart.

The support may further comprise a plurality of diffuser vanes positioned circumferentially around the outer circumference defined by the impeller.

The support may further comprise a plurality of stationary pre-swirl vanes positioned within in inlet.

A portion of a surface of the internal volume of the main body of the casing and/or a portion of an outer surface of the impeller may comprise spiraling grooves configured to facilitate secondary flow paths of blood between the impeller and the casing.

In some embodiments, a method of treating congestive heart failure in a patient comprises installing a mechanical circulation support within the descending aorta of the patient. The mechanical circulation support comprises a centrifugal blood pump configured to provide a pressure rise between about 40 mmHg and about 80 mmHg in the blood flow and to maintain a flow rate of about 5 L/min.

The support may be installed in series with the descending aorta. The method may further comprise severing the aorta into upper and lower portions, wherein the installing comprises grafting the upper portion to an inlet of the support and grafting the lower portion to an outlet of the support The support may be installed in parallel with the descending aorta. The method may further comprise installing a one-way valve in the native aorta in parallel with the support, such that blood cannot flow upstream through the native aorta to recirculate through the support.

The support may be installed such that both an inlet to the support and an outlet from the support are oriented at a non-linear angle to the native aorta.

The support may be installed such that both an inlet to the support and an outlet from the support are oriented to be substantially collinear with the native aorta.

The support may be installed such that both an inlet to the support and an outlet from the support are oriented to be parallel with the native aorta.

The patient may have stage III or stage IV congestive heart failure.

The patient may have late stage III or early stage IV congestive heart failure.

In various embodiments, the MCS device comprises one or more propellers which are configured to be installed within the lumen of a blood vessel, such as the descending aorta. The one or more propellers may be anchored within the lumen by an anchoring mechanism which surrounds the one or more propellers. In some embodiments, the one or more propellers may be driven by one or more motors which may be extra-corporeal or intravascular. In some embodiments, at least some of the propeller blades may be magnetic and the one or more propellers may be driven by a stator comprising electromagnets, the stator being positioned concentrically around the propeller blades. The stator may be configured to be placed intravascularly or may be placed around the outside of the blood vessel. The MCS device may include one or more pairs of contra-rotating impellers for modulating the tangential velocity component of the blood flow. The MCS device may include pre-swirler and/or de-swirler vanes coupled to the propeller or the anchoring mechanism. The blades of the one or more propellers may be foldable and the anchoring mechanism collapsible so that they may be delivered percutaneously via a catheter. A controller implanted within the body or positioned outside the body may provide power to the MCS device and control the electrical operations. In some embodiments, the MCS device may be powered by internal and/or external batteries. The internal batteries may be recharged and/or power may be delivered from external batteries through transcutaneous or percutaneous energy transfer systems. In various embodiments, the MCS device is specifically suited for late stage II and/or early stage III CHF and generates pressures rises between about 20 to about 50 mmHg and maintains a flow rate of approximately 5 L/min.

In some embodiments, a mechanical circulatory support for assisting the heart comprises at least one propeller. The at least one propeller comprises a plurality of blades arranged around an axis of rotation, the blades being configured to pump blood in a substantially axial direction parallel to the axis of rotation. In some embodiments, at least one of the plurality of blades is magnetic. The support further comprises a shaft aligned along the axis of rotation of the at least one propeller. The support further comprises an anchoring mechanism configured to anchor the at least one propeller within a lumen of a blood vessel. The anchoring mechanism comprises a proximal hub coupled to a proximal end of the shaft; a distal hub coupled to a distal end of the shaft; a collapsed configuration for installing the anchoring mechanism in the blood vessel; and an expanded configuration wherein at least a portion of the anchoring mechanism is configured to be pressed against a wall of the lumen of the blood vessel. The support further comprises at least one ring-shaped stator. The at least one stator comprises one or more electromagnets positioned around the circumference of the stator. The at least one stator is configured to be positioned concentrically around the blades of the at least one propeller to electromagnetically drive rotation of the at least one magnetic blade.

All of the blades of the at least one propeller may be configured to be foldable substantially along the shaft such that in the collapsed configuration of the anchoring mechanism the blades are in a folded position. The collapsed configuration may be configured for percutaneously installing the anchoring mechanism in the blood vessel through a catheter.

The at least one propeller may comprise a pair of contra-rotating propellers configured to rotate in opposite directions.

The support may further comprise a plurality of stationary de-swirler vanes coupled to either the shaft or the anchoring mechanism. The de-swirler vanes may be positioned downstream of the at least one propeller and may be configured to remove or reduce a tangential velocity component of blood flow as it leaves the support.

The support may further comprise a plurality of stationary pre-swirler vanes coupled to either the shaft or the anchoring mechanism. The pre-swirler vanes may be positioned upstream of the at least one propeller and may be configured to increase a tangential velocity component of blood flow entering the support.

The at least one stator may be configured to be positioned around an outer circumference of the blood vessel.

The at least one stator may comprise a hinge configured to allow the stator to open and close. The stator may have a circumference and may be configured to open along the circumference for positioning the stator around the blood vessel and to close for securing the stator around the outer circumference of the blood vessel.

The at least one stator may be configured to be positioned along an inner circumference of the lumen of the blood vessel.

The at least one stator may comprise a collapsed configuration for percutaneous delivery via a catheter and an expanded configuration.

The at least one stator may be coupled to or integral with the anchoring mechanism.

The at least one stator may comprise first and second discrete ring-shaped components. The first and second discrete ring-shaped components may each comprise circumferentially offset electromagnets, wherein the electromagnets of the second discrete ring-shaped component are configured to be positioned circumferentially between the electromagnets of the first discrete-ring shaped component.

The at least one propeller may comprise a plurality of propellers configured to rotate together.

At least one propeller may not comprise any magnetic blades.

All the blades of all the propellers may be magnetic.

A radial tip of at least one blade from each propeller may be connected via a magnetic connector extending substantially along an outer diameter of the plurality of propellers.

The at least one ring-shaped stator may comprise a plurality of ring shaped stators, each stator being axially aligned with one of the plurality of propellers.

The at least one magnetic blade may comprise a magnet positioned within or coupled to a radial tip of the blade.

The at least one magnetic blade may comprise a magnetic winglet coupled to the radial tip of the blade.

The at least one magnetic blade may comprise a magnetic ring coupled to the radial tip of the blade. The magnetic ring may join a plurality of blades of the at least one propeller.

The at least one magnetic blade may be formed from a magnetic material.

The support may further comprise a ferrous ring configured to be placed in the blood vessel between the propellers and the blood vessel wall.

The at least one propeller may be configured to rotate around the shaft. A bearing may be positioned between the shaft and the at least one propeller.

The shaft may be configured to rotate with the at least one propeller. A bearing may be positioned between the shaft and the proximal hub and a bearing may be positioned between the shaft and the distal hub.

The blades may be deformable so as to be foldable toward the shaft.

The support may comprise a partially disassembled configuration and a fully assembled configuration. The propeller may comprise a channel for receiving the shaft. The distal hub may comprise a first mechanical feature for coupling to a second mechanical feature on the shaft. The shaft may be fixedly coupled to the proximal hub. The shaft, proximal hub, and distal hub may not be rigidly secured together in the partially disassembled configuration. A tensioning line may connect the shaft and the distal hub in the partially disassembled configuration. The tensioning line may extend through the propeller channel. Applying tension to the tensioning line may place the support in the fully assembled configuration. In the fully assembled configuration, the shaft may extend through the propeller channel and the first mechanical feature and the second mechanical feature may be coupled together rigidly securing the shaft, proximal hub, and distal hub together. The plurality of blades may be configured to extend in a substantially perpendicular direction to the shaft in the assembled configuration.

The at least one propeller may comprise two blades. The blades may be foldable along the shaft in opposite directions.

The proximal hub may be adjustably displaceable along the shaft such that the proximal hub can be moved closer to the distal hub to place the anchoring mechanism in an expanded configuration and/or the proximal hub can be moved further from the distal hub to place the anchoring mechanism in a collapsed configuration.

The anchoring mechanism may comprise a proximal half and a distal half. The proximal half of the anchoring mechanism may be separate or separable from the distal half of the anchoring mechanism. The shaft may comprise a proximal half and a distal half. The proximal half of the shaft may be separable from and attachable to the distal half of the shaft.

The shaft may comprise a plurality of joints dividing the shaft into at least three foldable portions. The shaft may be in a straightened configuration when the foldable portions are aligned along the axis of rotation and the shaft may be in a folded configuration when the foldable portions are folded. The at least one propeller may be coupled to a foldable portion positioned between the most proximal fordable portion and the most distal foldable portion of the shaft such that the plurality of blades of the at least one propeller may be aligned substantially parallel to the most proximal foldable portion and the most distal foldable portion in the folded configuration.

The shaft may comprise two joints configured to allow the shaft to assume a z-shape configuration in the folded configuration.

The shaft may comprise four joints configured to allow the shaft to assume a c-shape configuration in the folded configuration.

The support may further comprise a securing shaft configured to be inserted through an internal lumen of the shaft to lock the shaft into a straightened configuration.

The anchoring mechanism may comprise a plurality of leaflet springs coupled to the propeller. The leaflet springs may be configured to extend in a radially outward direction from the propeller to contact the blood vessel wall and anchor the propeller within the blood vessel. The leaflet springs may comprise a deformed configuration configured to allow the anchoring mechanism to be compressed for percutaneous delivery via a catheter.

The anchoring mechanism may be configured to be installed in the descending aorta. The support may be configured to provide a pressure rise between about 20 mmHg and about 50 mmHg in the blood flow and to maintain a flow rate of about 5 L/min.

The support may be configured to produce a right handed helical blood flow comprising a vorticity about equal to that of the native descending aorta at an output of the support.

The anchoring mechanism may comprise a plurality of struts extending between the proximal hub and the distal hub. The struts may be bendable or flexible.

In some embodiments, a method of treating congestive heart failure in a patient comprises installing a mechanical circulation support within the lumen of the descending aorta of the patient. The support comprises at least one propeller;

a shaft aligned along the axis of rotation of the at least one propeller; an anchoring mechanism; and at least one ring-shaped stator. The at least one propeller comprises a plurality of blades arranged around an axis of rotation. The blades are configured to pump blood in a substantially axial direction parallel to the axis of rotation. In some embodiments, at least one of the plurality of blades is magnetic. The anchoring mechanism is configured to anchor the at least one propeller within the lumen. The anchoring mechanism comprises a proximal hub coupled to a proximal end of the shaft and a distal hub coupled to a distal end of the shaft. The anchoring mechanism further comprises a collapsed configuration for installing the anchoring mechanism in the descending aorta and an expanded configuration wherein at least a portion of the anchoring mechanism is configured to be pressed against a wall of the lumen of the descending aorta. The at least one ring-shaped stator comprises one or more electromagnets positioned around the circumference of the stator. The at least one stator is configured to be positioned concentrically around the blades of the at least one propeller to electromagnetically drive rotation of the at least one magnetic blade.

The support may be configured to provide a pressure rise between about 20 mmHg and about 50 mmHg in the blood flow and to maintain a flow rate of about 5 L/min.

Installing the support may comprise percutaneously installing the rotor and the anchoring mechanism in the lumen through a catheter. The anchoring mechanism may assume the collapsed configuration during delivery. Installing the support may further comprise expanding the anchoring mechanism into an expanded configuration such that the anchoring mechanism anchors the rotor within the lumen.

Installing the support may further comprise percutaneously installing the at least one stator in the lumen through a catheter.

The at least one stator may be coupled to the anchoring mechanism.

The at least one stator may be installed prior to the anchoring mechanism.

The at least one stator may comprise first and second discrete ring-shaped components. The first and second discrete ring-shaped components may each comprise circumferentially offset electromagnets. The installing the at least one stator may comprise installing the first discrete ring-shaped component and subsequently installing the second discrete ring shaped component so that the electromagnets of the second discrete ring-shaped components are positioned circumferentially between the electromagnets of the first discrete-ring shaped component.

Installing the support may further comprise surgically installing the at least one stator around an outer circumference of the descending aorta such that the at least one stator is axially aligned with the at least one propeller.

The at least one stator may comprise a hinge allowing the stator to assume an open configuration and a closed configuration. Installing the stator may comprise positioning the stator around the descending aorta in an open configuration and closing the stator.

Installing the support may comprise making a surgical incision in the descending aorta and installing the anchoring mechanism into the lumen through the incision.

The patient may have stage II or stage III congestive heart failure.

The patient may have late stage II or early stage III congestive heart failure.

In some embodiments, a mechanical circulatory support for assisting the heart comprises at least one propeller; a shaft aligned along the axis of rotation of the at least one propeller; an anchoring mechanism; and at least one motor configured to drive rotation of the at least one propeller. The at least one propeller comprises a plurality of blades arranged around an axis of rotation. The blades are configured to pump blood in a substantially axial direction parallel to the axis of rotation. In some embodiments, at least one of the plurality of blades is magnetic. The anchoring mechanism is configured to anchor the at least one propeller within a lumen of a blood vessel. The anchoring mechanism comprises a proximal hub coupled to a proximal end of the shaft and a distal hub coupled to a distal end of the shaft. The anchoring mechanism further comprises a collapsed configuration for installing the anchoring mechanism in the blood vessel and an expanded configuration wherein at least a portion of the anchoring mechanism is configured to be pressed against a wall of the lumen of the blood vessel.

All of the blades of the at least one propeller may be configured to be foldable substantially along the shaft such that in the collapsed configuration of the anchoring mechanism the blades are in a folded position. The collapsed configuration may be configured for percutaneously installing the anchoring mechanism in the blood vessel through a catheter.

The at least one propeller may comprise a pair of contra-rotating propellers configured to rotate in opposite directions.

The support may further comprise a plurality of stationary de-swirler vanes coupled to either the shaft or the anchoring mechanism. The de-swirler vanes may be positioned downstream of the at least one propeller and may be configured to remove or reduce a tangential velocity component of blood flow as it leaves the support.

The support me further comprise a plurality of stationary pre-swirler vanes coupled to either the shaft or the anchoring mechanism. The pre-swirler vanes may be positioned upstream of the at least one propeller and may be configured to increase a tangential velocity component of blood flow entering the support.

The at least one motor may be configured to be extracorporeal. The motor may be configured to drive rotation of the propeller via a driveline percutaneously extending through the body of a patient and connecting the motor to the shaft.

The at least one motor may be configured to be positioned within the lumen of the blood vessel. The motor may be configured to rotate the shaft to drive rotation of the propeller.

The at least one motor may comprise a plurality of motors configured to be positioned within the lumen and the at least one propeller may comprise a plurality of propellers. Each motor may be configured to drive rotation of one of the plurality of propellers.

The at least one propeller may comprise a pair of contra-rotating propellers which are mechanically connected. The at least one motor may comprise a single motor configured to drive the pair of contra-rotating propellers in opposite directions.

In some embodiments, a temporary, removable mechanical circulatory support heart-assist device comprises at least two propellers or impellers, each propeller or impeller comprising a plurality of blades arranged around an axis of rotation, the blades being configured to pump blood, wherein two propellers or impellers of the at least two propellers or impellers rotate in opposite directions.

In some embodiments, the device may be configured to be implanted and removed with minimally invasive surgery. In some embodiments, the device may include an electric device configured to deliver power to motors, wherein the electric device is configured to be intra-corporeal and placed near the at least two propellers or impellers. In some embodiments, at least two propellers or impellers are configured to be placed in the vasculature to assist with perfusion. In some embodiments, the at least two propellers or impellers are configured to hold a heart valve in an open position to assist with perfusion. In some embodiments, the device may include a first gearbox placed between a motor and a downstream propeller or impeller of the at least two propellers or impellers, and a second gearbox between the upstream and downstream propeller or impeller of the at least two propellers or impellers. In some embodiments, diameters of the gears in the first and second gearboxes are configured to achieve equal rpm between the at least two propellers or impellers. In some embodiments, diameters of the gears in the first and second gearboxes are configured to achieve different rpm between the at least two propellers or impellers. In some embodiments, the blades are flexible. In some embodiments, the blades are foldable. In some embodiments, the blades are placed in a surrounding cage. In some embodiments, the cage and blades are configured to be folded and inserted in the blood vessel. In some embodiments, the device may include a balloon, wherein the balloon is configured to expand to fill the difference between minimum and maximum aorta sizes. In some embodiments, the device may include two motors, wherein the two motors are arranged back-to-back, wherein the two motors are connected to two propellers or impellers of the at least two propellers or impellers rotating in opposite directions. In some embodiments, the device may include a lubrication channel, where the lubricant is biocompatible and dispersed in the body. In some embodiments, the device may include one rotor and first and second stators, wherein a first stator is configured to be located upstream and a second stator is configured to be located downstream. In some embodiments, the device may include a gearbox comprising two concentric output shafts driving two propellers or impellers of the at least two propellers or impellers in opposite directions, and one input shaft connected via a flexible shaft to an electric motor or gearmotor. In some embodiments, the electric motor or gearmotor is intracorporeal. In some embodiments, the electric motor or gearmotor is extracorporeal. In some embodiments, an upstream propeller or impeller of the at least two propellers or impellers is driven by an epicyclic-type gearbox, a downstream propeller or impeller of the at least two propellers or impellers is driven in the opposite direction to the upstream impeller or propeller by a second epicyclic-type gearbox. In some embodiments, the suns of both epicyclic gearboxes are driven by sun gears connected via an input shaft to an electric motor. In some embodiments, the electric motor or gearmotor is intracorporeal. In some embodiments, the electric motor or gearmotor is extracorporeal. In some embodiments, the blades of the two propellers or impellers of the at least two propellers or impellers rotating in opposite directions comprise flexible connections to impeller hubs to accommodate insertion and removal with folded blades, and operation with unfolded blades. In some embodiments, the blades of the two propellers or impellers of the at least two propellers or impellers rotating in opposite directions comprise mechanical connections to the impeller hubs to accommodate insertion and removal with folded blades in a catheter, and operation with unfolded blades. In some embodiments, the mechanical folding mechanism for the blades variably folds open. In some embodiments, the inlet to the pump is configured to be anastomosed to a chamber of the heart, and the outlet of the pump is configured to be anastomosed to the vascular system. In some embodiments, the device may include an anchoring mechanism, the anchoring mechanism being configured to anchor the at least one propeller within a lumen of a blood vessel. In some embodiments, the anchoring mechanism comprises a collapsed configuration for installing the anchoring mechanism in the blood vessel and an expanded configuration wherein at least a portion of the anchoring mechanism is configured to be pressed against a wall of the lumen of the blood vessel. In some embodiments, the anchoring mechanism comprises 3D struts. In some embodiments, the anchoring mechanism comprises a balloon. In some embodiments, the device consists of two propellers. In some embodiments, the device may include a pre-swirler configured to increase a tangential velocity component of blood flow entering the support. In some embodiments, the device may include a de-swirler. In some embodiments, the device may include at least one stator. In some embodiments, the at least two propellers or impellers comprises a plurality of propellers configured to rotate together. In some embodiments, at least two propellers or impellers comprises a plurality of propellers configured to rotate independently. In some embodiments, the plurality of blades of a propeller or an impeller of the at least two propellers or impellers has a fixed open diameter. In some embodiments, the plurality of blades of a propeller or an impeller of the at least two propellers or impellers has a variable open diameter. In some embodiments, the propeller of the at least two propellers or impellers and a motor comprise a magnetic coupling. In some embodiments, the device may include one or more lubrication channels. In some embodiments, the device may include an articulated sleeve for insertion. In some embodiments, the device may include a motor configured to be placed within the body of the patient. In some embodiments, the device may include a motor configured to be placed outside the body of the patient. In some embodiments, the device may include at least one gearbox reducing shaft speed. In some embodiments, the device may include at least one gearbox providing contra-rotation. In some embodiments, the device may include at least one planetary gearbox.

In some embodiments, a method of treating congestive heart failure in a patient, the method comprises installing a mechanical circulation support within the lumen of the descending aorta of the patient, wherein the mechanical circulation heart-assist device comprises at least two propellers or impellers, each propeller or impeller comprising a plurality of blades arranged around an axis of rotation, the blades being configured to pump blood, wherein two propellers or impellers of the at least two propellers or impellers rotate in opposite directions.

In some embodiments, the device is configured to provide a pressure rise between about 20 mmHg and about 40 mmHg in the blood flow and to maintain a flow rate of about 5 L/min. In some embodiments, installing the device comprises inflating a balloon. In some embodiments, installing the device comprises expanding one or more struts. In some embodiments, the method can include expanding a pre-swirler or de-swirler. In some embodiments, the method can include expanding the plurality of blades to a fixed diameter. In some embodiments, the method can include expanding the plurality of blades to a variable diameter. In some embodiments, the device is implanted and removed with minimally invasive surgery. In some embodiments, the at least two propellers or impellers assist with perfusion. In some embodiments, the at least two propellers or impellers hold a heart valve in an open position to assist with perfusion. In some embodiments, the method can include a first gearbox placed between a motor and a downstream propeller or impeller of the at least two propellers or impellers to provide contra-rotation of the at least two propellers or impellers. In some embodiments, the at least two propellers or impellers rotate at equal rpm. In some embodiments, the at least two propellers or impellers rotate at different rpm. In some embodiments, the method can include folding the blades for insertion. In some embodiments, the method can include expanding a balloon to fill the difference between minimum and maximum aorta sizes. In some embodiments, the method can include at least one intracorporeal motor. In some embodiments, the method can include at least one extracorporeal motor. In some embodiments, the method can include pumping a biocompatible lubricant through at least a portion of the device. In some embodiments, a system, device, or method can include, exclude (e.g., not comprise), consist essentially of, or consist of any number of features or combinations of features of this disclosure.

In some embodiments, a temporary, removable mechanical circulatory support heart-assist device is provided. The device can include at least two propellers or impellers, each propeller or impeller comprising a plurality of blades arranged around an axis of rotation, the blades being configured to pump blood. In some embodiments, two propellers or impellers of the at least two propellers or impellers rotate in opposite directions. In some embodiments, the device can include an hour glass support. In some embodiments, a section of the hour glass support has a constant diameter when expanded. In some embodiments, the hour glass support and blades are configured to be folded and inserted in the blood vessel. In some embodiments, the device is configured to be implanted and removed with minimally invasive surgery. In some embodiments, the at least two propellers or impellers are configured to be placed in the vasculature to assist with perfusion. In some embodiments, the at least two propellers or impellers are configured to hold a heart valve in an open position to assist with perfusion. In some embodiments, the blades are flexible. In some embodiments, the blades are foldable. In some embodiments, the device can include a lubrication channel, where the lubricant is biocompatible and dispersed in the body. In some embodiments, the device can include a gearbox comprising two concentric output shafts driving two propellers or impellers of the at least two propellers or impellers in opposite directions, and one input shaft connected via a flexible shaft to an electric motor or gearmotor. In some embodiments, the electric motor or gearmotor is intracorporeal. In some embodiments, the electric motor or gearmotor is extracorporeal. In some embodiments, an upstream propeller or impeller of the at least two propellers or impellers is driven by an epicyclic-type gearbox, a downstream propeller or impeller of the at least two propellers or impellers is driven in the opposite direction to the upstream impeller or propeller by a second epicyclic-type gearbox. In some embodiments, the suns of both epicyclic gearboxes are driven by sun gears connected via an input shaft to an electric motor. In some embodiments, the electric motor or gearmotor is intracorporeal. In some embodiments, the electric motor or gearmotor is extracorporeal. In some embodiments, the blades of the two propellers or impellers of the at least two propellers or impellers rotating in opposite directions comprise flexible connections to impeller hubs to accommodate insertion and removal with folded blades, and operation with unfolded blades. In some embodiments, the blades of the two propellers or impellers of the at least two propellers or impellers rotating in opposite directions comprise mechanical connections to the impeller hubs to accommodate insertion and removal with folded blades in a catheter, and operation with unfolded blades. In some embodiments, the device can include two propellers. In some embodiments, the device can include a pre-swirler configured to increase a tangential velocity component of blood flow entering the support. In some embodiments, the device can include a de-swirler. In some embodiments, the device can include at least one stator. In some embodiments, the at least two propellers or impellers comprises a plurality of propellers configured to rotate together. In some embodiments, at least two propellers or impellers comprises a plurality of propellers configured to rotate independently. In some embodiments, the plurality of blades of a propeller or an impeller of the at least two propellers or impellers have a fixed open diameter. In some embodiments, the plurality of blades of a propeller or an impeller of the at least two propellers or impellers have a variable open diameter. In some embodiments, the propeller of the at least two propellers or impellers and a motor comprise a magnetic coupling. In some embodiments, the device can include one or more lubrication channels. In some embodiments, the device can include an articulated sleeve for insertion. In some embodiments, the device can include a motor configured to be placed within the body of the patient. In some embodiments, the device can include a motor configured to be placed outside the body of the patient. In some embodiments, the device can include at least one gearbox reducing shaft speed. In some embodiments, the device can include at least one gearbox providing contra-rotation. In some embodiments, the device can include at least one planetary gearbox.

In some embodiments, a method of treating a patient is provided. The method can include installing a mechanical circulation support within the lumen of the descending aorta of the patient. The mechanical circulation heart-assist device can include at least two propellers or impellers. In some embodiments, each propeller or impeller comprises a plurality of blades arranged around an axis of rotation. In some embodiments, the blades being configured to pump blood. In some embodiments, two propellers or impellers of the at least two propellers or impellers rotate in opposite directions. In some embodiments, the device is configured to provide a pressure rise between about 20 mmHg and about 40 mmHg in the blood flow and to maintain a flow rate of about 5 L/min. In some embodiments, installing the device comprises inflating a balloon. In some embodiments, installing the device comprises expanding one or more struts. In some embodiments, the method can include expanding a pre-swirler or de-swirler. In some embodiments, the method can include expanding the plurality of blades to a fixed diameter. In some embodiments, the method can include expanding the plurality of blades to a variable diameter. In some embodiments, the device is implanted and removed with minimally invasive surgery. In some embodiments, the at least two propellers or impellers assist with perfusion. In some embodiments, the at least two propellers or impellers hold a heart valve in an open position to assist with perfusion. In some embodiments, the method can include a first gearbox placed between a motor and a downstream propeller or impeller of the at least two propellers or impellers to provide contra-rotation of the at least two propellers or impellers. In some embodiments, the at least two propellers or impellers rotate at equal rpm. In some embodiments, the at least two propellers or impellers rotate at different rpm. In some embodiments, the method can include folding the blades for insertion. In some embodiments, the method can include expanding a balloon to fill the difference between minimum and maximum aorta sizes. In some embodiments, the method can include at least one intracorporeal motor. In some embodiments, the method can include at least one extracorporeal motor. In some embodiments, the method can include pumping a biocompatible lubricant through at least a portion of the device. In some embodiments, the method can treat any number of Acute Cardiogenic Shock (CGS), Percutaneous Coronary Intervention (PCI), acute decompensated heart failure (ADHF), Cardio Renal Syndrome (CRS), and/or temporary relief of the native heart in early or late stages of congestive heart failure. Other uses of the devices are contemplated.

In some embodiments, a mechanical circulatory support heart-assist device is provided. The device can include a pumping head comprising at least one set of two contra-rotating impellers. In some embodiments, contra-rotation is configured to occur at equal or unequal revolutions per minute. In some embodiments, at least one impeller is configured to allow for axial flow. In some embodiments, at least one impeller is a screw impeller. In some embodiments, an inlet to the pumping head is configured to be anastomosed to a heart of a patient, and an outlet of the pumping head is configured to be anastomosed to a vascular system of the patient. In some embodiments, an inlet and an outlet of the pumping head are configured to be anastomosed to the vascular system. In some embodiments, an upstream impeller of the at least one set of impellers rotates at a different rotational speed than a downstream impeller of the at least one set of impellers in order to achieve substantially equal pressure rise per impeller. In some embodiments, a vortex flow pattern established by a first impeller is totally removed by a second impeller, such that a flow velocity vector downstream is in the axial direction, thus maximizing pressure rise and efficiency. In some embodiments, a vortex flow pattern established by a first impeller is substantially but not fully removed by a second impeller, allowing 2-3 flow rotations in about 30 cm of flow downstream, to mimic a vortex pattern in a descending aorta of a healthy heart, and provide additional perfusion to side arteries. In some embodiments, the device can include helical screw blades between the two contra-rotating impellers. In some embodiments, the helical screw blades are mounted downstream of the set of impellers on the device.

In some embodiments, a mechanical circulatory support heart-assist device is provided. The device can include one impeller. In some embodiments, a set of stationary pre-swirler vanes is installed upstream of the impeller, and a set of stationary de-swirler vanes are installed downstream of the impeller, effectively returning the flow downstream of the device in the axial direction, thus maximizing pressure rise and efficiency. In some embodiments, a vortex flow pattern established by a first impeller is substantially but not fully removed by a second impeller, allowing 2-3 flow rotations in about 30 cm of flow downstream, to mimic a vortex pattern in a descending aorta of a healthy heart, and provide additional perfusion to side arteries, and wherein the one impeller is the only impeller present on the device.

In some embodiments, a mechanical circulatory support heart-assist device is provided. The device can include a pumping head comprising a plurality of impellers configured to contra-rotate with respect to each other. In some embodiments, the contra-rotation is configured to occur at equal or unequal revolutions per minute. In some embodiments, the impellers are configured to be actuated mechanically and are not configured to be actuated via magnetic elements.

In some embodiments, a mechanical circulatory support heart-assist device is provided. The device can include a pumping head comprising two contra-rotating impellers. In some embodiments, the two contra-rotating impellers are configured to be driven by a first gearbox achieving contra-rotation between the two contra-rotating impellers. In some embodiments, the gearbox is configured to be intra-corporeally located. In some embodiments, the gearbox is configured to be extra-corporeally located. In some embodiments, the device can include a plurality of gearboxes, each gearbox located at the hub of each rotor impeller. In some embodiments, the gearbox is downstream of the two contra-rotating impellers. In some embodiments, the gearbox is between the two contra-rotating impellers. In some embodiments, the gearbox is upstream of the two contra-rotating impellers. In some embodiments, the gearbox is configured to be driven by an intra-corporeal motor. In some embodiments, the gearbox is configured to be driven by an intra-corporeal motor. In some embodiments, the two contra-rotating impellers are configured to be driven by an intra-corporeal single-input shaft double-output shaft gearbox, with the gearbox located downstream of the two contra-rotating impellers, and wherein the gearbox is driven by a flexible shaft powered by an extra-corporeal motor and motor controller. In some embodiments, the gearbox is configured to be driven by an extra-corporeal motor. In some embodiments, the pumping head comprises collapsible blades and is installed in a collapsible hourglass-shaped frame cage. In some embodiments, the pumping head comprises collapsible blades, the gearbox is positioned downstream and directly adjacent to the collapsible blades, and the pumping head and the gearbox are within a collapsible hourglass-shaped frame cage. In some embodiments, the pumping head comprises collapsible blades, the gearbox is positioned immediately downstream of the pumping head, the intra-corporeal motor is positioned immediately downstream of the gearbox, and pumping head, gearbox, and the motor are within a collapsible hourglass-shaped frame cage. In some embodiments, the two contra-rotating impellers are driven by two coaxial flexible contra-rotating shafts, wherein the single-input shaft double-output shaft gearbox, and motor, and motor controller are all configured to be extra-corporeal. In some embodiments, the two contra-rotating impellers, gearbox and motor are configured to be intra-corporeal, and power is transmitted to the intra-corporeal motor via electric conductors from an extracorporeal power supply and controller. In some embodiments, the gearbox, coaxial contra-rotating flexible shafts, and impeller hubs are lubricated by a biocompatible fluid. In some embodiments, the coaxial contra-rotating flexible shafts and impeller hubs are lubricated by a biocompatible fluid.

In some embodiments, a mechanical circulatory support device is provided. The device can include a pump head positioned in a waist section of an hourglass-shaped cage, such that an inlet of an inlet section and an outlet of an outlet section of the hourglass shaped cage are of varying diameter and the inlet and the outlet are configured to be secured on blood vessels of various diameter sizes, thus accommodating one size of waist section and turbomachine pump head for all sizes of blood vessels. In some embodiments, the waist section of the hourglass shaped cage is a memory-alloy frame cage covered with biocompatible material, so that the inlet of the inlet section and outlet of the outlet section of the hourglass shaped cage are configured to be secured against an inside of blood vessels of various sizes, so that the whole length of the hourglass shaped cage is collapsible along its axis, and the inlet and the outlet accommodate one size of waist section and turbomachine pump head for all sizes of blood vessels. In some embodiments, the inlet section of the hourglass shaped cage has perforations allowing some blood to go through the perforations and perfuse the region between the outside of the hourglass shaped cage and the inside of blood vessel, wherein the waist of the hourglass shaped cage and a diffuser of the hourglass shaped cage are covered. In some embodiments, the pump head has at least one rotating blade row of collapsible blades installed in the waist section of the hourglass shaped cage. In some embodiments, the impeller is driven by an extra-corporeal motor. In some embodiments, the impeller is driven by an intra-corporeal motor. In some embodiments, the pump head has at least one pair of contra-rotating blade rows. In some embodiments, the blade rows are powered by an intra-corporeal gearbox and an intra-corporeal motor. In some embodiments, the blade rows are powered by an intra-corporeal gearbox and an extra-corporeal motor. In some embodiments, the blade rows are powered by an extra-corporeal gearbox and an extra-corporeal motor. In some embodiments, no blood flow is permitted from the outlet to the inlet on the outside of the hourglass. In some embodiments, the device prevents backflow and is configured to perfuse intercostal vessels. In some embodiments, the inlet section of the hourglass shaped cage is covered. In some embodiments, the collapsing of the blade row and the hourglass shaped cage are achieved by a runner moving downstream and a sheath moving upstream. In some embodiments, the collapsing of the blade row and the hourglass shaped cage are achieved a sheath moving upstream, without the use of a runner.

In some embodiments, a mechanical circulatory support device is provided. The device can include a frame comprising a first end, a second end, and a central portion. In some embodiments, the frame comprises a first diameter at the first end, a second diameter at the second end, and a third diameter at the central portion. In some embodiments, the third diameter is smaller than the first diameter and the second diameter. In some embodiments, the frame comprises a sidewall and a lumen therethrough. The device can include a pump head positionable within the lumen of the frame proximate the central portion. In some embodiments, the frame comprises a compressed state and a radially expanded state configured to be secured within a blood vessel. In some embodiments, the pump head comprises a plurality of impellers with at least one pair of contra-rotating impellers, wherein the device does not comprise any magnetic elements configured to actuate the impellers. In some embodiments, the frame gradually decreases in diameter from the first end to the central portion. In some embodiments, a mechanical hub is provided for use with heart-assist devices, comprising a hub configured to bend with a worm and a screw. In some embodiments, a mechanical hub is provided for use with heart-assist devices, comprising a hub configured to bend with an axle and pin. In some embodiments, a mechanical hub is provided for use with heart-assist devices, comprising a hub configured to bend by axial displacement of the center-shaft. In some embodiments, a mechanical hub is provided for use with heart-assist devices, comprising a hub configured to bend by one or more of a tube, rod, lattice, or strip. In some embodiments, a mechanical hub is provided for use with heart-assist devices, comprising one strip or lattice of strips in the hub causing stiffness in folding along the direction of the resultant force of lift and drag forces, predominantly upstream or downstream, and lower stiffness accommodating folding in the perpendicular. In some embodiments, a turbomachine blade row and hub are provided cut of one cylindrical section of memory shaped alloy. In some embodiments, additional material is added to each horizontal segment of the hub to form a folding blade shape with appropriate thickness distribution from leading edge to trailing edge and chord distribution from hub to tip. In some embodiments, the hub is manufactured stiffer to bend either upstream or downstream, and less stiff in the opposite direction. In some embodiments, a turbomachine blade row and hub are provided cut of one cylindrical section of memory shaped alloy. In some embodiments, each horizontal segment of the hub is further cut into a lattice to form either the camber line, or the suction side, or the pressure side of the blade shape, which is then matched with another lattice structure to make the overall shape of the blade, and covered with a biocompatible material to make a folding blade shape with appropriate thickness distribution from leading edge to trailing edge and chord distribution from hub to tip, and where the hub is manufactured stiffer to bend either upstream or downstream, and less stiff in the opposite direction. In some embodiments, the lattice and surrounding biocompatible material is configured to shrink chordwise, thus allowing folding and storage into a sheath. In some embodiments, a mechanical hub for use with heart-assist devices is provided comprising a flat-plate blade bent to blade shape during manufacturing. In some embodiments, a mechanical hub for use with heart-assist devices is provided, comprising a plurality of blades extending radially outward from the hub, wherein the blades are configured to tilt in a downstream direction at a rest configuration and rotate horizontal with respect to the hub during an operational configuration. In some embodiments, a mechanical hub for use with heart-assist devices is provided, comprising a stop mechanism to prevent blades bending upstream in an undesired direction. In some embodiments, a device comprising two contra-rotating turbomachine blade rows is provided that can be folded around a shaft inside a sheath while contracting. In some embodiments, a device comprising turbomachines under hubs to reduce recirculation is provided. In some embodiments, a mechanical hub for use with heart-assist devices is provided and configured to allow bending upstream. In some embodiments, a mechanical hub for use with heart-assist devices is provided and configured to allow bending downstream. In some embodiments, a mechanical circulatory support is provided comprising a single blade row. In some embodiments, a mechanical circulatory support comprising more than one blade row is provided, wherein a subset of which comprises contra-rotating impellers.

In some embodiments, a mechanical circulatory support heart-assist device is provided an configured to be inserted with minimally invasive surgery wherein the pumping head comprises two contra-rotating impellers. In some embodiments, contra-rotation may be at equal or unequal revolutions per minute. In some embodiments, an inlet to the pumping head is configured to be anastomosed to a heart, and an outlet of the pumping head is configured to be anastomosed to a vascular system. In some embodiments, the inlet and the outlet of the pumping head are configured to be anastomosed to a vasculature. In some embodiments, the contra-rotating rotors are collapsible, and the contra-rotating rotors are configured to be installed in a collapsible hourglass-shaped frame cage covered with biocompatible material. In some embodiments, the contra-rotating rotors are configured to be driven by an intra-corporeal gearbox which is driven by an intra-corporeal motor, and the whole device is collapsible into a catheter sheath for implantation and removal. In some embodiments, where the contra-rotating rotors are configured to be driven by an intra-corporeal gearbox which is driven by an extra-corporeal motor, and the intra-corporeal parts of the device are collapsible into a catheter sheath for implantation and removal. In some embodiments, the two contra-rotating impellers are configured to be driven by two coaxial flexible contra-rotating shafts, wherein the single-input shaft double-output shaft gearbox, and motor, and motor controller are extra-corporeal. In some embodiments, an inlet of an hourglass-shaped frame cage is perforated in order to provide blood perfusion between the outside of the hourglass-shaped frame cage and the inside of the blood vessel. In some embodiments, a rotor tip diameter is between 6 mm and 34 mm. In some embodiments, the rotors operate between 1,000 and 60,000 rpm. In some embodiments, a gap between rotor tip and inside diameter of an hourglass-shaped frame cage is between 0.03 mm and 12 mm. In some embodiments, the device can include an hourglass shaped cage wherein the waist diameter is 5 mm to 33 mm, and where the inlet section has diameter 0.2 times the waist diameter to 8.0 times the waist diameter, and length 0.2 times the waist diameter to 16.0 times the waist diameter. In some embodiments, the device can include an hourglass shaped cage wherein the waist diameter is 5 mm to 33 mm, and where the inlet section has diameter 1.0 times the waist diameter to 5.0 times the waist diameter, and length 0.2 times the waist diameter to 16.0 times the waist diameter. In some embodiments, the device can include an hourglass shaped cage wherein the waist diameter is 5 mm to 33 mm, and where the outlet diffuser section has diameter 0.2 times the waist diameter to 8.0 times the waist diameter, and length 0.2 times the waist diameter to 16.0 times the waist diameter. In some embodiments, the device can include an hourglass shaped cage wherein the waist diameter is 5 mm to 33 mm, and where the outlet diffuser section has diameter 1.0 times the waist diameter to 5.0 times the waist diameter, and length 0.2 times the waist diameter to 16.0 times the waist diameter.

In some embodiments, a mechanical circulatory support heart-assist device is provided and inserted with minimally invasive surgery wherein the pumping head comprises only a single impeller with a stationary set of pre-swirler blades upstream of the impeller and a stationary set of de-swirler blades downstream of the impeller. In some embodiments, the impeller tip diameter is about 5 mm-about 33 mm diameter. In some embodiments, the turbomachine rotates at about 1,000 to about 50,000 rpm. In some embodiments, where the impeller tip diameter is about 5 mm-about 33 mm diameter and the turbomachine rotates at about 1,000 to about 50,000 rpm. In some embodiments, the waist diameter is about 5 mm to about 33 mm. In some embodiments, the inlet section has a diameter of between about 0.2 times the waist diameter to about 8.0 times the waist diameter. In some embodiments, the inlet section has a length of about 0.2 times the waist diameter to about 16.0 times the waist diameter. In some embodiments, the waist diameter is about 5 mm to about 33 mm, and where the inlet section has diameter about 0.2 times the waist diameter to about 8.0 times the waist diameter, and length about 0.2 times the waist diameter to about 16.0 times the waist diameter. In some embodiments, the waist diameter is about 5 mm to about 33 mm. In some embodiments, the inlet section has a diameter of about 1.0 times the waist diameter to about 5.0 times the waist diameter. In some embodiments, inlet section has a length of about 0.2 times the waist diameter to about 16.0 times the waist diameter. In some embodiments, the waist diameter is about 5 mm to 33 mm, and where the outlet diffuser section has diameter about 1.0 times the waist diameter to about 5.0 times the waist diameter, and length about 0.2 times the waist diameter to about 16.0 times the waist diameter. In some embodiments, the device utilizes contra-rotation with the pressure rise and flow rate. In some embodiments, the device has a pressure rise of about 5-150 mm Hg. In some embodiments, the device has a flow rate of about 0.1-10 Lt/min. In some embodiments, the device is configured for about 10-40 mmHg pressure rise. In some embodiments, the device is configured for about 2-6 L/min flow rate. In some embodiments, the device is configured for 30 mm Hg pressure rise and 5 Lt/min flow rate. In some embodiments, the device is configured for about 10-60 mm Hg pressure rise and about 0.1-8 L/min flow rate.

In some embodiments, a fully-removable temporary heart-assist device is provided and installed in a blood vessel, not across the aortic valve, where in the unfurled position the impeller tip diameter is 0.2 to 1.0 times the diameter of the adult-sized blood vessel. In some embodiments, the device is a folding device.

In some embodiments, a temporary, removable mechanical circulatory support heart-assist device is provided. The device can include at least two non-magnetic propellers or impellers, each propeller or impeller comprising a plurality of foldable blades arranged around an axis of rotation. In some embodiments, the at least two propellers or impellers of the at least two propellers or impellers are configured to rotate in opposite directions with respect to each other.

In some embodiments, the device can include a generally hourglass shaped support surrounding the at least two non-magnetic propellers or impellers, the support comprising a proximal section, a distal section, and a waist section in between the proximal section and the distal section, the support sized and configured to be placed within an arterial vessel. In some embodiments, the waist section has a constant diameter when expanded. In some embodiments, the support and blades are configured to be folded and inserted in the blood vessel in a radially compressed configuration. In some embodiments, the device is configured to be implanted and removed with minimally invasive surgery, and the support is atraumatic with respect to the arterial vessel. In some embodiments, the at least two propellers or impellers are configured to rotate at about, or no more than about 60,000 rpm, 30,000 rpm, 15,000 rpm, 12,000 rpm, 10,000 rpm, 9,000 rpm, 8,000 rpm, or less. In some embodiments, the at least two propellers or impellers are configured to hold a heart valve in an open position to assist with perfusion. In some embodiments, the blades are flexible. In some embodiments, the blades are foldable. In some embodiments, the device can include a lubrication reservoir, where the lubricant is biocompatible. In some embodiments, the device can include a gearbox comprising two concentric output shafts driving two propellers or impellers of the at least two propellers or impellers in opposite directions, and one input shaft connected via a flexible shaft to an electric motor or gearmotor. In some embodiments, the electric motor or gearmotor is intracorporeal. In some embodiments, the electric motor or gearmotor is extracorporeal. In some embodiments, an upstream propeller or impeller of the at least two propellers or impellers is driven by an epicyclic-type gearbox, a downstream propeller or impeller of the at least two propellers or impellers is driven in the opposite direction to the upstream impeller or propeller by a second epicyclic-type gearbox. In some embodiments, suns of both of the epicyclic gearboxes are driven by sun gears connected via an input shaft to an electric motor. In some embodiments, the electric motor or gearmotor is configured to be intracorporeal. In some embodiments, the electric motor or gearmotor is configured to be extracorporeal. In some embodiments, the blades of the two propellers or impellers of the at least two propellers or impellers rotating in opposite directions comprise flexible connections to impeller hubs to accommodate insertion and removal with folded blades, and operation with unfolded blades. In some embodiments, the blades of the two propellers or impellers of the at least two propellers or impellers rotating in opposite directions comprise mechanical connections to the impeller hubs to accommodate insertion and removal with folded blades in a catheter, and operation with unfolded blades. In some embodiments, the device can include two propellers. In some embodiments, the device can include a pre-swirler configured to increase a tangential velocity component of blood flow entering the support. In some embodiments, the device can include a de-swirler. In some embodiments, the device can include at least one stator. In some embodiments, the at least two propellers or impellers comprises a plurality of propellers configured to rotate together. In some embodiments, at least two propellers or impellers comprises a plurality of propellers configured to rotate independently. In some embodiments, the plurality of blades of a propeller or an impeller of the at least two propellers or impellers have a fixed open diameter. In some embodiments, the plurality of blades of a propeller or an impeller of the at least two propellers or impellers have a variable open diameter. In some embodiments, the propeller of the at least two propellers or impellers and a motor comprise a magnetic coupling. In some embodiments, the device can include one or more lubrication channels. In some embodiments, the device can include an articulated sleeve for insertion. In some embodiments, the device can include a motor configured to be placed within the body of the patient. In some embodiments, the device can include a motor configured to be placed outside the body of the patient. In some embodiments, the device can include at least one gearbox reducing shaft speed. In some embodiments, the device can include at least one gearbox providing contra-rotation. In some embodiments, the device can include at least one planetary gearbox.

In some embodiments, a method of treating a patient is provided. The method can include deploying a mechanical circulation support within the lumen of the descending aorta of the patient. In some embodiments, the mechanical circulation heart-assist device can include at least two propellers or impellers. In some embodiments, each propeller or impeller comprising a plurality of blades arranged around an axis of rotation. In some embodiments, the blades are configured to pump blood. In some embodiments, two propellers or impellers of the at least two propellers or impellers rotate in opposite directions. The method can include transforming the plurality of blades from a folded configuration to an unfolded configuration. The method can include rotating the blades to enhance circulation in the patient.

In some embodiments, the device is configured to provide a pressure rise between about 5 mmHg and about 40 mmHg in the blood flow and to maintain a flow rate of about 5 L/min. In some embodiments, deploying the device comprises inflating a balloon. In some embodiments, installing the device comprises expanding one or more struts. In some embodiments, the method can include expanding a pre-swirler or de-swirler. In some embodiments, the method can include expanding the plurality of blades to a fixed diameter. In some embodiments, the method can include expanding the plurality of blades to a variable diameter. In some embodiments, deploying the mechanical circulation support is accomplished via minimally invasive surgery. In some embodiments, the method can include activating the at least two propellers or impellers sufficient to assist with perfusion. In some embodiments, the at least two propellers or impellers hold a heart valve in an open position to assist with perfusion. In some embodiments, the method can include a first gearbox placed between a motor and a downstream propeller or impeller of the at least two propellers or impellers to provide contra-rotation of the at least two propellers or impellers. In some embodiments, the at least two propellers or impellers rotate at equal rpm. In some embodiments, the at least two propellers or impellers rotate at different rpm. In some embodiments, the method can include folding the plurality of blades prior to deploying the mechanical circulation support. In some embodiments, the method can include expanding a balloon to fill the difference between minimum and maximum aorta sizes. In some embodiments, rotating the blades is achieved utilizing at least one intracorporeal motor. In some embodiments, rotating the blades is achieved utilizing at least one extracorporeal motor. In some embodiments, the method can include pumping a biocompatible lubricant through at least a portion of the device.

In some embodiments, a mechanical circulatory support heart-assist device is provided. The device can include a pumping head comprising at least one set of two contra-rotating impellers. In some embodiments, contra-rotation is configured to occur at equal or unequal revolutions per minute and at about 8,000 rpm, or less than about 8,000 rpm.

In some embodiments, at least one impeller is configured to allow for axial flow. In some embodiments, at least one impeller is a screw impeller. In some embodiments, an inlet to the pumping head is configured to be anastomosed to a heart of a patient, and an outlet of the pumping head is configured to be anastomosed to a vascular system of the patient. In some embodiments, an inlet and an outlet of the pumping head are configured to be anastomosed to the vascular system. In some embodiments, an upstream impeller of the at least one set of impellers rotates at a different rotational speed than a downstream impeller of the at least one set of impellers in order to achieve substantially equal pressure rise per impeller. In some embodiments, wherein a vortex flow pattern established by a first impeller is totally removed by a second impeller, such that a flow velocity vector downstream is in the axial direction, to facilitate pressure rise and efficiency. In some embodiments, a vortex flow pattern established by a first impeller is substantially but not fully removed by a second impeller, allowing 2-3 flow rotations in about 30 cm of flow downstream, to mimic a vortex pattern in a descending aorta of a healthy heart, and provide additional perfusion to side arteries. In some embodiments, the device can include helical screw blades between the two contra-rotating impellers. In some embodiments, the helical screw blades are mounted downstream of the set of impellers on the device.

In some embodiments, a mechanical circulatory support heart-assist device is provided. The device can include at least one impeller. The device can include a first set of stationary pre-swirler vanes upstream of the impeller. The device can include a second set of stationary de-swirler vanes downstream of the impeller, effectively returning the flow downstream of the device in the axial direction, thus improving pressure rise and efficiency. In some embodiments, a vortex flow pattern established by a first impeller is substantially but not fully removed by a second impeller, allowing 2-3 flow rotations in about 30 cm of flow downstream, to mimic a vortex pattern in a descending aorta of a healthy heart, and provide additional perfusion to side arteries, and wherein the one impeller is the only impeller present on the device.

In some embodiments, a mechanical circulatory support heart-assist device is provided. The device can include a pumping head comprising a plurality of impellers configured to contra-rotate with respect to each other. In some embodiments, the contra-rotation is configured to occur at equal or unequal revolutions per minute. In some embodiments, the impellers are configured to be actuated mechanically and are not configured to be actuated via magnetic elements. In some embodiments, the impellers rotate at no more than about 8,000 rpm.

In some embodiments, a mechanical circulatory support heart-assist device is provided. The device can include a pumping head comprising two contra-rotating impellers. In some embodiments, the two contra-rotating impellers are configured to be driven by a first gearbox achieving contra-rotation between the two contra-rotating impellers.

In some embodiments, the gearbox is configured to be intra-corporeally located. In some embodiments, the gearbox is configured to be extra-corporeally located. In some embodiments, the device can include a plurality of gearboxes, each gearbox located at the hub of each rotor impeller. In some embodiments, the gearbox is downstream of the two contra-rotating impellers. In some embodiments, the gearbox is between the two contra-rotating impellers. In some embodiments, the gearbox is upstream of the two contra-rotating impellers. In some embodiments, the gearbox is configured to be driven by an intra-corporeal motor. In some embodiments, the gearbox is configured to be driven by an extra-corporeal motor. In some embodiments, the two contra-rotating impellers are configured to be driven by an intra-corporeal single-input shaft double-output shaft gearbox, with the gearbox located downstream of the two contra-rotating impellers, and wherein the gearbox is driven by a flexible shaft powered by an extra-corporeal motor and motor controller. In some embodiments, the gearbox comprises an epicyclic gearbox. In some embodiments, the pumping head comprises collapsible blades and is installed in a collapsible hourglass-shaped frame cage. In some embodiments, the pumping head comprises collapsible blades, the first gearbox is positioned downstream and directly adjacent to the collapsible blades, and the pumping head and the first gearbox are within a collapsible hourglass-shaped frame cage. In some embodiments, the pumping head comprises collapsible blades, the first gearbox is positioned immediately downstream of the pumping head, and an intra-corporeal motor is positioned immediately downstream of the gearbox, and the pumping head, gearbox, and the motor are within a collapsible hourglass-shaped frame cage. In some embodiments, the two contra-rotating impellers are driven by two coaxial flexible contra-rotating shafts, wherein a single-input shaft double-output shaft gearbox, and motor, and motor controller are all configured to be extra-corporeal. In some embodiments, the two contra-rotating impellers, first gearbox and a motor are configured to be intra-corporeal, and power is transmitted to the intra-corporeal motor via electric conductors from an extracorporeal power supply and controller. In some embodiments, the gearbox, coaxial contra-rotating flexible shafts, and impeller hubs are lubricated by a biocompatible fluid. In some embodiments, the coaxial contra-rotating flexible shafts and impeller hubs are lubricated by a biocompatible fluid.

In some embodiments, a mechanical circulatory support device is provided. The device can include a pump head comprising at least one impeller positioned within a central waist section of an hourglass-shaped cage, such that an inlet of an inlet section and an outlet of an outlet section of the hourglass shaped cage are of varying diameter and the inlet and the outlet are configured to be secured within blood vessels of various diameter sizes, thus accommodating one size of waist section and turbomachine pump head for all sizes of blood vessels.

In some embodiments, the waist section of the hourglass shaped cage is a memory-alloy frame cage covered with biocompatible material, so that the inlet of the inlet section and outlet of the outlet section of the hourglass shaped cage are configured to be secured against an inside of blood vessels of various sizes, so that the whole length of the hourglass shaped cage is collapsible along its axis, and the inlet and the outlet accommodate one size of waist section and turbomachine pump head for all sizes of blood vessels. In some embodiments, the inlet section of the hourglass shaped cage comprises perforations allowing blood permeability through the perforations and perfuse the region between the outside of the hourglass shaped cage and the inside of blood vessel, wherein the waist of the hourglass shaped cage and a diffuser of the hourglass shaped cage are non-permeable to blood. In some embodiments, the pump head has at least one rotating blade row of collapsible blades installed in the waist section of the hourglass shaped cage. In some embodiments, the impeller is driven by an extra-corporeal motor. In some embodiments, the impeller is driven by an intra-corporeal motor. In some embodiments, the pump head has at least one pair of contra-rotating blade rows. In some embodiments, the blade rows are powered by an intra-corporeal gearbox and an intra-corporeal motor. In some embodiments, the blade rows are powered by an intra-corporeal gearbox and an extra-corporeal motor. In some embodiments, the blade rows are powered by an extra-corporeal gearbox and an extra-corporeal motor. In some embodiments, no blood flow is permitted from the outlet to the inlet on the outside of the frame. In some embodiments, the device prevents backflow and is configured to perfuse intercostal vessels. In some embodiments, the inlet section of the hourglass shaped cage is covered. In some embodiments, the collapsing of the blade row and the hourglass shaped cage are achieved by a runner moving downstream and a sheath moving upstream. In some embodiments, the collapsing of the blade row and the hourglass shaped cage are achieved a sheath moving upstream, without the use of a runner.

In some embodiments, a mechanical circulatory support device is provided. The device can include a frame comprising a first end, a second end, and a central portion. In some embodiments, the frame comprises a first diameter at the first end, a second diameter at the second end, and a third diameter at the central portion. In some embodiments, the third diameter is smaller than the first diameter and the second diameter, wherein the frame comprises a sidewall and a lumen therethrough. The device can include a pump head positionable within the lumen of the frame proximate the central portion. In some embodiments, the frame comprises a compressed state and a radially expanded state configured to be secured within a blood vessel.

In some embodiments, the pump head comprises a plurality of impellers configured to contra-rotate with respect to each other, wherein the device does not comprise any magnetic elements configured to actuate the impellers. In some embodiments, the frame decreases in diameter from the first end to the central portion. In some embodiments, a mechanical hub for use with heart-assist devices, comprising a hub configured to bend with a worm and a screw is provided. In some embodiments, mechanical hub for use with heart-assist devices, comprising a hub configured to bend with an axle and pin is provided. In some embodiments, a mechanical hub for use with heart-assist devices, comprising a hub configured to bend by axial displacement of the center-shaft is provided. In some embodiments, a mechanical hub for use with heart-assist devices, comprising a hub configured to bend by one or more of a tube, rod, lattice, or strip is provided. In some embodiments, a mechanical hub for use with heart-assist devices, comprising one strip or lattice of strips in the hub causing stiffness in folding along the direction of the resultant force of lift and drag forces, predominantly upstream or downstream, and lower stiffness accommodating folding in the perpendicular is provided. In some embodiments, a turbomachine blade row and hub cut of one cylindrical section of memory shaped alloy, where additional material is added to each horizontal segment of the hub to form a folding blade shape with appropriate thickness distribution from leading edge to trailing edge and chord distribution from hub to tip, and where the hub is manufactured stiffer to bend either upstream or downstream, and less stiff in the opposite direction is provided. In some embodiments, a turbomachine blade row and hub cut of one cylindrical section of memory shaped alloy, where each horizontal segment of the hub is further cut into a lattice to form either the camber line, or the suction side, or the pressure side of the blade shape, which is then matched with another lattice structure to make the overall shape of the blade, and covered with a biocompatible material to make a folding blade shape with appropriate thickness distribution from leading edge to trailing edge and chord distribution from hub to tip, and where the hub is manufactured stiffer to bend either upstream or downstream, and less stiff in the opposite direction is provided. In some embodiments, the lattice and surrounding biocompatible material is configured to shrink chordwise, thus allowing folding and storage into a sheath. In some embodiments, a mechanical hub for use with heart-assist devices, comprising a flat-plate blade bent to blade shape during manufacturing is provided. In some embodiments, a mechanical hub for use with heart-assist devices, comprising a plurality of blades extending radially outward from the hub, wherein the blades are configured to tilt in a downstream direction at a rest configuration and rotate horizontal with respect to the hub during an operational configuration is provided. In some embodiments, a mechanical hub for use with heart-assist devices, comprising a stop mechanism to prevent blades bending upstream in an undesired direction is provided. In some embodiments, a device comprising two contra-rotating turbomachine blade rows that can be folded around a shaft inside a sheath while contracting is provided. In some embodiments, a device comprising turbomachines under hubs to reduce recirculation is provided. In some embodiments, a mechanical hub for use with heart-assist devices, configured to allow bending upstream is provided. In some embodiments, a mechanical hub for use with heart-assist devices, configured to allow bending downstream is provided. In some embodiments, a mechanical circulatory support comprising a single blade row is provided. In some embodiments, mechanical circulatory support comprising more than one blade row, wherein a subset of which comprises contra-rotating impellers is provided. In some embodiments, a mechanical circulatory support heart-assist device configured to be inserted with minimally invasive surgery wherein the pumping head comprises two contra-rotating impellers is provided. In some embodiments, contra-rotation may be at equal or unequal revolutions per minute.

In some embodiments, an inlet to the pumping head is configured to be anastomosed to a heart, and an outlet of the pumping head is configured to be anastomosed to a vascular system. In some embodiments, the inlet and the outlet of the pumping head are configured to be anastomosed to a vasculature. In some embodiments, the contra-rotating rotors are collapsible, and the contra-rotating rotors are configured to be installed in a collapsible hourglass-shaped frame cage covered with biocompatible material. In some embodiments, the contra-rotating rotors are configured to be driven by an intra-corporeal gearbox which is driven by an intra-corporeal motor, and the whole device is collapsible into a catheter sheath for implantation and removal. In some embodiments, where the contra-rotating rotors are configured to be driven by an intra-corporeal gearbox which is driven by an extra-corporeal motor, and the intra-corporeal parts of the device are collapsible into a catheter sheath for implantation and removal. In some embodiments, the two contra-rotating impellers are configured to be driven by two coaxial flexible contra-rotating shafts, wherein the single-input shaft double-output shaft gearbox, and motor, and motor controller are extra-corporeal. In some embodiments, an inlet of an hourglass-shaped frame cage is perforated in order to provide blood perfusion between the outside of the hourglass-shaped frame cage and the inside of the blood vessel. In some embodiments, a rotor tip diameter is between 6 mm and 34 mm. In some embodiments, the rotors operate between 1,000 and 60,000 rpm. In some embodiments, a gap between rotor tip and inside diameter of an hourglass-shaped frame cage is between 0.1 mm and 12 mm. In some embodiments, the device can include an hourglass shaped cage wherein the waist diameter is 5 mm to 33 mm, and where the inlet section has diameter 0.2 times the waist diameter to 8.0 times the waist diameter, and length 0.2 times the waist diameter to 16.0 times the waist diameter. In some embodiments, the device can include an hourglass shaped cage wherein the waist diameter is 5 mm to 33 mm, and where the inlet section has diameter 1.0 times the waist diameter to 5.0 times the waist diameter, and length 0.2 times the waist diameter to 16.0 times the waist diameter. In some embodiments, the device can include an hourglass shaped cage wherein the waist diameter is 5 mm to 33 mm, and where the outlet diffuser section has diameter 0.2 times the waist diameter to 8.0 times the waist diameter, and length 0.2 times the waist diameter to 16.0 times the waist diameter. In some embodiments, the device can include an hourglass shaped cage wherein the waist diameter is 5 mm to 33 mm, and where the outlet diffuser section has diameter 1.0 times the waist diameter to 5.0 times the waist diameter, and length 0.2 times the waist diameter to 16.0 times the waist diameter.

In some embodiments, a mechanical circulatory support heart-assist device is provided, inserted with minimally invasive surgery wherein the pumping head comprises only a single impeller with a stationary set of pre-swirler blades upstream of the impeller and a stationary set of de-swirler blades downstream of the impeller.

In some embodiments, a cardiac assist device is provided. The device can include one or more of the following. In some embodiments, the device can include at least one impeller, the impeller comprising a tip diameter of between about 5 mm and about 33 mm. In some embodiments, the at least one impeller rotates from between 1,000 and about 50,000 rpm. In some embodiments, the at least one impeller is housed within a support comprising an inlet, a waist, and an outlet. In some embodiments, the waist diameter is about 5 mm to about 33 mm. In some embodiments, the inlet section has a diameter of between about 0.2 times the waist diameter to about 8.0 times the waist diameter. In some embodiments, the inlet section has a length of about 0.2 times the waist diameter to about 16.0 times the waist diameter. In some embodiments, the waist diameter is about 5 mm to about 33 mm. In some embodiments, the inlet section has diameter about 0.2 times the waist diameter to about 8.0 times the waist diameter, and length about 0.2 times the waist diameter to about 16.0 times the waist diameter. In some embodiments, the inlet section has a diameter of about 1.0 times the waist diameter to about 5.0 times the waist diameter. In some embodiments, the waist diameter is about 5 mm to 33 mm. In some embodiments, the outlet comprises a diffuser. In some embodiments, the outlet comprising a diameter from about 1.0 times the waist diameter to about 5.0 times the waist diameter, and a length of from about 0.2 times the waist diameter to about 16.0 times the waist diameter. In some embodiments, the device comprises a plurality of contra-rotating impellers with the pressure rise and flow rate. In some embodiments, the device has a pressure rise of about 5-150 mm Hg. In some embodiments, the device has a flow rate of about 0.1-10 L/min. In some embodiments, the device is configured for about 10-40 mmHg pressure rise. In some embodiments, the device is configured for about 2-6 L/min flow rate. In some embodiments, the device is configured for 30 mm Hg pressure rise and 5 L/min flow rate. In some embodiments, the device is configured for about 10-60 mm Hg pressure rise and about 0.1-8 L/min flow rate.

In some embodiments, a temporary, removable mechanical circulatory support heart-assist device is provided. The device can include an expandable support member comprising an open proximal end, an open distal end, and a central lumen therebetween. In some embodiments, the expandable member comprising a proximal segment, a distal segment, and a waist segment between the proximal segment and the distal segment, and a sidewall extending from the proximal segment, waist segment, and distal segment. In some embodiments, the device can include one or more propellers or impellers. In some embodiments, each propeller or impeller is configured to reside within the waist segment of the expandable member and comprising a plurality of blades arranged around an axis of rotation, the blades configured to pump blood. In some embodiments, the sidewall of the proximal segment is permeable to fluid. In some embodiments, the sidewall of the waist segment and the distal segment are impermeable to fluid.

In some embodiments, the sidewall of the waist segment has a constant diameter in an expanded configuration. In some embodiments, the proximal segment decreases in diameter from its open proximal end in an expanded configuration. In some embodiments, the expandable support member does not comprise any penetrating anchors. In some embodiments, the one or more propellers or impellers are non-magnetic.

In some embodiments, a method of temporarily supporting cardiac function is provided. The method can include positioning a circulatory support device in a descending aorta of a patient such that the device axially spans at least one intercostal and/or spinal artery at their branch point off the descending aorta. In some embodiments, the circulatory support device comprises a support member comprising an open proximal end, an open distal end, and a central lumen therebetween. In some embodiments, the support member comprises at least one pump housed within the central lumen. In some embodiments, the method can include transforming the support member from a first configuration to a second expanded configuration. In some embodiments, the method can include activating the pump sufficient to support cardiac function. In some embodiments, the at least one intercostal and/or spinal artery remain perfused following the positioning of the circulatory support device.

In some embodiments, the support member further comprises a proximal segment, a distal segment, and a waist segment between the proximal segment and the distal segment, and a sidewall extending from the proximal segment, waist segment, and distal segment. In some embodiments, the sidewall of the proximal segment is permeable to blood. In some embodiments, the sidewall of the waist segment and the distal segment are impermeable to blood. In some embodiments, at least one of the waist segment and the distal segment axially span at least one branch point. In some embodiments, blood flows through the sidewall of the proximal segment and outside of the sidewall of at least one of the waist segment and the distal segment to perfuse the at least one intercostal and/or spinal artery.

In some embodiments, the device spans at least two intercostal and/or spinal arteries. In some embodiments, the sidewall of the waist segment has a constant diameter in an expanded configuration. In some embodiments, the proximal segment decreases in diameter from its open proximal end in an expanded configuration.

In some embodiments, method of temporarily supporting cardiac function is provided. The method can include positioning a circulatory support device in a descending aorta of a patient. In some embodiments, the circulatory support device comprising a support member comprising an open proximal end, an open distal end, and a central lumen therebetween. In some embodiments, the support member also comprises at least one pump housed within the central lumen. The method can include transforming the support member from a first configuration to a second expanded configuration. The method can include activating the pump such that the pump rotates at less than about 9,000 rpm, is sufficient to cause a pressure rise of at least about 20 mmHg in the descending aorta. In some embodiments, hemolysis is limited to less than about 40 mg/dL of plasma-free hemoglobin in the patient's blood after activating the pump.

In some embodiments, the pump causes a pressure rise of between about 20 mm Hg and about 100 mm Hg in the descending aorta. In some embodiments, the pump causes a pressure rise of between about 20 mm Hg and about 80 mm Hg in the descending aorta. In some embodiments, the pump causes a pressure rise of about 30 mm Hg in the descending aorta. In some embodiments, the pump rotates at between about 5,000 rpm and about 9,000 rpm. In some embodiments, the pump rotates at between about 6,000 rpm and about 8,000 rpm. In some embodiments, the hemolysis is limited to less than about 30 mg/dL of plasma-free hemoglobin in the patient's blood after activating the pump. In some embodiments, the hemolysis is limited to less than about 20 mg/dL of plasma-free hemoglobin in the patient's blood after activating the pump. In some embodiments, the hemolysis is limited to less than about 10 mg/dL of plasma-free hemoglobin in the patient's blood after activating the pump. In some embodiments, the hemolysis is determined at or after about 72 hours after activating the pump.

In some embodiments, a method of temporarily supporting cardiac function is provided. The method can include positioning a circulatory support device in an artery of a patient entirely distal to the aortic valve. In some embodiments, the circulatory support device comprising at least one impeller. In some embodiments, when the at least one impeller is unfurled within the blood vessel a tip diameter of the impeller is between about 0.2× and about 0.90×, or between about 0.2× and about 0.99× the diameter of the artery. In some embodiments, the method can include transforming the device from an unfolded configuration to a folded configuration.

In some embodiments, the device includes one non-magnetic propeller or impeller, two non-magnetic propellers or impellers, three non-magnetic propellers or impellers, four non-magnetic propellers or impellers, five non-magnetic propellers or impellers, six non-magnetic propellers or impellers, at least one non-magnetic propellers or impellers, at least two non-magnetic propellers or impellers, at least three non-magnetic propellers or impellers, at least four non-magnetic propellers or impellers, at least five non-magnetic propellers or impellers, at least six non-magnetic propellers or impellers or any range of the foregoing values.

In some embodiments, the device includes one blade per propeller or impeller, two blades per propeller or impeller, three blades per propeller or impeller, four blades per propeller or impeller, five blades per propeller or impeller, six blades per propeller or impeller, at least one blade per propeller or impeller, at least two blades per propeller or impeller, at least three blades per propeller or impeller, at least four blades per propeller or impeller, at least five blades per propeller or impeller, at least six blades per propeller or impeller or impellers or any range of the foregoing values.

In some embodiments, two propellers or impellers are configured to rotate in opposite directions with respect to each other. In some embodiments, at least two propellers or impellers are configured to rotate in opposite directions with respect to each other. In some embodiments, two propellers or impellers are configured to rotate simultaneously. In some embodiments, two propellers or impellers are configured to rotate independently. In some embodiments, two propellers or impellers are configured to rotate separately. In some embodiments, two propellers or impellers are configured to rotate at different speeds. In some embodiments, two propellers or impellers are configured to rotate at the same speed. In some embodiments, two propellers or impellers are configured to rotate at variable speeds.

In some embodiments, wherein the propeller or impeller is configured to rotate at 1,000 rpm, 2,000 rpm, 3,000 rpm, 4,000 rpm, 5,000 rpm, 6,000 rpm, 7,000 rpm, 8,000 rpm, 9,000 rpm, 10,000 rpm, 20,000 rpm, 30,000 rpm, 40,000 rpm, 50,000 rpm, 60,000 rpm, 70,000 rpm, at least 1,000 rpm, at least 2,000 rpm, at least 3,000 rpm, at least 4,000 rpm, at least 5,000 rpm, at least 6,000 rpm, at least 7,000 rpm, at least 8,000 rpm, at least 9,000 rpm, at least 10,000 rpm, at least 20,000 rpm, at least 30,000 rpm, at least 40,000 rpm, at least 50,000 rpm, at least 60,000 rpm, 70,000 rpm, no more than 1,000 rpm, no more than 2,000 rpm, no more than 3,000 rpm, no more than 4,000 rpm, no more than 5,000 rpm, no more than 6,000 rpm, no more than 7,000 rpm, no more than 8,000 rpm, no more than 9,000 rpm, no more than 10,000 rpm, no more than 20,000 rpm, no more than 30,000 rpm, no more than 40,000 rpm, no more than 50,000 rpm, no more than 60,000 rpm, no more than 70,000 rpm, between 1,000 and 10,000 rpm, between 10,000 and 60,000 rpm, or any range of the foregoing values. In some embodiments, two propellers or impellers rotate at equal or the same rpm. In some embodiments, two propellers or impellers rotate an unequal or different rpm. In some embodiments, an upstream impeller of rotates at a different rotational speed than a downstream impeller. In some embodiments, the contra-rotation is configured to occur at equal revolutions per minute. In some embodiments, the contra-rotation is configured to occur at unequal revolutions per minute.

In some embodiments, the devices be configured to provide a pressure rise of 5 mm Hg, 10 mm Hg, 15 mm Hg, 20 mm Hg, 25 mm Hg, 30 mm Hg, 35 mm Hg, 40 mm Hg, 45 mm Hg, 50 mm Hg, 55 mm Hg, 60 mm Hg, 65 mm Hg, 70 mm Hg, 75 mm Hg, 80 mm Hg, 85 mm Hg, 90 mm Hg, 95 mm Hg, 100 mm Hg, 105 mm Hg, 110 mm Hg, 115 mm Hg, 120 mm Hg, 125 mm Hg, 130 mm Hg, 135 mm Hg, 140 mm Hg, 145 mm Hg, 150 mm Hg, at least 5 mm Hg, at least 10 mm Hg, at least 15 mm Hg, at least 20 mm Hg, at least 25 mm Hg, at least 30 mm Hg, at least 35 mm Hg, at least 40 mm Hg, at least 45 mm Hg, at least 50 mm Hg, at least 55 mm Hg, at least 60 mm Hg, at least 65 mm Hg, at least 70 mm Hg, at least 75 mm Hg, at least 80 mm Hg, at least 85 mm Hg, at least 90 mm Hg, at least 95 mm Hg, at least 100 mm Hg, at least 105 mm Hg, at least 110 mm Hg, at least 115 mm Hg, at least 120 mm Hg, at least 125 mm Hg, at least 130 mm Hg, at least 135 mm Hg, at least 140 mm Hg, at least 145 mm Hg, at least 150 mm Hg, no more than 5 mm Hg, no more than 10 mm Hg, no more than 15 mm Hg, no more than 20 mm Hg, no more than 25 mm Hg, no more than 30 mm Hg, no more than 35 mm Hg, no more than 40 mm Hg, no more than 45 mm Hg, no more than 50 mm Hg, no more than 55 mm Hg, no more than 60 mm Hg, no more than 65 mm Hg, no more than 70 mm Hg, no more than 75 mm Hg, no more than 80 mm Hg, no more than 85 mm Hg, no more than 90 mm Hg, no more than 95 mm Hg, no more than 100 mm Hg, no more than 105 mm Hg, no more than 110 mm Hg, no more than 115 mm Hg, no more than 120 mm Hg, no more than 125 mm Hg, no more than 130 mm no more than Hg, 135 mm Hg, no more than 140 mm Hg, 145 mm Hg, no more than 150 mm Hg, between 10 mm Hg and 30 mm Hg, between 15 mm Hg and 35 mm Hg, between 20 mm Hg and 40 mm Hg, between 20 mm Hg and 30 mm Hg, between 30 mm Hg and 40 mm Hg, between 10 mm Hg and 50 mm Hg, between 5 mm Hg and 150 mm Hg, between 10 mm Hg and 40 mm Hg, between 10 mm Hg and 60 mm Hg, or any ranges including two of the foregoing values. In some embodiments, the remaining pressure rise is given by the diseased native heart.

In some embodiments, devices be configured to provide a flow rate of 1 L/min, 2 L/min, 3 L/min, 4 L/min, 5 L/min, 6 L/min, 7 L/min, 8 L/min, 9 L/min, 10 L/min, at least 1 L/min, at least 2 L/min, at least 3 L/min, at least 4 L/min, at least 5 L/min, at least 6 L/min, at least 7 L/min, at least 8 L/min, at least 9 L/min, at least 10 L/min, no more than 1 L/min, no more than 2 L/min, no more than 3 L/min, no more than 4 L/min, no more than 5 L/min, no more than 6 L/min, no more than 7 L/min, no more than 8 L/min, no more than 9 L/min, no more than 10 L/min, between 4 L/min and 6 L/min, between 2 L/min and 7 L/min, between 3 L/min and 5 L/min, between 5 L/min and 7 L/min, between 0.1 and 10 L/min, between 2 and 6 L/min, between 0.1 and 8 L/min, or any ranges including two of the foregoing values.

In some embodiments, there can be a number of rotations in about length of of flow downstream. In some embodiments, there can be 1 rotation, 2 rotations, 3 rotations, 4 rotations, 5 rotations, 6 rotations, 7 rotations, 8 rotations, 9 rotations, 10 rotations, at least 1 rotation, at least 2 rotations, at least 3 rotations, at least 4 rotations, at least 5 rotations, at least 6 rotations, at least 7 rotations, at least 8 rotations, at least 9 rotations, at least 10 rotations, no more than 1 rotation, no more than 2 rotations, no more than 3 rotations, no more than 4 rotations, no more than 5 rotations, no more than 6 rotations, no more than 7 rotations, no more than 8 rotations, no more than 9 rotations, no more than 10 rotations, between 1 and 2 rotations, between 2 and 3 rotations or any ranges including two of the foregoing values; in a length of 5 cm of flow downstream, 10 cm of flow downstream, 15 cm of flow downstream, 20 cm of flow downstream, 25 cm of flow downstream, 30 cm of flow downstream, 35 cm of flow downstream, 40 cm of flow downstream, 45 cm of flow downstream, 50 cm of flow downstream, or any range of the foregoing values.

In some embodiments, the rotor tip diameter is 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, at least 1 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, at least 30 mm, at least 31 mm, at least 32 mm, at least 33 mm, at least 34 mm, at least 35 mm, at least 36 mm, at least 37 mm, at least 38 mm, at least 39 mm, at least 40 mm, no more than 1 mm, no more than 2 mm, no more than 3 mm, no more than 4 mm, no more than 5 mm, no more than 6 mm, no more than 7 mm, no more than 8 mm, no more than 9 mm, no more than 10 mm, no more than 11 mm, no more than 12 mm, no more than 13 mm, no more than 14 mm, no more than 15 mm, no more than 16 mm, no more than 17 mm, no more than 18 mm, no more than 19 mm, no more than 20 mm, no more than 21 mm, no more than 22 mm, no more than 23 mm, no more than 24 mm, no more than 25 mm, no more than 26 mm, no more than 27 mm, no more than 28 mm, no more than 29 mm, no more than 30 mm, no more than 31 mm, no more than 32 mm, no more than 33 mm, no more than 34 mm, no more than 35 mm, no more than 36 mm, no more than 37 mm, no more than 38 mm, no more than 39 mm, no more than 40 mm, between 1 mm and 10 mm, between 10 mm and 20 mm, between 20 mm and 30 mm, between 30 mm and 40 mm, between 6 mm and 34 mm, between 5 mm and 35 mm, or any range of the foregoing values.

In some embodiments, a gap between rotor tip and inside diameter of a frame cage, including an hourglass-shaped frame cage, is 0.01 mm, 0.1 mm, 0.2 mm, 0.3 mm, 0.4 mm, 0.5 mm, 0.6 mm, 0.7 mm, 0.8 mm, 0.9 mm, 1.0 mm, 2 mm, 3 mm, 4 mm, 5 mm, 6 mm, 7 mm, 8 mm, 9 mm, 10 mm, 11 mm, 12 mm, at least 0.01 mm, at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1.0 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, no more than 0.01 mm, no more than 0.1 mm, no more than 0.2 mm, no more than 0.3 mm, no more than 0.4 mm, no more than 0.5 mm, no more than 0.6 mm, no more than 0.7 mm, no more than 0.8 mm, no more than 0.9 mm, no more than 1.0 mm, no more than 2 mm, no more than 3 mm, no more than 4 mm, no more than 5 mm, no more than 6 mm, no more than 7 mm, no more than 8 mm, no more than 9 mm, no more than 10 mm, no more than 11 mm, no more than 12 mm, no more than 13 mm, no more than 14 mm, no more than 15 mm, between 1 mm and 2 mm, between 2 mm and 3 mm, between 3 mm and 4 mm, between 0.1 mm and 1 mm, between 0.1 mm and 5 mm, or any range of the foregoing values.

In some embodiments, the waist diameter is 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, at least 1 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, at least 30 mm, at least 31 mm, at least 32 mm, at least 33 mm, at least 34 mm, at least 35 mm, at least 36 mm, at least 37 mm, at least 38 mm, at least 39 mm, at least 40 mm, no more than 1 mm, no more than 2 mm, no more than 3 mm, no more than 4 mm, no more than 5 mm, no more than 6 mm, no more than 7 mm, no more than 8 mm, no more than 9 mm, no more than 10 mm, no more than 11 mm, no more than 12 mm, no more than 13 mm, no more than 14 mm, no more than 15 mm, no more than 16 mm, no more than 17 mm, no more than 18 mm, no more than 19 mm, no more than 20 mm, no more than 21 mm, no more than 22 mm, no more than 23 mm, no more than 24 mm, no more than 25 mm, no more than 26 mm, no more than 27 mm, no more than 28 mm, no more than 29 mm, no more than 30 mm, no more than 31 mm, no more than 32 mm, no more than 33 mm, no more than 34 mm, no more than 35 mm, no more than 36 mm, no more than 37 mm, no more than 38 mm, no more than 39 mm, no more than 40 mm, between 5 mm and 20 mm, between 20 mm and 35 mm, between 5 mm and 33 mm, between 5 mm and 35 mm, or any range of the foregoing values.

In some embodiments, the inlet section has diameter a multiple times the waist diameter, where the inlet section has diameter 0.1 times the waist diameter times the waist diameter, where the inlet section has diameter 0.5 times the waist diameter, where the inlet section has diameter 1 times the waist diameter, where the inlet section has diameter 2 times the waist diameter, where the inlet section has diameter 3 times the waist diameter, where the inlet section has diameter 4 times the waist diameter, where the inlet section has diameter 5 times the waist diameter, where the inlet section has diameter 6 times the waist diameter, where the inlet section has diameter 7 times the waist diameter, where the inlet section has diameter 8 times the waist diameter, where the inlet section has diameter 9 times the waist diameter, where the inlet section has diameter 10 times the waist diameter, between 1 and 2 times the waist diameter, between 0.2 and 8 times the waist diameter, between 1 and 5 times the waist diameter, or any range of the foregoing values.

In some embodiments, the inlet section has length a multiple times the waist diameter, where the inlet section has length 0.1 times the waist diameter times the waist diameter, where the inlet section has length 0.5 times the waist diameter, where the inlet section has length 1 times the waist diameter, where the inlet section has length 2 times the waist diameter, where the inlet section has length 3 times the waist diameter, where the inlet section has length 4 times the waist diameter, where the inlet section has length 5 times the waist diameter, where the inlet section has length 6 times the waist diameter, where the inlet section has length 7 times the waist diameter, where the inlet section has length 8 times the waist diameter, where the inlet section has length 9 times the waist diameter, where the inlet section has length 10 times the waist diameter, where the inlet section has length 11 times the waist diameter, where the inlet section has length 12 times the waist diameter, where the inlet section has length 13 times the waist diameter, where the inlet section has length 14 times the waist diameter, where the inlet section has length 15 times the waist diameter, where the inlet section has length 16 times the waist diameter, where the inlet section has length 17 times the waist diameter, where the inlet section has length 18 times the waist diameter, where the inlet section has length 19 times the waist diameter, where the inlet section has length 20 times the waist diameter, between 5 and 10 times the waist diameter, between 0.2 and 16 times the waist diameter, or any range of the foregoing values.

In some embodiments, the outlet diffuser has diameter a multiple times the waist diameter, where the outlet diffuser has diameter 0.1 times the waist diameter times the waist diameter, where the outlet diffuser has diameter 0.5 times the waist diameter, where the outlet diffuser has diameter 1 times the waist diameter, where the outlet diffuser has diameter 2 times the waist diameter, where the outlet diffuser has diameter 3 times the waist diameter, where the outlet diffuser has diameter 4 times the waist diameter, where the outlet diffuser has diameter 5 times the waist diameter, where the outlet diffuser has diameter 6 times the waist diameter, where the outlet diffuser has diameter 7 times the waist diameter, where the outlet diffuser has diameter 8 times the waist diameter, where the outlet diffuser has diameter 9 times the waist diameter, where the outlet diffuser has diameter 10 times the waist diameter, between 1 and 2 times the waist diameter, between 2 and 8 times the waist diameter, between 1 and 5 times the waist diameter, or any range of the foregoing values.

In some embodiments, the outlet diffuser has length a multiple times the waist diameter, where the outlet diffuser has length 0.1 times the waist diameter times the waist diameter, where the outlet diffuser has length 0.5 times the waist diameter, where the outlet diffuser has length 1 times the waist diameter, where the outlet diffuser has length 2 times the waist diameter, where the outlet diffuser has length 3 times the waist diameter, where the outlet diffuser has length 4 times the waist diameter, where the outlet diffuser has length 5 times the waist diameter, where the outlet diffuser has length 6 times the waist diameter, where the outlet diffuser has length 7 times the waist diameter, where the outlet diffuser has length 8 times the waist diameter, where the outlet diffuser has length 9 times the waist diameter, where the outlet diffuser has length 10 times the waist diameter, where the outlet diffuser has length 11 times the waist diameter, where the outlet diffuser has length 12 times the waist diameter, where the outlet diffuser has length 13 times the waist diameter, where the outlet diffuser has length 14 times the waist diameter, where the outlet diffuser has length 15 times the waist diameter, where the outlet diffuser has length 16 times the waist diameter, where the outlet diffuser has length 17 times the waist diameter, where the outlet diffuser has length 18 times the waist diameter, where the outlet diffuser has length 19 times the waist diameter, where the outlet diffuser has length 20 times the waist diameter, between 5 and 10 times the waist diameter, between 0.2 and 16 times the waist diameter, or any range of the foregoing values.

In some embodiments, hemolysis is limited to less an amount of plasma-free hemoglobin in the patient's blood after activating the pump including less than about 50 mg/dL, less than about 40 mg/dL, less than about 30 mg/dL, less than about 20 mg/dL, less than about 10 mg/dL, between 10 mg/dL and 50 mg/dL, or any range of the foregoing values. In some embodiments, hemolysis is determined at 24 hours after activating the pump, 48 hours after activating the pump, 72 hours after activating the pump, 96 hours after activating the pump, between 24 and 48 hours after activating the pump, between 48 and 72 hours after activating the pump, between 72 and 96 hours after activating the pump, or any range of the foregoing values.

In some embodiments, when the at least one impeller is unfurled within the blood vessel a tip diameter of the impeller is a multiple times the diameter of the artery, where the tip diameter of the impeller is 0.1 times the diameter of the artery, where the tip diameter of the impeller is 0.2 times the diameter of the artery, where the tip diameter of the impeller is 0.3 times the diameter of the artery, where the tip diameter of the impeller is 0.4 times the diameter of the artery, where the tip diameter of the impeller is 0.5 times the diameter of the artery, where the tip diameter of the impeller is 0.6 times the diameter of the artery, where the tip diameter of the impeller is 0.7 times the diameter of the artery, where the tip diameter of the impeller is 0.8 times the diameter of the artery, where the tip diameter of the impeller is 0.9 times the diameter of the artery, where the tip diameter of the impeller is 1 times the diameter of the artery, or any range of the foregoing values.

In some embodiments, a system or device can comprise, consist essentially of, or consist of any number of features of the disclosure. A method of treatment, installing a system or device, or removing a system or device can comprise, consist essentially of, or consist of any number of features of the disclosure.

BRIEF DESCRIPTION OF THE DRAWINGS

Embodiments of the invention will now be described, by way of example only, with reference to the accompanying drawings in which corresponding reference symbols indicate corresponding parts, and in which:

FIGS. 1A-1G schematically illustrate various examples of operating configurations of the MCS device.

FIGS. 4A-4C schematically illustrate examples of MCS devices configured for installation in the lumen of a blood vessel.

FIGS. 5A-5C schematically illustrate examples of an MCS device comprising various motor arrangements and features to facilitate insertion.

FIGS. 9A-9D schematically illustrate operating configurations of the MCS device comprising two gearboxes.

FIGS. 11A-11B schematically illustrate operating configurations of the MCS device comprising two gearboxes.

FIGS. 14A-14C schematically illustrate operating configurations of the MCS device opening in an hour glass configuration.

FIGS. 16A-16C schematically illustrate positions of the motor.

FIGS. 17A-17D schematically illustrate stages of delivery.

FIGS. 18A-18C schematically illustrate folding and unfolding of the blades and cage sections.

FIGS. 21A-21D illustrates lubrication and/or cooling with an extra-corporeal motor.

FIGS. 22A-22C illustrate bearings.

FIGS. 24A-24F illustrate blade deflection.

FIGS. 26A-26F illustrate blade construction.

DETAILED DESCRIPTION

Figure 2C:
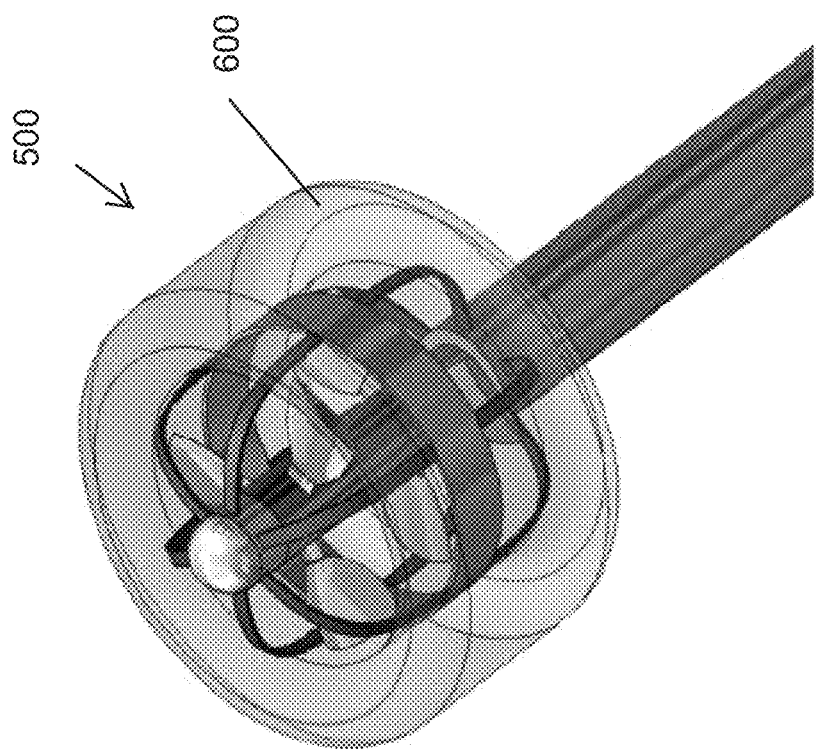
FIGS. 2A-2C schematically illustrate operating configurations of the MCS device comprising a balloon.

This invention relates in some aspects to various embodiments of percutaneously implantable cardiovascular support (PICS) devices. PICS devices can include percutaneously implantable Mechanical Circulatory Support Devices (MCSD). In some embodiments, PICS may be configured for implantation in the aorta via the femoral artery. In some methods of use, PICS may be intended for implantation percutaneously. In some methods of use, PICS may be intended for implantation with minimally invasive surgery. Cardiovascular support devices can be configured for either long-term implantation or short-term (e.g., temporary) implantation. Some embodiments may be designed for early New York Heart Association (NYHA) class III CHF (before Interagency Registry for Mechanically Assisted Circulator Support (INTERMACS level 7) and more severe conditions. In some embodiments, devices may be configured for in-series implantation in the aorta. Thus, in some embodiments, the adult specification can include about a 5 L/min flow rate and from about 20 to about 40 mm Hg pressure rise, where the remaining pressure rise is given by the diseased native heart.

Some embodiments may be designed with operating conditions specifically configured for particular state of the patient, including the stage of disease. For instance, a MCS designed for late stage II or early stage III CHF may provide a lesser pressure rise, while a MCS designed for late stage III or early stage IV CHF may provide a greater pressure rise, to better supplant the failing heart. In some embodiments, devices be configured to provide a flow rate of about, at least about, or no more than about 1 L/min, 2 L/min, 3 L/min, 4 L/min, 5 L/min, 6 L/min, 7 L/min, 8 L/min, 9 L/min, 10 L/min, or any ranges including two of the foregoing values. In some embodiments, the devices be configured to provide a pressure rise of about, at least about, or no more than about 5 mm Hg, 10 mm Hg, 15 mm Hg, 20 mm Hg, 25 mm Hg, 30 mm Hg, 35 mm Hg, 40 mm Hg, 45 mm Hg, 50 mm Hg, 55 mm, Hg 60 mm Hg, 65 mm Hg, 70 mm Hg, 75 mm Hg, 80 mm Hg, 85 mm Hg, 90 mm Hg, 95 mm Hg, 100 mm Hg, 105 mm Hg, 110 mm Hg, 115 mm Hg, 120 mm Hg, 125 mm Hg, 130 mm Hg, 135 mm Hg, 140 mm Hg, 145 mm Hg, 150 mm Hg, between 20 mm Hg and 40 mm Hg, between 20 mm Hg and 50 mm Hg, or any ranges including two of the foregoing values. In some embodiments, the remaining pressure rise is given by the diseased native heart. In some embodiments, devices can be configured with operating conditions to replicate the conditions of a healthy patient. In some embodiments, the device is configured to provide a pressure rise of between about 10-40 mmHg. In some embodiment, the device is configured for a flow rate of about 2-6 L/min. In some embodiments, the device is configured for a pressure rise of about 30 mm Hg and a flow rate of about 5 L/min. In some embodiments, the device is configured for a pressure rise of about 10-60 mm Hg and a flow rate of about 0.1-8 L/min. The ranges in the foregoing paragraph can be used in combination with, for example, contra-rotation for permanent and temporary MCSD.

Some devices may be designed to be implanted in-series with the heart. As described herein, such arrangements may effectively reduce the load on the heart. Some devices may be configured to lower the resistance to blood flow. As described herein, such arrangements provide the heart increased potential for regeneration of diseased tissue. Devices may be configured to require less power, and therefore be lighter in weight and more compact. Devices may be configured to pump blood at a continuous flow. Devices may be configured to pump blood at a pulsated flow. Devices may be configured to pump blood at a flow rate advantageous to complement the pulsing heart.

Ventricular Assist Devices (VAD) are heart assist pumps that can include an inlet anastomosed to one of the four chambers of the native diseased heart. In some methods of use, the VAD device is anastomosed to the left ventricle. This configuration is more common. In some methods of use, the VAD device is anastomosed to the right ventricle. In some methods of use, the VAD device is anastomosed to one of the atria. In some embodiments, a mechanical circulatory support heart-assist device is provided where the pump comprises impellers rotating in opposite directions. In some embodiments, the inlet to the pump is configured to be anastomosed to a chamber of the heart, and the outlet of the pump is configured to be anastomosed to the vascular system.

Mechanical circulatory support devices (MCSD) are also heart assist pumps. MCSDs, in contrast to VADs, are typically installed in the vasculature. MCSDs, in contrast to VADs, are not typically attached to any part of the diseased native heart. Usually the MCSDs are designed for a less invasive implantation procedure than the VADs.

Permanent MCSDs are devices that may be used over a short or over a long period of time. Due to their design, permanent MCSDs have some components that once installed in the human body, these components are configured to stay in the patient's body, even if some other parts of the MCSD are later removed. In some embodiments, a cage or support structure stays within the body after removal of other components. In some embodiments, a motor or power source stays within the body after removal of other components. In some embodiments, one or more components is permanently coupled to a structure within the body of the patient.

Temporary MCSDs can be specifically configured for short-term use with the intent that after the temporary use all components of the device will be fully removed from the patient's body. Thus a key characteristic of a temporary MCSD in some embodiments is that no part of the device will stay in the patient's body after use. In some embodiments, the Temporary MCSD is configured to be removed as a unit. In some embodiments, two or more components of the Temporary MCSD are configured to be removed separately or independently. In some methods of use, the Temporary MCSD is removed in a single surgical procedure. In some methods of use, the Temporary MCSD may be configured for removal via the femoral artery. In some methods of use, the Temporary MCSD may be configured for removal percutaneously. In some methods of use, the Temporary MCSD may be configured for removal with minimally invasive surgery. In some cases, temporary devices may be referred to as pVADs (percutaneous VADs).

Some devices indicated for at least class III CHF (INTERMACS levels 5, 6, 7) may be designed with the rotor of the turbomachine and electric motor being designed for implantation, periodic removal and re-implantation. In some methods of use, the devices may be configured for periodic removal via the femoral artery. In some methods of use, the devices may be configured for periodic removal percutaneously. In some methods of use, the devices may be configured for periodic removal with minimally invasive surgery. In some methods of use, the devices may be configured for re-implantation via the femoral artery. In some methods of use, the devices may be configured for re-implantation percutaneously. In some methods of use, the devices may be configured for re-implantation with minimally invasive surgery. In some methods of use, the devices can be implanted and re-implanted via the same type of procedure. In some methods of use, the devices can be implanted and re-implanted via different types of procedures. As an example, the devices may be configured for implantation, periodic removal and re-implantation via the femoral artery in the aorta.

As described herein, devices may be Permanent MCSDs such that one or more components are permanently installed. In some embodiments, the stator of the motor may be permanently installed. In some methods of use, the stator of the motor may be permanently installed around and outside the aorta, surrounding the location of the rotor. In some methods of use, the stator may be configured to be positioned around an outer circumference of the blood vessel. In some methods of use, the stator may be configured to be positioned around another structure of the patient. The stator may include a hinge or other mechanical feature to allow the stator to be positioned there around. The stator may include an anchoring structure to permanently attach to the patient. As described herein, the stator can include one or more electromagnets positioned around the circumference of the stator. The stator is configured to be positioned concentrically around the blades of a propeller or impeller to electromagnetically drive rotation of the at least one magnetic blade.

However, other components may be removed after use, or intermediately removed during use. As one example, the rotor of the turbomachine and/or electric motor may be designed to be removed. In some embodiments, all components of some devices are configured to be permanently installed.

Some devices with the above flow rate and pressure rise specifications may be configured for short term use. In some embodiments, the device is configured to be used for a few hours, e.g., about, at least about, or no more than about 1 hour, 2 hours, 4 hours, 8 hours, 12 hours, 16 hours, 20 hours, 24 hours, or a few days, e.g., 1 day, 2 days, 3 days, 4 days, 5 days, 6 days, 7 days, or any range including any two of the foregoing values. In some embodiments, the device is configured to be used less than a week, less than 5 days, less than 3 days, less than 1 day, less than 12 hours, more than 1 hour, more than 4 hours, more than 12 hours, more than 1 day, more than 3 days, more than 5 days, or any range of the foregoing values. In some embodiments, the device is configured to be used between a few hours and up to about 5 days. Devices may be configured for implantation and then complete removal of all components from the human body. Devices may be configured to address Acute Cardiogenic Shock (CGS). Devices may be configured to address Percutaneous Coronary Intervention (PCI). Devices may be configured to address acute decompensated heart failure (ADHF). Devices may be configured to address Cardio Renal Syndrome (CRS). Devices may be configured to provide temporary relief of the native heart in early or late stages of congestive heart failure. Other uses of the devices are contemplated.

Some embodiments include percutaneously implantable Temporary MCSDs configured for implantation. In some methods of use, the device may be configured for implantation in the aorta via the femoral artery. In some methods of use, the device may be configured for implantation in the aorta percutaneously. In some methods of use, the device may be configured for implantation in the aorta with minimally invasive surgery. The device may be intended for short term, temporary use, ranging from a few hours to up to about five days. At the end of use, all components of the device are removed from the patient's body.

In some embodiments, a device could include axial, and/or centrifugal impellers. Some devices may be configured to provide support during Percutaneous Coronary Intervention (PCI), including high risk PCI for those who are hemodynamically unstable after acute heart attack, for acute decompensated heart failure (ADHF), for cardio-renal syndrome (CRS) patients and acute cardiogenic shock (ACS), as well as for early NYHA class II CHF (before INTERMACS level 7) and more-severe conditions. In some embodiments, the Temporary MCSD devices described herein can be designed in series. Some devices may be configured for in-series implantation in the aorta.

Some devices can be a temporary MCSD as described herein. Devices can provide any flow rate and pressure rise described herein. However, some devices may be configured for short term use, typically varying between a few hours and up to about 5 days. All components of temporary devices can be configured to be removed after the short term use. For instance, in some embodiments, no component is configured to be permanently attached to the body of the patient. Unlike some permanently implantable devices, temporary MCSDs can be configured for implantation and then complete removal of all components from the human body. In this way, temporary devices may be configured to addresses PCI, ADHF, CRS, ACS, and temporary relief of the native heart in very early stages of CHF.

Clinical experience performed by an inventor suggests that a device with the specifications as disclosed elsewhere herein can be used effectively as an alternative to other percutaneous systems during percutaneous coronary intervention (PCI). Clinical experience performed by an inventor also suggests that the implantation location of the device (e.g., in the descending aorta) can also provide additional but substantial therapeutic advantages due to increasing perfusion to the kidneys. Other clinical advantages are contemplated.

Some illustrations of devices are included in FIGS. 1A-13. In some embodiments, features described as related to temporary devices may be incorporated into permanently implantable devices and features described as related to permanently implantable devices may be incorporated into temporary devices. Temporary devices may include any feature of any device described herein. Permanent devices may include any feature of any device described herein.

Mechanical circulatory support devices (MCSD) can include a pumping head. In some embodiments, the pumping head comprises two impellers rotating in opposite directions (contra-rotation). In some embodiments, the pumping head comprises two or impellers, with at least two impellers rotating in opposite directions. The impellers can be foldable or collapsible during insertion. In some embodiments, the contra-rotating impellers have equal rpm and opposite rotation. In some embodiments, the contra-rotating impellers have unequal rpm and opposite rotation. The impellers and surrounding support structure, if utilized, are placed in the folded position. The MCS device can be inserted via a catheter in the aorta upstream of the kidneys. This may be in the descending aorta, as shown in the figures, or further upstream in the aorta, anywhere up to the aortic valve. Once the catheter is removed, the blades and surrounding support structure spring into the unfolded position. After use, the pumping head may be removed via the reverse procedure by folding it and capturing it into a catheter.

The pumping head may be connected to one or more motors. The motor may have its own internal speed-reducing gearbox. The motor may be integrally connected to the pumping head intra-corporeally. The motor may be connected via a short bending shaft to the pumping head intra-corporeally. In some embodiments, in these intra-corporeal configurations, power may be delivered to the motor via an electric cable. In some embodiments, the electric cable may also transmit control signals from the device to outside the body or vice versa. In some embodiments, the electric cable may also transmit measured data from the device to outside the body. In some embodiments, a biocompatible lubricant may be pumped from outside the body to the intra-corporeal motor and/or gearbox or gearboxes.

In some embodiments, the device may include gearboxes and an intra-corporeal motor. In some embodiments, one shaft extending out of the intra-corporeal motor or gearmotor drives two epicyclic gearboxes in series, which achieves output contra-rotation. In some embodiments, one gearbox of the same type as the gearbox described herein with the extra-corporeal motor, can also be used.

In some embodiments, the device may include an extra-corporeal motor. In some embodiments, the impellers and gearbox achieving contra-rotation are placed intra-corporeally in the descending aorta, and they are connected to an extra-corporeal motor or gearmotor via a flexible drive shaft. The flexible drive shaft may be encased in a non-rotating sleeve. In some embodiments, a biocompatible lubricant may be pumped from outside the body to the internal components via the gap between the flexible drive shaft and the sleeve.

In some embodiments, the device may include a gearbox and an extra-corporeal motor. With an extra-corporeal motor, rotation of the two impellers in opposite directions is achieved via a gearbox, described herein. This gearbox may be just upstream of the impellers, just downstream of the impellers, or between the impellers. The gearbox receives input power and rotation from one shaft, and provides output via two contra-rotating shafts to the two impellers as described herein.

In some embodiments, the device may include blades. In some embodiments, the device may include blades that fold. In some embodiments, the impellers are four-bladed, but any number from 2 to 32 blades or more may be used in each impeller. In some embodiments, the blades have a flexible section near their hub to allow bending or folding upstream. In some embodiments, the blades have a flexible section near their hub to allow bending or folding downstream. In some embodiments, the blades bend or fold to place the blades in the catheter, as described herein. In some embodiments, the blades are folded upstream via mechanical activation. In some embodiments, the blades are folded downstream via mechanical activation. Several mechanical activation mechanisms can be employed. In some embodiments, mechanical activation is via a runner-stretcher mechanism like umbrellas. In some embodiments, mechanical activation is via a screw/gear activation mechanism like foldable marine propellers. Examples of all folding mechanisms are described herein. The blades can be foldable by any mechanical means. The blades based can be coupled to the hub via a foldable mechanism. The foldable mechanism can include a worm gear. The foldable mechanism a screw. The foldable mechanism can include a rack and pinion. The foldable mechanism can include one or more gears. The foldable mechanism can include an axle. The foldable mechanism can include a pin. The foldable mechanism can be actuated. The foldable mechanism can be self-expandable. The foldable mechanism can include a shape memory material. The foldable mechanism can include a springy or biased material. The foldable mechanism can allow the blades to be expanded. The foldable mechanism can allow the blades to be compressed.

In some embodiments, devices may include two or more foldable impellers or propellers rotating in opposite directions, e.g., contra-rotation with respect to each other. In some embodiments, contra-rotating blades rotate with equal and opposite rpm. In some embodiments, contra-rotating blades rotate with unequal rpm. The impellers, and surrounding support, are placed in the folded position via a catheter in the aorta upstream of the kidneys. In some methods of use, this may be in the descending aorta, or further upstream in the aorta, anywhere up to the aortic valve. Once the catheter is removed the blades and surrounding support spring into the unfolded position. In some methods of use, the temporary device is removed via the reverse procedure by folding it and capturing it into a catheter.

Some devices may be connected to a motor, which may have its own internal speed-reducing gearbox. The motor may be integrally connected to the devices intra-corporeally, or connected via a short bending shaft to the devices intra-corporeally. In some embodiments, a downstream gearbox can be included. The downstream gearbox can be intracorporeal. The downstream gearbox can be extra-corporeal. In some embodiments, power will be delivered to the motor via an electric cable. In some embodiments, the impellers and gearbox achieving contra-rotation are placed intra-corporeally in the descending aorta, and they are connected to an extra-corporeal motor or gear motor via a flexible drive shaft. The contra-rotating blades may have unequal rpm or equal rpm, based in part on the associated gearboxes. The electric motor may have integral with it an epicyclic gearbox reducing motor rpm the first time, e.g., a gear motor, then additional gearboxes reduce the motor rpm a second time before the impellers. In some embodiments, rotation of the two impellers in opposite directions is achieved via a gearbox. This gearbox may be just upstream of the impellers, just downstream of the impellers, or between the impellers. The gearbox receives input power and rotation from one shaft, and provides output via one or more two contra-rotating shafts to the two impellers. In some embodiments, the impellers are actuated purely mechanically, and not via any internal or external magnetic elements.

In some embodiments, a gearbox can be an epicyclic gearbox, some variants of which are used in mechanical watches, but for the first time in heart-assist pumps, to the inventors' knowledge. An epicyclic gearbox can include, for example one or more (e.g., only one in some cases) input shaft and one or more (e.g., only one in some cases) output shaft, and a plurality of sets of gears, such as two, three, four, five, or more gears, or ranges including any two of the foregoing values. In some embodiments, the gearbox can include exactly three, or three or more sets of gears: sun gears, planet gears and rotor gears. In some embodiments, an epicyclic gearbox can include, or have exactly one input and two coaxial output drive shafts that are contra-rotating, including sun gears and planet gears, but not ring gears. In some embodiments, a gearbox can include any number of sun gears, planet gears, rotor gears, and/or ring gears. In some embodiments, a gearbox does not include one or more of sun gears, planet gears, rotor gears, and/or ring gears.

The input to the gearboxes can be via sun gears, both driven by one center shaft. For instance, the downstream impeller may be driven by the planet carrier of the downstream epicyclic gearbox (ring fixed), and the upstream impeller may be driven by the ring of the upstream epicyclic gearbox (planet carrier fixed to nose cone, and via struts to stationary motor casing) to achieve contra rotation. The gear ratios can be adjusted by the diameters of their internal components to achieve exact contra-rotation, i.e. the rpm of the two rotors is equal and opposite. Alternatively, the diameters of internal gear components can be used to make the rpm of the downstream rotor higher or lower than the rpm of the upstream rotor, to accommodate contra-rotation at different impeller rpm, for example for optimal flow dynamics or for balancing reasons.

Some illustrations of devices are included in FIGS. 1A-13. In some embodiments, features described as related to temporary devices may be incorporated into permanently implantable devices and features described as related to permanently implantable devices may be incorporated into temporary devices. Temporary devices may include any feature of any device described herein. Permanent devices may include any feature of any device described herein.

In some embodiments, devices may include two or more foldable impellers or propellers rotating in opposite directions, e.g., contra-rotation with respect to each other. In some embodiments, contra-rotating blades rotate with equal and opposite rpm. In some embodiments, contra-rotating blades rotate with unequal rpm. The impellers, and surrounding support, are placed in the folded position via a catheter in the aorta upstream of the kidneys. In some methods of use, this may be in the descending aorta, or further upstream in the aorta, anywhere up to the aortic valve. Once the catheter is removed the blades and surrounding support spring into the unfolded position. In some methods of use, the temporary device is removed via the reverse procedure by folding it and capturing it into a catheter.

Contra-rotation blades may have unequal rpm. Contra-rotation blades may have equal rpm. In some embodiments, embodiments of the gearboxes described herein can produce the rpm configuration, either equal rpm or unequal rpm. Contra-rotation blades rotate in opposite directions. As described herein, contra-rotation does not necessarily mean equal and opposite rpm, just opposite directions of rotation. In some embodiments, a mechanical circulatory support heart-assist device is provided which comprises two impellers rotating in opposite directions. In some embodiments, a mechanical circulatory support heart-assist device is provided which comprises at least two impellers (e.g., two, three, four, five, six, seven, eight, or any range of the foregoing values). In some embodiments, two of the at least two impellers are configured to rotate in opposite directions. The contra-rotation impellers may be adjacent in an axial direction. The contra-rotation impellers may be spaced apart in an axial direction. The contra-rotation impellers may be separated by one or more additional impellers in an axial direction. The contra-rotation impellers may be separated by one or more additional mechanical structures in an axial direction. The contra-rotation impellers may be separated by one or more support structures in an axial direction.

In some embodiments, devices described herein are placed in the vasculature in order to assist with perfusion. In some embodiments, devices described herein are placed in the vasculature to assist with opening a heart valve. The device may be placed to hold one of the four heart valves in an open position.

Some devices may be connected to a motor, which may have its own internal speed-reducing gearbox. The motor may be integrally connected to the devices intra-corporeally, or connected via a short bending shaft to the devices intra-corporeally. In some embodiments, power will be delivered to the motor via an electric cable. In some embodiments, the impellers and gearbox achieving contra-rotation are placed intra-corporeally in the descending aorta, and they are connected to an extra-corporeal motor or gear motor via a flexible drive shaft. The contra-rotating blades may have unequal rpm or equal rpm, based in part on the associated gearboxes. The electric motor may have integral with it an epicyclic gearbox reducing motor rpm the first time, e.g., a gear motor, then additional gearboxes reduce the motor rpm a second time before the impellers. In some embodiments, rotation of the two impellers in opposite directions is achieved via a gearbox. This gearbox may be just upstream of the impellers, just downstream of the impellers, or between the impellers. The gearbox receives input power and rotation from one shaft, and provides output via one or more two contra-rotating shafts to the two impellers.

The electric motor may have integral with it an epicyclic gearbox. The epicyclic gearbox may reduce motor rpm the first time. In some embodiments, this electric motor may be described as a gearmotor. In some embodiments, an additional gearbox reduces the motor rpm a second time before the impellers. The epicyclic gearboxes may be different types. The epicyclic gearboxes may be referred to by different names. For instance, in the case in which the sun is the input, planet carrier is the output, and ring gear is fixed, this type of gearbox may be referred to as planetary. For instance, in the case in which the planet carrier is fixed and ring moving, this type of gearbox may be referred to as star.

Other configurations of fixed and movable components may have different names in the art.

In some embodiments, contra-rotation of impellers is achieved with one or more gearboxes. In some embodiments, a gearbox may be placed near the pump head. The gearbox may have two concentric output shafts driving the impellers in opposite directions. The gearbox may have one input shaft connected via a flexible shaft to an electric motor or gearmotor. The electric motor or gearmotor may be intracorporeal. The electric motor or gearmotor may be extracorporeal. In some embodiments, the upstream impeller is driven by an epicyclic-type gearbox. The downstream impeller may be driven in the opposite direction to the upstream impeller by a second epicyclic-type gearbox. The suns of both epicyclic gearboxes may be driven by sun gears connected via an input shaft to an electric motor. Other configurations are contemplated.

The input to the gearboxes can be via sun gears, both driven by one center shaft. For instance, the downstream impeller may be driven by the planet carrier of the downstream epicyclic gearbox (ring fixed), and the upstream impeller may be driven by the ring of the upstream epicyclic gearbox (planet carrier fixed to nose cone, and via struts to stationary motor casing) to achieve contra rotation. The gear ratios can be adjusted by the diameters of their internal components to achieve exact contra-rotation, i.e. the rpm of the two rotors is equal and opposite. Alternatively, the diameters of internal gear components can be used to make the rpm of the downstream rotor higher or lower than the rpm of the upstream rotor, to accommodate contra-rotation at different impeller rpm, for example for optimal flow dynamics or for balancing reasons.

In some embodiments, the device is a fully-removable temporary heart-assist device installed in a blood vessel. In some embodiments, the device is not across the aortic valve. In the unfurled position, the impeller tip diameter is 0.2 to 1.0 times the diameter of the adult-sized blood vessel. In some embodiments, the impeller tip diameter is about, at least about, or no more than about 0.1 times the diameter of the adult-sized blood vessel, 0.2 times the diameter of the adult-sized blood vessel, 0.3 times the diameter of the adult-sized blood vessel, 0.4 times the diameter of the adult-sized blood vessel, 0.5 times the diameter of the adult-sized blood vessel, 0.6 times the diameter of the adult-sized blood vessel, 0.7 times the diameter of the adult-sized blood vessel, 0.8 times the diameter of the adult-sized blood vessel, 0.9 times the diameter of the adult-sized blood vessel, 1.0 times the diameter of the adult-sized blood vessel, 1.1 times the diameter of the adult-sized blood vessel, 1.2 times the diameter of the adult-sized blood vessel, 1.3 times the diameter of the adult-sized blood vessel, 1.4 times the diameter of the adult-sized blood vessel, 1.5 times the diameter of the adult-sized blood vessel, 1.6 times the diameter of the adult-sized blood vessel, 1.7 times the diameter of the adult-sized blood vessel, 1.8 times the diameter of the adult-sized blood vessel, 1.9 times the diameter of the adult-sized blood vessel, 2.0 times the diameter of the adult-sized blood vessel, between 0.1 and 0.5 times the diameter of the adult-sized blood vessel, between 0.5 and 1 times the diameter of the adult-sized blood vessel, or any ranges including two of the foregoing values. In some embodiments, the devices be configured with a tip dimeter of about, at least about, or no more than about 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, between 1 mm and 5 mm, between 3 mm and 7 mm, or any ranges including two of the foregoing values. In some embodiments, the device is a folding device. In some embodiment, the device has solid blades. In some embodiments, the closed device is about, at least about, or no more than about 5 Fr, 6 Fr, 7 Fr, 8 Fr, 9 Fr, 10 Fr, 11 Fr, 12 Fr, 13 Fr, 14 Fr, 15 Fr, 16 Fr, 17 Fr, 18 Fr, 19 Fr, 20 Fr, 21 Fr, 22 Fr, 23 Fr, 24 Fr, 25 Fr, 26 Fr, 27 Fr, 28 Fr, 29 Fr, 30 Fr, 31 Fr, 32 Fr, 33 Fr, between 5 and 10 Fr, between 10 and 15 Fr, or any ranges including two of the foregoing values. In some embodiments, the open device is about, at least about, or no more than about 10 Fr, 11 Fr, 12 Fr, 13 Fr, 14 Fr, 15 Fr, 16 Fr, 17 Fr, 18 Fr, 19 Fr, 20 Fr, 21 Fr, 22 Fr, 23 Fr, 24 Fr, 25 Fr, 26 Fr, 27 Fr, 28 Fr, 29 Fr, 30 Fr, 31 Fr, 32 Fr, 33 Fr, between 15 and 20 Fr, between 20 and 25 Fr, or any ranges including two of the foregoing values.

In some embodiments, the device is collapsible. In some embodiments, the device is inserted through a sheath. In some embodiments, the device is expanded. In some embodiments, the device can deliver a blood flow and pressure rises as described herein. In some embodiments, the device can be inserted percutaneously. In some embodiments, the device can provide continuous axial flow by pumping blood from the left ventricle into the ascending aorta. In some embodiments, the device is a mechanical circulatory support system. In some embodiments, the device generates antegrade flow. In some embodiments, the device has a collapsible impeller. In some embodiments, the device is expandable about twice the initial configuration. In some embodiments, the device is expandable when unsheathed. In some embodiments, the device is driven by one or more motors, which can be internal or external. In some embodiments, the device is driven by one or more flexible drive shafts. In some embodiments, the device includes a cage or anchor to support the impellers.

The device is a next generation of temporary heart-assist devices (TAD), providing treatment for early or imminent heart failure during Percutaneous Coronary Intervention (PCI), Primary PCI (during PCI for heart attack), and support for renal failure during episodes of cardio-renal syndrome, using a new technology placed via a minimally invasive procedure. Clinical conditions that may need TAD include primary and high-risk percutaneous coronary intervention (PCI); cardiogenic shock; acute decompensated heart failure (ADHF); cardio-renal syndrome (CRS) (no other device addresses this); acute heart failure (AHF); and/or recurring events in many of the above cases. There is a need for a new and innovative temporary cardiovascular support device. There is a need to overcome shortfalls with the current catheter based technology which can include one or more of the following disadvantages: has a narrow fluid channel, doesn't increase blood pressure, causes significant damage to blood cells, and can't support renal function. This is an Underpenetrated and growing market with a huge unmet need. For instance, high-risk PCI patients have twice the mortality risk compared to other PCI patients using current technology and mortality risk of cardiogenic shock patients post AMI remains high at 50%.

TAD can include one or more of the following advantageous features. TAD can be placed in the descending aorta in the collapsed profile and unsheathed in situ. TAD can be driven by an external gearbox and motor. TAD can include self-stabilisation and anchoring, minimizes aortic wall trauma. TAD can be positioned in a descending aorta location. TAD can be delivered with a 12 Fr delivery system. TAD can include foldable blades and cage. TAD can be removable. TAD can include a contra-rotating pair of propeller blades. TAD can accommodate varying aorta sizes, where one size fits all. TAD can include a constant waist diameter for optimized efficiency. TAD can include a permeable inlet. This inlet can perfuse intercostal and spinal arteries. TAD can include low rotation speed which reduces hemolysis. TAD can include an optimized blood flow path in each component. TAD can prevent or eliminate backflow, with no recirculation. TAD can include a flexible drive shaft. TAD can include an external gear box and motor. TAD is the only device that adds significantly to downstream pressure and flow. This feature supports renal function and improves cardio-renal failure. TAD can be temporary. TAD is designed for use from a few hours and up to 5 days. TAD can include a cage. The propeller section of the cage can be shape memory material such as Nitinol. The cage can surround the impellers. TAD can include foldable propeller blades. The foldable blades can be shape memory material such as Nitinol. The foldable blades can have a unique folding propeller design. The propeller blades can be stowed for delivery. The propeller blades can form a nested configuration around the hub for delivery. The blades can expand outward in use. TAD can include bidirectional rotating propeller blades. The blades can be mounted on a unique bidirectional drive shaft attached to a gearbox.

In some embodiments, TAD has structures which active these clinical performance features. TAD can include an inlet structure and/or cage structure which facilitate anchoring. TAD can include structures which minimize wall contact such as vanes or other diffusor structures. The radial forces just sufficient to hold rotating shaft radially. The axial thrust partially held by friction against aortic wall (and possibly partially by axial shaft). In some embodiments, TAD is inserted and/or retrieved in folded position. TAD can include folding blades. TAD can include a folding waist or compressible structure. TAD can include a folding inlet. TAD can include a folding vane structure or outlet diffuser. TAD can include a catheter for retrieval. In some embodiments, blades folded upstream. In some embodiments, blades folded upstream downstream. The blades can be folded or facilitated to be folded by daggers from hub. The blades can be built up around daggers. In some embodiments, the cage of memory alloy is covered by biocompatible material. TAD can include contra-rotating pair of propeller blades. The blades can remove vortex of first rotor. The blades can convert flow to axial or leave a small vortex. All energy imparted to blades can be converted to downstream axial energy and momentum, thus minimizing flow-friction losses and maximizes efficiency, and maximizes perfusion. In some embodiments, these high efficiency blades are not magnetic. In some embodiments, these high efficiency blades need to fold upstream or downstream. TAD can include a permeable inlet structure. The inlet shape can optimized for flow, and for perfusion in inter-costal arteries. The inlet can supports renal function and improves cardio-renal failure, as organs need perfusion.

In some embodiments, the pressure downstream of impellers is higher than the pressure upstream of impellers. If the gap between rotor tips and surrounding casing is too large, there is a lot of backflow from downstream to upstream. If the gap is too small, there is too much friction. Thus optimizing the gap is important for minimizing backflow around the gap, minimizing friction, and optimizing efficiency. Concurrently, the set rotor tip diameter and set waist diameter optimizes performance in the waist. Then the inlet section, and outlet diffuser section, enable the one-size fits all or most. Optimal efficiency can be from waist aspects, but also can be from inlet size, and outlet diffuser size, rotor gap size, among other features. The total energy imparted from device to blood is the minimum (ideal) energy imparted to blood to achieve pressure rise and flow rate, plus the losses. The losses do not contribute to perfusion (pressure and flow), but they are converted to blood trauma (which leads to hemolysis). Thus all the above (contra-rotating blades, outlet diffuser, optimal gap, etc.) can contribute to lower total energy by minimizing losses, and lower hemolysis by minimizing losses. In some embodiments, there is no backflow. There can be a constant gap between rotor tip and inner diameter of waist section.

In some embodiments, TAD is drive with a unique drive system. TAD can include a flexible drive shaft. The drive shaft can allow insertion in blood vessel. The drive shaft can allow placement of pump head in descending aorta. There can be variations in placement of the gearbox. An external gearbox can require a contra-rotating drive shaft from motor to near pump head. An intra-corporeal gearbox can allow a single drive shaft to gear box, and two shafts from gearbox to pump head. The drive shaft can be lubricated. The drive shaft can be unlubricated. The drive shaft can be coated. TAD can include an extra-corporeal gear box and/or motor. TAD can include an intra-corporeal gear box and/or motor. TAD can add to both downstream pressure and flow. Other devices may only impact flow rate without pressure rice.

TAD can be temporary. TAD can be designed for use for 1 hour, 2 hours, 3 hours, 4 hours, 5 hours, 6 hours, 12 hours, 24 hours/1 day, 2 days, 3 days, 4 days, 5 days, between 1 and 5 days, less than 1 day, less than 5 days, or any ranges including two of the foregoing values.

FIGS. 1A-1G schematically illustrate examples of MCS devices 500 configured for installation in the lumen of a blood vessel. MCS devices 500 can be permanent or temporary implantable devices. In some embodiments, the MCS 500 may comprise one or more rotors 510. The rotor 510 can have any configuration of rotors described herein. In some embodiment, the rotor 510 may be designed to operate with a stator. The rotors 510 may comprise one, two, or more propellers 511. The propeller 511 can have any configuration of propellers described herein. The propellers 511 may comprise one or more radially extending blades 520 configured to transfer force to the blood flowing through the vasculature. The blades 520 can have any configuration of blades described herein. In some embodiments, the MCS 500 may comprise one or more impellers 200 described herein. The impellers 200 can have any configuration of impellers described herein.

FIGS. 1A and 1B illustrate an example of a MCS device 500 with two rotors 510. In some embodiments, the MCS devices 500 can include any number of rotors, e.g., one rotor, two rotors, three rotors, etc. In some embodiments, the MCS device 500 may comprise more than one rotor 510. In some embodiments, each rotor 510 may comprise a propeller 511 configured to rotate independently of the propellers of other rotors. In some embodiments, each rotor 510 may comprise a propeller 511 configured to rotate simultaneously with the propeller of another rotor.

Each propeller 511 includes a number of blades. In the illustrated example, each propeller 511 may include four blades 520. The propeller 511 may have two pairs of diametrically opposed blades 520. The four blades 520 may be circumferentially spaced, e.g., spaced apart by approximately 90 degrees. The four blades 520 may be unevenly spaced apart. In the illustrated example, each propeller 511 includes one row of blades. In some embodiments, the propeller 511 can include two or more rows of blades. In some embodiments, the blades of the impellers rotating in opposite directions have flexible connections to the impeller hubs. The flexible connections may accommodate insertion and removal with folded blades. The flexible connections may accommodate operation when the blades are unfolded. The flexible connections may be a shape memory structure disposed within the blades.

The propeller 511 may be comprised of one or more radially extending blades 520. In some embodiments, the blades 520 may be aligned at a given axial position of the MCS device 500. In some embodiments, the blades 520 may be axially spaced along the axis of the MCS device 500. In some embodiments, one or more rotors 510 may comprise more than one propeller 511. In some embodiments, one or more rotors 510 may comprise more than one row of blades 520. In some embodiments, the propellers 511 of the same rotor 510 may be configured to rotate simultaneously. The propellers 511 may impart a velocity on blood flowing through the vasculature in which the MCS device 500 is installed. The one or more rotors 510 may be aligned along an axial dimension of the blood vessel. The axial dimension may extend parallel to the overall direction of blood flow within the vessel (upstream to downstream) and define a central axis of the MCS device 500. The axis of rotation of the one or more rotors 510 may be aligned substantially along the central axis of the MCS device 500. The axis of rotation of each of the rotors 510 may be aligned such that they are coaxial.

In some embodiments, magnetic elements may be used in the blades. In some embodiments, the whole blades may be magnetic. In some embodiments, the blades can be driven by a coil outside of the blades. For example, the coil may be outside of the blood vessel or aorta for permanent implantation. For example, the coil may be located inside the vessel, for instance in a support structure. Because axial blades are smaller than helical blades, most of the blade (e.g., a majority of the blade) may be a magnet.

In some embodiments, the blades may be made of shape memory materials. The material of the blades may enable folding into or against the hub for implantation and/or removal. In some embodiments, the components of the MCS device must be able to carry the fluid and magnetic forces exerted on them. If the blades are too pliable, the blades will be unable to carry the fluid forces. For example, if blades can twist to become axial, centrifugal, or helical they may not be able to carry the fluid or magnetic force necessary to generate mixed axial and centrifugal flow characteristics, wherein centrifugal would be pure losses.

In some embodiments, the optimal number of blades may be 2, 3, 4, 5, or 6 blades per rotating blade row. In some embodiments, the propeller or impeller has 1 blade in a single blade row, 2 blades in a single blade row, 3 blades in a single blade row, 4 blades in a single blade row, 5 blades in a single blade row, or 6 blades in a single blade row, one row, two rows, or three rows, or any combination of the foregoing configurations. In some embodiments, the rotor may include 1, 2, 3, 4, 5, or 6 blade rows. Each blade row may be rotated by the same rotor.

In some embodiments, the optimum stagger angle may be between approximately 40 and 90 degrees from the hub direction. In some embodiments, the optimum stagger angle is between 40 and 50 degrees, between 50 and 60 degrees, between 60 and 70 degrees, between 70 and 80 degrees, between 80 and 90 degrees, between 40 and 60 degrees, between 50 and 70 degrees, between 60 and 80 degrees, between 70 and 90 degrees, between 40 and 70 degrees, between 50 and 80 degrees, between 60 and 90 degrees, or any range including any two of the foregoing values. In some embodiments, the MCS device may comprise an optimized number of blades. In some embodiments, the MCS device may comprise an optimized stagger angle of the blades.

MCS devices may include axial propeller type blades, as described elsewhere herein. Axial propeller type blades are generally distinct from helical screws, in that they comprise distinct turbomachine geometries. Cutting azimuthal segments of helical devices does in some cases not result in as efficient 3D axial turbomachines as turbomachines comprising axial propeller type blades.

The MCS device 500 may comprise an anchoring mechanism 600 for anchoring the turbomachinery within the aorta or blood vessel. The anchoring mechanism 600 may be a cage, circumferential band, or other support structure configured to surround the turbomachinery and to allow blood flow to pass through. In some embodiments, the cage structure may comprise upstream and downstream points substantially aligned with the axis of rotation of the one or more rotors 510. The anchoring mechanisms 600 may be configured to hold the MCS device 500 in place within the blood vessel through pressure exerted on the blood vessel wall at points where the anchoring mechanism 600 contacts the blood vessel. The anchoring mechanism 600 may be expandable as described elsewhere herein.

For temporary devices, the anchoring mechanism 600 may be designed to temporary anchor the device within the aorta or blood vessel. The anchoring mechanism 600 may be atraumatic to rest against the vessel wall. For permanent devices, the anchoring mechanism 600 may be designed to permanently engage the tissue of the patient. The anchoring mechanism 600 may take on various forms to achieve the desired level of fixation.

FIG. 1A illustrates a collapsed configuration. FIG. 1B illustrates an expanded configuration. The MCS devices 500 may have one or more intermediate configurations between the collapsed configuration and the expanded configuration. In the collapsed configuration, the one, two, or more blades are configured to collapse to a low profile configuration. In the expanded configuration, the one or more blades are moved laterally outward. In some embodiments, the MCS device may be implanted in a collapsed state and deployed inside descending aorta, ascending aorta, or left ventricle via the aortic valve.

FIGS. 1C and 1D illustrate the MCS devices 500 within a blood vessel 150. FIGS. 1C and 1D schematically illustrate the surgical installation of the MCS device 500. In FIG. 1C, the anchoring mechanism 600 is removed, showing the rotors.

FIG. 1E illustrate a perspective view of the MCS devices 500 with two rotors 510. Each rotor 510 includes a propeller 511 that includes three blades 520. The three blades 520 may be circumferentially spaced, e.g., spaced apart by approximately 120 degrees. In some embodiments, one or more propellers 511 include a single blade. In some embodiments, one or more propellers 511 include two blades. The two blades 520 can be circumferentially spaced, e.g., spaced apart by approximately 180 degrees, or unevenly space. In some embodiments, the two or more propellers 511 have the same number of blades. In some embodiments, the two or more propellers 511 have the same configuration of blades, such as the same spacing between blades. In some embodiments, the two or more propellers 511 have a different number of blades. In some embodiments, the two or more propellers 511 have a different configuration of blades, such as different spacing between blades.

In some embodiments, the anchoring mechanism 600 may have a barrel-shape configuration as shown in FIG. 1E. In some embodiments, the anchoring mechanism 600 can be designed to minimize contact with the vessel wall. In some embodiments, the anchoring mechanism 600 is the point or points of contact with the vessel wall. In some embodiments, the anchoring mechanism 600 may act as a centering mechanism for the rotors.

FIG. 1F illustrates an example of a contra rotors device including a pair of contra-rotating propellers 512, 514. In some embodiments, the second propeller 514 may reverse the direction of the tangential velocity component. In some embodiments, the second propeller 514 may add to the axial velocity component of the blood flow such that the axial velocity of the blood is continually increased as it passes through the MCS device 500. In some embodiments, MCS devices 500 may include contra-rotating blades. Contra-rotating blades may be highly beneficial to minimize hemolysis. Contra-rotating blades may be able to operate efficiently at a lower rpm than devices without contra-rotating blades. The MCS devices 500 can include any number of propellers, including any number of contra-rotating propellers. The MCS devices 500 can include any arrangement of propellers, including any arrangement of contra-rotating propellers. In the illustrated embodiment, the pair of contra-rotating propellers 512, 514 are axially aligned. In the illustrated embodiment, the pair of contra-rotating propellers 512, 514 have the same number of blades. In the illustrated embodiment, the pair of contra-rotating propellers 512, 514 have blades that are equally spaced around the circumference.

In some embodiments, the magnitude of angular velocities of two propellers within a pair of contra-rotating propellers 512, 514 may be equal. Contra-rotating propellers 512, 514 with equal angular velocity magnitudes may result in output velocity vectors comprising small tangential velocity components, such as that necessary to replicate natural helical blood flow in the aorta. In some embodiments, the magnitude of angular velocities of two propellers within a pair of contra-rotating propellers 512, 514 may be unequal.

The final velocity vector at the output of the MCS device 500 may be modulated by the blade geometry. The blades of the propeller 511 and/or the contra-rotating propellers 512, 514 can be selected to have the desired flow characteristics. The blades of the propeller 511 and/or the contra-rotating propellers 512, 514 can be selected based on the size of the blades. The blades of the propeller 511 and/or the contra-rotating propellers 512, 514 can be selected based on the tilt of the blades. The blades of the propeller 511 and/or the contra-rotating propellers 512, 514 can be selected based on the total number of blades of the propeller. The blades of the propeller 511 and/or the contra-rotating propellers 512, 514 can be selected based on the direction of rotation of the propeller 511 and/or the contra-rotating propellers 512, 514. The blades of the propeller 511 and/or the contra-rotating propellers 512, 514 can be selected based on the desired distance between the two or more propellers 511 and/or contra-rotating propellers 512, 514 in the MCS device 500. The blades of the propeller 511 and/or the contra-rotating propellers 512, 514 can be selected based on the ordering of the propellers in an axial direction in the MCS device 500. The blades of the propeller 511 and/or the contra-rotating propellers 512, 514 can be selected based on the desired number of propellers to achieve a blood flow characteristic. The blades of the propeller 511 and/or the contra-rotating propellers 512, 514 can be selected based on the desired angular velocities of the propeller 511 and/or the contra-rotating propellers 512, 514 to achieve a blood flow characteristic.

In some embodiments, the propellers 511, the contra-rotating propellers 512, 514, impellers, or contra-rotating impellers may have a diameter taking most of the available blood vessel diameter. This configuration can have advantages. The RPM of the one or more propellers or impellers may be minimized for the pressure rise and flow rate specification, thus minimizing blood trauma. In some embodiments, the propellers 511, the contra-rotating propellers 512, 514, impellers, or contra-rotating impellers may have a diameter less than the available blood vessel diameter. In some embodiments, one or more support structures have a diameter that fills a portion of the available blood vessel diameter.

In some embodiments, the propellers 511, the contra-rotating propellers 512, 514, impellers, or contra-rotating impellers are coupled to a motor. The motor can have any features of motors described herein. MCS device 500 can include any structure or hub to contain or house the motor. In some embodiments, one or more contra-rotating motors may be located in the hub of propellers or impellers. MCS device 500 can include any structure to deliver power to the motor. MCS device 500 can include any structure to deliver control signals to the motor. In some embodiments, one or more catheter based conduits are provided for carrying conductors for power delivery and control signals.

TAD can include contra-rotating impellers. In some embodiments, the impellers rotate in opposite directions, as viewed from an external reference point. In some embodiments, one impeller rotates clockwise and the other impeller rotates counter-clockwise. In some embodiments, the impellers rotate in the same direction, as viewed from an external reference point. In some embodiments, both impellers rotate clockwise. In some embodiments, both impellers rotate counter-clockwise. In some embodiments, the impellers face opposite directions, as viewed from an external reference point. In some embodiments, the impellers are mounted end-to-end. In some embodiments, the impellers face the same direction, as viewed from an external reference point. In some embodiments, the impellers are mounted end-to-face. In some embodiments, the impellers are of opposing handedness, as viewed from an external reference point. In some embodiments, one of the impellers is a left-handed impeller and the other impeller is a right handed impeller. In some embodiments, the impellers have the same handedness, as viewed from an external reference point. In some embodiments, both of the impellers are a left-handed impellers. In some embodiments, both of the impellers are right handed impellers. In some embodiments, the contra-rotating impellers are within the same cage. In some embodiments, the contra-rotating impellers pump blood in the same direction. In some embodiments, the contra-rotating impellers pump blood in opposite directions.

FIG. 1G illustrates an example of a single rotor with a pre-swirler 540 and a de-swirler 542. The MCS device 500 can include one or more pre-swirlers. The MCS device 500 can include one or more de-swirlers. The pre-swirlers and de-swirlers may comprise 3D conformations. The blades may include a complex 3D configuration. This configuration of the pre-swirlers may impart a desired flow characteristic on the blood prior to entry into the propeller. This configuration of the de-swirlers may impart a desired flow characteristic on the blood after engagement with the propeller.

The pre-swirlers and de-swirlers may provide improved hydrodynamics over simple 2D struts. For example, 2D struts may not be able to impart the desired flow characteristics. In some embodiments, the pre-swirlers and/or de-swirlers are compared to those which are 2D in shape. These 2D struts may be extruded from a tube. These 2D struts may have poor flow characteristics. In contrast, the 3D pre-swirl and de-swirl vanes may be configured to have vane-angle changes from hub to tip. This configuration can impart better flow characteristics on the blood. In some embodiments, the 3D pre-swirl and de-swirl vanes are not planar. In some embodiments, the 3D pre-swirl and de-swirl vanes extend in three planes. In some embodiments, the 3D pre-swirl and de-swirl vanes extend in multiple directional vectors in a thickness dimension. In some embodiments, the 3D pre-swirl and de-swirl vanes have a longitudinal twist. In some embodiments, the 3D pre-swirl and de-swirl vanes have a longitudinal curvature.

The pre-swirlers and de-swirlers may have a compressed configuration and an expanded configuration, similar to the blades. The pre-swirlers and de-swirlers may be foldable against a hub or other structure of the MCS device 500. In some embodiments, the pre-swirlers and de-swirlers may be removable from the remainder of the device. In some embodiments, the pre-swirlers and de-swirlers may be permanently coupled to the device.

Figure 2B:
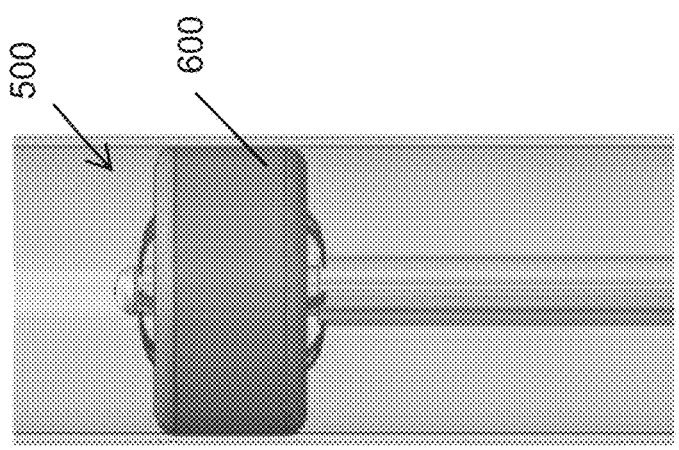
Figure 2A:
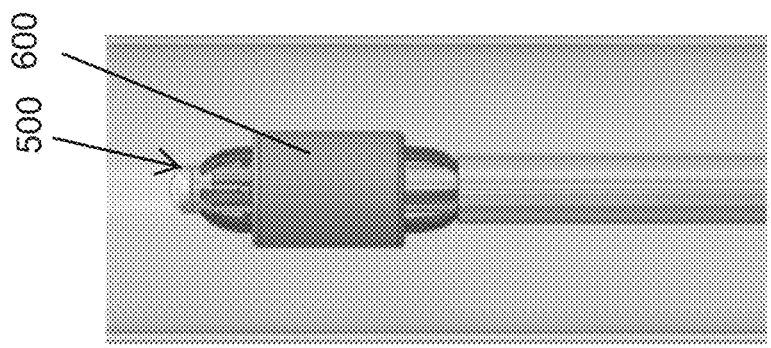

FIGS. 2A-2C illustrate an anchoring mechanism 600 for anchoring the turbomachinery within the blood vessel. FIG. 2A illustrates a folded device 500 with a deflated balloon. FIGS. 2B and 2C illustrate an unfolded device 500 with an inflated balloon. The anchoring mechanism 600 may include a balloon configured to surround the turbomachinery and to allow blood flow to pass through. The balloon can be selectively inflated within the blood vessel or aorta. In some embodiments, the balloon fills a portion of the diameter of the blood vessel. In some embodiments, the balloon is designed to rest against the blood vessel and be a point of contact with the blood vessel. The anchoring mechanism 600 may also include one or more struts. The struts can rest against the inside diameter of the balloon. The struts can center the turbomachinery within the lumen of the balloon.

In some embodiments, the balloon may have a tube configuration as shown in FIG. 2C. In some embodiments, the balloon may comprise an upstream and downstream periphery substantially offset from the axis of rotation of the one or more rotors 510. The balloon may be configured to hold the MCS device 500 in place within the blood vessel through pressure exerted on the blood vessel wall at the side surface where the balloon contacts the blood vessel. The balloon may be expandable such as through inflation medium. In some methods of use, the balloon is inflated when within the blood vessel or aorta. The inflation medium can be delivered through one or more conduits to the balloon. The inflation medium can be a biocompatible material such as saline. In some embodiments, the inflation medium is a gas. In some embodiments, the inflation medium is a liquid. In some embodiments, the inflation medium is a solid, solid-forming, or curable material. The balloon may be expandable by absorption of liquid, such as blood. In some embodiments, the balloon is permeable to liquid allowing the balloon to expand. In some embodiments, the balloon can be deflated. In some embodiments, the balloon is configured to be a permanent structure within the body of the patient.

Figure 3A:
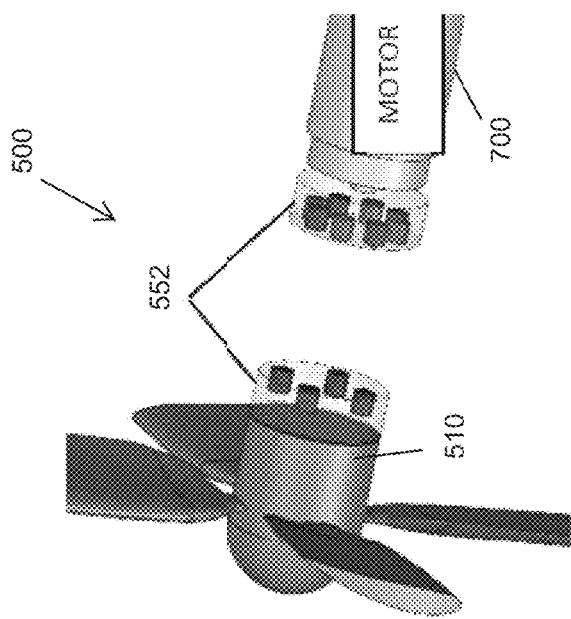
FIGS. 3A-3E schematically illustrate various examples of internal features of the MCS device.
Figure 3B:
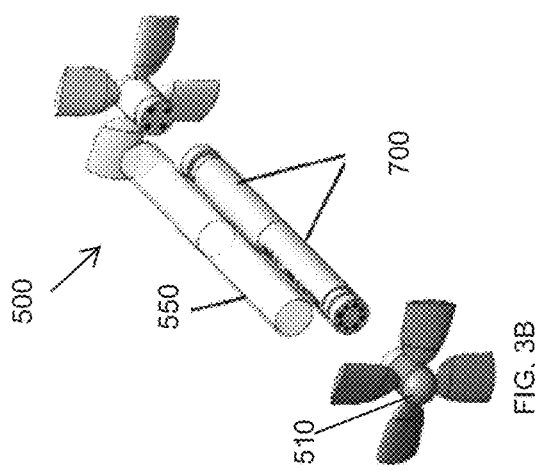

FIGS. 3A-3B illustrate intra-corporeal motors. The MCS device 500 may comprise one or more motors 700 coupled to the one or more rotors 510 to provide rotational force to the one or more rotors 510. In embodiments comprising more than one rotor 510, some or all of the rotors 510 may be driven by different motors. FIG. 3B illustrate a plurality, e.g., two intra-corporeal motors 700 positioned back to back. Each intra-corporeal motor 700 provides rotational force to an independent rotor. The two intra-corporeal motors 700 are positioned within a sealed capsule 550 to prevent the passage of blood into the motors 700. FIG. 3A illustrates the assembled device with the sealed capsule. For TAD, the motor can be easily removed with the removal of the device.

Figure 3C:
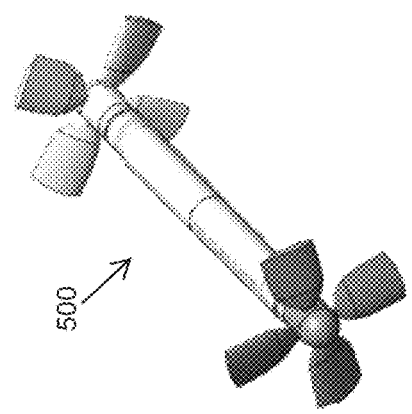

FIG. 3C illustrates a magnetic coupling 552. The magnetic coupling is illustrated between the rotor 510 and the motor 700. The rotor is the hub of the propeller and provides a location for coupling to the motor. The coupling can be any mechanical couple to transmit rotational movement from the motor to the rotor. In some embodiments, the rotor and/or propeller may be coupled to the motor by any magnetic means. In the illustrated embodiment, magnets are provided on the rotor and the motor. In some embodiments, the rotor and/or propeller may be directly rotated by the motor stator and may be referred to as part of the motor 700. For instance, magnets driven by the electromagnetic stator of the motor may be coupled to or installed within the rotor or rotors 510. Other configurations of coupling are contemplated. In some embodiments, the coupling of the turbomachine to the motor may be accomplished via a shaft. In some embodiments, the coupling of the turbomachine to the motor may be accomplished via magnetic coupling.

In some embodiments, there is provided one or more couplings between the motors, where multiple motors are provided. The coupling between the motors may be via magnetic coupling, connectors, and/or bearings. In some embodiments, bearings at the proximal and distal end of the MCS device may be hydrodynamic. In some embodiments, bearings at the proximal and distal end of the MCS device may be magnetic. In some embodiments, bearings at the proximal and distal end of the MCS device may be self-lubricating using circulating blood.

Figure 3D:
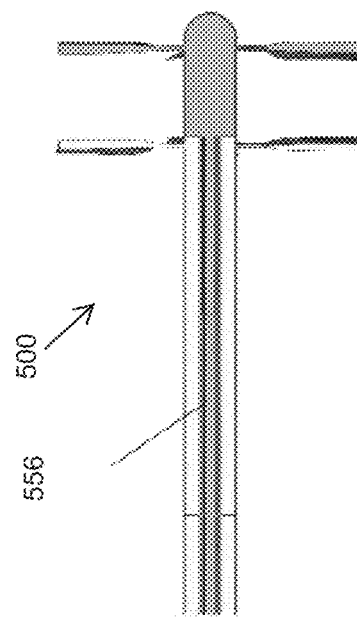

FIG. 3D illustrates another embodiment of a motor. One or more epicyclic gears 554 (also known as planetary gears) may be used to achieve contra-rotation between the two rotors. Other configurations of motors are contemplated.

Figure 3E:
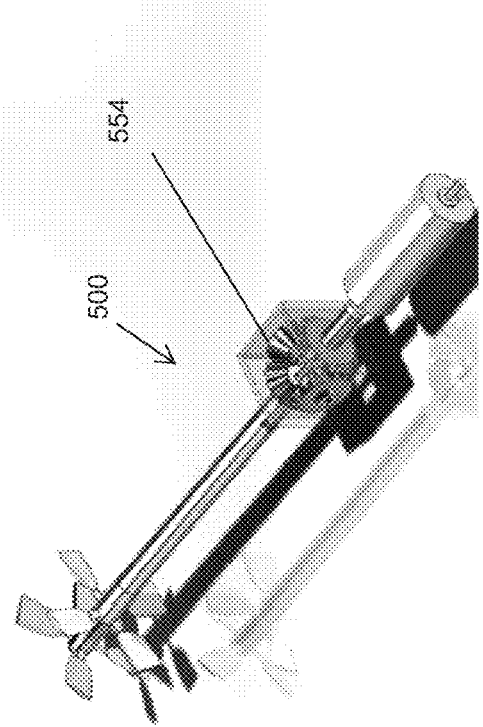

FIG. 3E illustrates lubrication channels 556. In some embodiments, a lubricating fluid may be provided through the catheter to lubricate the driveline. For example, a lubricating fluid may be transported through small channels in the catheter to a proximal bearing of the rotor 510 and returned through a line comprising the driveline. In some embodiments, the distal bearing of the rotor 510 may be lubricated by blood flow.

FIGS. 4A-4C illustrate the MCS device 500 positioned within a blood vessel 150. The MCS device 500 can be inserted in a low profile configuration until the MCS device 500 reaches a target vessel. The MCS device 500 can be unfolded or deployed to expand the one or more blades 520. In embodiments comprising an intra-corporeal motor, the motor or motors may be positioned within the lumen of the blood vessel (intravascular).

FIG. 5A illustrates articulated sleeves for insertion 560. The articulated sleeves can allow the MCS device 500 to bend as the MCS device 500 travels to the target vessel. FIG. 5B illustrates tail to tail motors 700 within the articulate sleeve 560. The motors 700 can be positioned tail to tail to operate rotors at each end of the sleeve. FIG. 5C illustrates head to tail motors 700 within the articulate sleeve. The motors 700 can be positioned in any configurations within the articulate sleeve or other capsule. The motors can be easily removed with the removal of the device.

Figure 6A:
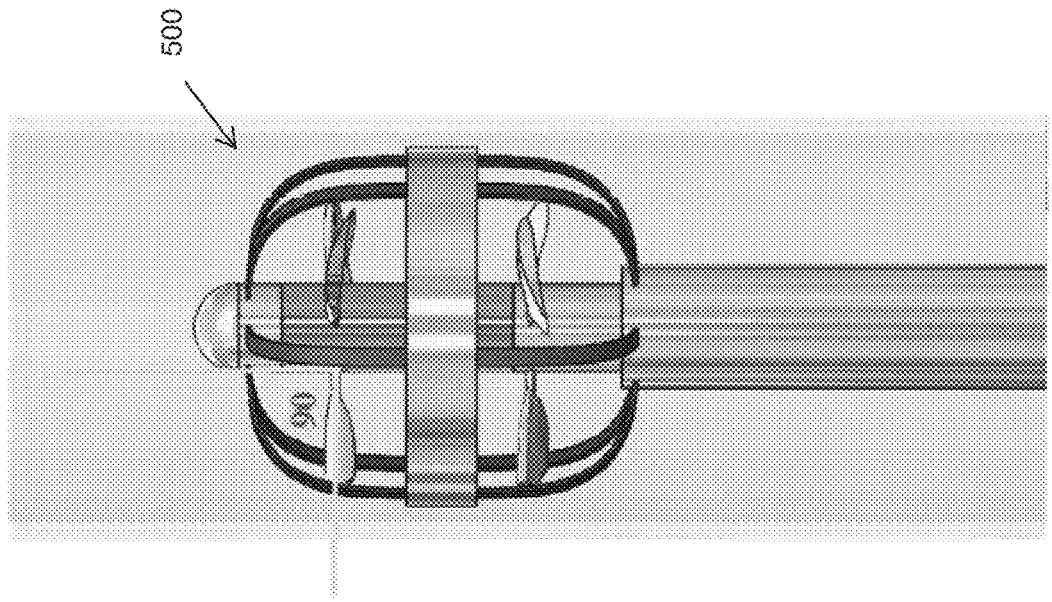
FIGS. 6A-6B schematically illustrate operating configurations of the MCS device opening in an umbrella-like fashion.
Figure 6B:
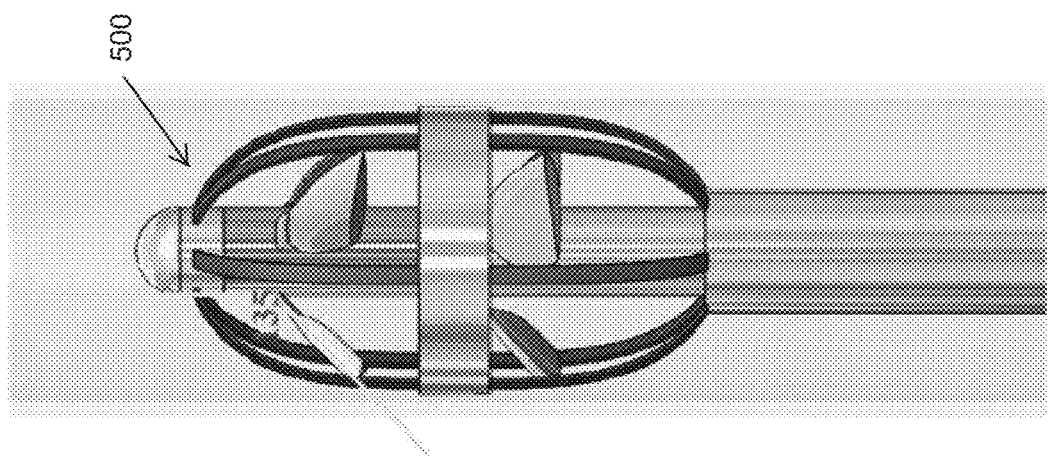

FIGS. 6A-6B illustrate the opening of blades in an umbrella-like fashion. FIG. 6A illustrates partial opening in a smaller aorta. The blades form an angle of about 135 degrees with the longitudinal axis of the MCS device 500. FIG. 6B illustrates full opening in a larger aorta. The blades form an angle of 90 degrees with the longitudinal axis of the MCS device 500. The tip diameter of the propeller is smaller in FIG. 6A than in FIG. 6B. The MCS device may be configured to maintain a substantially constant gap size between the blade tips and the anchoring mechanism regardless of size of the aorta. In some embodiments, the MCS device 500 can include an impeller designed to open in an umbrella-like fashion. In some embodiments, the blades of the impellers have flexible connections to the corresponding impeller hubs. The flexible connections may facilitate insertion and removal with folded blades. The flexible connections may facilitate operation when the blades are unfolded. In some embodiments, the mechanical folding mechanism for the blades is like an umbrella. In some embodiments, the mechanical folding mechanism may include a runner and a stretcher. In some embodiments, the mechanical folding mechanism may include a screw and cam. In some embodiments, the mechanical folding mechanism can include a locking mechanism that locks the blades in an open configuration. In some embodiments, the mechanical folding mechanism can include a locking mechanism that locks the blades in a closed configuration. In some embodiments, the mechanical folding mechanism can by any mechanism that folds and unfolds the blades. In some embodiments, the blades are folded and unfolded by the action of a larger catheter or sheath.

In some embodiments, the MCS device 500 may include one or more foldable propellers and/or impellers. The foldable impellers may be inserted collapsed against the hub of the device, and then opened in an umbrella-like fashion at the desired aortic location to various degrees. The tip diameter of the impeller or propeller varies by the amount of opening of the umbrella. The propellers or impellers may be enclosed within a cage or other anchoring mechanism 600. The propellers or impellers may open partially to a variable umbrella opening, resulting in variable tip diameter. The umbrella design may keep the turbomachine tip-to-cage gap at optimum levels as described herein. The MCS device 500 may comprise an adjustable operating impeller or propeller diameter configured to maintain a substantially constant gap size between the blade tips and the anchoring mechanism. The MCS device 500 may comprise an adjustable operating impeller or propeller diameter configured to maintain a substantially constant gap size between the blade tips and the blood vessel wall. In some embodiments, the MCS device 500 has a variable impeller diameter to maintain the desired gap with a one size impeller.

In some embodiments, the impellers or propellers of the MCS device 500 may be intended to be either fully open or fully closed. The impellers or propellers of the MCS device 500 possess a fixed tip diameter in the open position. This embodiment can be an alternative to the umbrella-like opening described above. The diameter of the fixed diameter propellers or impellers may be set, for example, at approximately 10 mm, 12 mm, 14 mm, 16 mm, 18 mm, 20 mm, 22 mm, 24 mm, 26 mm, 28 mm, 30 mm, 32 mm, between 10 mm and 20 mm, between 20 mm and 30 mm, less than 30 mm, less than 22 mm, less than 20 mm, less than 18 mm, more than 10 mm, more than 14 mm, more than 16 mm, or any range including two of the foregoing values.

In some embodiments, the blades may be inserted in a collapsed state whether designed to partially open or fully open. The blades can be loaded into one or more sleeves for delivery. The blades may be spring-loaded and ready to expand upon removal of the sleeves. Once expanded to the full extent or to a partial extent, as described herein, the centrifugal action of rotation may keep the blades in an open configuration. In the case of partial opening, the blades may be locked in position. In some embodiments, the blades are locked from the hub side.

MCS devices may include a tip-diameter dimension. The interior diameter of the aorta at the implantation location varies from patient to patient, for instance, between approximately 20 mm and 32 mm. This varying dimension may present a series of problems, as there is generally a desire to limit the gap between the propeller or impeller tip and the surrounding device or blood vessel structure. Optimal gaps, balancing requirements between hydraulic efficiency and hemolysis, may be between approximately 0.2 and 2 mm, e.g., 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 2 mm or any range including two of the foregoing values. Optimal gaps, balancing requirements between efficiency and hemolysis, are between 0.2 and 1 mm, e.g., 0.2 mm, 0.3 mm, 0.4 mm, 0.5 mm, 0.6 mm, 0.7 mm, 0.8 mm, 0.9 mm, 1 mm, or any range including two of the foregoing values. For example, in some embodiments, the preferred or nominal gap size may be approximately 0.5 mm. In some embodiments, the nominal gap size may be approximately 0.0 mm, 0.1 mm, 0.2 mm, 0.3 mm, 0.4 mm, 0.5 mm, 0.6 mm, 0.7 mm, less than 0.7 mm, less than 0.5 mm, less than 0.3 mm, or any range including two of the foregoing values. Larger gaps may result in regurgitant flow from the device outlet to the device inlet, and thus reduced hydraulic efficiency, as well as increased mixing and hemolysis.

However, providing a device with a fixed large diameter to reduce the gap may make the device unsuitable (too large) to be accommodated in specific patient anatomies. In some embodiments, there is provided a customized device. In some embodiments, there is provided an adjustable size device. In some embodiments, the MCS device accommodates variable sized blood vessels using adjustability. In some embodiments, the MCS device is available in a potential matrix of device sizes, from smaller to larger diameters. In some embodiments, there is the ability to select a device from a range of device sizes from smaller diameters to larger diameters, to accommodate the desirable gaps in each case. In some embodiments, the MCS device is available in a variety of dimeter sizes in the fully open position to accommodate varying aorta sizes.

In some embodiments, the propeller or impeller can be designed to operate in conjunction with an expandable member, e.g., a balloon. FIGS. 2A-2C provide an example balloon. The MCS device may include a cylindrical-sleeve shaped balloon. The balloon may include an open center to accommodate along its axis the open (unfolded) propeller or impeller. The balloon can be used to adjust the size of the gap between the blade tips and the balloon. The internal diameter of the balloon can be varied via a level of inflation to adjust for the desired gap size as well as accommodate the propeller or impeller blades and balloon in the blood vessel.

In some embodiments, the balloon may serve as the anchoring mechanism for the MCS device. In some embodiments, the balloon may be coupled to an outer diameter of the cage or struts. In some embodiments, the balloon may be coupled to an inner diameter of the cage or struts. In some embodiments, two balloons may be used, one coupled to each side (internal, external) of the cage or struts. The MCS device may comprise an impeller or propeller having a fixed operative diameter as described herein. The impeller or propeller having a fixed operative diameter may be surrounded by a balloon that inflatable to various sizes such that the gap between the propeller or impeller tip and the inner diameter of the balloon is adjustable. In some embodiments, the inner diameter of the balloon is adjustable, such as the central lumen through which the turbomachinery passes. In some embodiments, the outer diameter of the balloon may be adjustable. The outer diameter may be advantageously adjusted to fit against the wall of the vessel.

By utilizing a cylindrical-sleeve type balloon with an open center to accommodate in its axis the open propeller or impeller, the balloon internal diameter can be varied to adjust for the desired gap size. By utilizing a cylindrical-sleeve type balloon, the balloon external diameter can be varied to fit the impeller plus balloon into the blood vessel. In some embodiments, the MCS device may have a variable impeller tip diameter and variable balloon inflation to accommodate blood vessel diameter while keeping tip-to-balloon gap at optimum levels balancing hemolysis with tip leakage. In some embodiments, the MCS device may have a few impeller size devices and variable balloon inflation to fit desired gap in varying blood-vessel diameters.

In some embodiments, the balloon may comprise an axial length configured to extend axially beyond the one or more propellers or impellers. In some embodiments, the balloon may comprise an axial length configured to extend distally beyond the one or more propellers or impellers. In some embodiments, the balloon may comprise an axial length configured to extend proximally beyond the one or more propellers or impellers. In some embodiments, the balloon may comprise an axial length configured to extend both proximally and distally beyond the one or more propellers or impellers. Extending the length of the balloon may optimize blood flow through the MCS device. This increased axial length can have many advantages including reducing hemolysis, protecting against backflow, optimizing fluid dynamics, and/or avoiding vortices.

The balloon may be a generally cylindrical tube like structure as illustrated herein. In some embodiments, the balloon is spherical. In some embodiments, the balloon is conical. In some embodiments, the balloon comprises two or more balloons. In some embodiments, the balloon comprises two or more axial balloons. In some embodiments, the balloon comprises two or more circumferential balloons. In some embodiments, the balloon comprises two or more circumferential lobes. For example, the balloon can include a cloverleaf design with four lobes. Other configurations are contemplated.

The balloon can include one or more surfaces configured to contact the blood vessel. The balloon can include one or more rounded edges. The balloon may comprise shaped inlet and/or outlet regions. For example, the inlet and/or outlet regions may be shaped as smooth-shaped bodies of revolution above and/or below the propeller or impeller structure. The inlet and/or outlet regions may be designed to smooth the inflow into the propeller/impellers and outflow out of the propeller or impellers. The inlet and/or outlet regions may be designed in a manner minimizing recirculating flow patterns, dead-flow regions, and/or minimizing losses. The inlet and/or outlet regions may be shaped with optimization techniques similar to aircraft inlets and diffusers. In some embodiments, the MCS device may include shaped balloon inlets and/or outlets.

The MCS device can include the cage or anchoring mechanism 600. The cage or anchoring mechanism 600 can be deployed in embodiments with or without a balloon. The cage or anchoring mechanism 600 can be deployed in embodiments with one or more rotors/propellers. The cage or anchoring mechanism 600 can be deployed in embodiments with one or more contra-rotating rotors/propellers. In some embodiments, the structures of the perimeter struts forming the cage or anchoring mechanism 600 may be shaped to open into 3D blades directing the flow in the desired direction. For example, the struts may form blades that extend in an axial and circumferential direction from proximal to distal ends. The blades may extend radially inward in a proximal to distal direction. The blades may extend radially outward in a proximal to distal direction. The blades may have a uniform thickness as they extend along the proximal to distal direction. The blades may have a variable thickness as they extend along the proximal to distal direction. The blades may have the same or similar features as pre-swirler and/or de-swirler blades described herein.

The MCS device can include one or more coils. The coils may be used in an addition to or alternatively to the balloon. In some embodiments, the coils can be used to form funnels (3D bodies of revolution) at the inlet and/or outlet of the MCS device. In some embodiments, the coils can provide strength to the balloon. In some embodiments, the coils can improve flow characteristics. In some embodiments, the coils can be provide at the inlet, the outlet, or both the inlet and the outlet. In some embodiments, the coils can serve the function as pre-swirlers and/or de-swirlers. In some embodiments, the coils can accommodate the differences in blood-vessel diameter from the tip and cage diameter. In some embodiments, the coils can be expanded and uncoiled, as well as compressed and stretched to change shape. In some embodiments, the coils can form the desired gap between the blade tips and the coils.

Figure 7D:
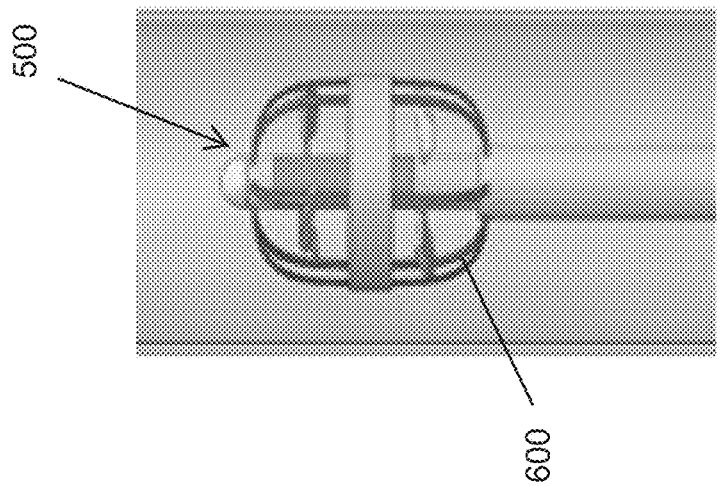
FIGS. 7A-7D schematically illustrate operating configurations of the MCS device comprising various motor and support configurations.
Figure 7C:
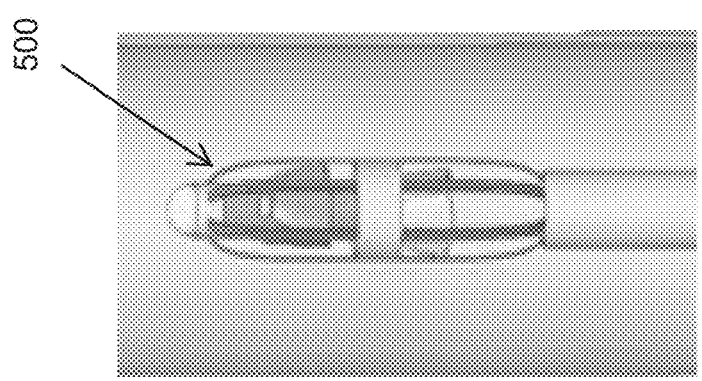
Figure 7B:
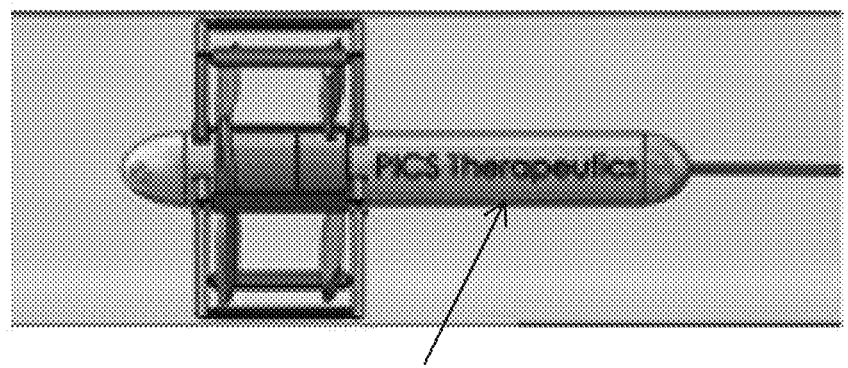
Figure 7A:
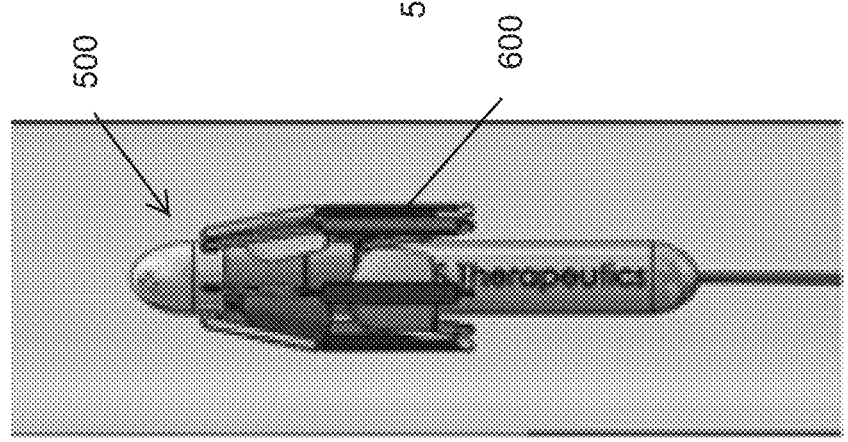

FIGS. 7A-7D illustrate an example of perimeter struts forming the cage or anchoring mechanism 600. In some embodiments, the impellers or propellers of the MCS device may be intended to be either fully open and possess a fixed tip diameter in the open position. In some embodiments, the impellers or propellers of the MCS device may be intended to be opened in an umbrella like fashion. FIG. 7A illustrates an embodiment of a collapsed configuration. The blades of the propeller are against the hub of the device. The anchoring mechanism 600 extends distally along the hub of the device. The anchoring mechanism 600 can include one or more hinges or other mechanical structures that enable the anchoring mechanism 600 to fold. FIG. 7B illustrates an embodiment of an expanded configuration of the embodiment of FIG. 7A. The blades of the propeller are laterally extended from the rotor. The anchoring mechanism 600 is also laterally extended. The propellers of the MCS device 500 may have a fixed tip diameter in the open position between the blade tips and the struts of the anchoring mechanism 600. In the illustrated embodiment, each strut of the anchoring mechanism 600 extends laterally away, then distally, then laterally toward the device. The strut forms two 90 degree angles or similar angles when expanded. Other configurations are contemplated. FIGS. 7A-7B illustrate an intra-corporeal motor with folding cage support.

FIG. 7C illustrates an embodiment of a collapsed configuration. The blades of the propeller are in a low profile, insertion, and/or removal configuration. FIG. 7D illustrates an embodiment of an expanded configuration of the embodiment of FIG. 7C. The blades of the propeller and the anchoring mechanism 600 are laterally extended. The propellers of the MCS device 500 may have a fixed tip diameter in the open position between the blade tips and the struts of the anchoring mechanism 600. The propellers of the MCS device 500 may have a variable tip diameter in the open position between the blade tips and the struts of the anchoring mechanism 600. In the illustrated embodiment, each strut of the anchoring mechanism 600 curves or forms an arch in the proximal-distal direction. Other configurations are contemplated. FIGS. 7C-7D illustrate an extra-corporeal motor with a thicker drive shaft. FIGS. 7A-7D illustrate the MCS device deployed in a blood vessel. FIGS. 7A-7D illustrate an intra-corporeal motor with folding cage support, and extra-corporeal motor (thicker drive shaft), both in a blood vessel.

In some embodiments, the MCS device may comprise pre-swirler and/or de-swirler stationary vanes. The pre-swirler and/or de-swirler stationary vanes may also serve as the support structures of the hub of the turbomachine. In some embodiments, the pre-swirler and/or de-swirler stationary vanes may form the cage or anchoring mechanism surrounding the one or more rotors. In some embodiments, the MCS device may comprise struts opening in blade shapes. The struts may function as the pre-swirler and/or de-swirler. The struts functioning as a pre-swirler and/or a de-swirler can have a 3D configuration when expanded. In some embodiments, the MCS device may comprise a simpler stator-rotor-stator configuration. In some embodiments, the MCS device may comprise one rotating impeller with upstream pre-swirler and downstream de-swirler stationary vanes. The upstream pre-swirler and downstream de-swirler stationary vanes may also be the support structures of the hub of the turbomachine to the cage or support around the rotor. In some embodiments, the MCS device may comprise support struts configured to open in blade shapes.

In some embodiments, more than one impeller or propeller may be positioned between pre-swirler and de-swirler stationary vanes (e.g., 2, 3, 4, 5, or more impellers or propellers). In some embodiments, one impeller or propeller may be positioned between pre-swirler and de-swirler stationary vanes. In some embodiments two or more contra-rotating impellers or propeller may be positioned between pre-swirler and de-swirler stationary vanes. In some embodiments, the stationary vanes may only serve the function of the pre-swirler. In some embodiments, the stationary vanes may only serve the function of the de-swirler.

Whether with one rotor or a pair of contra-rotating rotors, the structures of the perimeter struts forming the cage may be shaped to open into 3D blades. The 3D blades may be designed for directing the flow in the desired direction. In some embodiments, the MCS device may comprise pre-swirler and/or de-swirler struts to optimize flow angles and turbomachinery efficiency. The 3D blades can be pre-formed to have the desired configuration when expanded. The 3D blades can be formed of a shape memory material.

In some embodiments, the cage or anchoring mechanism 600 may be a solid cylinder. The cage or anchoring mechanism 600 may comprise one or more supporting rings at the proximal and distal end. The cage or anchoring mechanism 600 may comprise one or more supporting rings located at the axial location of the propeller or impeller tips. The cage or anchoring mechanism 600 may comprise axial elements between the supporting rings that expand to fit inside the blood vessel. The axial elements may be 3D blades. The cage or anchoring mechanism 600 may be made of flexible materials that expand to the required shape. In some embodiments, the MCS device may comprise a cage and/or supporting structure. In some embodiments, the MCS device may comprise an installation procedure including the deployment of a cage or anchoring mechanism 600.

In some methods of use, the cage or anchoring mechanism 600 may be implanted separately from the impeller device or other turbomachinery. In some methods of use, the cage or anchoring mechanism 600 can be implanted similar to a stent cage. The cage or anchoring mechanism 600 may comprise a balloon or other space-occupying feature. In some methods of use, the cage or anchoring mechanism 600 is expanded prior to insertion of the turbomachinery. The cage or anchoring mechanism 600 expands against the wall of the vessel. In some embodiments, the cage or anchoring mechanism 600 may include a central lumen for insertion of the turbomachinery. In some embodiments, the cage or anchoring mechanism 600 is designed to ensure the central lumen of the cage or anchoring mechanism 600 matches the diameter of the propeller or impeller with the appropriate gap. In some embodiments, the design ensures that there is not an excessive gap between the tip of propeller or impeller blades and the wall of vessel. In some embodiments, the design ensures that there is not an excessive gap between the tip of propeller or impeller blades and the wall of anchoring mechanism or cage in the stent tube configuration.

In some embodiments, MCS devices may include interior sleeves or stents. The sleeves or stents may be in one piece or multi-pieces. The sleeves or stents may be implanted against the interior blood vessel wall. The sleeves or stents may be implanted such that a supporting structure can be attached to hold the bearings and main shaft of the propellers or impellers. Other configurations of support structures are contemplated.

In some embodiments, if the stent cage is delivered independently, the impeller device may have pre-swirlers and/or post-swirlers. The pre-swirlers and/or post-swirlers may be self-expanding. The pre-swirlers and/or post-swirlers may be mechanically expanded disks. In some embodiments, the pre-swirlers and/or post-swirlers may function to centralize the propeller or impeller and prevent collision with vessel wall. In some embodiments, the pre-swirlers and/or post-swirlers may be collapsible for when removal is required. Variable diameters of blood vessel may be accommodated using different openings comprising 3D pre-swirlers and/or de-swirlers.

In some methods of use, the cage or anchoring mechanism 600 may be implanted simultaneously with the impeller device or other turbomachinery. In some methods of use, the cage or anchoring mechanism 600 and the blades can be expanded simultaneously. In some methods of use, the cage or anchoring mechanism 600 and the blades can be expanded independently and/or sequentially. In some methods of use, the cage or anchoring mechanism 600 and the blades can be expanded to varying degrees. In some embodiments, the design ensures that there is not an excessive gap between the tip of propeller or impeller blades and the wall of vessel and/or the wall of anchoring mechanism or cage.

In some embodiments, the MCS device may comprise two contra-rotating propellers or impellers. In some embodiments, such a configuration may result in maximum hydraulic efficiency. In some embodiments, such a configuration may result in minimum rotor RPM. In some embodiments, such a configuration may result in minimum hemolysis. In some embodiments, the MCS device may include a pair of contra-rotating impellers maximizing efficiency and minimizing hemolysis.

Figure 8C:
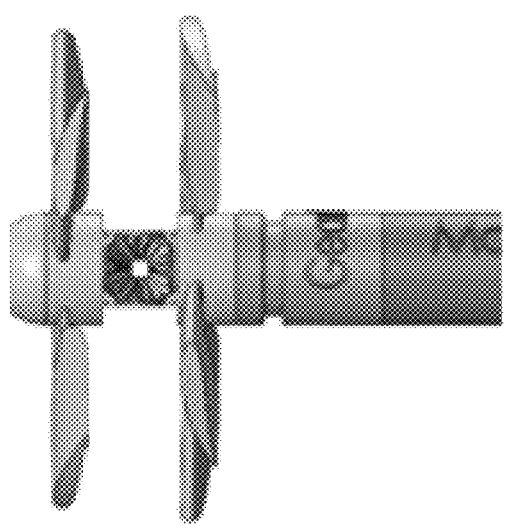
FIGS. 8A-8C schematically illustrate operating configurations of the MCS device comprising a bevel gearbox for contra-rotation.
Figure 8B:
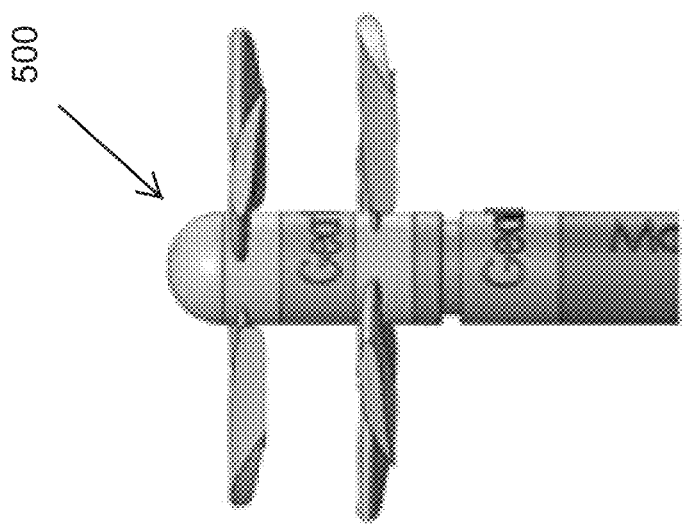
Figure 8A:
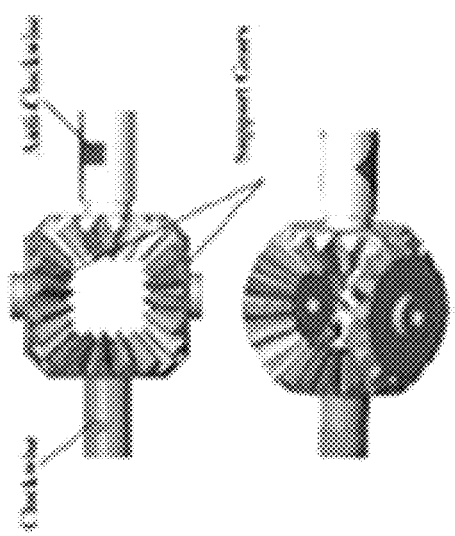

FIGS. 8A-8C illustrate a configuration comprising two contra-rotating propellers. FIG. 8A illustrates the bevel gearbox achieving contra-rotation. The first shaft moves clockwise and the second shaft moves counter clockwise. The support gears are also illustrated. The MCS device is shown in FIG. 8B. The positioning of the bevel gearbox is shown in FIG. 8C. FIGS. 8A-8C illustrate an intra-corporeal motor, a first gearbox reducing the shaft speed, a first rotor, a bevel gearbox achieving a contra-rotation from the first rotor, and then the second rotor. The bevel gearbox achieving a contra-rotation from the first rotor is illustrated in FIGS. 8A and 8C.

In some embodiments, power may be delivered to blades by a miniature electric motor (or motors). The motor, controller, and power supply may be extra-corporeal, as described elsewhere herein. The motor may be extra-corporeal and catheters may serve as drive shafts. The motor may be intra-corporeal. The motor may be located in the hub of turbomachines. The catheter in the installed and operating condition may be an electric cable delivering power from outside the body to the motor location in the aorta. The motor may be intra-corporeal with the controller and power supply being located extra-corporeally.

In some embodiments, a gearing mechanism may be needed between the motor and the rotating impeller or propeller. The gearing mechanism may be located next to the motor. The gearing mechanism may be located next to the one or more impellers. The gearing mechanism may be intra-corporeal or extra-corporeal. In some embodiments, the motor, gearing mechanism, and propeller/impeller are all intra-corporeal, and only the electric cable goes through the rotor. In some embodiments, one or more of the motor, gearing mechanism and propeller/impeller are intra-corporeal. In some embodiments, one or more of the motor, gearing mechanism and propeller/impeller are extra-corporeal.

One or more epicyclic gears (also known as planetary gears) may be used to achieve contra-rotation between the two rotors. Epicyclic gears have four main elements: a sun; planets; a planet carrier; and a ring. One of three components is held stationary: the planet carrier and planets; or the ring; or rarely the sun. Depending on which component is held stationary different gear ratios are achieved, and concurrently the output shaft may be co-rotating or contra-rotating from the input shaft to the gearbox. The epicyclic gearbox or boxes may be intra- or extra-corporeal.

FIG. 9A-9D illustrate a configuration with two gearboxes or gearing mechanisms 554. The first gear 554 and the motor 770 are within a sealed capsule. The second gear 554 is located between the rotors 510. The ring of the second gear is connected to the second rotor 510. FIG. 9A illustrates the two gearboxes. FIG. 9B illustrates the external view of the MCS device 500. FIGS. 9C and 9D illustrate the location of the two gear boxes within the device. This is one example of several arrangements of planetary gearboxes, other configurations are contemplated. The planetary gearboxes achieve contra-rotation. The MCS device comprises an intra-corporeal motor with two planetary gearboxes in series. The motor shaft is driving the sun of the first gearbox. The ring is stationary. The planet carrier is the output shaft for the first rotor and is connected to the sun of the second gearbox. The planets of the second gearbox are stationary and connected to the front stationary hub. The rotating ring of the second gearbox is the output. In this arrangement, the first rotor is contra-rotating from the motor shaft. In this arrangement, the second rotor is co-rotating with the rotor shaft. The size of the gear teeth can be used to modify the gear ratios as needed. The cage may be supported by the stationary motor. FIG. 9A-9D illustrate gear 1 and motor inside the sealed capsule and gear 2 with the ring connected to the second rotor. While the motor 700 is illustrated as having a 5 W (watt) power, other configurations are contemplated, e.g., 1 W, 2 W, 5 W, 10 W, 15 W, 20 W, 25 W, 30 W, or any range of the foregoing values.

FIG. 9A-9D illustrate an intra-corporeal motor with two epicyclic gearboxes in series achieving contra-rotation of two rotors. The input to the gearboxes is via sun gears, both driven by one center shaft. For instance, the downstream impeller may be driven by the planet carrier of the downstream epicyclic gearbox (e.g., ring fixed), and the upstream impeller may be driven by the ring of the upstream epicyclic gearbox (e.g., planet carrier fixed to nose cone, and via struts to stationary motor casing) to achieve contra rotation. The gear ratios can be adjusted by the diameters of their internal components to achieve exact contra rotation, i.e. the rpm of the two rotors is equal and opposite. In some embodiments, the diameters of internal gear components can be used to make the rpm of the downstream rotor higher or lower than the rpm of the upstream rotor, to accommodate contra-rotation at different impeller rpm, for optimal flow dynamics, or for balancing reasons.

Figure 10:
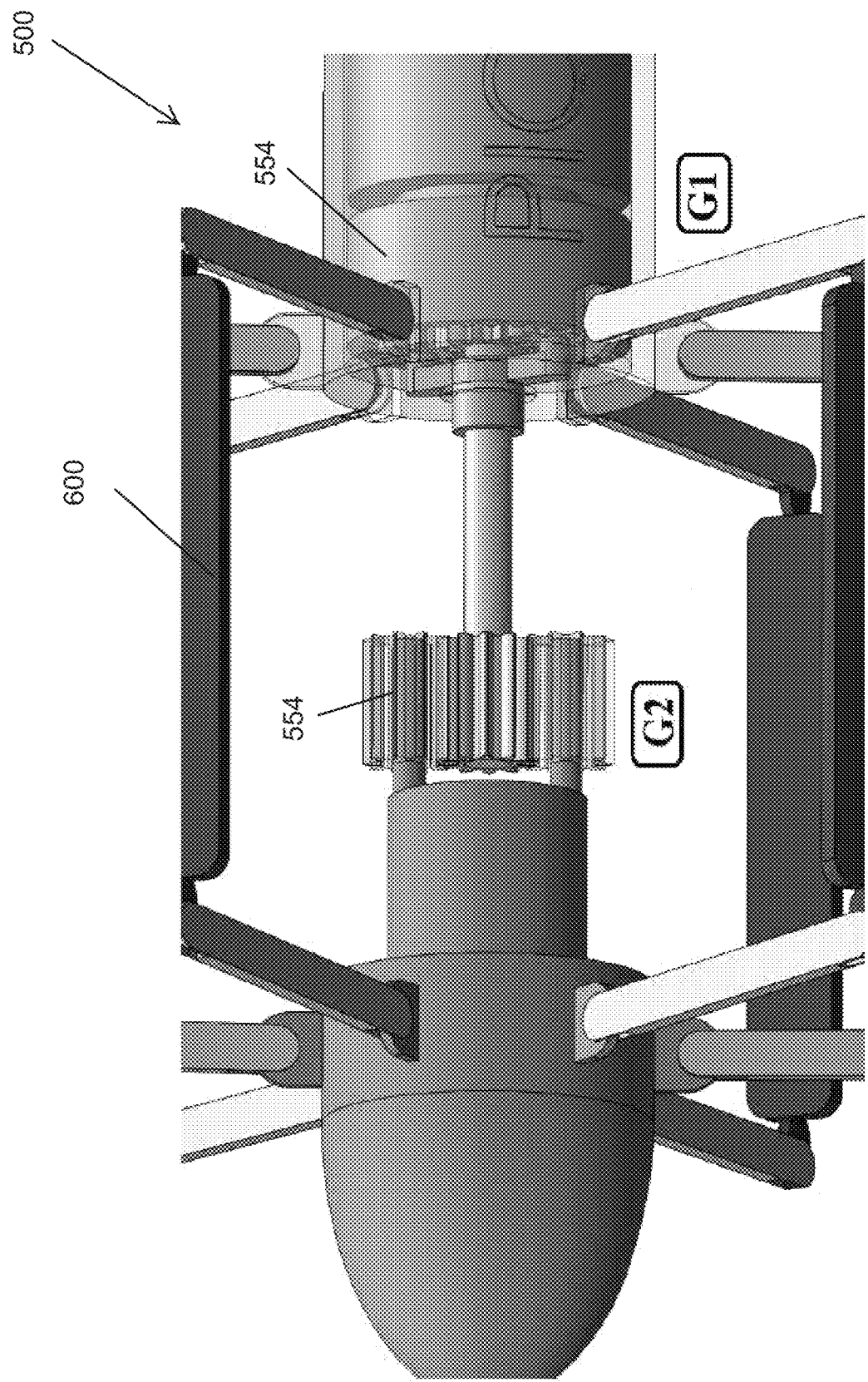
FIG. 10 schematically illustrates an operating configuration of the MCS device comprising two gearboxes.

FIG. 10 illustrates another configuration with two gearboxes 554. The rotors are omitted from the figures. The cage 600 is shown. The first gear G1 and the motor are within a sealed capsule. The ring is fixed with the first gear. In some embodiments, the first gear will operate the first rotor. In some embodiments, the second gear G2 is located between the rotors. The planets are fixed with the second gear. The cage may be supported by the stationary ring of the first gearbox and by the stationary hub. FIG. 10 illustrates G1 wherein the ring is fixed and G2 wherein the planets are fixed.

In some embodiments, in a contra-rotating configuration, there may be one motor with a differential-type gearing device. In some embodiments, bevel gears are provided. The bevel gears may provide contra-rotation to two shafts from one motor. This gearing may be intra-corporeal or extra-corporeal. If in this arrangement the motor is extracorporeal, then there may be one shaft from the motor to the intra-corporeal gearing. In this arrangement, there can be two contra-rotating shafts on the outlet of the bevel gearing, at the same axial end of the bevel gear, or in the opposite ends of the bevel gear. In some embodiments, the bevel gearing may be extra-corporeal, located next to the extra-corporeal motor. In this arrangement, two concentric shafts may be placed along the blood vessel to the contra-rotating impellers. Other configurations of intra-corporeal and extra-corporeal gearing mechanisms are contemplated.

In some embodiments, intra-corporeal motors may be configured tail-to-tail. In some embodiments, intra-corporeal motors may be configured head-to-tail. In some embodiments, intra-corporeal motors may be arranged in the axial direction. In some embodiments, intra-corporeal motors may be configured to articulate for installation. The intra-corporeal motors may be articulated, for example, by being located in an articulating sleeve.

In embodiments comprising one or more intra-corporeal motors in one or more turbomachine hubs, the electric cables may be installed around the perimeter of the cage or anchoring mechanism 600. In some embodiments, the electric cables may be installed along the hub of the device.

FIG. 10 is one example of several arrangements of epicyclic (planetary) gearboxes used to achieve contra-rotation, which comprises an intra-corporeal motor with two epicyclic (planetary) gearboxes in series to achieve contra-rotation. The motor shaft is driving the sun of the first planetary gearbox. The ring is stationary. The planet carrier is the output shaft for the first rotor, and is connected to the sun of the second gearbox. The planets of the second gearbox are stationary, and connected to the front stationary hub. The rotating ring of the second gearbox is the output. In this arrangement the first rotor is contra-rotating from the motor shaft, and the second rotor is co-rotating with the rotor shaft. The size of gear teeth can be used to modify gear ratios as needed. In this example the cage is supported by the stationary motor or stationary ring of the first gearbox, and by the stationary hub, as shown in FIG. 10.

FIGS. 11A-11B illustrate an embodiment of the MCS device 500. In some embodiments, the MCS device 500 may comprise a nose propeller 570. The MCS device 500 may include foldable caging, forming a support structure 600. The MCS device 500 may include one or more hydrodynamic bearings 572. The MCS device 500 may include one or more blades 520. The MCS device 500 may include one or more gearboxes 554. The MCS device 500 may include a motor 700. The MCS device 500 may include a sealed capsule 550 for the motor 700. The MCS device 500 may include a cord 574 extending from the sealed capsule. The foldable cage 600 extends from the nose propeller and the sealed capsule. The nose propeller and the sealed capsule include hubs that allow the foldable cage 600 to connect thereto.

Figure 12:
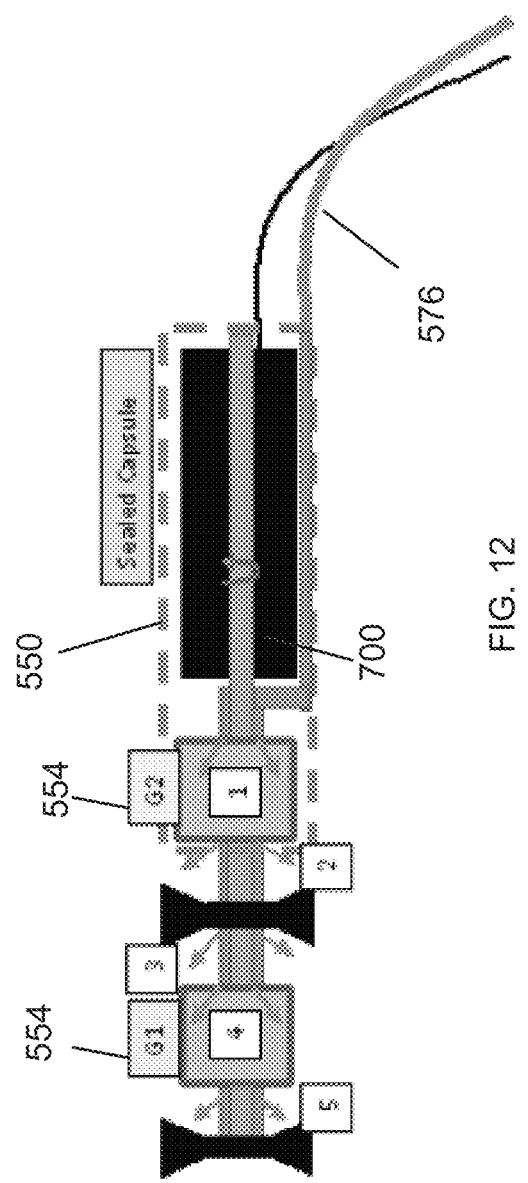
FIG. 12 schematically illustrates an operating configuration of the MCS device comprising a lubrication path.

FIG. 12 illustrates an example of lubrication path 576. The lubrication path extends through the sealed capsule 550. The lubrication path extends through the gearboxes 554 G1, 554 G2. A biocompatible lubricant may be pumped through the motor 700 and/or gearbox or gearboxes 554. One example, in which the lubricant is diffused in the blood stream, is shown in the figures. The lubricant may be returned outside the body. FIG. 12 illustrates lubrication and/or cooling with an intra-corporeal motor. With suitable choice of components, the device may run unlubricated or dry. In some embodiments, a biocompatible fluid may be pumped to lubricate and/or cool the components.

Figure 13:
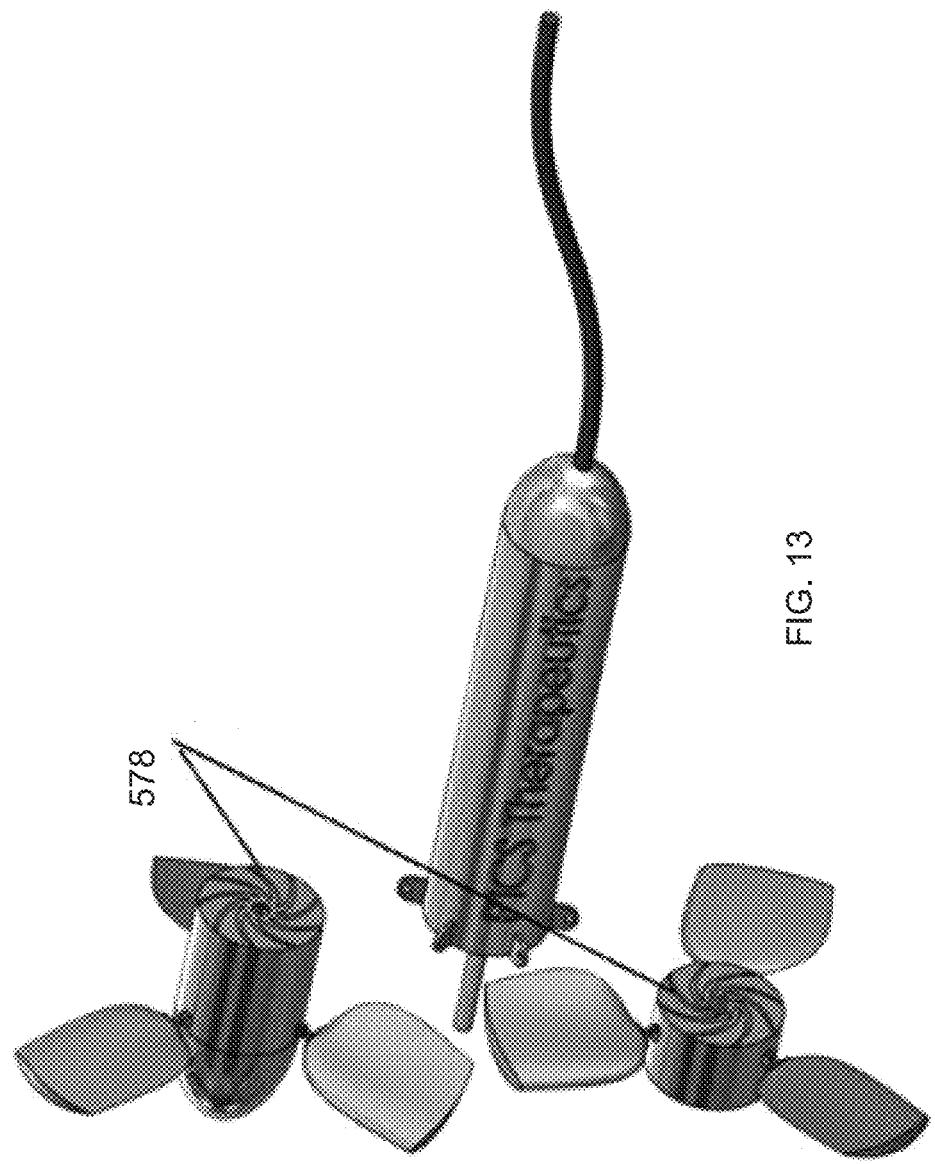
FIG. 13 schematically illustrates an operating configuration of the MCS device comprising spiral grooves.

FIG. 13 illustrates spiral grooves 578. The pump-out spiral grooves may improve the wash-out flow in the critical regions. Spiral grooves may be used between rotating and stationary elements in the pump head to remove stagnant blood flow between rotating and stationary components. FIG. 13 illustrates pump-out spiral grooves to improve the wash-out flow in the critical regions.

FIGS. 14A-14C illustrate the opening of blades within an hour glass support 600. FIG. 14A illustrates full opening in a larger aorta. The hour glass support 600 is opened to the maximum inner diameter of the aorta. The outer diameter may be approximately 19 mm. The edges of the struts extend to the maximum aortic diameter. The blades form an angle of 90 degrees with the longitudinal axis of the MCS device 500. FIG. 14B illustrates partial opening of the hour glass support 600 in a smaller aorta. The hour glass support 600 is opened to the minimum inner diameter of the aorta. The blades form an angle of 90 degrees with the longitudinal axis of the MCS device 500.

The tip diameter of the propeller is approximately the same in FIG. 14A and FIG. 14B. The MCS device 500 may be configured to maintain a substantially constant gap size between the blade tips and the hour glass support 600 regardless of size of the aorta. In some embodiments, the MCS device 500 can include an anchoring mechanism designed to open in an hour glass like fashion. The impellers or propellers of the MCS device 500 may possess a fixed tip diameter relative to the hour glass support in the open position. The diameter of the fixed diameter propellers or impellers may be set, for example, at approximately 10 mm, 12 mm, 14 mm, 16 mm, 18 mm, 20 mm, 22 mm, 24 mm, 26 mm, 28 mm, 30 mm, 32 mm, between 10 mm and 20 mm, between 20 mm and 30 mm, less than 30 mm, less than 22 mm, less than 20 mm, less than 18 mm, more than 10 mm, more than 14 mm, more than 16 mm, or any range including two of the foregoing values.

MCS devices may include a tip-diameter dimension. The interior diameter of the aorta at the implantation location varies from patient to patient, for instance, between approximately 20 mm and 32 mm. This varying dimension may present a series of problems, as there is generally a desire to limit the gap between the propeller or impeller tip and the surrounding device or blood vessel structure. Optimal gaps, balancing requirements between hydraulic efficiency and hemolysis, may be between approximately 0.2 and 2 mm, e.g., 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 2 mm, or any range including two of the foregoing values. Optimal gaps, balancing requirements between efficiency and hemolysis, are between 0.2 and 1 mm, e.g., 0.2 mm, 0.3 mm, 0.4 mm, 0.5 mm, 0.6 mm, 0.7 mm, 0.8 mm, 0.9 mm, 1 mm, or any range including two of the foregoing values. For example, in some embodiments, the preferred or nominal gap size may be approximately 0.5 mm. In some embodiments, the nominal gap size may be approximately 0.0 mm, 0.1 mm, 0.2 mm, 0.3 mm, 0.4 mm, 0.5 mm, 0.6 mm, 0.7 mm, less than 0.7 mm, less than 0.5 mm, less than 0.3 mm, or any range including two of the foregoing values.

FIG. 14C illustrates the collapsed configuration. The top struts and the bottom struts are stretched axially. In some embodiments, the blades of the impellers have flexible connections to the corresponding impeller hubs. The flexible connections may facilitate insertion and removal with folded blades. The flexible connections may facilitate operation when the blades are unfolded. In some embodiments, the MCS device 500 may include one or more foldable propellers and/or impellers. The foldable impellers may be inserted collapsed against the hub of the device, and then opened at the desired aortic location. The tip diameter of the impeller or propeller can be maintained at a constant gap due to the constant diameter of a middle portion of the hour glass. The hour glass design may keep the turbomachine tip-to-cage gap at optimum levels as described herein.

In some embodiments, the blades may be inserted in a collapsed state. The blades may be spring-loaded and ready to expand upon removal of the sleeves. Once expanded, the centrifugal action of rotation may keep the blades in an open configuration. In some embodiments, the blades may be locked in position. In some embodiments, the blades are locked from the hub side.

The hour glass support 600 may be implanted first and separately from the MCS device 500. The hour glass support 600 may be implanted alone. The hour glass support 600 may be implanted like a stent cage. The hour glass support 600 may have a balloon or space occupying feature to ensure the central lumen matches the diameter of the impeller. The hour glass support 600 may have a balloon or space occupying feature to ensure that there is not excessive gap between tip of impeller blades and wall of vessel/or wall of hour glass support 600. If the hour glass support 600 is delivered independently, the MCS device 500 may have pre-swirlers and post-swirlers. In some embodiments, the pre-swirlers and post-swirlers are self-expanding or mechanically expanded disks. In some embodiments, the pre-swirlers and post-swirlers may centralize the impeller and prevent collision with vessel wall. In some embodiments, the pre-swirlers and post-swirlers may be collapsible if the device is to be removed.

In some embodiments, the hour glass support 600 is an adjustable size device. In some embodiments, the hour glass support 600 accommodates variable sized blood vessels using adjustability. In some embodiments, the hour glass support 600 is available in a potential matrix of device sizes, from smaller to larger diameters. In some embodiments, there is the ability to select a device from a range of device sizes from smaller diameters to larger diameters. In some embodiments, the hour glass support 600 is available in a variety of diameter sizes in the fully open position to accommodate varying aorta sizes. For instance, each the hour glass support 600 may be designed to operate within a range of aortic sizes.

In some embodiments, the hour glass support 600 is an expandable member. The hour glass support 600 may include a cylindrical-sleeve portion in which the impellers operate. The hour glass support 600 may include an open center to accommodate the open propeller or impeller. In some embodiments, the hour glass support 600 and the blades each have a fixed diameter such that the gap between the two can be fixed. In some embodiments, the hour glass support 600 includes top struts and bottom struts. The top struts and bottom struts can be used to adjust the size of the hour glass support 600 to the aortic diameter. The top struts and bottom struts can be varied to adjust for the aortic or blood vessel size. The top struts and bottom struts may be coupled to a stent like structure. The stent like structure can be an hour glass shape as shown in FIG. 14A or cylindrical as shown in FIG. 14B. The top struts and bottom struts may stretch the stent like structure toward the aortic diameter. The top struts and bottom struts may facilitate locating the hourglass cage axially. The structures of the struts may be shaped to open into 3D blades. The top struts and bottom struts may assist in directing the flow in the desired direction.

In some embodiments, the impellers are folded in an hourglass-shaped cage. The hourglass-shaped cage may form an inlet upstream of the first rotor. The inlet may be configured to accelerate the axial component of flow velocity. In some embodiments, the device includes a flow diffuser downstream of the second rotor.

The flow diffuser may be configured to decelerate the axial component of flow velocity. In some embodiments, the cage diameter between the inlet and the diffuser is constant. The inlet may taper inward toward the constant diameter. The flow diffuser may taper outward from the constant diameter. In some embodiments, the constant cage diameter between the inlet and the diffuser may be designed to make one size of rotor diameters fit anatomically different larger inside diameters of the blood vessel. In some embodiments, the constant cage diameter is selected to correspond to a single diameter rotor. In some embodiments, the constant cage diameter is selected based on the desired gap between the cage and the blades. As illustrated in FIGS. 14A and 14B, the constant cage diameter accommodates the same size blade and gap, regardless of the size of the inlet and flow diffuser. In some embodiment, the waist section near the middle of the support has a constant diameter, sized to accommodate an impeller of fixed diameter and thus a fixed gap between blade tips and inner diameter of waist section. In some embodiments, the gap between the impeller and diameter of the waist is fixed. The gap may be chosen to minimize blood trauma by friction in the blood while minimizing backflow across the impellers from the high pressure region to the low pressure region of the pump. In some embodiments, the pump rotors are axially secured by connecting members or struts to a surrounding cage. In some embodiments, the cage is secured to the perimeter of the surrounding blood vessel, so that the cage protects the inside perimeter of the blood vessel.

In some embodiment, the hour glass support 600 is made of shape memory alloy. In some embodiment, the hour glass support 600 is made of Nitinol or another shape memory material. In some embodiment, the hour glass support 600 is an open weave braided structure. In some embodiment, the hour glass support 600 is a tubular structure. In some embodiment, the hour glass stent structure may be covered with a biocompatible material. In some embodiments, the biocompatible material is configured to prevent blood flow through the biocompatible material.

The impellers and surrounding hour glass support 600 may be placed in the folded position. The impellers and surrounding hour glass support 600 may be inserted via a catheter in the aorta upstream of the kidneys. The impellers and surrounding hour glass support 600 may be positioned in the descending aorta or further upstream in the aorta, anywhere up to the aortic valve. Once the catheter is removed, the impellers and surrounding hour glass support 600 may spring into the unfolded position. After use, the impellers and surrounding hour glass support 600 may be removed via the reverse procedure by folding and capturing the impellers and surrounding hour glass support 600 into a catheter.

Figure 15A:
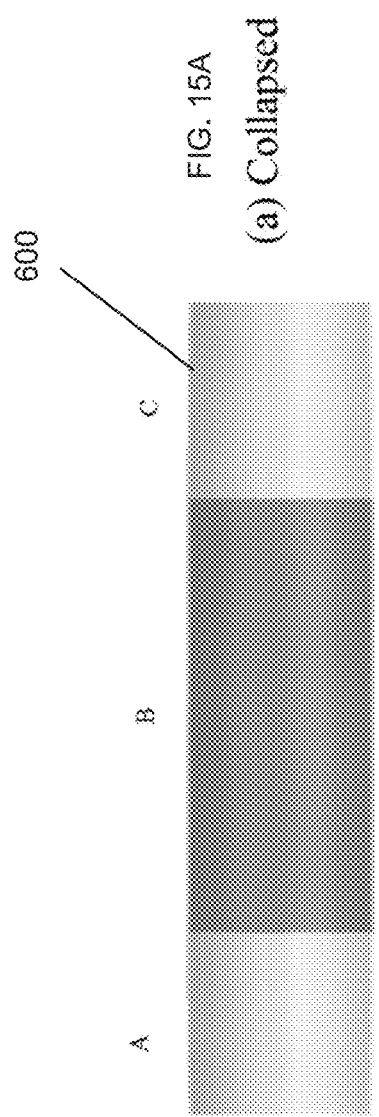
FIGS. 15A-15B schematically illustrate operating configurations of the hour glass configuration.
Figure 15B:
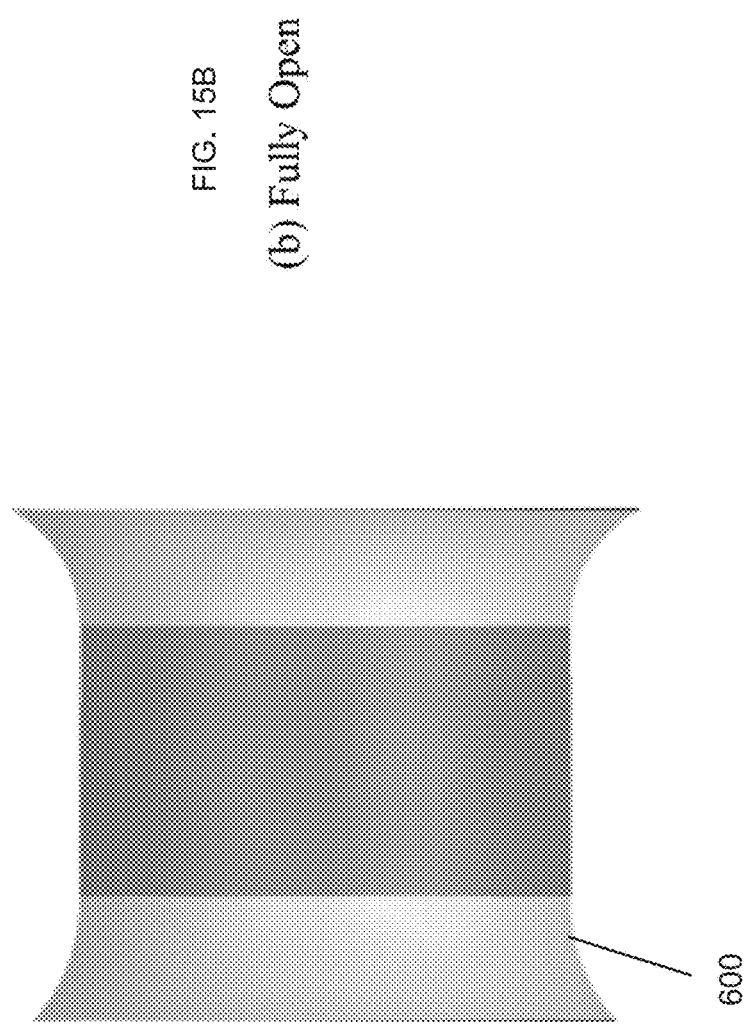

The contra-rotating impellers can provide various advantages. In some embodiments, two contra-rotating impellers result in maximum efficiency, minimum rotor rpm, and/or minimum hemolysis. In some embodiments, the downstream rotor reduces the swirling flow imparted by the upstream rotor in order to achieve near-axial downstream flow velocity, thus emulating the blood flow in healthy conditions of about one clockwise flow rotation downstream from aortic arch to renal arteries, while maximizing pumping efficiency, reducing impeller rpm, and reducing friction and turbulence from swirling flow downstream of the pump. In some embodiments, the pre-swirler and de-swirler struts optimize flow angles and turbomachinery efficiency. The structures of the struts may be shaped to open into 3D blades directing the flow in the desired direction FIGS. 15A-15B schematically illustrate operating configurations of the hour glass support 600. FIG. 15A illustrates a collapsed configuration. FIG. 15B illustrates an expanded configuration. The hour glass support 600 may include section A, section B, and section C. In some embodiments, each section is expandable. In some embodiments, sections A and section C flare outward.

FIGS. 16A-16C schematically illustrate positions of the gearmotor. FIGS. 16A and 16B illustrate an extra-corporeal motor or gearmotor. FIG. 16A illustrates a gearmotor and the anatomical position of the device. FIG. 16B illustrates an extra-corporeal motor. The extra-corporeal motor can be integral with its own speed-reducing gearbox. The controller can be extra-corporeal. The monitoring algorithm can be extra-corporeal. The display can be extra-corporeal. The lubricant pump can be extra-corporeal. One or more of the motor, controller, monitoring algorithm, display and lubricant pump can be integrated in a housing or unitary device. FIG. 16C illustrates a configuration in which the motor or gearmotor is placed in the vicinity of the pump head. The motor can be an intra-corporeal motor. The location of the device is illustrated. The device may be used with either an external motor design or an internal motor design. The motor can be positioned in the descending aorta. The flexible drive shaft or cables may be external. The control and power to the motor can be external. FIG. 16C illustrates an internal motor and an external supply of power, control, monitoring and display. The display can be connected via a cable via the femoral artery. In some embodiments, one or more of the power, control, or monitoring functions is intracorporeal.

FIGS. 17A-17D schematically illustrate stages of delivery. FIG. 17A illustrates insertion. During insertion, the hour glass support 600 may be compressed. During insertion, the blades may be folded. The MCS device 500 can be positioned within a sheath or larger catheter. The MCS device 500 may be guided into position with a smaller guide catheter. The guide catheter may be connected to a portion of the MCS device 500. The hour glass support 600 may be a PTFE-coated stent-like frame.

FIG. 17B illustrates opening. During opening, the hour glass support 600 may be partially expanded. The upstream end can be laterally expanded. During opening, the blades may be partially unfolded. The upstream impeller can be unfolded. The downstream impeller can remain folded. The MCS device 500 can be uncovered at least partially from the sheath or larger catheter. The sheath can be retracted. The sheath can be moved downstream.

FIG. 17C illustrates pumping. During pumping, the hour glass support 600 may be fully expanded. The upstream and downstream end of the stent-like frame can be laterally expanded. The hour glass support 600 can be anchored. During pumping, the blades of the two or more impellers may be fully unfolded. The upstream and downstream impellers can be unfolded. The MCS device 500 can be uncovered from the sheath or larger catheter. The sheath can be fully retracted. The contra-rotating impellers can be rotated to pump blood. The hour glass support 600 can maintain a desired gap between the blade tips and the support.

FIG. 17D illustrates removal. During removal, the hour glass support 600 may be partially compressed. The downstream end can be laterally compressed. During removal, the blades may be partially folded. The downstream impeller can be folded. The MCS device 500 can be covered at least partially from the sheath or larger catheter. The sheath can be advanced. The sheath can be moved upstream. The sheath can be reapplied. The motion of the sheath can compress the hour glass support 600. The motion of the sheath can fold the blades.

In some embodiments, the folding, hour glass support 600 can be designed such that one device fits all anatomic sizes. The pumping head of the MCS device 500 may be placed in an hour glass support 600 which has a relatively long waist section B. The hour glass support 600 may be made of memory-shape alloy so it can be collapsed or expanded. The hour glass support 600 may be covered by a biocompatible material so that blood does not flow through its sides. In some embodiments, the minimum internal diameter of the patient's aorta is 19-20 mm, and the maximum is 32 mm, though these exact dimensions may vary. Thus the internal diameter of the hour glass support 600 at the waist section B may be 19 mm, and the impeller diameters 18 mm, allowing for impeller tip to waist internal diameter gap of about 0.5 mm. The sections of the hourglass upstream and downstream of the impellers allow for the diameter variations in aorta from minimum of about 19 mm to a maximum size that can be 32 mm, or larger.

FIGS. 18A-18C schematically illustrate folding and unfolding of the blades and cage sections into the larger catheter. This concept can be used in both extra-corporeal and intra-corporeal motor embodiments described herein. In some embodiments, the folding and unfolding is better suited to the extra-corporeal motor. The distance between the upstream top of the drive shaft T to the contra-rotating gearbox G downstream is fixed. The hour glass support 600 comprises sections A, B and C. The hourglass shape of the hour glass support 600 has memory-shape alloy struts T.S. upstream and bottom struts B.S. downstream. In some embodiments, the struts at their hubs may have bearings, such as journal bearings. The downstream bearing may be integral to the gearbox, blood lubricated, or lubricated via biocompatible lubricant. Separately, the upstream bearing at the hub of top struts T.S. may blood lubricated, or with biocompatible lubricant.

In FIGS. 18A-18C, the top T and the bottom gearbox G are at the same positions. The hour glass support 600 is divided in three sections. Section B may be larger than the distance between the blades to accommodate different openings from maximum to minimum aorta inner diameter. In some embodiments, the hour glass support 600 forms a Nitinol frame. In some embodiments, struts attached to the hour glass support 600. At the center of the struts, the struts can carry journal bearings. In the widest aortic inner diameter, the bottom struts B.S. already set for insertion in catheter. If aortic inner diameter is smaller, than bottom struts B.S. are in an even better position to enter into catheter. Advantages include that there can be the same gap between the one or more rotors and the section B. Advantages include that there can be the same length between the tip T and the gearbox G. Advantages include that the segments are already positioned for insertion to catheter or sheath for blade folding and removal.

Figure 19A:
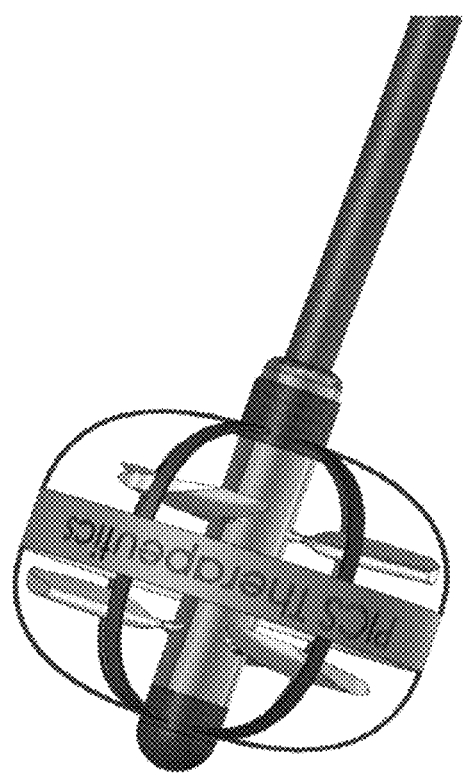
FIGS. 19A-19C schematically illustrate an extra-corporeal motor and associated gearbox for the pumping head.
Figure 19B:
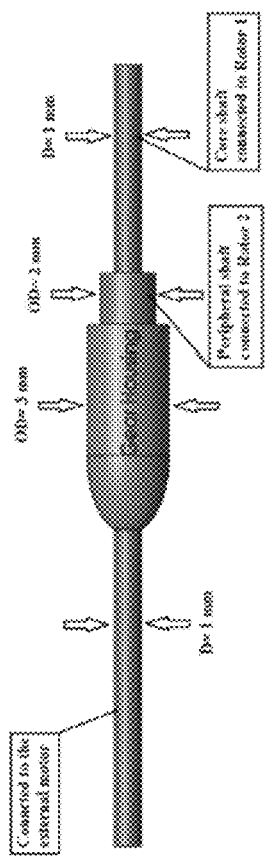
Figure 19C:
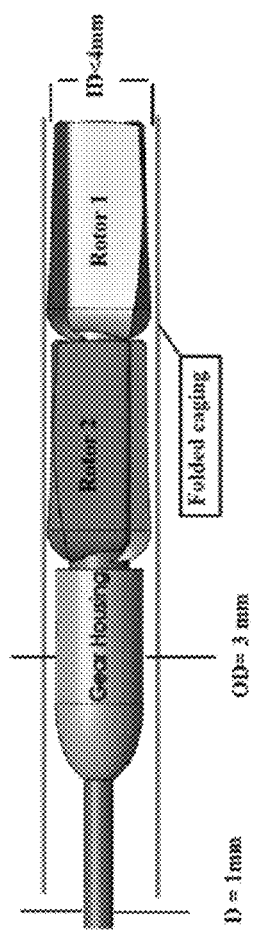

FIGS. 19A-19C schematically illustrate an extra-corporeal motor and associated gearbox for the pumping head. FIG. 19A is a perspective view and FIGS. 19B-19C are side views. The gearbox achieving contra-rotation may be upstream of the rotors, between the rotors, or downstream of the rotors. In FIGS. 19A-19C, the gearbox is downstream of the two rotors. The blades may be folded upstream or downstream. In FIGS. 19A-19C, the upstream folding configuration is illustrated. All dimensions are for illustration purposes only, and exact dimensions will vary, including that of the overall catheter. The gearbox is connected to an external motor. The gearbox can have a larger diameter than the shaft connected to the rotor. The peripheral shaft can be connected to one of the rotors (Rotor 2) and the core shaft can be connected to another rotor (Rotor 1). The support 600 is illustrated in FIG. 19C. The inner diameter of the support can be larger than the diameter of the rotors when folded.

Figure 20A:
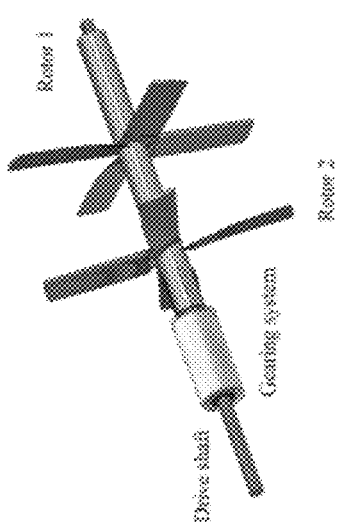
FIGS. 20A-20D illustrates the rotation of a peripheral shaft relative to the core shaft.
Figure 20B:
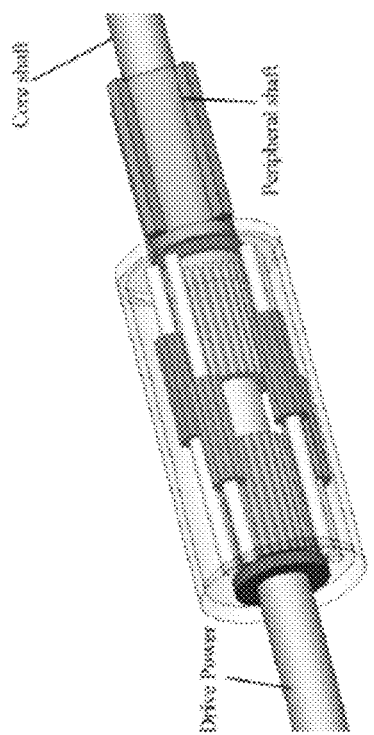
Figure 20C:
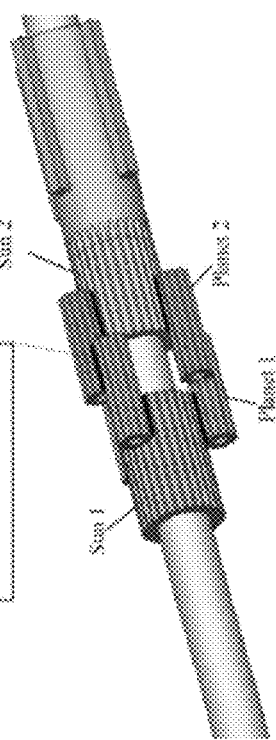
Figure 20D:
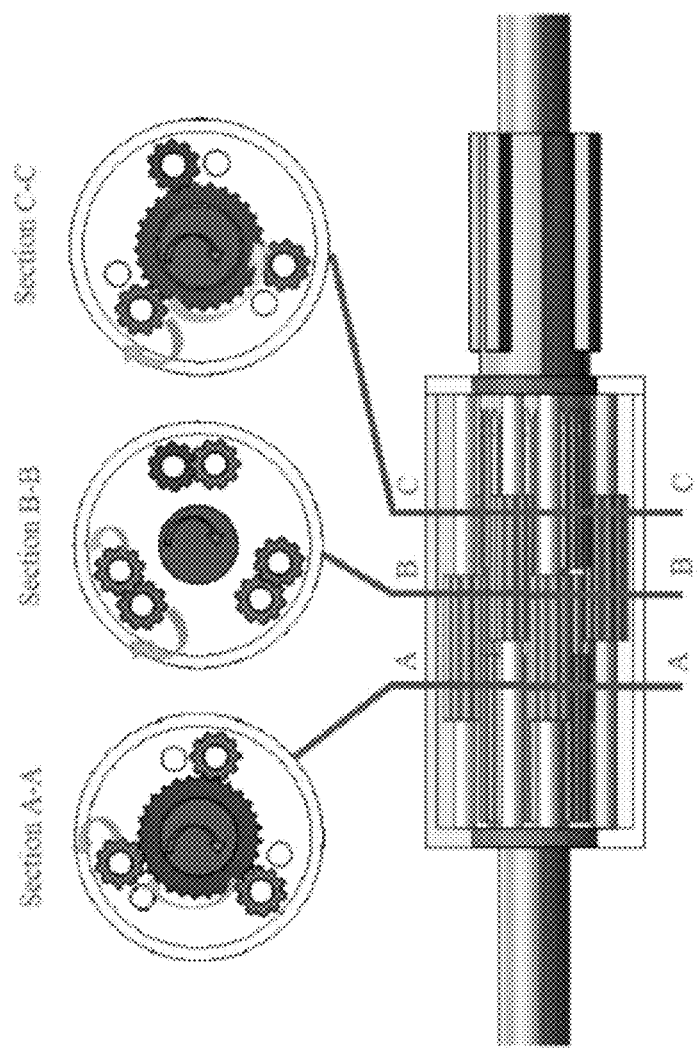
Figure 20E:
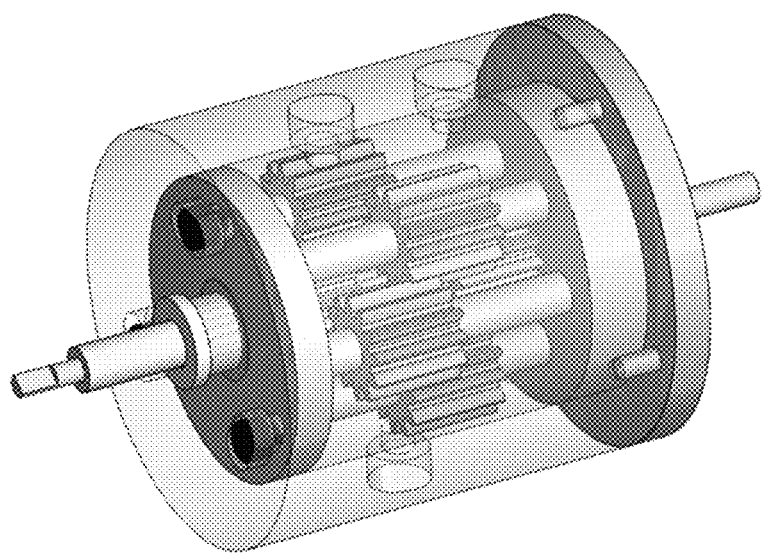
FIG. 20E illustrates another embodiment of a gearbox.

FIGS. 20A-20D illustrates the rotation of a peripheral shaft relative to the core shaft. The peripheral or key shaft may rotate in an equal and opposite direction to the core or hexagonal shaft. Two epicyclic gearboxes in series, like those used in the intra-corporeal motor embodiment described herein, may be used to achieve contra-rotation. In some embodiments, the gearboxes produce unequal impeller rpm. FIG. 20A illustrates the drive shaft, the gearing system, and the two rotors in a perspective view. FIG. 20B illustrates the gearing system. The drive power shaft extends from a first end of the gearing system. The core shaft and the peripheral shaft extend from the second end of the gearing system. The core shaft can have a first cross-sectional configuration and the peripheral shaft can have a second cross-sectional configuration, different than the first cross-sectional configuration. The core shaft can have a hexagonal configuration and the peripheral shaft can have a keyed configuration. FIG. 20B illustrates the gearing system with the casing removed. The two sun gears (Sun 1, Sun 2) are illustrated. The planet gears (Planet 1, Planet 2) are also illustrated. Rotation of the first sun gear (Sun 1) by the drive shaft causes contra-rotation of the second sun gear (Sun 2). The gear ratio can produce equal or unequal rpm. FIG. 20D illustrates three cross-sectional views of the rotation of the gear box. In section A-A, rotation of the Sun 1 causes rotation of Planet 1. In section B-B, rotation of the Planet 1 causes rotation of Planet 2. In section C-C, rotation of the Planet 2 causes rotation of Sun 2. In section A-A, rotation of the Sun 1 (clockwise) causes contra-rotation of Planet 1 (counterclockwise). In section B-B, rotation of the Planet 1 (counterclockwise) causes contra-rotation of Planet 2 (clockwise). In section C-C, rotation of the Planet 2 (clockwise). causes contra-rotation of Sun 2 (counterclockwise). FIG. 20D illustrates contra-rotation between Sun 1 and Sun 2. FIG. 20E illustrates another embodiment of an epicyclic gearbox.

Figure 21D:
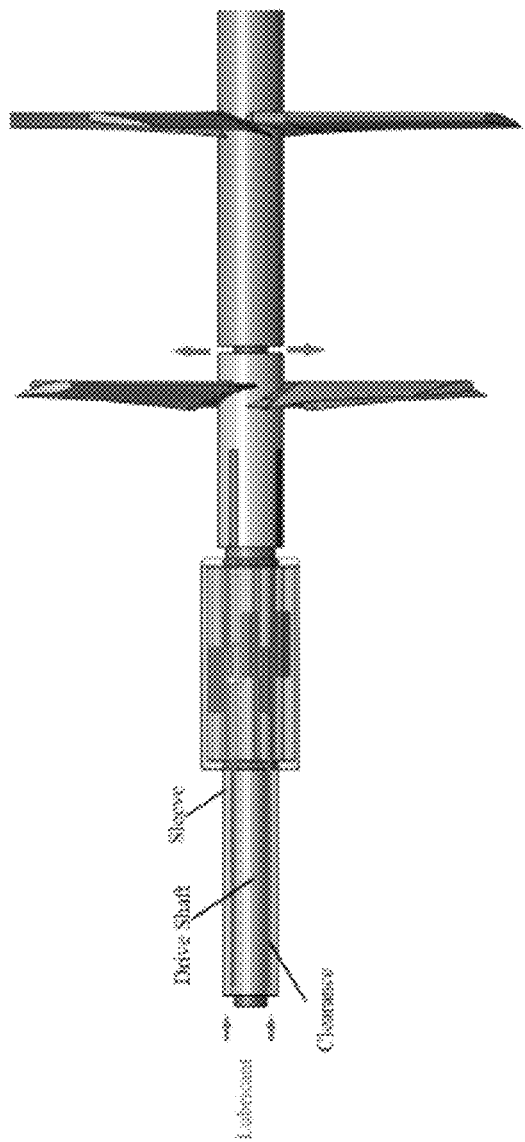

FIGS. 21A-21D illustrate lubrication and/or cooling with an extra-corporeal motor. With suitable choice of components, the device may run unlubricated. In some embodiments, a biocompatible fluid may be pumped to lubricate the components. In some embodiments, a biocompatible fluid may be pumped to cool the components. FIG. 21A illustrate the sealed journal bearings of the gearbox. FIG. 21A also illustrates the clearance between the peripheral shaft and the core shaft. FIG. 21B is another view. FIG. 21C illustrates the active lubricant passing through the device. The lubricant travels through the drive shaft and sleeve, through the gearing, and through the clearance. FIG. 21D illustrates the active lubricant passing through the device. The lubricant travels through the drive shaft and sleeve, through the gearing, and between the rotors. The rotor (Rotor 2) can allow the lubricant to pass through.

Figure 22C:
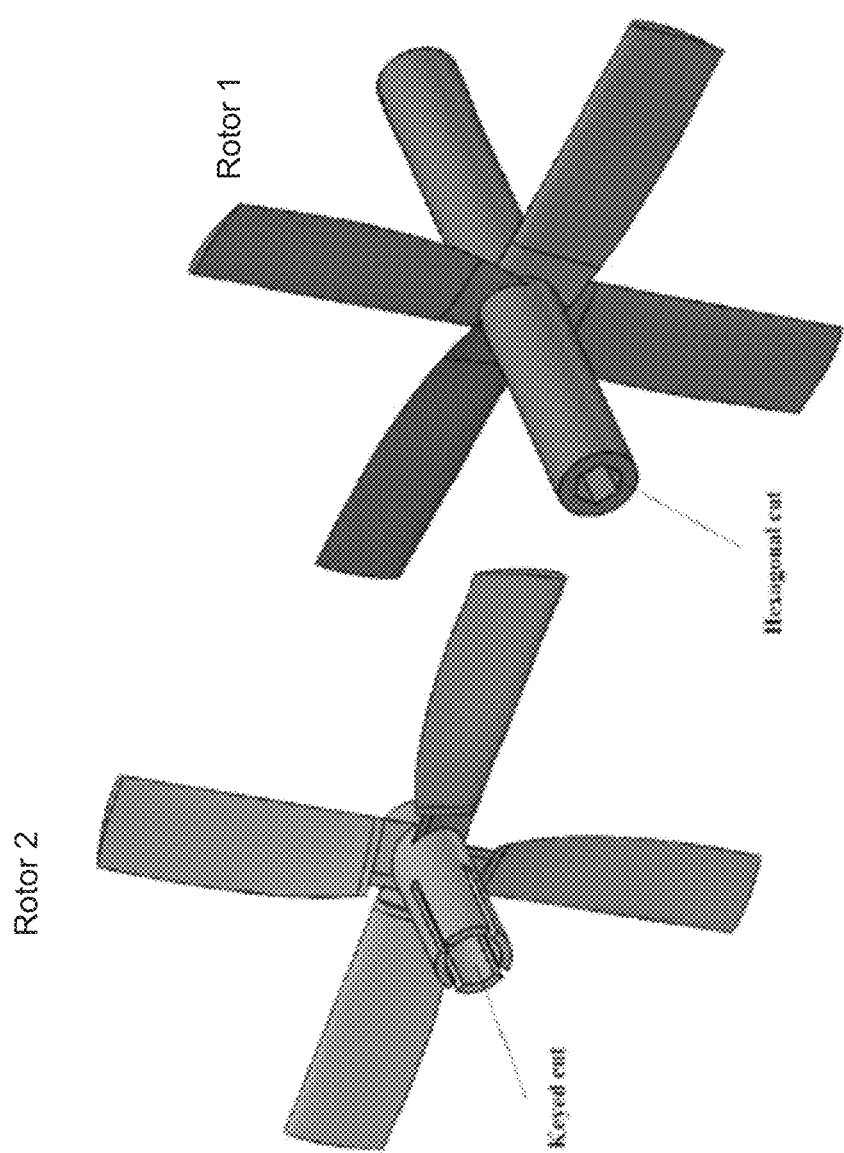

FIGS. 22A-22C illustrate bearings. The bearings may be any type of bearings. In some embodiments, the bearings are journal bearings. FIG. 22A illustrates the shaft, the gearing system, and the rotors (Rotor 1, Rotor 2). FIG. 22B illustrates the shafts. The drive shaft may be circular shaft. The bearing may be coupled to the circular shaft. The peripheral shaft may be keyed. The core shaft may be hexagonal. The device may include a circular tip. The bearing may be coupled to the circular tip. FIG. 22C illustrates the rotors. The rotor (Rotor 2) may include a keyed cut. The keyed cut may couple with the keyed shaft. The rotor (Rotor 1) may include a hexagonal cut. The hexagonal cut may couple with the hexagon shaft. The core shaft, the peripheral shaft, and the rotors may have any configuration to allow the components to couple and transmit rotation and/or torque.

Figure 23A:
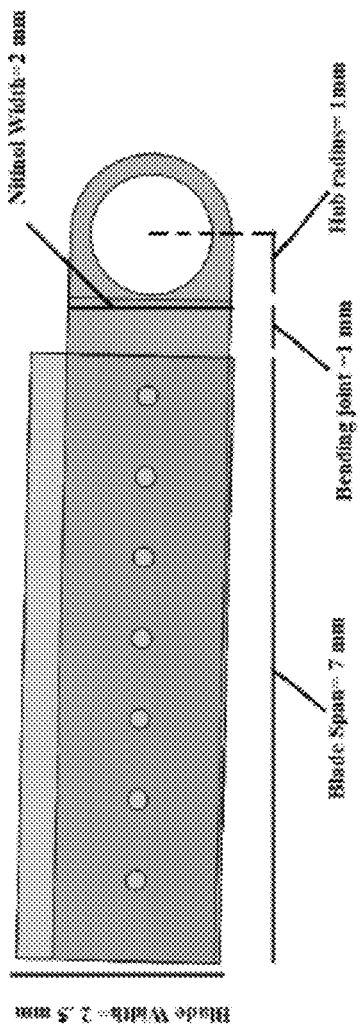
FIGS. 23A-23B illustrate bending blades.
Figure 23B:
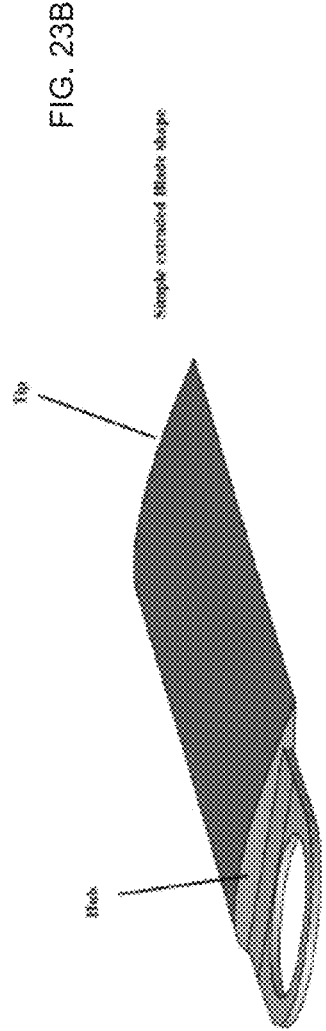

FIGS. 23A-23B illustrate embodiments of bending blades. The blades may be connected to the hub with thin segments of memory-shape alloy. In some embodiments, the memory-shape alloy is Nitinol. The memory-shape alloy can bend to insert in the catheter sheath for insertion, deploy and spring in the open position for operation, and then bend again for folding, recovery and removal. In some embodiments, the segment of the connecting part is made of appropriate shape to be fully inserted and not protrude out of the surface of the 3-dimensional blade. FIG. 23A illustrates a top view of the blade. The memory-shape alloy can extend along a portion of the length of the blade or the entire blade. FIG. 23B illustrates an embodiment of an extruded blade shape. The blade may have a twist along its span for fluid dynamic reasons. The connecting shape can be referred to as the dagger. The dagger is affixed to the hub at one end, and to the blade at the other.

Figure 24D:
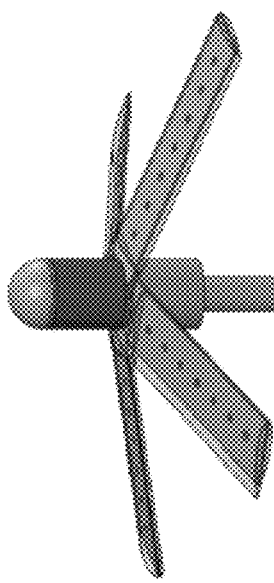
Figure 24E:
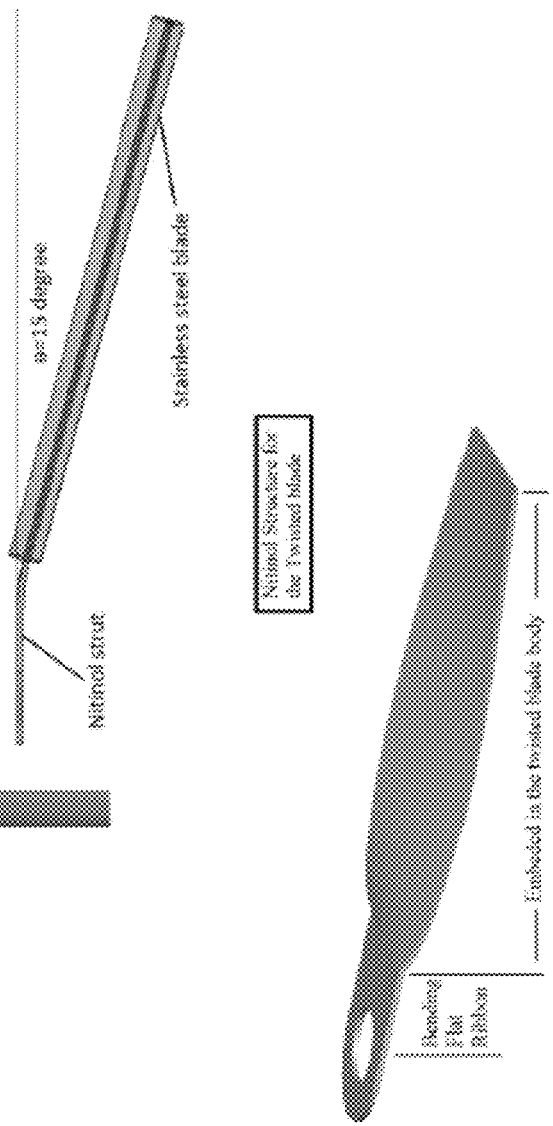
Figure 24F:
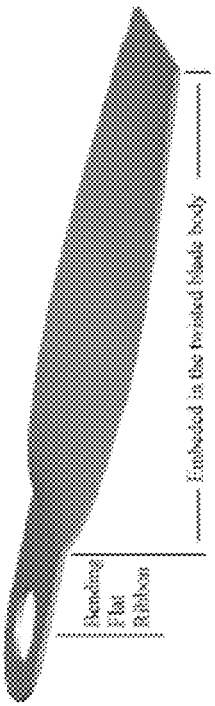

FIGS. 24A-24F illustrate blade deflection upstream and downstream. As the dagger is flexible, during operation the daggers and attached blades may be deflected upwards by the hydrodynamic force. For that reason the daggers in the relaxed position may be deflected downstream, for example by 15 degrees, in order to bring the blades to a horizontal position during normal operation. FIG. 24A illustrates the hydrodynamic force and the centrifugal force when the rotor is rotating. FIG. 24B illustrates the blades folded. The daggers are folded enabling the blades to fold. The blades are folded approximately 90 degrees. FIG. 24C illustrates the blades in relaxed position. This position may be the position of the blades before rotation. The blades may be deflected downstream, for example by 15 degrees. Other angles are contemplated, for example 5 degrees, 10 degrees, 15 degrees, 20 degrees, 25 degrees, or any range of the foregoing values. FIG. 24D illustrates another view of the blades in the relaxed position. The Nitinol struts are manufactures at about 15 degrees downward in the unrestrained original configuration. FIG. 24E illustrates the strut and the blade. The blade extends downward at approximately a 15 degree angle. The blade and the strut can be formed of different materials. The strut can be formed of a shape memory material such as Nitinol and the blade can be formed of a more rigid material such as stainless steel. The strut can bend to allow folding of the blade. FIG. 24F illustrates an embodiment of a Nitinol structure for the twisted blade. The structure can include a bending flat ribbon. The ribbon can allow the blade to fold. The structure can include a twisted structure to be embedded in the twisted blade body. The twisted structure can follow the bend of the blade such that the twisted structure is completely embedded. The ribbon can protrude from the blade.

Figures 25A, 25B:
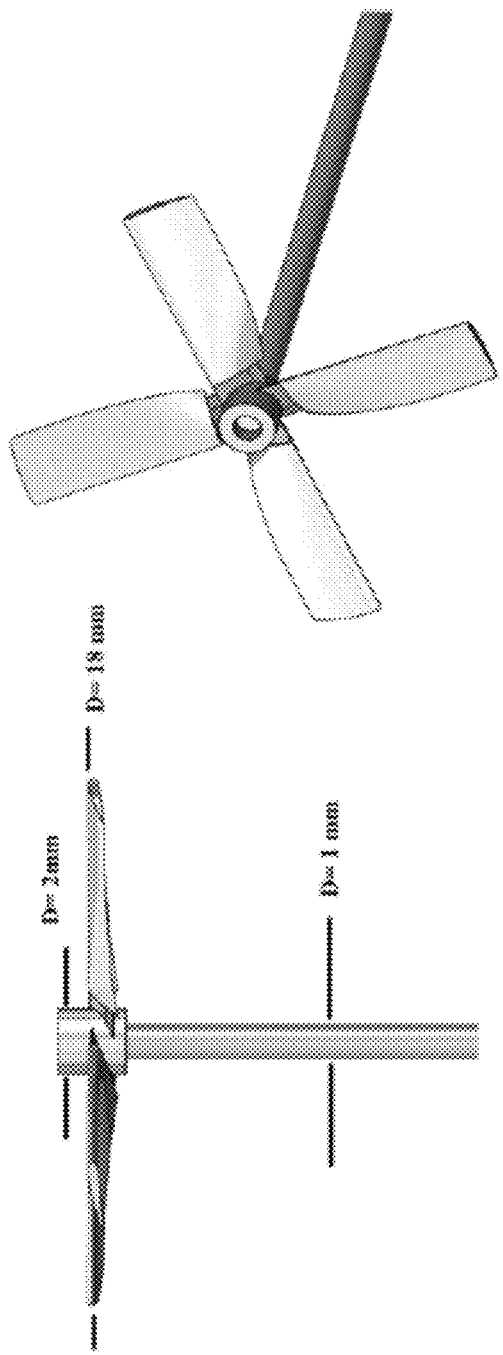
FIGS. 25A-25E illustrate blade folding.
Figure 25E:
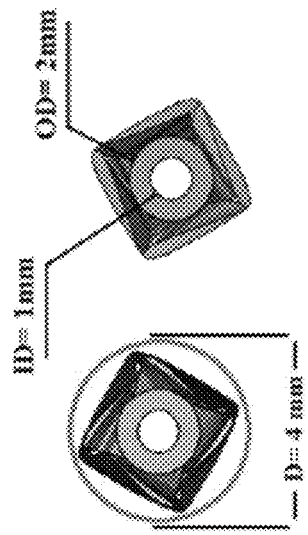
Figure 25D:
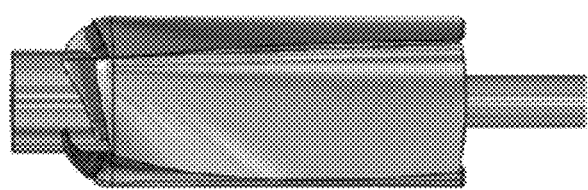
Figure 25C:
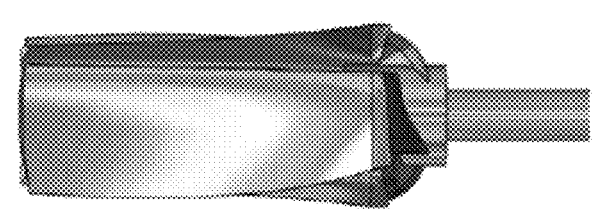

FIGS. 25A-25E illustrate blade folding. FIGS. 25A-25E illustrate approximate dimensions with blades folding upstream or downstream. The daggers may be affixed at an angle to the hub are shown, or may be affixed orthogonal to the hub. FIG. 25A illustrates the blade with an orthogonal dagger. FIG. 25B illustrates another view of FIG. 25A. FIG. 25C illustrates the blades folded upwards. FIG. 25D illustrates the blades folded downwards. FIG. 25E illustrates top and bottom views of the folded blades. In some embodiments, the blades can only fold in one direction, e.g., either upward or downward. In some embodiments, the blades can fold in both directions.

Figure 26E:
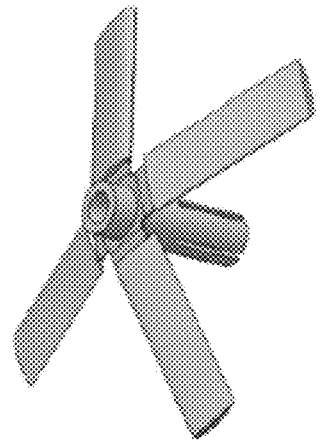
Figure 26D:
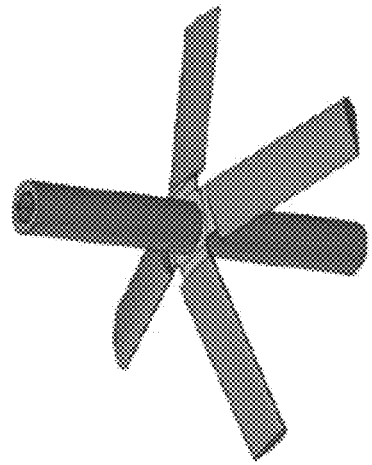
Figure 26F:
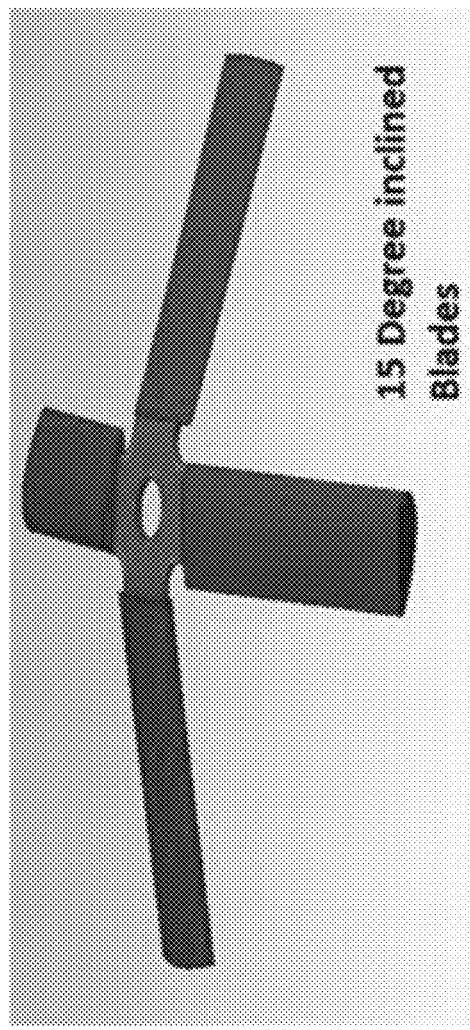

FIGS. 26A-26F illustrate blade construction. The daggers may be constructed in layers of Nitinol or other materials. The daggers may be constructed of layers of selected shapes. The layers may have different cross-sections to accommodate requirements of shear stress in bending, folding and unfolding. The layers may have different cross-sections to accommodate requirements of normal stress in joints to the blade and hub. The layers may have different cross-sections to accommodate requirements of selective weakening for bending. The layers may have different cross-sections to accommodate requirements of shape constraints for insertion of the 3D blades. The daggers may be two-dimensional, orthogonal to the hub axis, or twisted. FIG. 26A illustrates an embodiment of the layer construction. FIG. 26A illustrates four daggers that can be connected to four blades. The central opening can couple to a rotor. FIG. 26B illustrates the hubs of the rotors. Rotor 1 may include a hexagonal cut and Rotor 2 may include a keyed cut. FIG. 26C illustrates the dagger coupled to a rotor. The dagger may include highly twisted Nitinol ribbons to be accommodated into the blades. The blades can be formed onto the dagger in any manner known in the art or the dagger can be inserted into the blades. FIG. 26D illustrates the two rotors with the blade assemblies. FIG. 26E illustrates the inclined blades. The dagger can position the blades at a tilt. In some embodiments, the blades are positioned at a 15 degree inclined angle.

Figure 27:
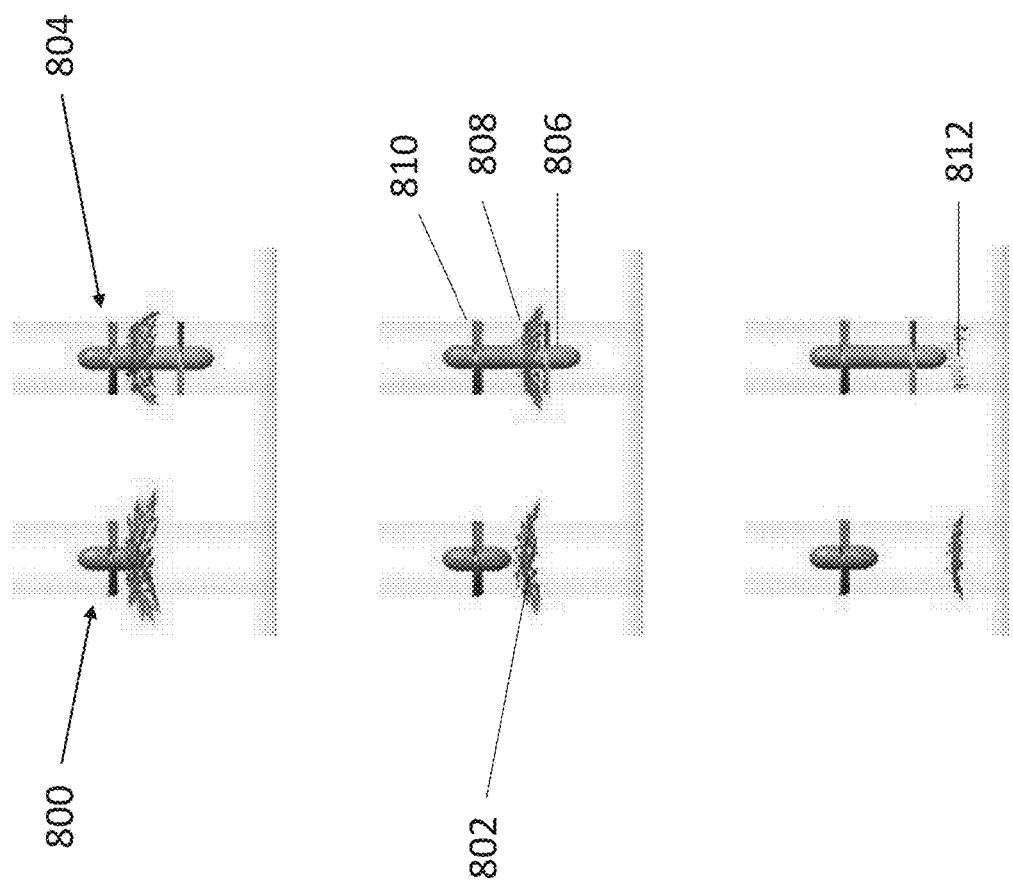
FIGS. 27-155 illustrate additional impeller and component concepts.

The case of axial impellers in a cylindrical flow passage is shown in FIG. 27. FIG. 27 shows an example embodiment of impellers. A single impeller 800 (left side) imparts a vortex pattern 802 downstream of the impeller. The vortex pattern 802 continues down the cylindrical flow passage. An impeller system 804 which incorporates a second contra-rotating impeller 806 (right side) substantially removes the vortex pattern 808 that is generated downstream of the first impeller 810. The contra-rotating impeller 806 establishes a substantially axial flow 812. Flow 812 is primarily in the axial direction, with little or no rotation, thus maximizing pressure rise and efficiency.

The results can be similar for the case of helical screw impellers, in some embodiments. A single helical screw impeller may tend to generate a flow with a substantial vortex pattern which can continue downstream of the impeller. A helical screw impeller with a contra-rotating impeller can correct this flow resulting in a primarily axial flow.

FIGS. 28A-28C show two dimensional velocity diagrams related to the impeller system 804. The nomenclature used by Wilson and Korakianitis (2014) is used here. C: absolute velocity vectors; CU: tangential component of absolute velocity vector; U: rotor tangential velocity vectors: W: relative velocity vectors; 1: inlet to upstream rotor; 2: outlet of upstream rotor; 3: inlet to downstream rotor; 4: outlet of downstream rotor.

The velocity diagrams show axial inflow and outflow velocity vectors C1 and C4, in cases where the rotors are rotating at equal revolutions per minute (U1=U2), or at not equal revolutions per minute (U1 not equal to U2).

FIG. 29 illustrates the case where the absolute velocity C4 has a tangential component of velocity CU4 creating a relatively weak vortex flow pattern downstream of the impeller. The weak downstream vortex flow emulates healthy physiological conditions. This concept is further explained below.

Figure 30:
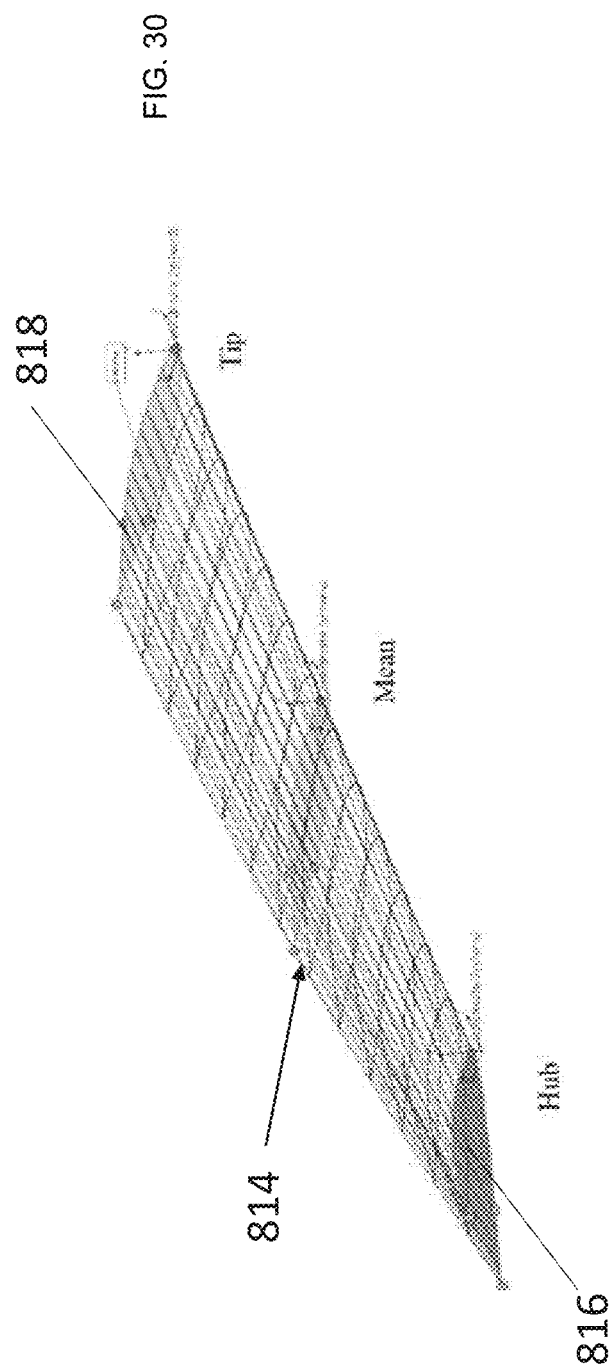

FIG. 30 depicts an example embodiment of a blade 814. In this embodiment, the velocity diagram and blade angles vary from hub 816 to tip 818 to meet radial equilibrium and de Haller ratio considerations. In some embodiments, the 2D cross-section of the blade 814 may remain invariant from hub to tip.

Figure 31:
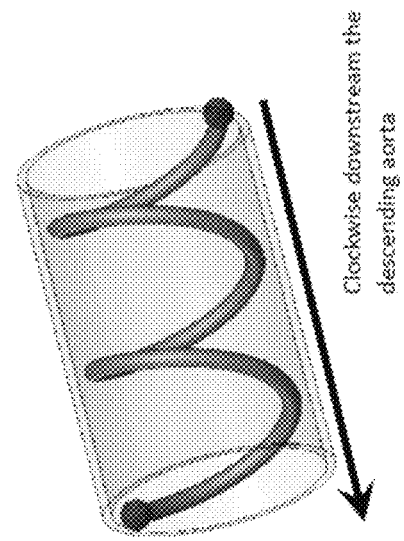

An example vortex flow pattern with tip diameter of, for example, between about 18-20 mm is shown in FIG. 31. The hub to tip distribution of flow angles and subsequent blade angles of an impeller can be designed to provide a downstream velocity component C4 that is slightly off the axial direction, such that velocity component C4 includes a small tangential component of velocity. The small tangential component of velocity may provide near healthy physiological flow. To exhibit a near healthy physiological flow, C4 may exhibit 1-3 rotations of the blood in about 30 cm length of descending aorta and exhibit an internal helical flow structure, as illustrated in FIG. 31. While FIG. 31 shows a particular example of a vortex flow pattern approximating a healthy physiological flow, many different vortex flow patterns may approximate a healthy physiological flow. Such vortex flow patterns may have a different number of turns in 30 cm at the tip, near the tip, near the mean, and near the hub. Correspondingly, while FIG. 31 shows a particular distribution of radius at the tip, near the tip, near the mean, and near the hub for a vortex flow pattern which approximates a healthy physiological flow, different dimensions may also correspond to a vortex flow approximating a healthy physiological flow. In some embodiments, there may be 3 helical patterns at the tip, 2 in the mid-section of the blades, and 0.5 in the hub section of the blades, all in the same length of aorta, e.g., a different number of helix hub to tip of blades.

Figure 32:
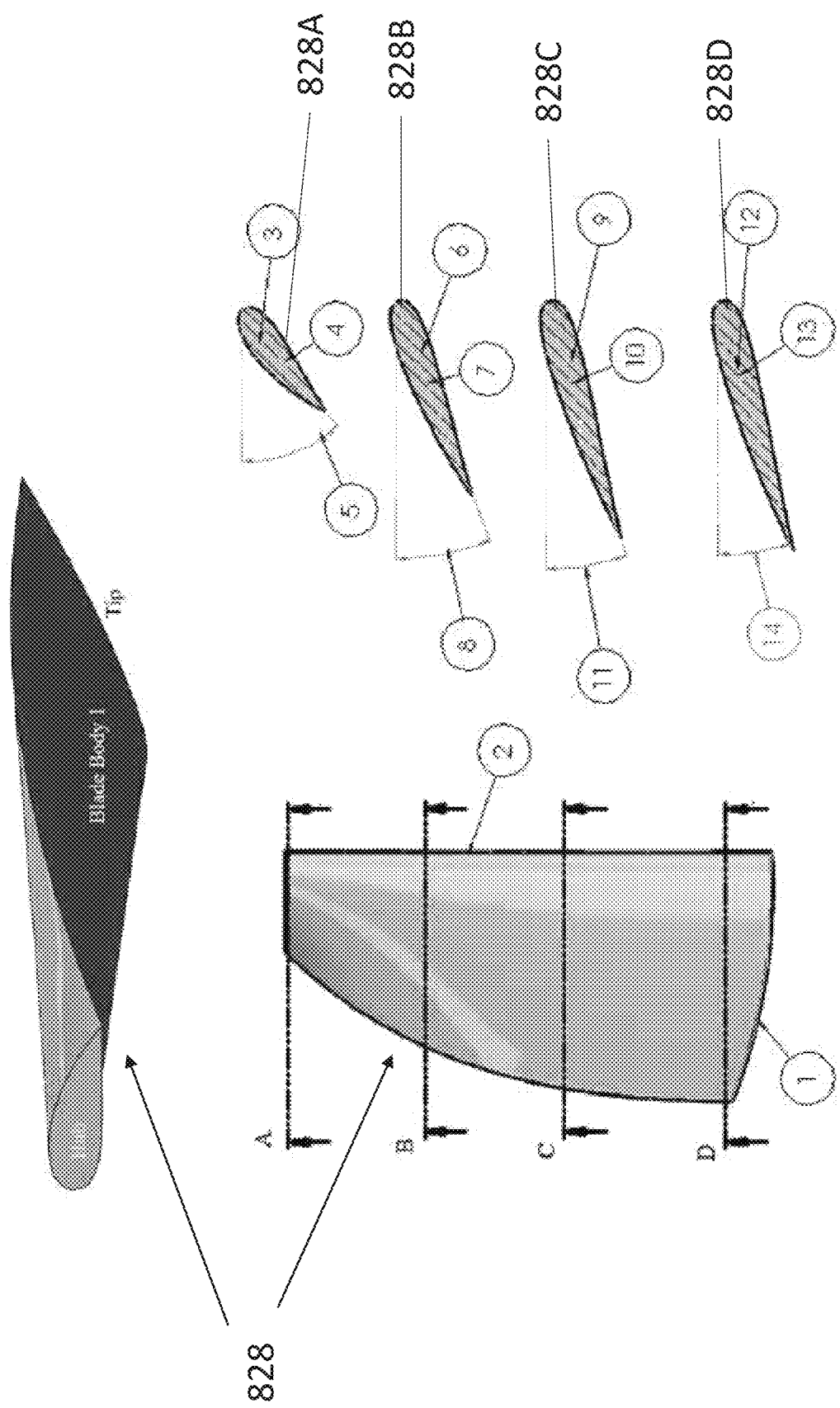

FIG. 32 depicts an example embodiment for an upstream rotor 828. The cross-sections A, B, C, and D are shown to the right of the rotor 828. While the depicted geometry distribution may be typical, other geometry distributions may be used. In some embodiments, the chord length variation from hub to tip may be increasing. In some embodiments, the chord length variation from hub to tip may be decreasing. In some embodiments, the chord length from hub to tip may be constant. In FIG. 32 the cord length is shown as increasing from the hub to the tip. Similarly, the leading edge may be radially curved as shown in FIG. 32. The leading edge can follow any curve.

Figure 33:
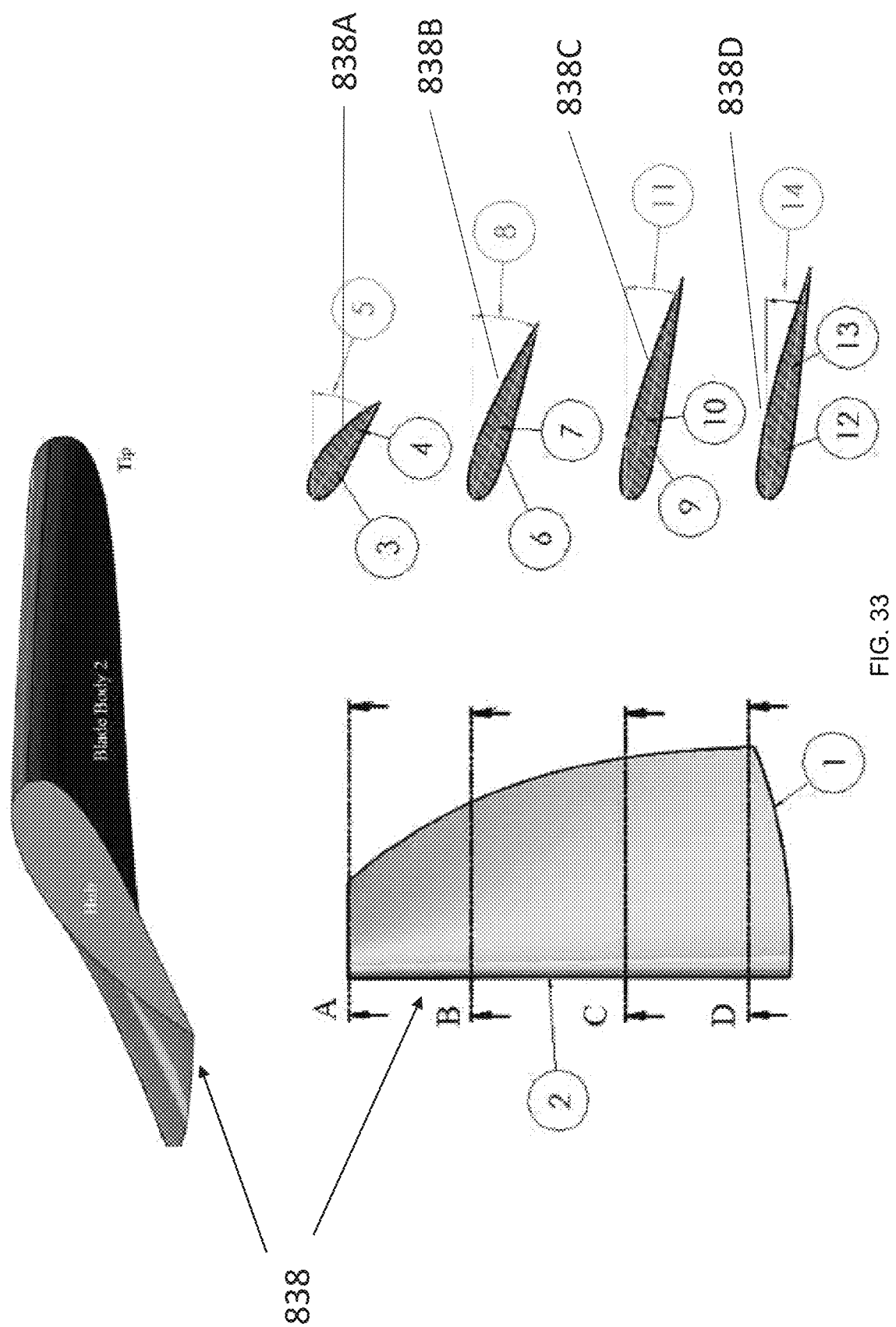

FIG. 33 depicts an example embodiment for a downstream rotor 838. The cross-sections A, B, C, and D are shown to the right of the rotor 838. While the depicted geometry distribution may be typical, other geometry distributions may be used. In some embodiments, the chord length variation from hub to tip may be increasing. In some embodiments, the chord length variation from hub to tip may be decreasing. In some embodiments, the chord length from hub to tip may be constant. In FIG. 34 the cord length is shown as increasing from the hub to the tip. Similarly, the leading edge may be radially curved or can follow any curve.

The depicted downstream rotor 838 corresponds to the depicted upstream rotor 828. The depicted downstream rotor 838 is not symmetric to the depicted upstream rotor 838. This difference is related to the relative flow vectors W1 to W4 in the velocity diagrams shown in FIGS. 28A, 28B, 28C, and 16 being not-symmetric).

In some embodiments, the flow diagrams and blade shapes may be chosen so that the upstream rotor 828 and downstream rotor 838 provide equal pressure rise. In some embodiments the upstream rotor 828 may be designed to provide higher, pressure rise than the downstream rotor 838. In some embodiments the upstream rotor 828 may be designed to provide lower pressure rise than the downstream rotor 838.

FIGS. 34, 35, and 36 depict an embodiment of a uni-rotor design. This design includes at least one blade row 848. This blade row 848 may be an impeller. The blade row 848 may be configured to fold inside a collapsible impeller cage 850. The collapsible cage inlet 852 and outlet 854 are shown secured in the inner diameter of the blood vessel 856. In some embodiments there is a pre-swirler membrane 858 upstream of the blade row 848. In some embodiments there is a de-swirler membrane 860 downstream of the blade row 848. The pre-swirler 858 and de-swirler 860 membrane carry the requisite forces by their securement between the axle 862 of the blade row and the collapsible impeller cage 852. The pre-swirler 858 and de-swirler 860 membranes may have a skeleton of memory alloy lattice covered by a biocompatible material like PTFE or may be made by thin sheets of 2D printed memory-shaped material, metal or plastic, like nitinol. In some embodiments, a membrane can include a flexible fine netting of memory-shaped material, metal or plastic, like nitinol used as a cover over the blade frame. In some embodiments, the membrane can include a biocompatible material netting. The nettings can be porous and flexible, but no blood can go through in some cases. In some embodiments there is a flexible shaft 862 carrying the rotational motion to the impeller 848 from an extra-corporeal motor. The device 846 may be collapsed into a sheath for removal and implantation as further described elsewhere herein.

FIG. 37 shows an example embodiment with contra-rotating rotors 872 and 874. These rotors may be driven by two concentric contra-rotating shafts. In one scenario the blades are collapsible and are installed in a collapsible hourglass cage frame. The frame can, in turn be installed in a descending aorta. The installation is further described later and can be similar to the installation process used for a uni-rotor design such as described in connection with the device 846.

FIGS. 38A, 38B, 39A, and 39B depict fluid flow in cases where the shaft 884 diameter is small. In these cases, the hydrodynamic blade loading near the hub becomes too high and the flow locally separates. The local separation induces recirculation flow regions 886 near the hub 888. Similar flow recirculation regions may occur near the hubs of foldable blades. The recirculation regions 886 reduce the efficiency of the impeller system. These recirculation flow regions can be removed by increasing device rpm. Alternatively, the recirculation regions can be removed with the addition of a second set of smaller-diameter impellers downstream of the main impellers. These smaller impellers may be axial impellers, or helical screws.

Figure 40A:
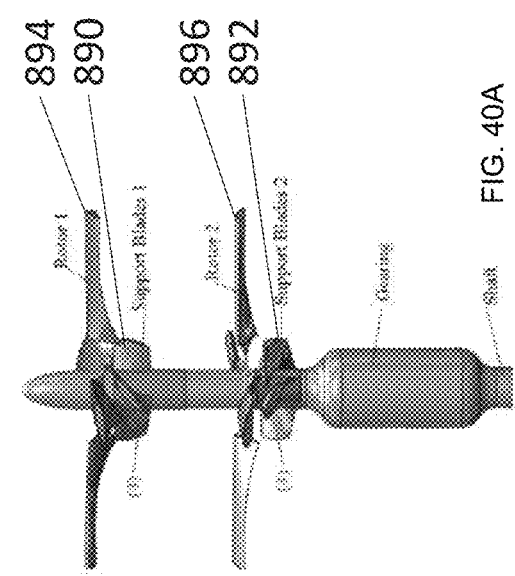
Figure 40B:
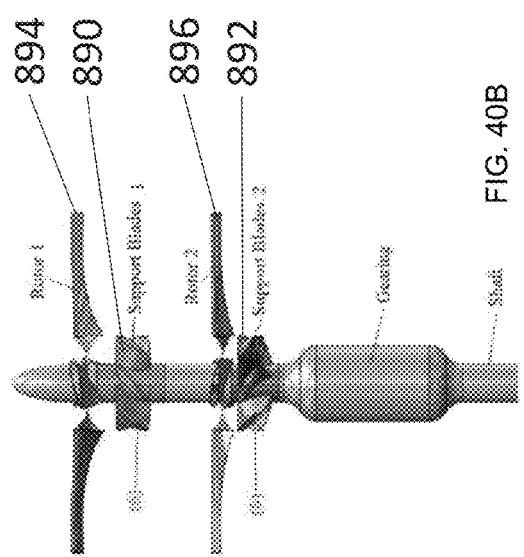

FIGS. 40A and 40B depict an embodiment of a contra-rotating impeller system 898 with first blades 890 and second blades 892. The blades can eliminate the separation region near the hub. The blades can function the same as the helical screws, described herein.

The blades 890 and 892 can be a second set of rotor blades with a tip diameter less than the tip diameter of the main blades 894 and 896. The blades 890 and 892 may be placed immediately downstream of the main contra rotating rotors to improve flow conditions near the hub. This arrangement helps to prevent back flow and separated flow regions.

The blades 890 and 892 may, in some embodiments be at the same azimuthal position as the main blades 894 and 896 located upstream. In some embodiments, the blades 890 and 892 may have a different azimuthal position then the main blades 894 and 896. As shown in FIG. 40A, the blade count on the support blades 890 and 892 may be the same as the main blades 894 and 896. As shown in FIG. 40B, the blade count on the blades 890 and 892 may be different than the main blades 894 and 896. In some embodiments the blades 890 may have the same blade count at the support blade 892. In other embodiments the blade count of blades 890 may vary from the blade count of support blade 892.

Figure 43:
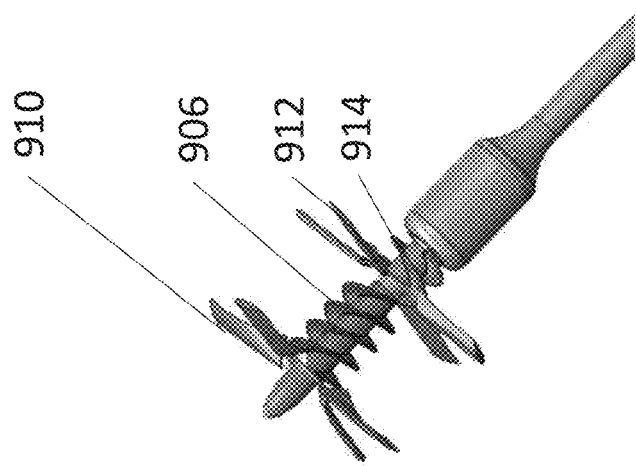
Figure 41:
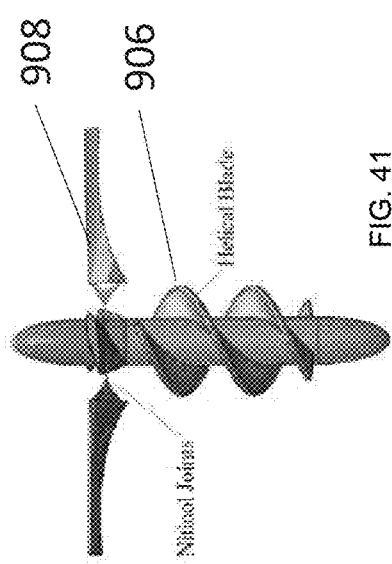
Figure 42:
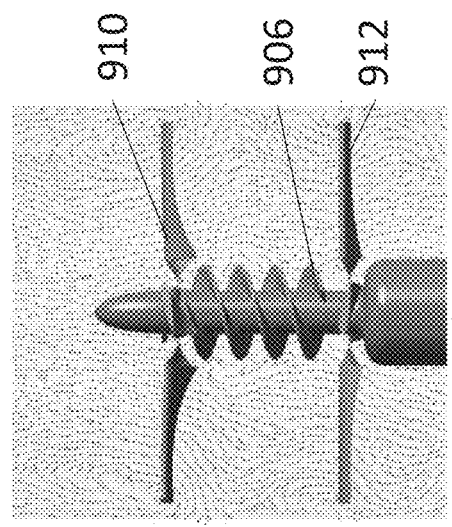

FIG. 41, 42, 43 depict an alternative arrangement. In FIG. 41 the depicted arrangement includes a helical secondary blade 906 positioned downstream of one main impellers 908. FIG. 42 depicts a helical secondary blade 906 positioned between two contra-rotating impellers 910 and 12. FIG. 43 depicts a helical secondary blade 906 located between contra-rotating impellers 910 and 912, it further depicts a second shorter helical secondary blade 914 locater downstream of the impeller 912. All of these arrangements can potentially function to provide a better flow condition near the hub, thereby reducing or preventing backflow and separated flow regions. The arrangement and geometry of the helical blades in absolute, and relative terms can vary. The revolution, pitch and number of the helical blades can all vary.

FIGS. 44A and 44B depict different arrangements with a combined helical blade 906, 914 and contra-rotating impellers 910, 912. The number of blades, on the helical screws 906, 914, can vary. The revolution and pitch characteristics of the helical screws 906, 914 may also vary. The helical screw 906 located between the contra-rotating blades, and the helical screw 914 located after the contra-rotating blades may have different helical screw characteristics including the pitch, revolution, step, and number.

As shown is FIG. 45, in some embodiments smaller helical screw 906 diameter, allows upstream folding of the blades. In this example embodiment the helical screw 906 and helical screw 914 have different diameters.

FIG. 46 and FIG. 47 depict example embodiments of a epicyclic gearboxe system 924 having a sun gear 926, which is surrounded by planet gears 928. The planet gears, or pinions, 928 can be connected to each other via a planetary carrier 930. In the depicted embodiment, the ring gear 932 surrounds the planet gears 928. In the depicted embodiment, the planetary carrier 930 fixes the locations of the planet gears 928 relative to each other. In the depicted embodiment, the internal teeth of the ring gear 932 mesh with the teeth on the planet gears 928. In the depicted embodiment, the teeth on the sun gear 926 mesh with the teeth on the planet gears 928.

During operation, when the sun gear 926 is rotated clockwise and the planetary carrier 930 is held stationary, the planet gears 928 move counterclockwise. The center of the planetary gears 928 do not move relative to the sun gear 926. In this configuration, the ring gear 932 turns clockwise. This mode of operation is depicted on the right side of FIG. 47. This configuration is sometime referred to as a star arrangement 934. The input and output shafts of the star arrangement 934 rotate in the same direction. This type of rotation can be referred to as co-rotation. In some embodiments, the input shaft may be connected to the sun gear 926. In some embodiments, the input shaft may be connected to the ring gear 932. In some embodiments, the output shaft may be connected to the sun gear 926. In some embodiments, the output shaft may be connected to the ring gear 932.

A second configuration is shown on the left side of FIG. 47. When the sun gear 926 is rotated clockwise and the ring gear 932 is held stationary, the planet gears 928 spin in counterclockwise around the sun gear 926. The centers of the planet gears 928 rotate around the sun gear 926. This motion results in a force turning the planet carrier 930 clockwise. This configuration is called the planetary arrangement 936. In the planetary arrangement and the input and output shafts rotate in opposite directions. This type of rotation is sometimes called contra-rotation. In some embodiments, the input shaft may be connected to the sun gear 926. In some embodiments, the input shaft may be connected to the planet carrier 930. In some embodiments, the output shaft may be connected to the sun gear 926. In some embodiments, the output shaft may be connected to the planet carrier 930.

There are many other simpler and more complex arrangements of epicyclic gearboxes, some of which are described elsewhere herein. Epicyclic gearboxes can achieve higher gear ratios than simpler gears of the same size and weight. Variants of the epicyclic gearbox have been used in many applications. Applications employing epicyclic gearboxes include automotive differentials, marine gears, clockmaking, aerospace applications, gearing the output rpm of electric motors, etc. To the inventors' knowledge, epicyclic gearboxes have not been used to vary the rpm and direction of rotation of heart-assist pump impellers, nor been applied in heart assist pumps of any type.

Epicyclic gears are advantageous in the context of heart-assist pumps to achieve contra-rotation of upstream and downstream impellers. Some advantages of contra-rotating impellers can be described elsewhere herein.

FIG. 48 depicts various example embodiments of contra-rotating rotor systems. In some embodiments, the upstream rotor 946 and downstream rotor 948 could be contra-rotating at equal rpm. In some embodiments the upstream rotor 946 and downstream rotor 948 could be contra-rotating at unequal rpm. In an example embodiment, the contra-rotating rotors are installed in the waist section of a collapsible hourglass-shaped cage frame. This arrangement is further described elsewhere herein.

In some embodiments, the gears 950 may be upstream of rotors. In some embodiments, the gears 950 may between rotors. In some embodiments, the gears 950 may be downstream of rotors. In some embodiments, the gears 950 may be epicyclic gears. In some embodiments, gears 950 that are downstream of the rotors are intra-corporeal. In some embodiments, gears 950 that are downstream of the rotors are extra-corporeal. In some embodiments, the motor driving the gears G may be intra-corporeal. In some embodiments, the motor driving the gears G may be extra-corporeal. In some embodiments, gears 950 that are upstream of the rotors may be fixed to a caging. In some embodiments, gears 950 that are between the rotors may be fixed to struts 952. Struts 952 may be fixed to a caging. In some embodiments, gears 950 that are downstream of the rotors may be fixed to a housing of a flexible shaft.

Figure 49:
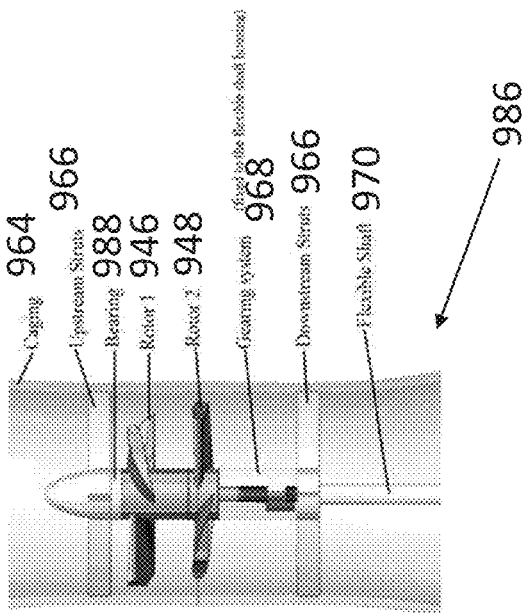

FIG. 49 depicts an example embodiment of an impeller system 962, also known as a pump head 962. Depicted in the figure are an upstream rotor 946, downstream rotor 948. Rotors 946 and 948 are fixed to an hourglass shaped caging 964 via struts 966. Upstream of the two rotors in an internal gearing 968. Driving the rotors 946 and 948 is the flexible shaft 970. The flexible shaft 970 is connected to the intra-corporeal pump head 962. The flexible shaft 970 travels trans-corporeally to connect to extra-corporeal components. The extra-corporeal components include a gearhead 972 coupled to a motor 974. The motor 974 is functionally connected to a controller 976. In some embodiments, the internal gearing 968 may be an epicyclic gear. This embodiment may be an example of upstream gearing with an extra-corporeal motor.

Figure 50:
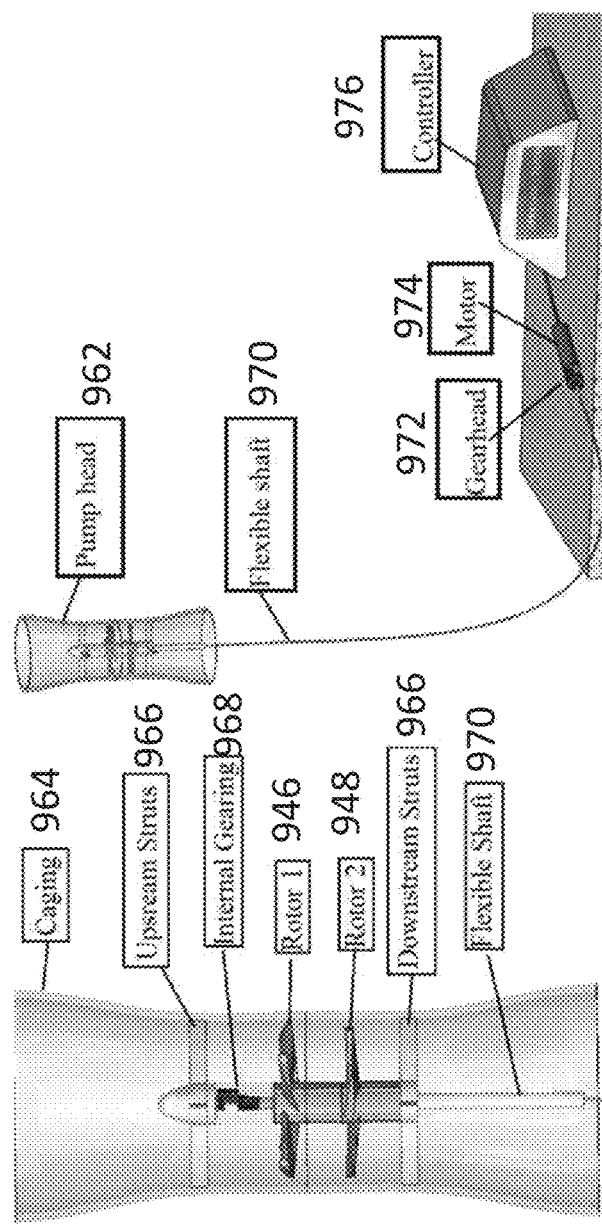

FIG. 50 depicts an example embodiment of downstream gearing with an extra-corporeal motor. This figure shows an intra-corporeal pump head 986. This pump head is similar to the pump head 962 with a few differences. A main difference is that the gearing system 968 is downstream of the Rotors 946 and 948. The depiction of pump head 986 includes a bearing 988 positioned between the rotor 946 and the upstream struts 966.

FIGS. 51-54 depict example embodiments of intra-corporeal gearing and intra-corporeal motors.

FIG. 51 depicts a system 998 with a first gearbox G1 1004 located downstream of the rotors 946 and 948. In the depicted system 998, the motor 1000 is located adjacent to the gearbox G1 1004. In some embodiments, the motor is further downstream than the gearbox G1 1004. In system 998, a second gearbox, G2 1006 may be located between the rotors 946 and 948. As shown by the arrows in FIG. 51 the rotors are contra-rotating. The motor may be powered by the power supplied through the connector 1002.

FIG. 52 depicts a rendering of system 998. FIG. 52 shows the parts shown in FIG. 51 except the connector 1002 is not shown.

FIG. 53 depicts another example system. The depicted system 1003 is similar to system 998 but the figure shows additional detail for the gears 1004 and 1006. In this depicted embodiment, gear 1006 is an epicyclic gear with the ring 1008 fixed. The motion of the planetary carrier 1010 drives the rotor 946. In the depicted embodiment the gear 1004 is an epicyclic gear with the planets 1012 fixed. The motion of the ring 1014 drives the rotor 948.

FIG. 54 depicts a rendering of system 1003.

FIGS. 55, 56, 57A, and 57B depict a system 1024. In the depicted embodiment, the planetary carriers 1026 are stationary planet carriers. In some embodiments, the planetary carriers are fixed to the motor 1000 and upstream hub 1028.

In some embodiments, in a first stage 1030, the ring 1032 rotates in the opposite direction of the sun 1034 via a planet gear pair 1036 between the sun 1034 and ring 1032.

In some embodiments, in a second stage 1038, the ring 1040 rotates in the same direction of the sun gear 1042 via an inner planet gear pair 1044 and an outer planet gear pair 1046.

Some advantages of this arrangement is that it may allow both sun gear 1042 and sun gear 1034 to be driven by a single motor shaft 1046. The sun gears 1042 and 1034 can be rotated the same direction while achieving contra-rotation of the rotors 946 and 948. This arrangement may simplify the drive system, and could make the system more reliable in operation and less expensive in manufacture. The following arrangements may also offer these advantages.

FIG. 58 depicts system 1024 with caging 1048 enclosing various components. In some embodiments the caging may be folding caging. In some embodiments the caging may encompass various combinations of components.

FIG. 59 depicts a system 1058 that is similar to the system 1024 with various differences. In some embodiments of system 1058, a first stage 1060 is included. The first stage 1060 may include a ring R1 that is held stationary. The planets P1, drive the planetary carrier P1 carrier. The planetary carrier P1 carrier drive the rotor Rotor 1.

In some embodiments, a second stage 1070 is included. The second stage 1070 may include stationary planets P2. In some embodiment the planets P2 may be connected to the motor via the caging 1048. The second stage 1070 may also include ring R2. The ring R2 may drive the rotor Rotor 2.

In some embodiments, the first sun (S1) and the second sun (S2) are driven by the motor shaft 1046.

FIG. 60 depicts a system 1080 that can include any number of features similar to the system 1024 with various differences.

Referring now to the first stage 1082, in some embodiments of the planets P1 are stationary. In some embodiments the planets are connected directly to the motor 1000 to remain stationary. In some embodiments the ring R1 is the rotor Rotor 1 driver.

Referring to the second stage 1084, in some embodiments the ring R2 is held stationary. In some embodiments, the ring R2 is held stationary by connecting the ring R2 to the motor via the shafts of the planetary gears P1. In some embodiments, the planets P2 drive the planetary carrier P2 carrier. In some embodiments, the planetary carrier P2 carrier drives the rotor Rotor 2.

In some embodiments, the first sun (S1) and the second sun (S2) are driven by the motor shaft 1046.

FIG. 61 depicts a system 1090 that can include any number of features similar to the system 1024 with various differences. Referring now to the first stage 1092. In some embodiments the ring R1 is held stationary. In some embodiments, the ring R1 is held stationary by connecting the ring R1 to the caging 1048. In some embodiments, the ring R1 is held stationary by connecting the ring R1 to the motor 1000. In some embodiments, the sun S1 drivers the planets P1. In some embodiments, the planets P1 drive the planetary carrier P1 carrier. In some embodiments, the planetary carrier P1 carrier drives the rotor Rotor 1.

Referring now to the second stage 1094. In some embodiments, the sun S2 drives the the planetary carrier P1 carrier. In some embodiments, the sun S2 drives the planets P2. In some embodiments, the planets P2 are stationary. In some embodiments, the planets P2 are held stationary by fixing the planets P2 to the caging 1048. In some embodiments, the planets P2 drive the ring R2. In some embodiments, the ring R2 drives the rotor Rotor 2.

The speed of the rotor Rotor 2 can be lower than the speed of the rotor Rotor 1 if the suns S1 and S2 are equal diameter. To improve the speed of the rotor Rotor 2, the diameter of sun S2 may be larger than the diameter of sun S1.

Figure 62:
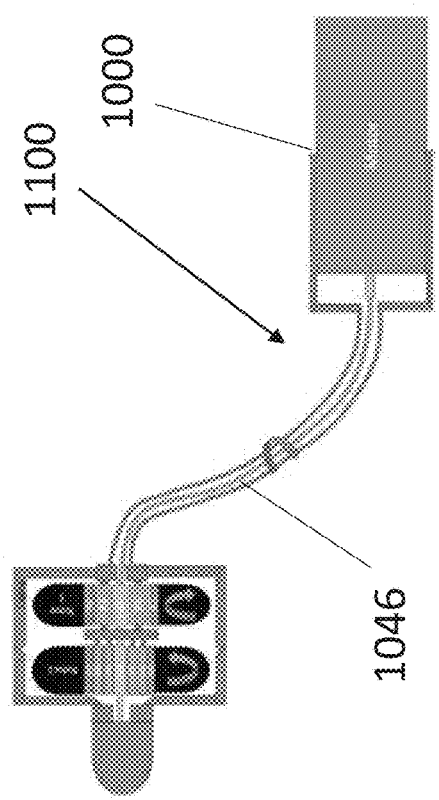

FIG. 62 depicts a system 1100. System 1100 can include any number of features similar to system 1024 with various differences. In some embodiments, the motor 1000 is extracorporeal and the motor shaft 1046 is trans-corporeal.

Figure 63:
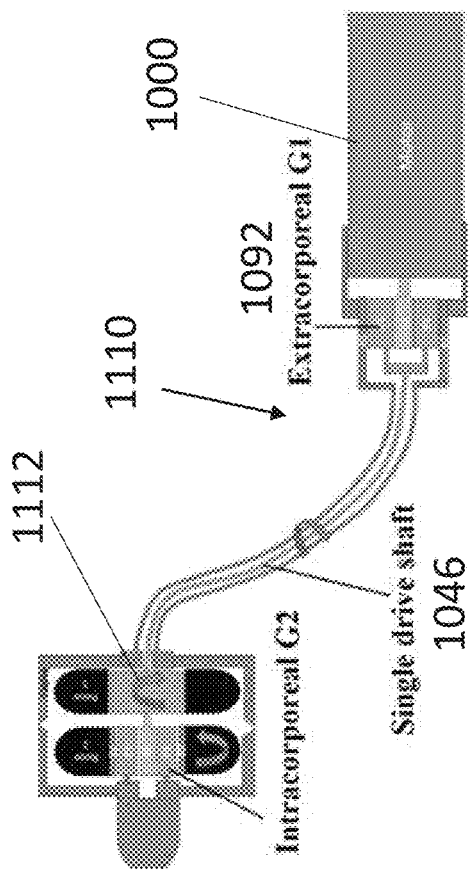

FIG. 63 depicts a system 1110. System 1110 can include any number of features similar to system 1090 with various differences. In some embodiments, the motor 1000 is located extracorporeally. In some embodiments, stage 1092 is substantially located extracorporeally. Stage 1092 may be located extracorporeally, except a drive component 1112, linked to stage 1092, may be located proximally to the rotor Rotor 1 to drive rotor Rotor 1. The motor shaft 1046 may be positioned trans-corporeally.

Figure 64:
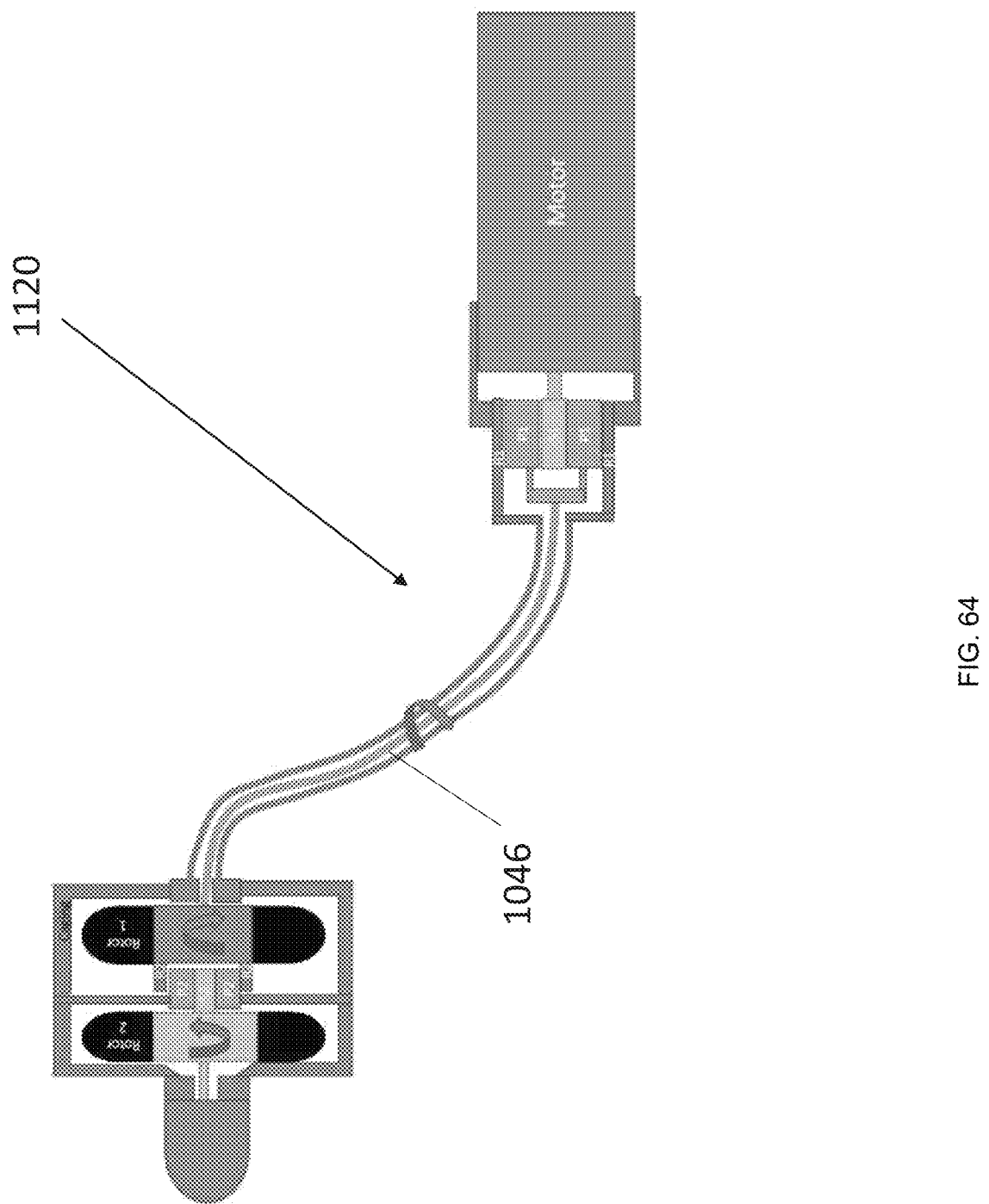
Figure 65:
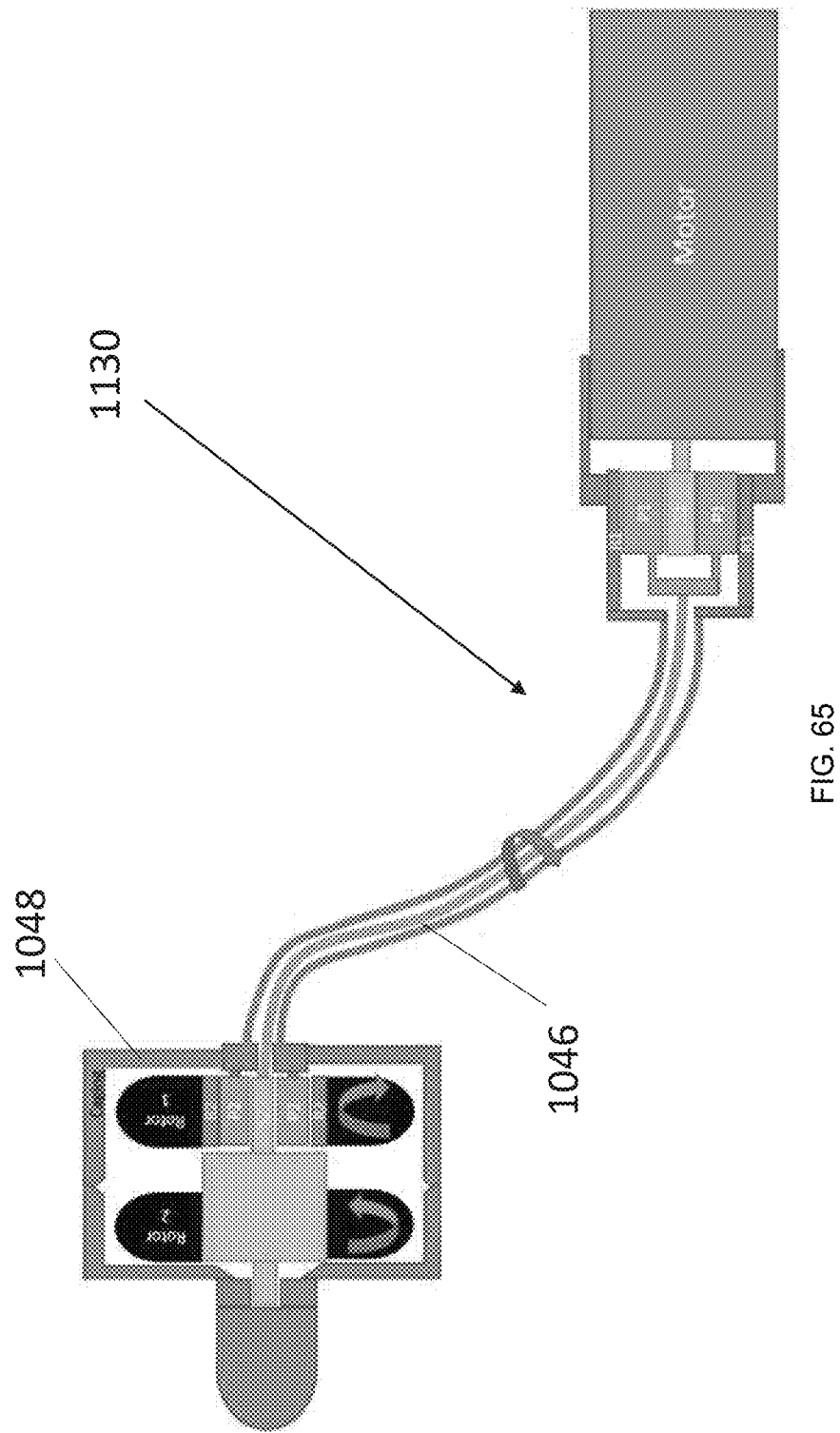
Figure 66:
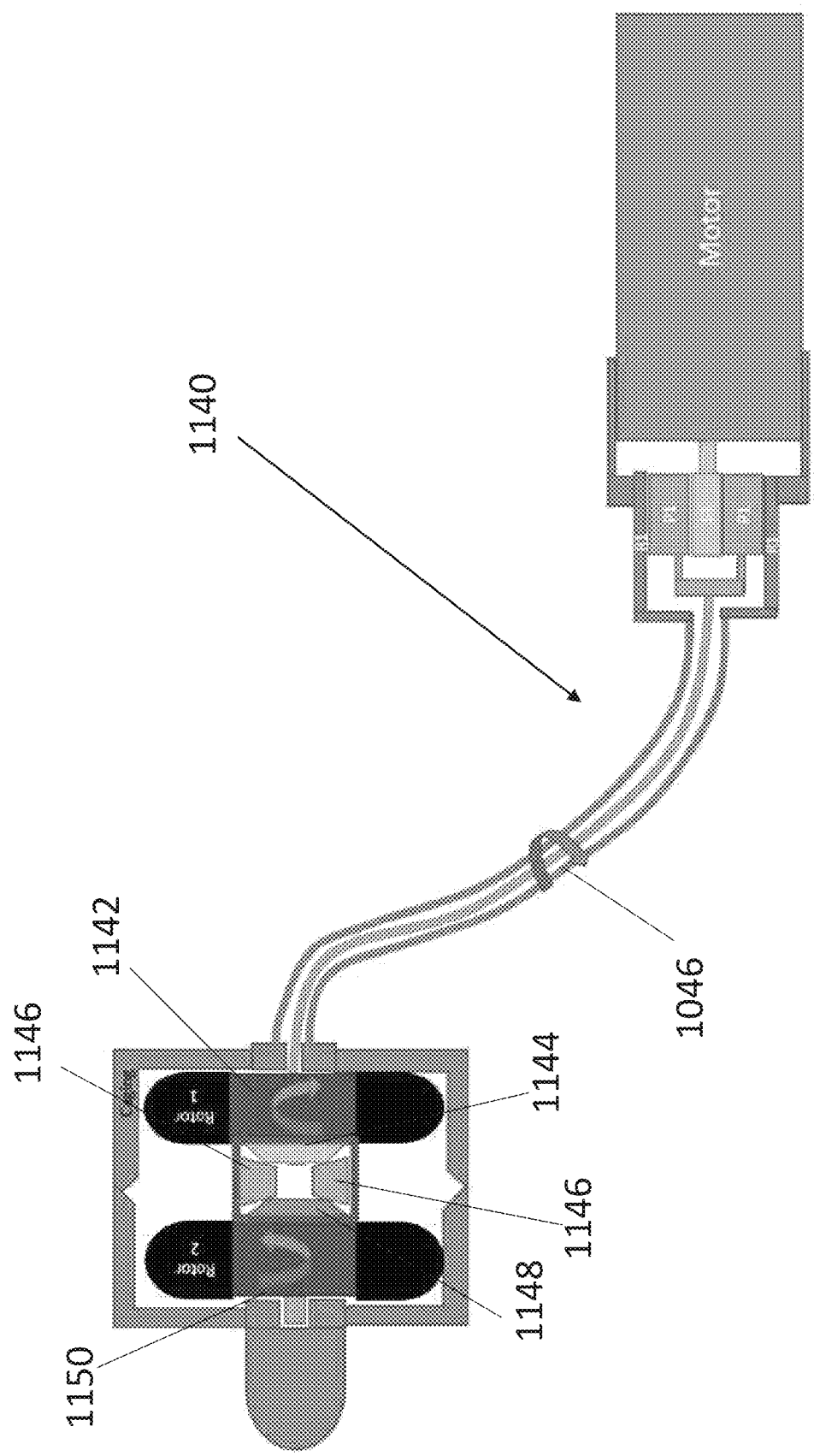

FIGS. 64-66 depicts various alternative gear arrangements that can include any number of features similar to system 1110.

FIG. 64 depicts a system 1120. In some embodiments, the drive shaft 1046 directly drives the ring R2. The ring R2 may drive the rotor Rotor R1. The ring R2 mat drive the planet gear pair P2. The ring R2 may drive both the planet gear pair P2 and the Rotor R1. The planets P2 may drive the sun S2. The sun S2 may be configured to have a large diameter region and a small diameter region. The planets P2 may interface with the small diameter region of the sun S2. The large diameter region of the sun S2 may drive the rotor Rotor 2.

FIG. 65 depicts a system 1130. In some embodiments, the drive shaft 1046 directly drives the sun gear S2. The sun S2 may be configured to have a large diameter region and a small diameter region. The small diameter region of the sun S2 may drive the planetary gears P2. The planet gears P2 may be stationary. The planet gears P2 may be held stationary by the cage 1048. The planetary gears P2 may drive the ring R2. The ring R2 may drive the rotor Rotor 1. The large diameter portion of the sun S2 may interface with and drive the rotor Rotor 2.

FIG. 66 depicts a system 1140. In some embodiments, the drive shaft 1046 drives the rotor Rotor 1. The drive portion 1142 of the rotor Rotor 1 may include a bevel gear 1144. The bevel gear 1144 may interface with two transition bevel gears 1146. The transition bevel gears 1146 may interface with a bevel gear 1148. The bevel gear 1148 may be included in a drive portion 1150. The drive portion 1150 may drive the rotor Rotor 2.

Figures 67, 68:
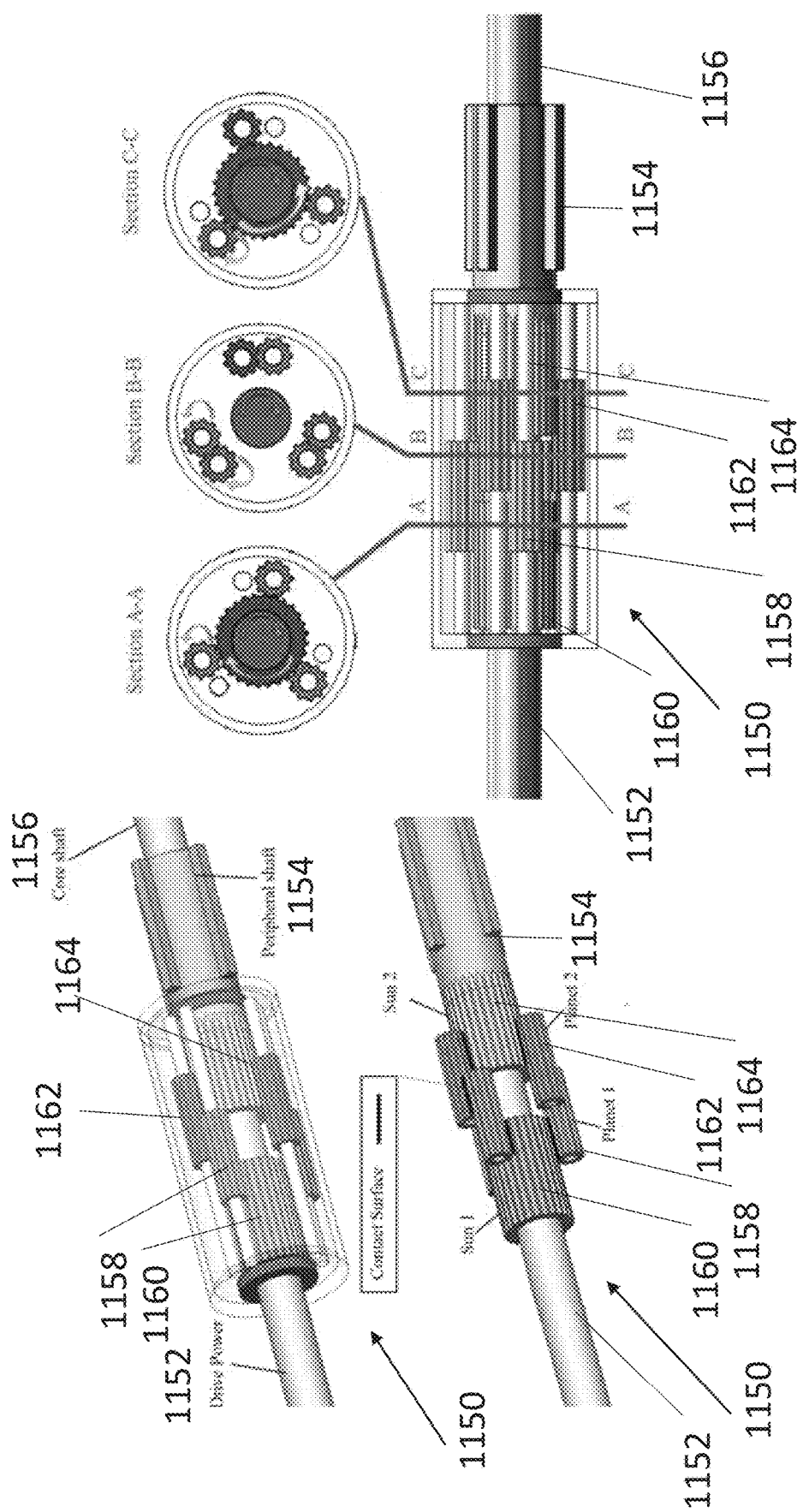

FIGS. 67 and 68 depicts various views of a system. The system can be an embodiment of the gearbox 1150 located downstream of the impellers. The gearbox 1150 may be intra-corporeal. The gearbox 1150 may be located immediately downstream of the impellers. The gearbox 1150 may be extra-corporeal. The gearbox 1150 may be placed near the extra-corporeal motor. In any case the gearbox 1150 may have one input drive shaft 1152 from the motor 1000 (not shown). The gearbox 1150 may have two contra-rotating output drive shafts. In some embodiments, one output shaft is a peripheral shaft 1154. In some embodiments, one output shaft is a core shaft 1156. The peripheral shaft 1154 and core shaft 1156 may be contra-rotating. The core shaft 1156 may be located within the peripheral shaft 1154 The example embodiment shows three planets 1158 engaging a sun 1160. In some embodiments, 2 or fewer planets 1158 may engage the sun 1160. In some embodiments, 4 or more planets 1158 may engage the sun 1160. The example embodiment shows three planets 1162 engaging a sun 1164. In some embodiments, 2 or fewer planets 1162 may engage the sun 1164. In some embodiments, 4 or more planets 1162 may engage the sun 1164.

In some embodiments, a step-up or step-down arrangement in the diameter of the planets 1162 engaging Sun 1164 at the location of section C-C, and a corresponding change in diameter of Sun 1164, allows for unequal rpm between the two contra-rotating output drive shafts. In some embodiments, the sun 1164 has a diameter equal to the diameter of the sun 1160. In some embodiments, the sun 1164 has a diameter larger than the diameter of the sun 1160. In some embodiments, the sun 1164 has a diameter smaller than the diameter of the sun 1160. In some embodiments, the planets 1158 have diameters equal to the diameters of the planets 1162. In some embodiments, the planets 1158 have diameters larger than the diameters of the planets 1162. In some embodiments, the planets 1158 have diameters smaller than the diameters of the planets 1162.

Figures 69, 70:
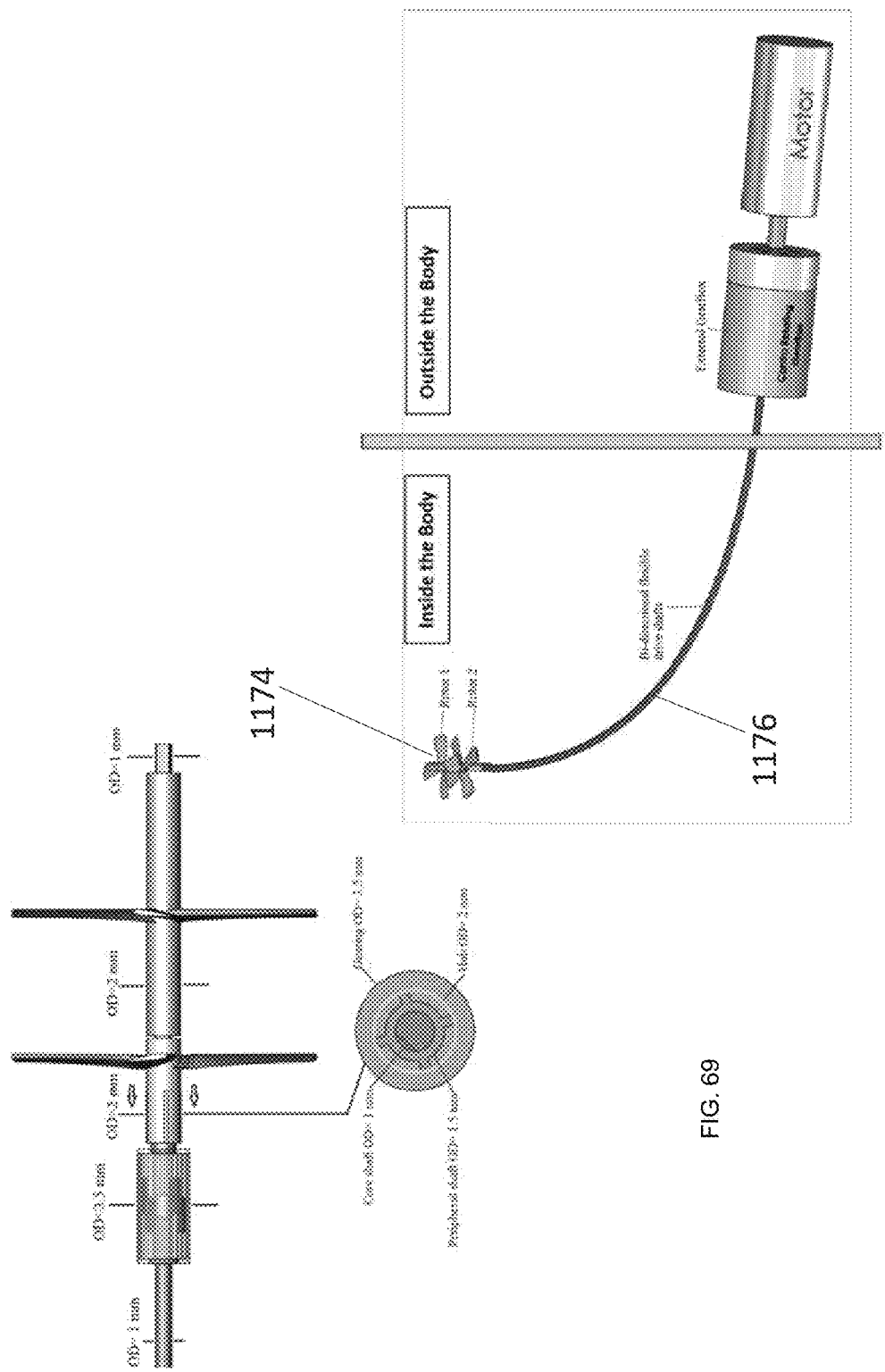

FIG. 69 depicts sample non-limiting dimensions for a gearbox 1150. These dimensions may correspond to an intra-corporeal gearbox 1150. The shown diameters are approximate. The lengths of the gear teeth may vary in order to carry the required torque for each impeller. If the gearbox is extra corporeal, then the diameters of components may be larger than shown.

Figures 71, 72:
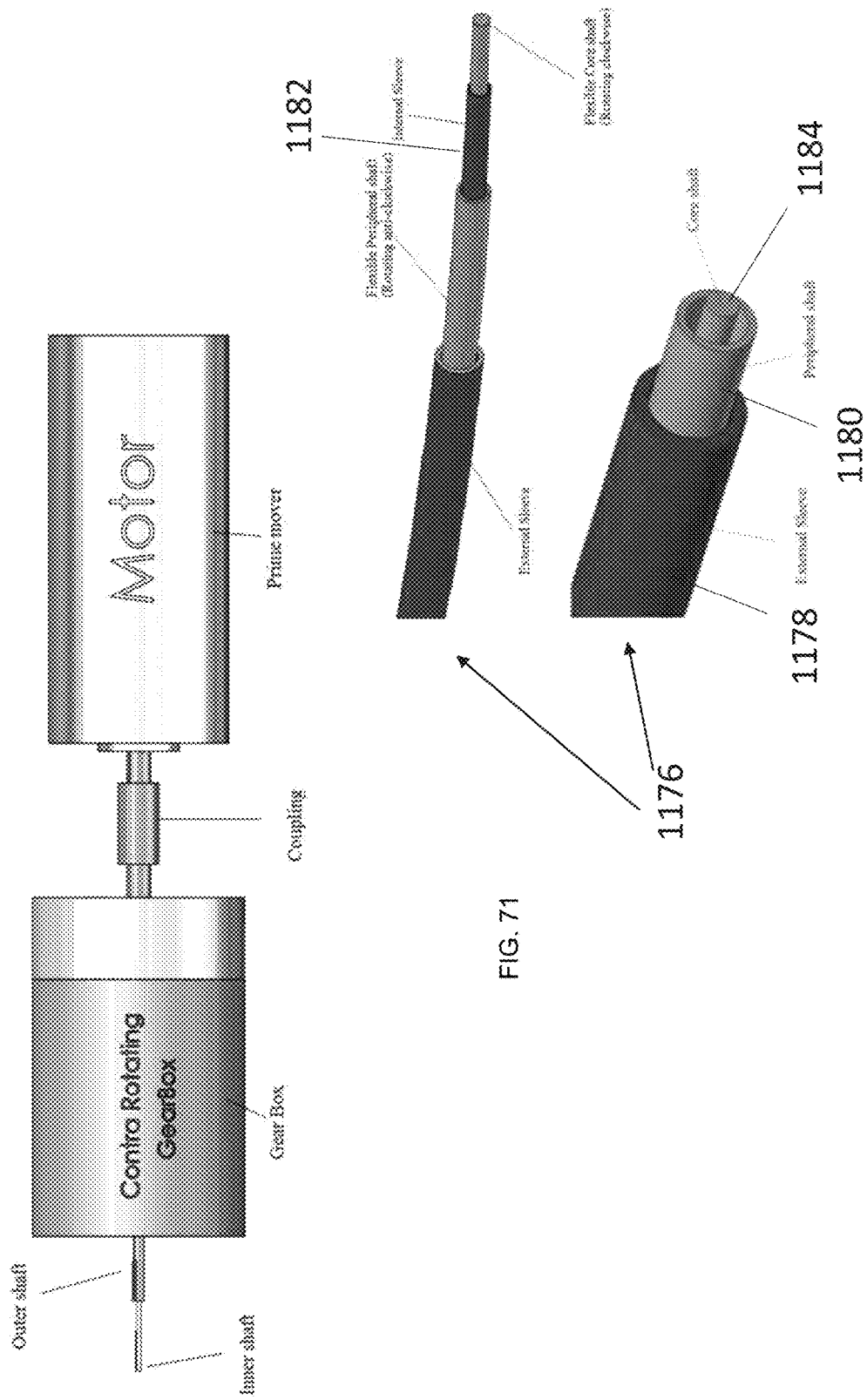

FIGS. 70-72 depict a gearbox 1170 located extra-corporeally. The two coaxial shaft system 1176 travels transcorporeally from the gearbox outlet to the intra-corporeal impellers 1174. FIG. 72 depicts the shaft system 1176. In some embodiments, the shaft system includes an external sleeve 1178. The external sleeve 1178 may protect the patient from the rotating peripheral shaft 1180. The peripheral shaft 1180 may located within the external sleeve 1178. The peripheral shaft is hollow. The inner diameter of the peripheral shaft 1180 may be configured to surround an internal sleeve 1182 and the core shaft 1184. In some embodiments, the internal sleeve 1182 is used. The internal sleeve 1182 may be positioned between the core shaft 1184 and the peripheral shaft 1182. In some embodiments, no internal sleeve 1182 is used (and the shafts do not have any sleeve or lubricant between them, and only an external sheath outside the outer shaft to prevent contact of blood with the rotating shaft), such that dry lubrication occurs for the duration of use.

FIG. 73 depicts the shaft system 1176 interfacing with the impellers. FIG. 60 depicts a case of extracorporeal gearbox and concentric contra-rotating drive shafts. In some embodiment, the upstream impeller 946 is driven by the core shaft 1184. In some embodiments, the downstream impeller 948 is driven by the peripheral shaft 1180.

FIGS. 74-75 depict how lubricant 1186 is conveyed to the gearbox 1188 for intracorporeal gearboxes. If the motor and gearbox are extra-corporeal, they can be lubricated as is known in the art. For intracorporeal gearboxes, the lubricant 1186 may conveyed in an interstitial space 1191 disposed between the sleeve 1190 and the drive shaft 1192. In some embodiments, the lubricant will be a bio-compatible lubricant.

In some embodiments, an intracorporeal gearbox 1188 can be dry lubricated (unlubricated) for a device designed for temporary use. In some embodiments the intracorporeal gearbox 1188 may be actively lubricated with a biocompatible lubricant 1186 supplied at a high pressure. The high pressure may ensure that a small amount of lubricant is pumped in the blood stream, thus preventing the flow of blood in the device crevices.

FIG. 76 depicts an intracorporeal motor 1000. Lubrication for the intracorporeal motor 1000 can be provided in a manner described above in connection to the intracorporeal gearbox 1188. In some embodiments, the lubrication system may also provide lubrication for the motor, then the gearbox, then the contra-rotating shafts. Biocompatible lubricant under pressure at points 1, 2, 3, 4 etc. prevents blood from entering the device.

FIG. 77 depicts spiral grooves 1200. In some embodiments, spiral grooves 1200 may be disposed at interfaces involving rotating parts. In some embodiments, spiral grooves 1200 may be disposed at the rotating surfaces of the impellers 946 and 948. Spiral grooves may improve lubrication flow in critical regions. The spiral grooves can be used with any device described herein.

FIGS. 78 and 79 depict an example lubrication mechanism for with a system including an intra-corporeal gearbox 1202. In some embodiments, a lubricant 1186 is pressurized by the purge system 1204. The lubricant may then be conveyed through the purge tubing 1206 and between the sleeve 1190 and the drive shaft 1192 as previously described.

FIG. 80 depicts a normal distribution of inner descending aorta diameter. The red distribution is females over 60. The blue distribution is men over 60. These distributions inform the design of a one size fits all dimensions for the aorta. Based at least partially on this data, some embodiments may have a rotor tip diameter of about 18 mm and maximum collapsible frame diameter of about 33 mm.

FIGS. 81A-81C depicts a collapsible supporting hourglass frame 1210 made of shape memory alloy. FIG. 81A depicts the hourglass frame 1210 in a first, expanded, configuration. FIG. 81B depicts the hourglass frame 1210 in a second, elongated, configuration. The frame in FIG. 81B is both elongated and collapsed. FIG. 81C depicts the hourglass frame 1210 in the expanded configuration with the two rotors 946 and 948 disposed inside. As the frame 1210 collapses, it may elongate. The elongation changes the diameter and length and may engage the tips of the blades of the rotors 946 and 948 to assist them in folding and unfolding.

FIGS. 82A-82D depicts the adjustable hourglass frame 1210. FIG. 82A depicts the frame 1210 is an expanded configuration. The Gearbox 1212 may be intra-corporeal or extra-corporeal. Motor 1000 (not shown) may be intra corporeal or extra corporeal. The frame may house a single impeller blade or contra-rotating blades 946 and 948 as shown. In the depicted embodiment, the caging 1216 is shown open. In some embodiments, the caging 1216 is supported by struts 1214.

In the case of single impeller, some differences in certain embodiments of the present technology compared with, for example, Cardiobridge's Reitan Catheter pump, Procyrion, and other collapsible devices suggesting membrane blades that cannot work is that the frame 1210 is secured at the inlet and outlet positions inside the blood vessel. There is no retrograde flow from device outlet to device inlet in some embodiments. This is an important advantage of some embodiments and distinguishes some devices in which the impeller diameter is smaller than the open passage upstream to downstream, resulting in retrograde flow, Procyrion, Reitan Catheter Pump, and some devices in development fall in that category.

FIG. 82B depicts the frame 1210 deployed in an aorta corresponding to the maximum size aorta. FIG. 82C depicts the frame 1210 deployed in an aorta corresponding to the minimum size aorta.

FIG. 82C depicts the frame 1210 in a collapsed configuration. In some embodiments, the blades of the rotors 946 and 948 may fold upstream or downstream. A runner 1218 may be used to pull bottom struts into sheath. In some embodiments, the pulling mechanism may have a runner 1218. In some embodiments, the pulling mechanism may use just the sheath 1220 (not shown). The depicted embodiment shows the system using the runner 1218 and the sheath 1220 (not shown).

In some embodiments, the gearbox 1212 is extra-corporeal, there is no runner 1218, and the sheath 1220 collapses the device by enclosing the bottom struts 1214.

Figure 83:
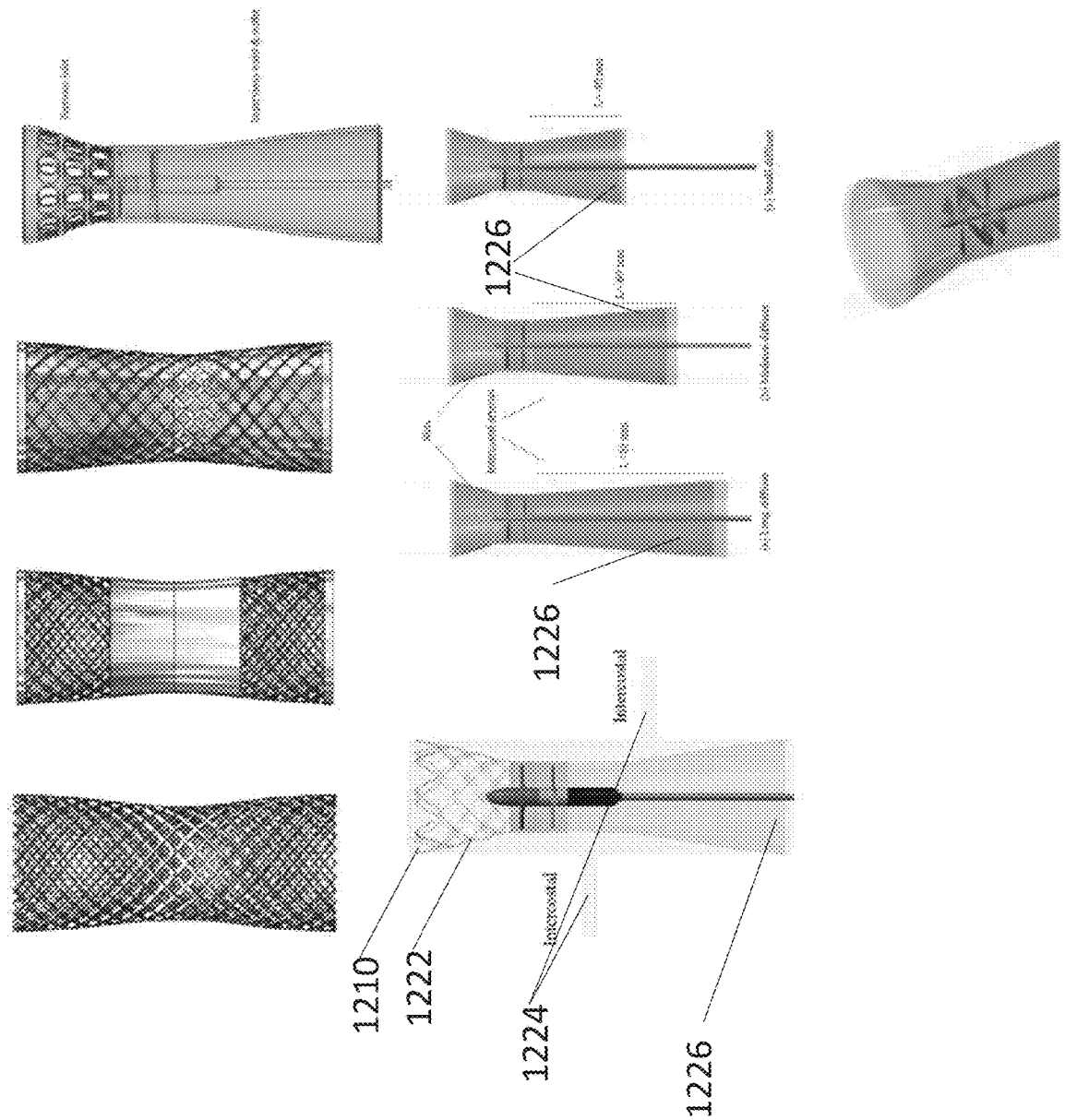

FIG. 83 depicts various embodiments of a shape memory alloy hourglass 1210. In some embodiments this hourglass 1210 may be covered by a biocompatible membrane. The biocompatible covering may be in all 3 sections (inlet, waist, outlet diffuser), or only in some of them (e.g., only in the inlet, only in the waist, only in the outlet diffuser, only in the inlet and waist, only in the inlet and diffuser, only in the waist and the diffuser, etc.). The biocompatible covering may be inside the hourglass, or outside, or inside in some sections and outside in some other sections. In some embodiments, the material is inside and outside as some polymers may need to bond to a second layer to ensure stability. In some embodiments, the hourglass 1210 may be porous in the inlet section 1222. In some embodiments inlet-section porosity is achieved by having no biocompatible covering of the frame at the inlet. In some embodiments, the porosity may be achieved with round holes. In some embodiments, the porosity may be achieved with slits. Some advantages of the porous inlet section 1222 is to provide perfusion between the hourglass shape and the vessel wall. There are intercostal arteries 1224 in the descending aorta, and one of them feeds the spine. If this intercostal artery is not perfused during the operation the patient may be paralyzed. There are currently no systems to provide the surgeon with an early warning. Provision for perfusion between hourglass and blood vessel can be a significant advantage in some embodiments. The perfusion of the intercostal arteries is achieved using the porous inlet section 1222. In some embodiments the inlet section is porous. In some embodiments the outlet section 1226 is porous. In some embodiments the entire hourglass 1210 is porous.

FIG. 83 also depicts various outlet diffuser 1226 lengths. Some embodiments may have a diffuser 1226 length of about 80 mm. Some embodiments may have a diffuser 1226 length of about 60 mm. Some embodiments may have a diffuser 1226 length of about 40 mm, or lengths greater or less than 40, 60, or 80 mm, or ranges including any two of the foregoing values.

FIG. 84 illustrates the catheter arrangement for the hourglass 1210 and a device, such as a perfusion device 1230. In some embodiments, a gearbox is needed to power contra-rotating impellers. In some embodiments, a single-impeller pump head is used and a gearbox may not be required. In some embodiments, a gearbox may be used to adjust the output RPM coming from the motor.

The catheter may include a sheath 1220, a runner 1218, a sleeve 1190 and a flexible shaft 1192. The sheath 1220 may be configured to accommodate the hourglass 1210 and the perfusion device 1230. In some embodiments, the hourglass 1210 and perfusion device 1230 collapse into the sheath 1220. In some embodiments, the sheath 1220 advancing upstream may push the bottom struts 1214 in to initiate folding of device 1230. In some embodiments, the Sheath 1220 advancing upstream may push the bottom struts 1214 in to complete folding of the device 1230.

In some embodiments the runner 1218 may be not be used. In some embodiments, the runner 1218 is used to pull the bottom struts downstream while pushing the sheath 1220 upstream.

In some embodiment, the gearbox and motor may be intracorporeal, in which case the flexible shaft 1192 is just an electric cable. In some embodiments, the gearbox and motor may be extracorporeal. In some embodiments, the device 1230 has contra-rotating blades. In some embodiments, the flexible shaft 1192 is two co-axial contra-rotating shafts as described elsewhere herein.

In some embodiments, gearbox may be intracorporeal and the motor extracorporeal. The flexible shaft 1192 may be a single shaft reaching to the intra-corporeal pump head. In an embodiment which includes contra-rotating blades, there may be a gearbox providing two output contra-rotating shafts, one for each impeller.

In some embodiments, the gearbox and motor may be extra-corporeal. In these embodiments, the flexible shaft 1192 may consist of two contra-rotating shafts.

With regards to the embodiments shown in FIGS. 85-91, the contra-rotating rotors 946 and 948 are driven by contra-rotating shafts engaging the hubs of the rotors carrying the blades. In some embodiments, the contra-rotation of the shafts may be arranged by direct drive contra-rotating shafts coupled to an extra-corporeal gearbox. In some embodiments, the shafts may be driven by an intracorporeal gearbox located upstream of both impellers. In some embodiments, the shafts may be driven by an intracorporeal gearbox located between the impellers. In some embodiments, the shafts may be driven by an intracorporeal gearbox located downstream of the impellers.

In some embodiments, the blades 1232 and 1234 may fold upstream. In some embodiments, the blades 1232 may fold downstream. In some embodiments, the upstream blades 1234 may fold upstream. In some embodiments, the downstream blades 1232 may fold downstream. In some embodiments, as the diameter of the hourglass frame collapses, portions of it may elongate upstream or downstream.

FIG. 85 depicts a system 1240 that includes upstream struts 1242 that are free to rotate about their corresponding hinge only upstream. In the depicted system 1240, the downstream struts 1244 are configured to turn downstream. In some embodiments, the hourglass frame 1210 is configured to collapse with the tips of the blades folding upstream. FIG. 85 shows the sequence of on elongation of segments of hourglass and shows the corresponding sequence of blade tip locations.

FIG. 86 depicts a system 1250 that can include any number of features similar to system 1240 with various differences. In some embodiments, the upstream and downstream struts 1242 and 1244 are free to rotate about their corresponding hinge in the downstream direction. In some embodiments, the blades 1232 and 1234 will likely fold downstream, but may also fold upstream.

FIG. 87 depicts the system 1250. If the blades 1234 fold upstream while the struts 1242 fold downstream, then the upstream struts 1242 may be positioned between the folding rotor blades 1234 resulting in the folded device being as short as possible.

FIG. 88 depicts the folding of the system 1250 or system 1240. Following the folding, the system may be inserted into the sheath 1220 for removal.

FIG. 89 depicts an upstream runner configuration. In some embodiments, the Sheath 1220 collapses the hourglass 1210 and the device elongates upstream. In such a configuration, the blades 1234 and 1232 may fold upstream or downstream.

FIGS. 90 and 91 depict a downstream runner configuration. In the figure, the runner 1218 pulls the hourglass 1210 downstream and collapses the device. In an alternative embodiment, there is no runner 1218. In some embodiments, the sheath 1220 pushes the bottom struts 1244 up, thus collapsing the mechanism.

FIG. 92 depicts an embodiment of the collapsible hourglass 1210. In some embodiments, the hourglass 1210 is made of memory-shaped material, metal or plastic, like nitinol. In some embodiments the, supporting struts 1242 and 1244 are made of memory-shaped material, metal or plastic, like nitinol. In some embodiments, the journal bearing hubs are made of memory-shaped material, metal or plastic, like nitinol. In some embodiments, a component made of memory-shaped material, metal or plastic, like nitinol may be made of one memory-shaped material, metal or plastic, like nitinol tube. In some embodiments the collapsible hourglass 1210, supporting struts 1242 and 1244 and journal bearing hubs may be made of one memory-shaped material, metal or plastic, like nitinol tube. In some embodiments, the runner may be an extension of the same memory-shaped material, metal or plastic, like nitinol tube.

FIGS. 93-96B depict a system 1260. System 1260 can include any number of features similar to system 1250 with various differences. System 1260 includes a device 1262. In some embodiments, a flexible tip 1264 may be attached to the distal end of the device. During the folding phase, the journal bearing 1266 may slide along the flexible tip 1264. The journal bearing 1266 free to move axially, and free to rotate. In some embodiments, the upstream struts 1268 may be fixed to the journal bearing 1266. During folding the upstream struts 1268 curve downwards. Downstream of the upstream struts 1268 may be the upstream propeller 1270 and the downstream propeller 1272. In some embodiments, upstream propeller 1270 is configured for the blades to tilt downstream during folding. In some embodiments, downstream propeller 1272 is configured for the blades to tilt downstream during folding. The gearbox 1274 provides contra-rotation to the propellers 1270 and 1272. The downstream struts 1276 may be fixed to the gearbox 1274 and curve downstream during folding. The flexible core 1277 is connected to the central axle of the gearbox 1274 and transmits torque form the gearbox 1274 to powered components. In some embodiments, the gearbox 1274 provides torque and speed to the propeller 1270. In some embodiments, the gearbox 1274 provides torque and speed to the propeller 1272. The flexible core 1277 may be covered in a sleeve, or plastic dressing, 1278. The sleeve 1278 may serve to protect the flexible core 1277 from blood exposure. The outer hourglass caging 1280 may comprise three segments—the inlet 1282, waist 1284 and outlet 1286. The waist 1284 may have a high radial strength and high longitudinal flexibility. In some embodiments the caging 1280 may be made of memory-shaped material, metal or plastic, like nitinol. Pulling strings 1288 connect the caging 1280 to the runner 1290. The pulling strings 1288 may be diffuser struts or strings. The runner 1290 is pulled by the operator to collapse the caging 1280. The collapsing may be similar to how an umbrella collapses. When the downstream struts 1276 are forced into the sheath, the waist 1284 elongates axially and shrinks radially. As a result, the journal bearing 1266 may be pushed further upstream.

Figures 96A, 96B:
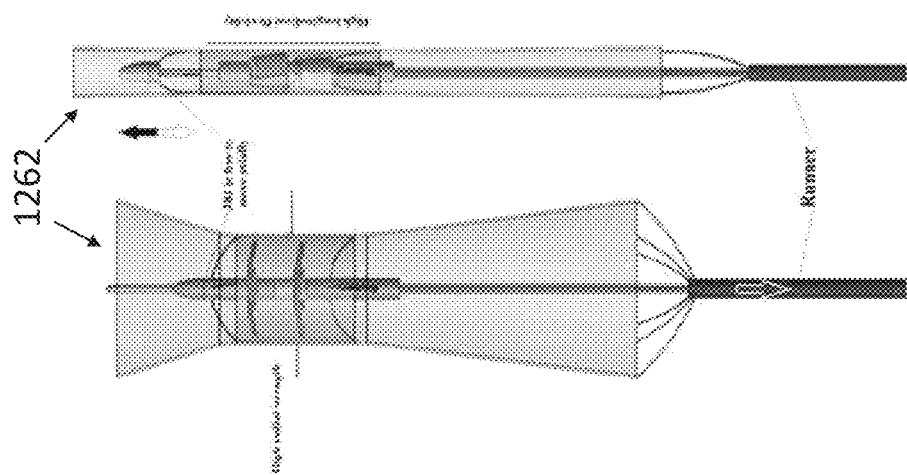
Figure 95:
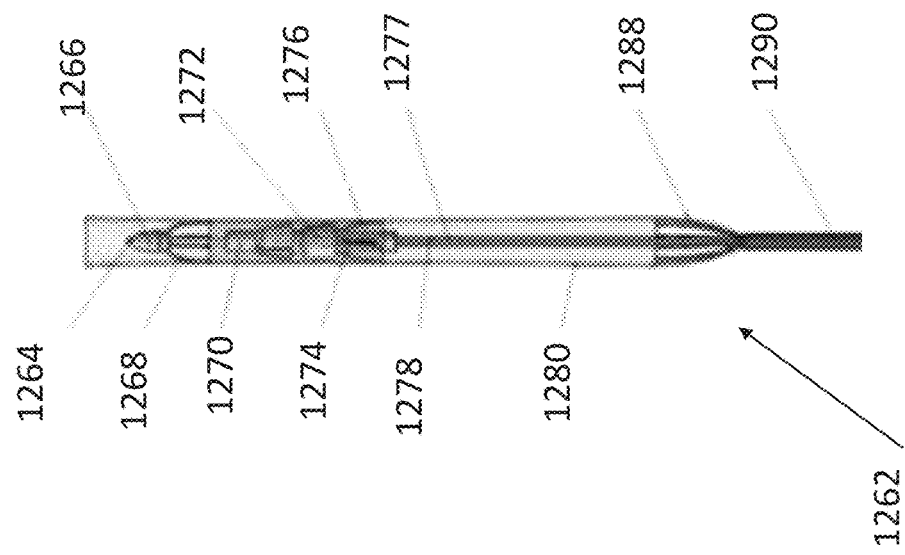

FIG. 96A depicts the device 1262 in an expanded configuration. FIG. 96B depicts the device 1262 in a collapsed configuration.

FIGS. 97-99B depict a device 1300. Device 1300 can include any number of features similar to device 1262 with various differences. In some embodiments, the upstream struts 1268 fold upstream. The downstream struts 1276 fold downstream. In this embodiment the journal bearing 1266 may be fixed in place. The upstream propeller 1270 hub rotates with the upstream propeller 1270. The upstream struts 1268 mat be configured to curve upstream during device folding. The downstream struts 1276 may curved downstream during device folding. When the runner 1290 is pulled against the drive shaft the struts fold to enable the device to transform into the collapsed configuration. The device 1300 may not include a flexible tip.

FIG. 99A depicts the device 1300 in an expanded configuration. FIG. 99B depicts the device 1300 in a collapsed configuration.

FIGS. 100-102 depict a system 1310. System 1310 is similar to system 1260 with various differences. The system 1310 includes the device 1312. Device 1312 is similar to device 1262 with various differences. System 1310 folds the device 1312 via the sheath 1220. No runner is used in some embodiments of system 1310. When the sheath 1220 is pushed upstream against the diffuser struts or strings 1288, and/or the caging 1280, the downstream struts 1276 tend to fold upstream and the upstream struts 1268 tend to fold downstream. In some embodiments, the journal bearing 1266 may be pushed further upstream. In some embodiment, the strings or diffuser struts 1268 may be connected to the caging 1280 on one end. In some embodiment, the strings or diffuser struts 1268 may be connected to the flexible shaft 1277 on a second end.

FIGS. 103A and 103B depicts system 1310. In this embodiment, the blades may tend to fold upwards. The blades may include a small upward inclination in the open position. This upward inclination may provide that when the blade tips are exposed to the radial force from folding caging, the blades fold upstream. FIG. 103A depicts the device 1312 in an expanded configuration. FIG. 103B depicts the device 1312 in a collapsed configuration.

FIGS. 104-107 depict example perfusion devices. In some embodiments, the rotating blade tips 1314 are 0.1 mm to 2 mm from the inside diameter of the waist 1284 of the hourglass cage frame 1280. The impeller axis is secured in place by struts, such as struts 1268, and bearings, such as journal bearing 1266. The struts are secured at one end on the bearings and at the other end on the frame 1280. There is also a similar arrangement securing the flexible shaft centerline with struts and a hub at the outlet of the diffuser (diffuser struts or strings).

In some embodiments, the whole cage 1280 and the struts 1268 and 1276 may be made of one memory-shaped material, metal or plastic, like nitinol tube. Manufacturing may in some cases require cutting out surplus segments and welding in some joints. The journal bearing hubs may be part of the same memory-shaped material, metal or plastic, like nitinol tube, see, e.g., FIGS. 106 and 107.

FIGS. 108 and 109 depict blades 1320 folding at the hub 1322. The blades 1320 may fold either upstream. The blades 1320 may fold downstream. The blades 1320 may fold in either direction. The blades 1320 may fold for insertion in a sheath. The blades 1320 may fold in a collapsible hourglass cage. In the example shown in FIG. 108, the blades 1320 are folded downstream for insertion. After insertion, the sheath 1220 is moved downstream in relation to the blades 1320 in order to unfold the mechanism. To fold and remove the mechanism, the sheath 1220 is moved upstream in relation to the rotors, and the blades 1320 fold upstream. In some embodiment the blades may be made of memory-shaped material, metal or plastic, like nitinol. In some embodiments, the blades may have a rotatable region 1322. In some embodiments, the rotatable region 1322 may be made of a flexible material.

Figure 111:
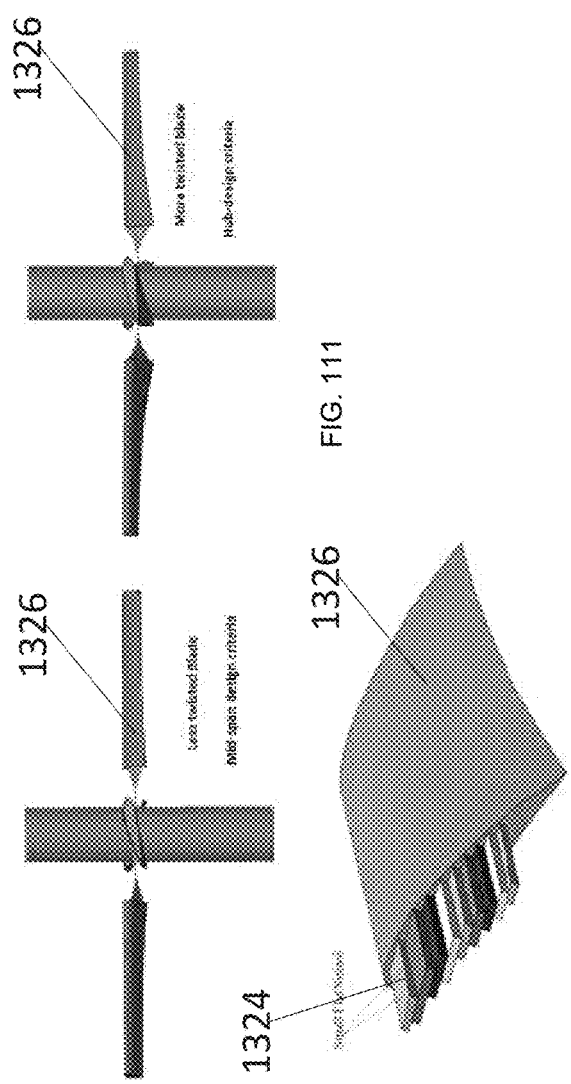

FIGS. 110 and 111 depict folding blades 1320. Each folding blade 1320 may have a center strut 1324 made of memory shape alloy. The center strut 1324 may be surrounded by an airfoil shape 1326. The airfoil 1326 may be made of biocompatible metal. The airfoil 1326 may be made of biocompatible plastic. In some embodiments the folding blade may include a memory-shaped material, metal or plastic, like nitinol frame in the shape of a blade, the blade covered by a biocompatible material. In these embodiments, the blades may wrap into the hourglass cage 1280 and the sheath 1220 for implantation and removal. The material surrounding the center strut 1324 may be twisted from hub to tip to accommodate flow considerations. In some embodiments the center strut 1324 will not protrude from the airfoil shape 1326. The center strut 1324 may be made in several thin layers using 2D deposition techniques.

Figure 112:
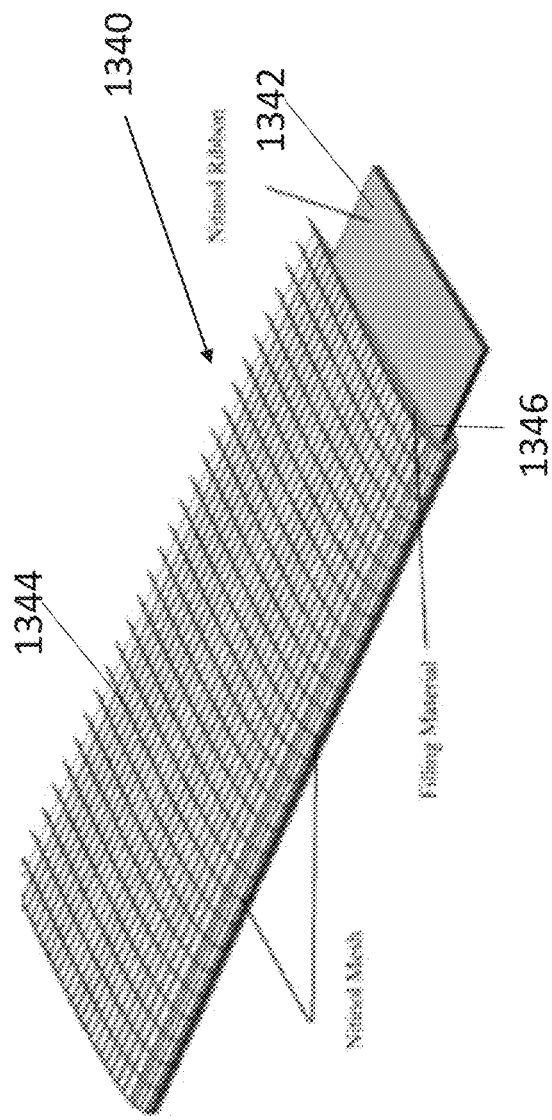

FIG. 112 depicts a rigid blade 1340 with flexible strut 1342. The central strut 1342 may be composed of a memory shape alloy. In some embodiments the shape memory alloy may be memory-shaped material, metal or plastic, like nitinol. The strut 1342 may be surrounded by a frame 1344. The strut 1342 may be comprised of memory-shaped material, metal or plastic, like nitinol. The frame 1344 may comprise memory-shaped material, metal or plastic, like nitinol. In some embodiments, the frame 1344 may be covered by biocompatible membrane. Any process may be used to do this including using a biocompatible material netting. In some embodiments, the frame 1344 may be covered by flexible memory-shaped material, metal or plastic, like nitinol sheets. Any process may be used to do this including using a flexible fine netting of memory-shaped material, metal or plastic, like nitinol. A filling material 1346 may be used. The overall blade 1340 is stiff enough to carry the requisite hydrodynamic forces but flexible enough at the hub to bend around the shaft in the collapsed state. In some embodiments, the strut 1342, may be a metal strip. In some embodiments, the strut 1342 may be a series of metal strips. In some embodiments, the strut 1342 may be a lattice of metal strips. The strut 1342 may be configured to be made stiff to bending along the direction of the resultant force of lift and drag. In some embodiments, the strut 1342 is predominantly stiff upstream making the strut 1342 suitable for pumping action. The strut 1342 may be weaker when bending perpendicular to this direction. In some embodiments, the strut 1342 may be predominantly less stiff downstream to enable folding. This concept is further explained elsewhere in this document.

FIG. 113 that the forces applied on a single strip 1358 connecting blade 1356 to hub 1354, results in bending of the strip 1358. If several strips 1360 are used to connect blade to hub, one strip bends and the remaining strips buckle.

Bending of strips in a particular inclination to the axis alpha is shown in the figure. The direction of blade bending can be as described herein.

FIG. 113 also shows the top views 1350 and 1352. These views show, upstream to downstream, of downstream blade with stagger angle with leading edge NW to trailing edge SE.

If hub 1354 turns clockwise, then blade 1356 turns counter-clockwise and upstream.

If hub 1354 turns counter-clockwise, then blade 1356 turns clockwise and downstream.

The upstream blades and their hub turn in the opposite direction to downstream blades. Their stagger angle is also in the opposite direction with leading edge NE and trailing edge SW. Therefore, the upstream blades will turn to bend upstream (or downstream) in the same direction the downstream blades bend.

FIG. 114 depicts a blade mesh in an unbent configuration and in a bent configuration. In some embodiments a blade 1370 can be a wide span non-rigid blade. In some embodiments, the blade 1370 can be made from a memory-shaped material, metal or plastic, like nitinol mesh. The large-span blade 1370 can help with the hydrodynamic performance. A memory-shaped material, metal or plastic, like nitinoll meshed blade may be able to deform under a certain loading. Deformation under loading may be functional for retraction.

FIGS. 115 and 116 depict the blades 1370 mounted to a hub 1372. In some embodiments, the blades 1370 may be covered in a thin layer of PTFE. In some embodiments, the blades 1370 are covered in another biocompatible membrane. Due to the blade 1370 flexibility, the blades 1370, such as meshed blades can be folded around the hub. Especially, it may allow the blades 1370 to be folder around the hub 1372 when the sheath 1220 is moved upward. This could be advantageous to reduce the overall system size. The blade 1370 could be welded directly to the hub 1372. Welding to the hub 1372 may enable maintaining the hydro dynamically designed twisted shape of the blades in the vicinity near the hub, without compromising performance. In some cases the blades may be flat plates bent to a blade shape. FIG. 126B, described herein below, illustrates a flat plate, bent to blade shape.

FIG. 117 shows an example embodiment wherein, in their relaxed and not rotating shape, the blade tips 1374 may be pointed slightly downstream. In some embodiments the blades may be pointed downwards by about 15 degrees. In operating conditions, the hydrodynamic forces plus the centrifugal forces bring the blade close to the horizontal position.

FIG. 118 depicts an embodiment of the blades 1370 wherein a stop mechanism 1376 may be attached at the hub to prevent the blades from bending too far upstream.

FIGS. 119 and 120 depict an example embodiment of a flexible hub. In this example embodiment the blades 1370 bend at the hub 1372. The bent blades 1370 can slide into the sheath 1220. In this example, the gear teeth 1376 shown inside the hub are the ring gear of an epicyclic gearbox. In some embodiment three flexible struts 1378 are used to connect each blade 1370 to the hub 1372.

FIG. 121 shows a blade system 1380. The blade supporting structure 1382 may be made of one tube of shape memory alloy. In some embodiments the shape memory alloy may be memory-shaped material, metal or plastic, like nitinol. In some embodiments, the tube is cut and with extra blade material is added around the base shape. In some embodiments, a manufacturing step may be to cut-out the blade shape from a selected memory-shaped material, metal or plastic, like nitinol tube. Another manufacturing step may be to deform the cut tube 1384 blade shape. In the depicted embodiment, the tube is cut into four pieces. In some embodiments, the minimum thickness of the memory-shaped material, metal or plastic, like nitinol frame may be determined by foldability considerations. In some embodiments, for each blade, the cut-out from the memory-shaped material, metal or plastic, like nitinol tubing should be deformed from the hub to tip into a prescribed curvature. In some embodiments, the prescribed curvature is selected to match the corresponding blade body curvature. In some embodiments the curvature varies from the hub to tip. The folding hub section of memory-shaped material, metal or plastic, like nitinol may have various shapes of cuts in it to weaken it for bending in some directions, and strengthening it against bending in other directions. In some embodiments, additional metal may be added to the cut memory-shaped material, metal or plastic, like nitinol tube to achieve a desired curvature and frame 1386 shape. In some embodiments, a biocompatible material may be added on top of the metal frame. In some embodiments, biocompatible material may be added to achieve a desired blade 1370 shape.

FIG. 122 depicts a set of blades 1370 attached to a hub 1372. In some embodiments, these blades are formed of a shape memory alloy, such as memory-shaped material, metal or plastic, like nitinol. The blades 1370 may be configured to wrap around the hub 1372. The blades 1370 may be configured such that they all can be wrapped around the hub simultaneously. The sheath 1220 may be sized and configured to accommodate these folded blades 1370. In some embodiments, the outer diameter of the sheath 1220 may be about 4 mm. In some embodiments, the outer diameter of the hub 1372 may be about 2 mm. In some embodiments, the hub 1372 and the folded blades 1372 may be configured to fit inside a 12 Fr tube. In some embodiment the blades 1370 may be made of a flexible material.

FIGS. 123A, 123B, and 123C depict the wrapping of various blade 1370 configurations around the hub 1372. Blades 1370 with wider chord length. FIG. 123A embodiments may be made thinner than the 4 mm chord blades in order to fit in a size 12 French catheter, for example. As the chord length of the blades increases, the amount of blade overlap may also increase. The effect is that higher chord length blades will sometimes tend to overlap more. This additional overlapping will tend to increase the minimum interior diameter of the sheath for a constant blade thickness. Alternatively, to maintain a constant interior diameter of the sheath, the blade thickness must decrease as blade chord length increases.

Figure 124:
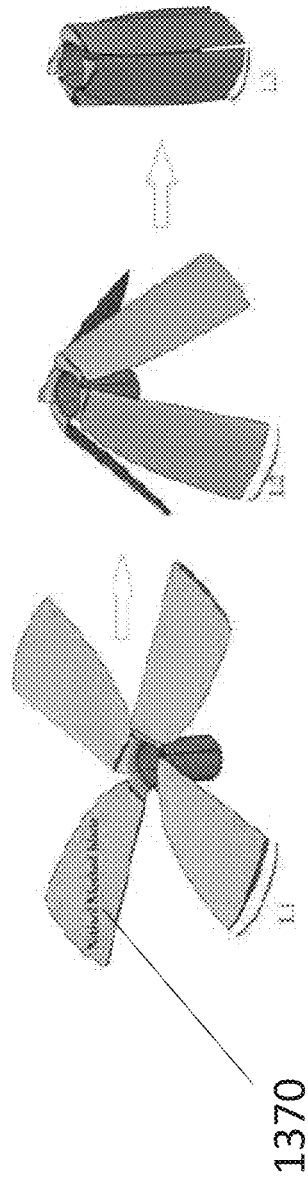
Figure 125:
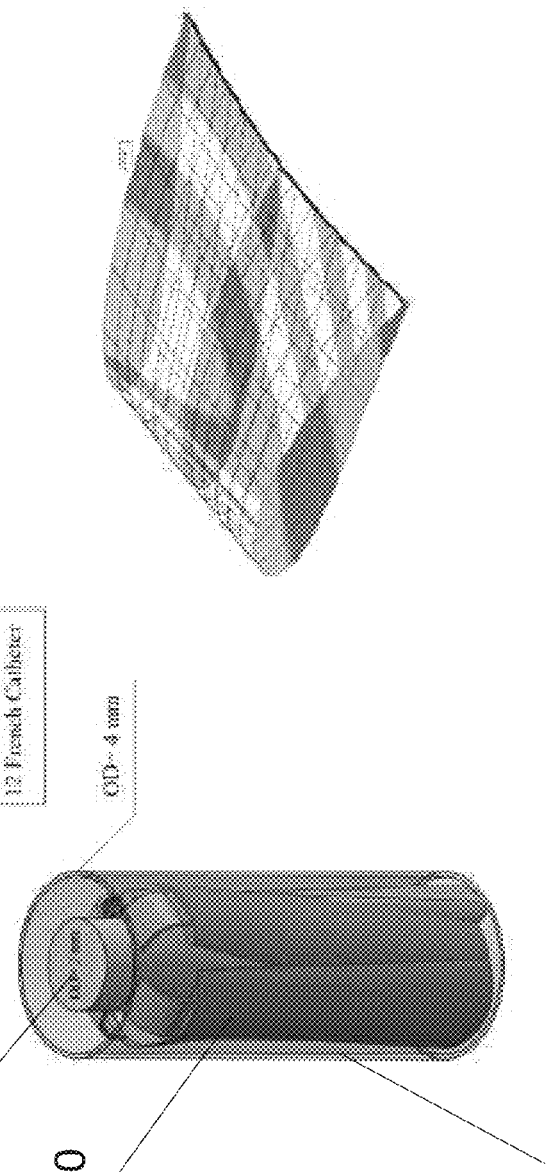

FIGS. 124 and 125 depict the deformable blade 1370. In some embodiments, the blade is made of a shape memory alloy lattice. In some embodiments, the lattice may be covered by PTFE. The shape memory alloy lattice may be advantageous to enable the chord L to be deformable in order to fit in the available space. In some embodiments the space may be limited by the configuration of the sheath 1220.

Figure 126A:
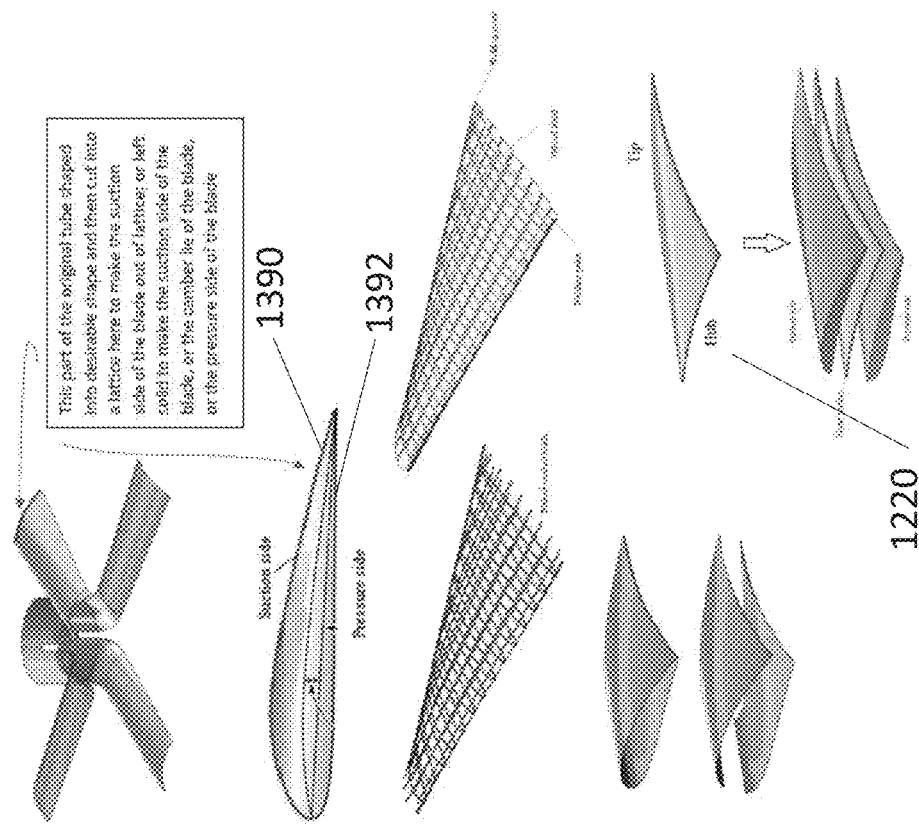

FIG. 126A depicts another example embodiment. In this embodiment, the blade 1370 is made by cutting a memory shape alloy tube into a lattice to form a first surface of the blade 1370. In some embodiments, the first surface may be the suction surface 1390. In some embodiments, the second surface is also made of a shape memory alloy mesh. In some embodiments, the second surface may be the pressure surface 1392. Welding, adhesives, or other coupling techniques may be used to couple the first surface to the second surface. In some embodiments, the shape memory alloy may be memory-shaped material, metal or plastic, like nitinol. In some embodiments, the pressure surface 1392 may be welded to the suction surface 1390 along the leading edge and the trailing edge. FIG. 126B illustrates a comparison of flat plate (bent to blade shape) versus aerofoil shape blades. In some embodiments, the flat plate is advantageous since it can be easier to manufacture and the performance penalty is small, although aerofoil cross-section blades can be utilized in other embodiments.

Figure 127:
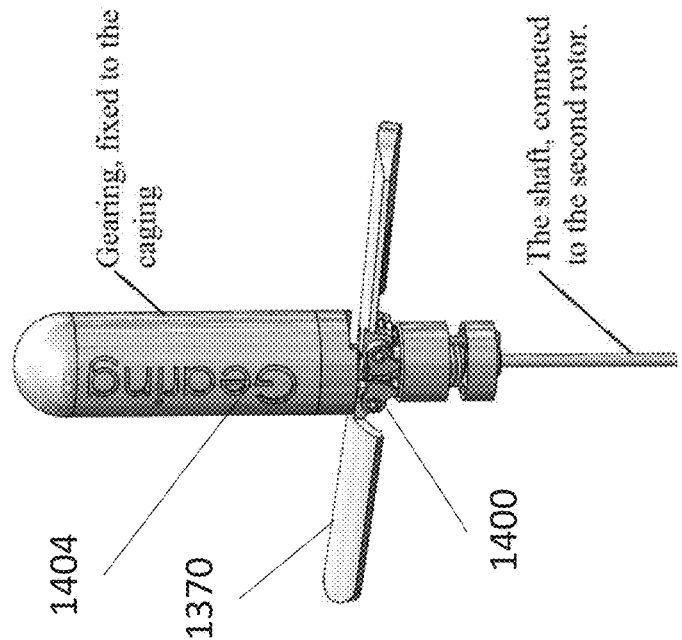

FIG. 127 depicts an embodiment of a screw-worm gear blade folding mechanism 1400. The mechanism 1400 includes foldable, or feathering blades 1370. This folding structure is a new application of foldable propeller to heart-assist pumps. The mechanism 1400 may include a stationary component of the structure upstream of the blades 1370, and another stationary component downstream of the blades 1370. In this example, the gearbox 1404 is shown upstream of the upstream impeller.

FIG. 128 depicts the gearing system 1404. In some embodiments, the gearing system 1404 is integrated at the tip, proximal to the heart. In some embodiments, the gearing system 1404 may be located the bottom, distal to the heart. The FIG. 128 shows the case with upstream gearing 1404. Two concentric shafts 1406, coming of the gearing 1404, rotate in opposite directions. The outer shaft 1410 may be connected to the first (upstream) rotor 946 (not shown). The inner shaft 1414 may be connected to the second (downstream) rotor 948 (not shown). In some embodiments, a worm screw shape 1408 may be disposed on the outer shaft 1410. A worm screw shape 1412 (not shown) may be disposed on the inner shaft 1414, connected to the second rotor 948 (distal, downstream rotor).

FIG. 129 depicts each blade 1370 equipped with a pinion 1416. In some embodiments, the pinion 1416 is configures to engage the worm screws 1412 or 1408. The system may further include two asymmetric cams 1418. The cams 1418 may secure the blades 1370 in upper slots 1420 (not shown) and lower slots 1422 (not shown). The slot that blade 1370 is secured to depends on the blade angle.

FIG. 130 depicts how, in some embodiments, as the worm screw turns 1412 or 1408 turns, the corresponding blade 1370 may open and close. This action may be comparable to a corkscrew opening a bottle of wine.

Figure 131:
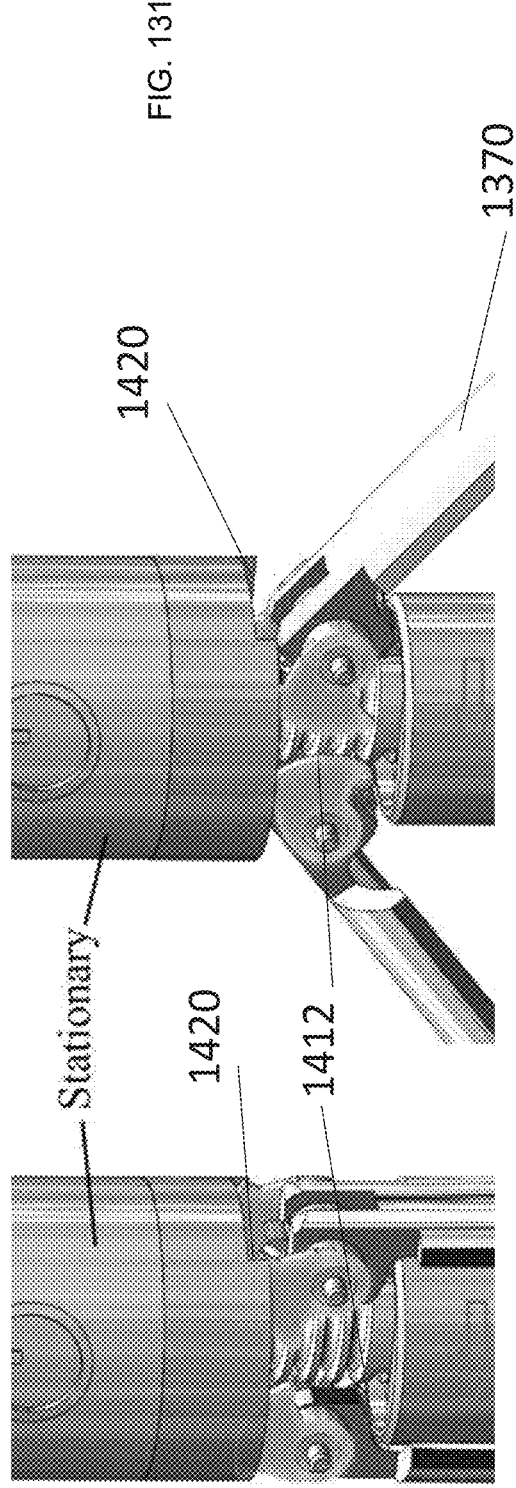

FIG. 131 depicts a configuration in which the blades 1370 are initially folded. In the folded position, the top edge of each cam 1418 is restricted in the top slot 1420 on the stationary gearing system. This configuration may prevent the blades 1370 from rotating. When the worm screw 1412 or 1408 turns, as long as the cams 1418 are in slots, the blades are unfolding. While the cams 1418 remain in the slots 1420 they prevent blade 1370 rotation.

Figure 132:
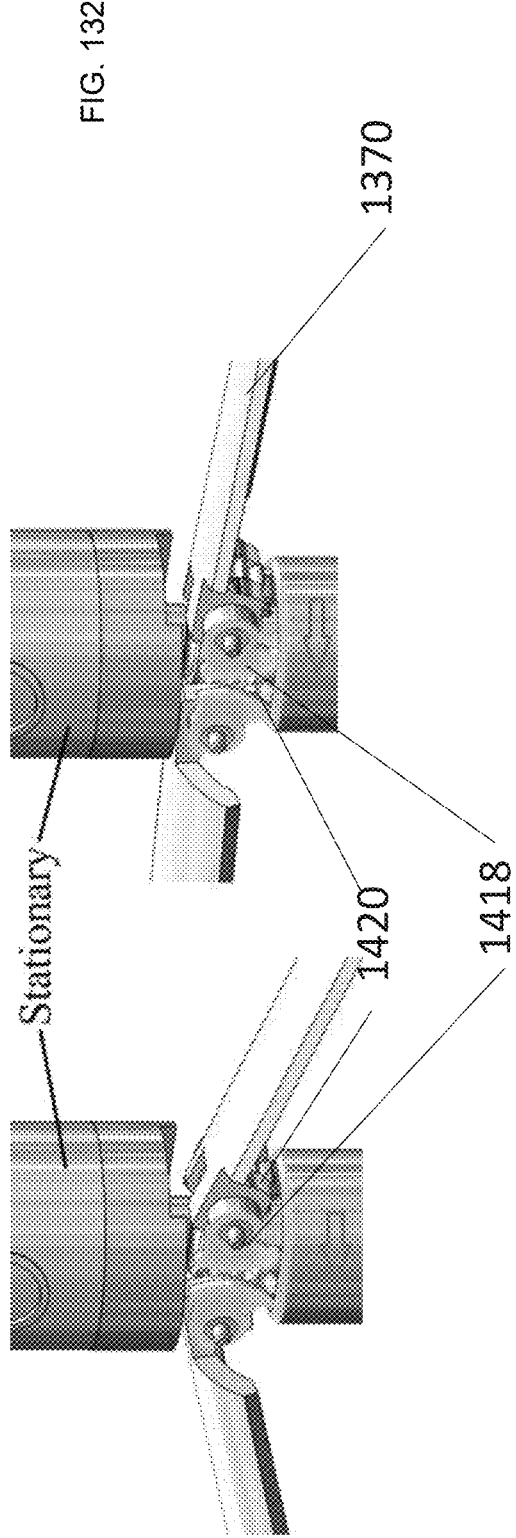

FIG. 132 depicts the screw worm gear folding system 1400. Specifically the FIG. 132 shows that as soon as the cams 1418 are released from the top slot 1420, the blades 1370 are free to rotate. At this point, the bottom tip of the cams 1418 engages the bottom slots 1422. In some embodiments, the bottom slots are coupled to the rotating shaft, so that the blades 1370 will spin with the shaft.

The same mechanism 1400 as described in FIG. 127-132 can be used for the downstream rotor. In some embodiments, the mechanism 1400 may have differences when applied to the upstream rotor and the downstream rotor.

FIG. 133 depicts a system 1430 that can include any number of features similar to mechanism 1400 with various differences. The system 1430 includes an alternative folding arrangement upstream. The blades 1370 fold upstream. The mechanism may be similar to feathering marine propellers.

In some embodiments, a pin is used to prevent blade 1370 rotation. The size of the hub diameter is for illustration purposes. In some embodiments, the hub diameter may be smaller than 4 mm. In some embodiments, the hub diameter may be larger than 4 mm.

FIG. 134 depicts prior art marine feathering propellers.

Figure 136:
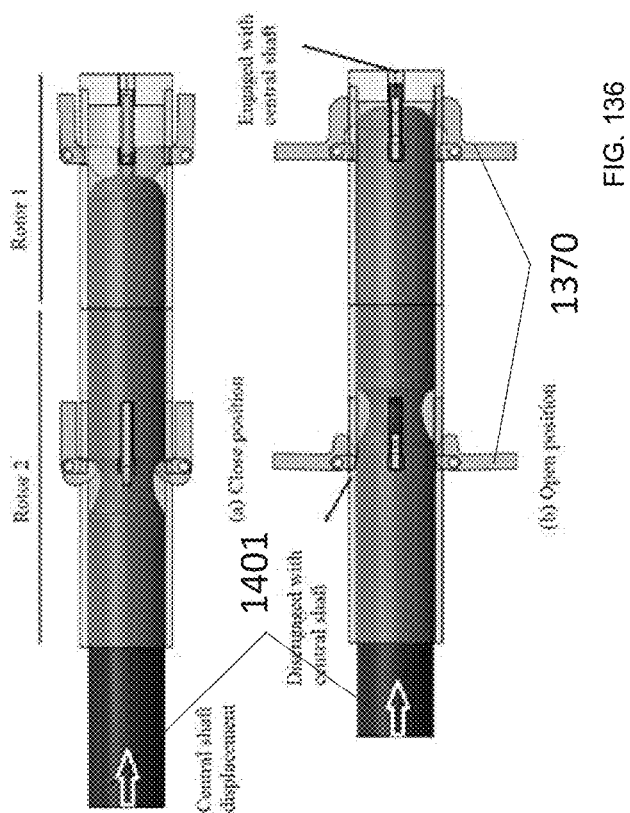
Figure 135:
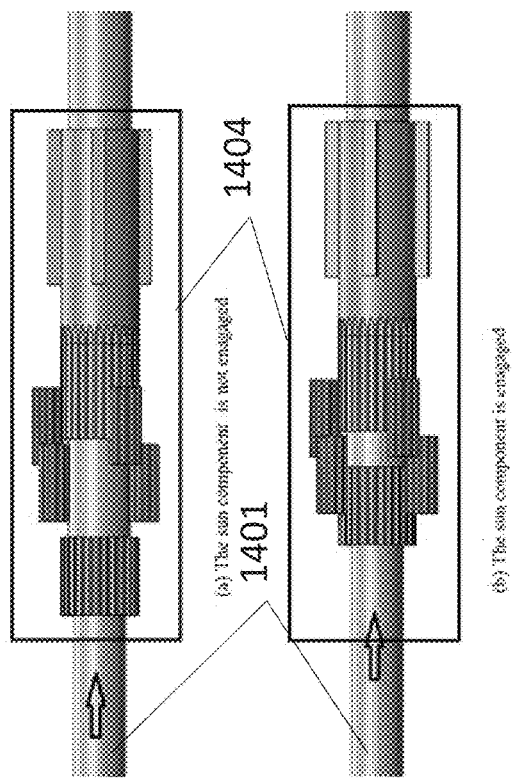

FIGS. 135 and 136 depict how the mechanism 1400 may utilize the axial displacement of the central shaft 1401 to engage and disengage the gearbox 1404. In some embodiments, this is achieved using a cam arrangement in the central shaft 1401 that in one position keeps the blades unfolded, and in another position allows them to fold upstream.

FIG. 136 depicts another embodiment in which a spring-loaded sliding pin 1440 may be used to lock the blades in the folded or unfolded position. The sliding pin 1440 and spring mechanism 1442 locks the blade 1370 in its position.

Figure 137:
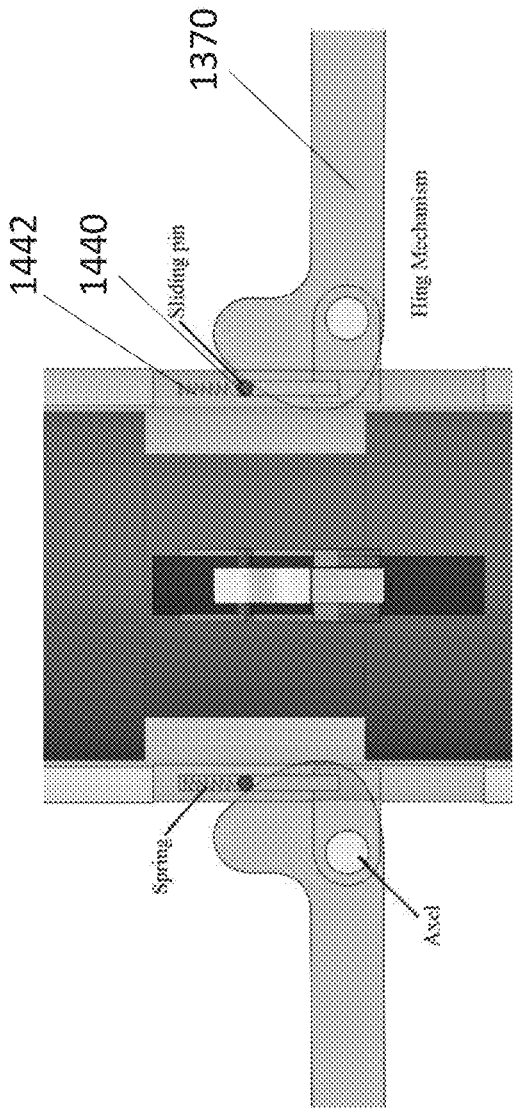
Figure 138:
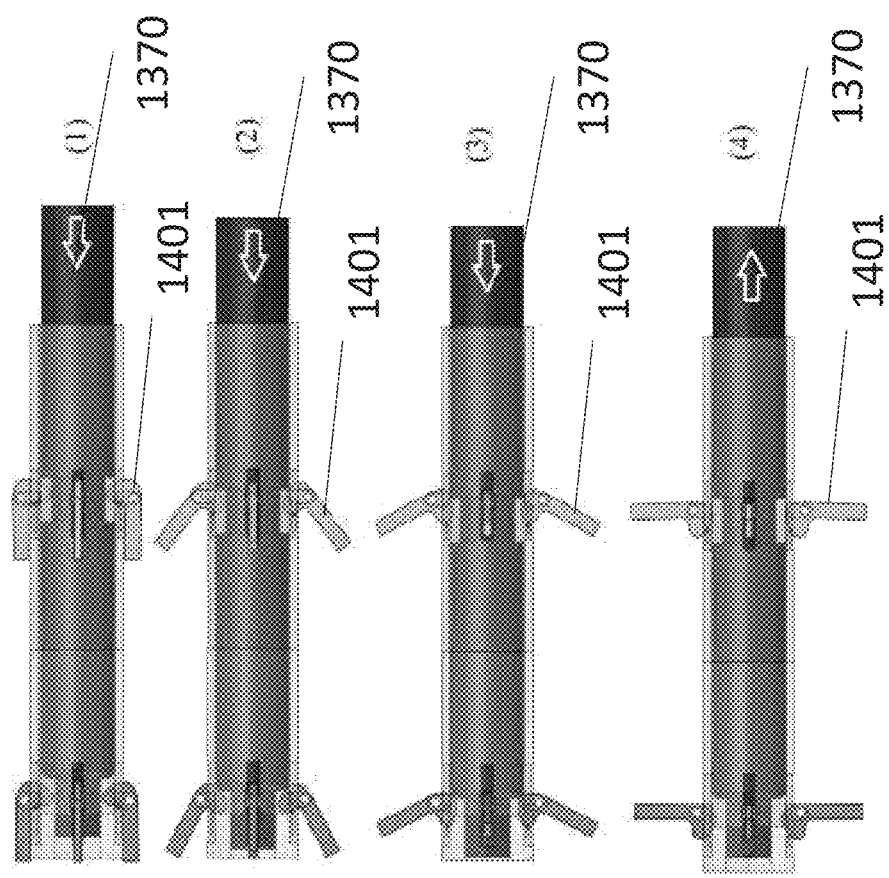
Figure 139:
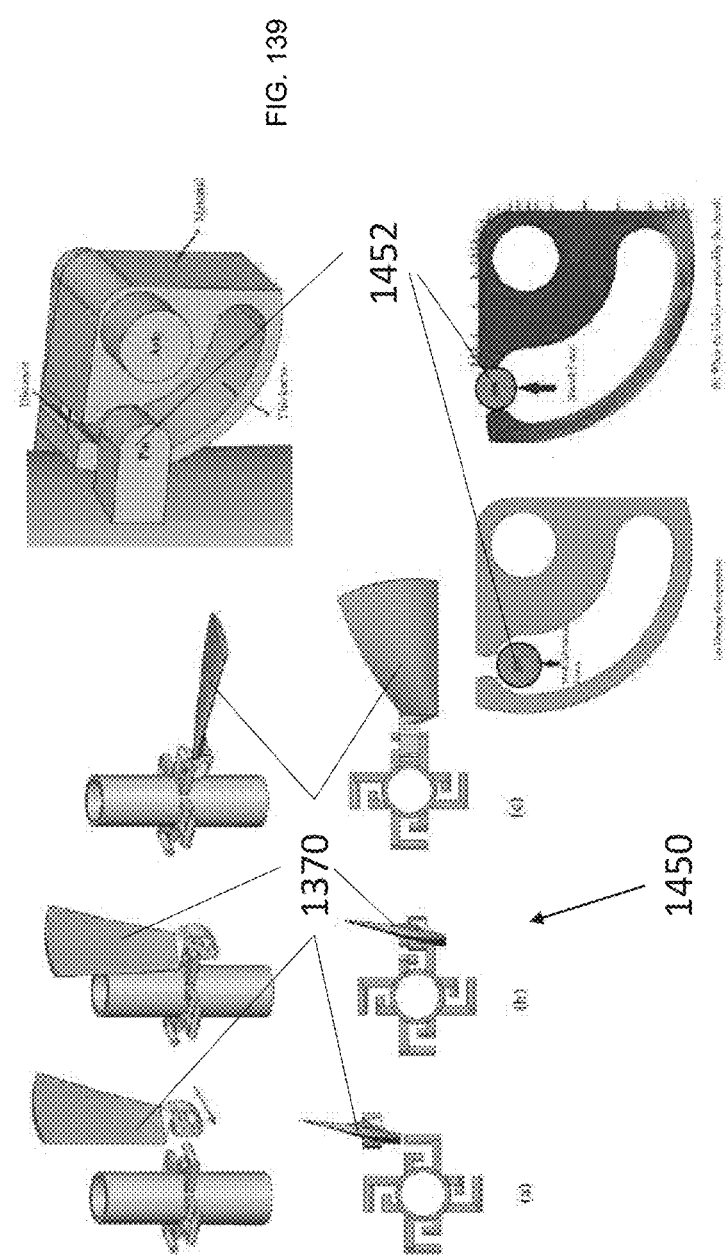

FIG. 137 depicts how the blades 1370 will be opened when the central shaft 1401 is pushed forward. FIG. 138 is another view of FIG. 137.

FIGS. 139-142 depicts an axle and pin locking mechanism 1450. In some embodiments, the blades 1370 are raised by popping them into place. The blades 1370 may be free to hang downstream for insertion in the folded state. Upon spinning the shaft, the centrifugal and hydrodynamic forces pop the blades 1370 into the open position, and keep them there until it is time for removal. In some embodiments, when it is time for removal, the device is set to a higher RPM, e.g. at 150% of maximum design rpm. At the higher RPM, the hydrodynamic forces pop the blades 1370 past the pin 1452 and into the upstream position. The blades 1370 in the upstream position are ready for removal. In another embodiment, the sheath 1220 pushes the blades 1370 upstream past the retaining clips.

Figure 140:
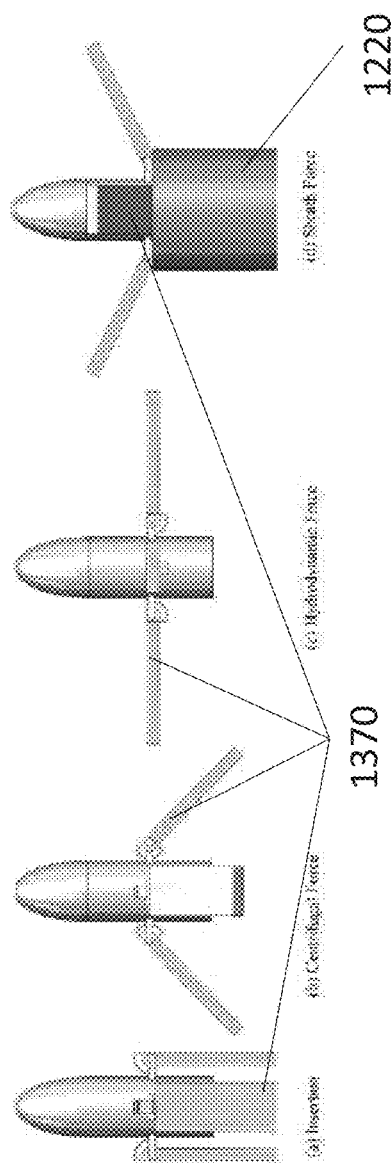

FIG. 140 depicts the various configuration of the axle and pin locking mechanism 1450.

Figures 141, 142:
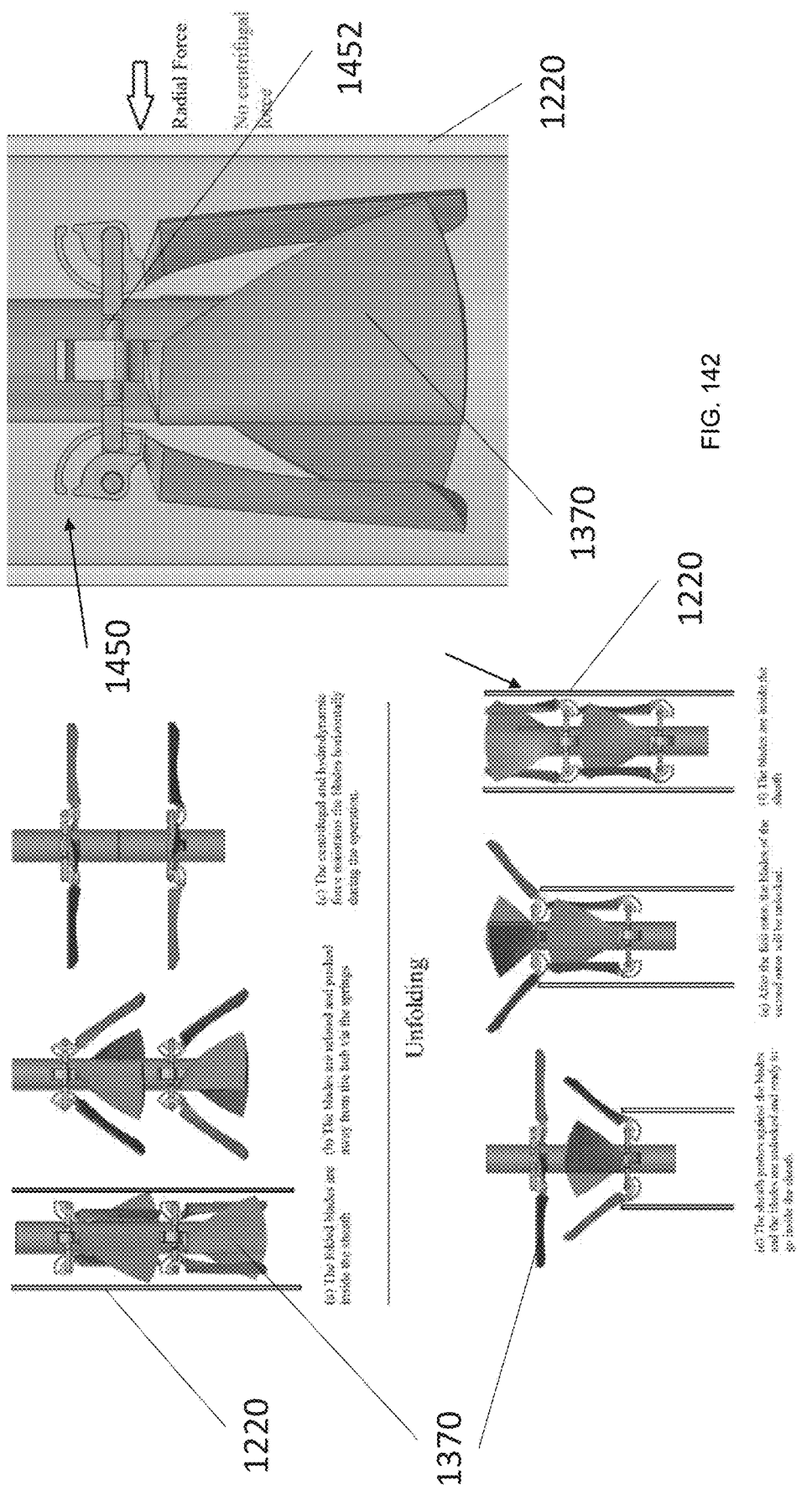

FIG. 141 depicts the axle and pin locking mechanism 1450. In some embodiments, the blades are kept in the horizontal position by hydrodynamic and centrifugal forces resulting from blades 1370 rotation. When the blades 1370 stop rotating they may tend to a folded position by gravity and/or blood flow downstream.

FIG. 143 depicts blades 1370 folded upstream on top of helical structures 1456. In some embodiments the blades 1370 could both fold downstream. In some embodiments one set of blades 1370 folds upstream and one set of blades 1370 folds downstream.

FIG. 144 depicts a catheter arrangement 1458 with runner 1460.

FIG. 145 depicts a catheter arrangement 1462 without a runner.

FIG. 146 depicts an hourglass cage 1464 with perforated inlets 1466. In some embodiments, the perforations may be slits 1468. In some embodiments, the perforations may be round.

Figure 152:
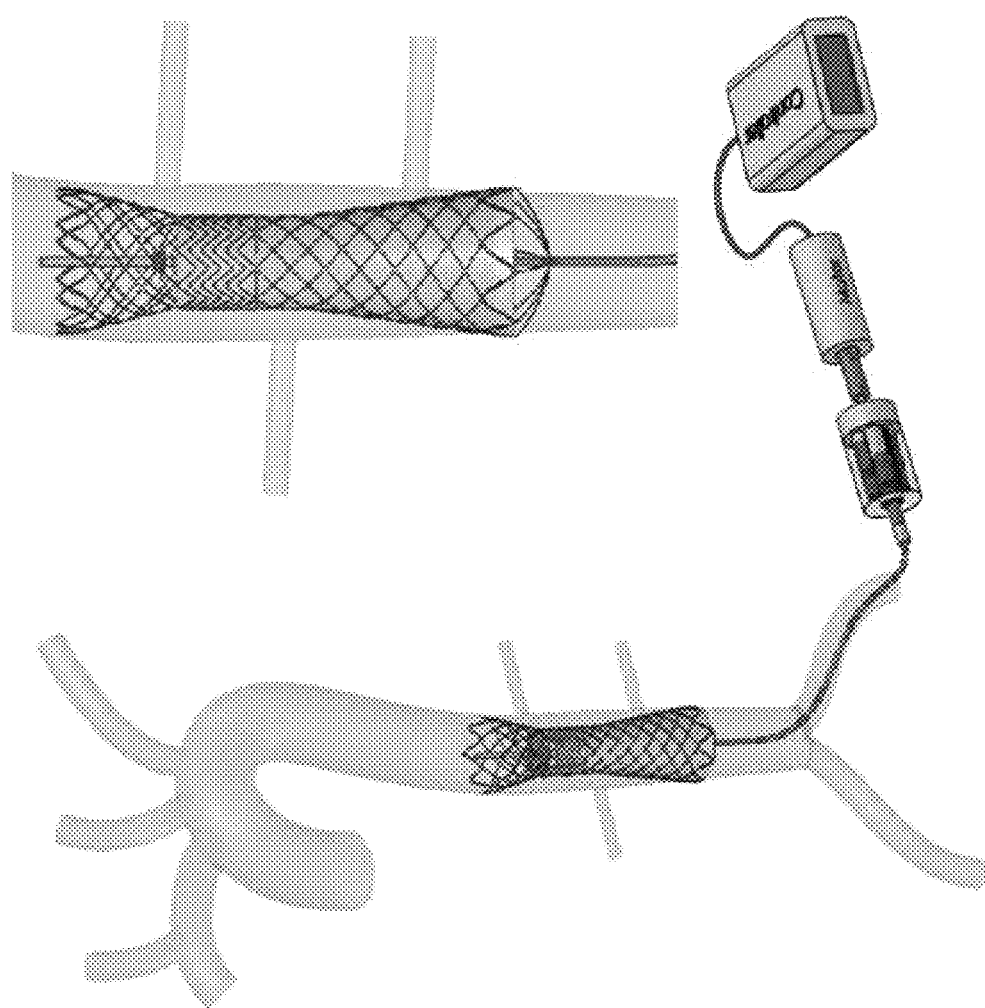

FIG. 147 depicts a heart perfusion system 1470. Some embodiments include contra-rotating rotors 1472 inside an hourglass cage 1474. The intra-corporeal gearbox 1476 may be just downstream of collapsed hourglass 1474. The intra-corporeal motor 1478 may be just downstream of gearbox 1476. The cable 1480 may supply electric power and communication to a controller 1482 outside the body. The system 1470 may be recoverable by sheath 1220. Items in line outside the collapsed hourglass 1474 fit in smaller catheter than if they were inside the hourglass 1474. In some embodiments, the heart perfusion system 1470 includes an inlet with wire frame only, as shown in FIG. 152 described herein.

In some embodiments, a runner may be used to assist in collapsing the hourglass 1474.

In some embodiments, the gearbox 1476 and motor 1478 fit inside the diffuser of the hourglass 1474.

Figure 148:
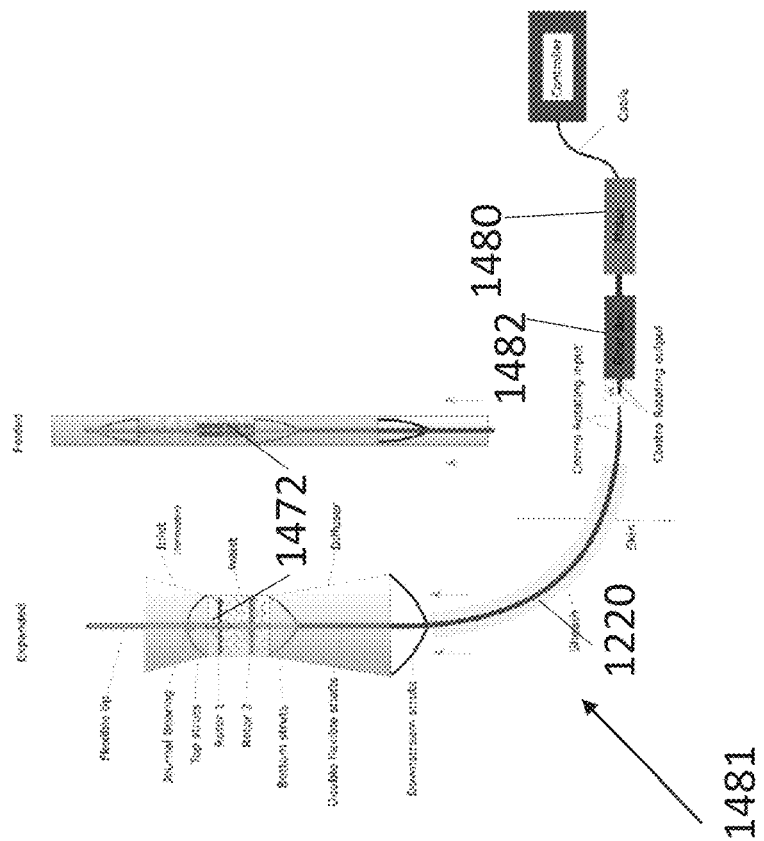

FIG. 148 depicts a system 1481. System 1481 is similar to system 1470 with various differences. Contra-rotating rotors 1472 with motor 1480 and gearbox 1482 extra-corporeal. Contra-rotating flex shafts 1484 supply power to pump head. In some embodiments, the system 1481 is recoverable by sheath 1220 only.

Figure 149:
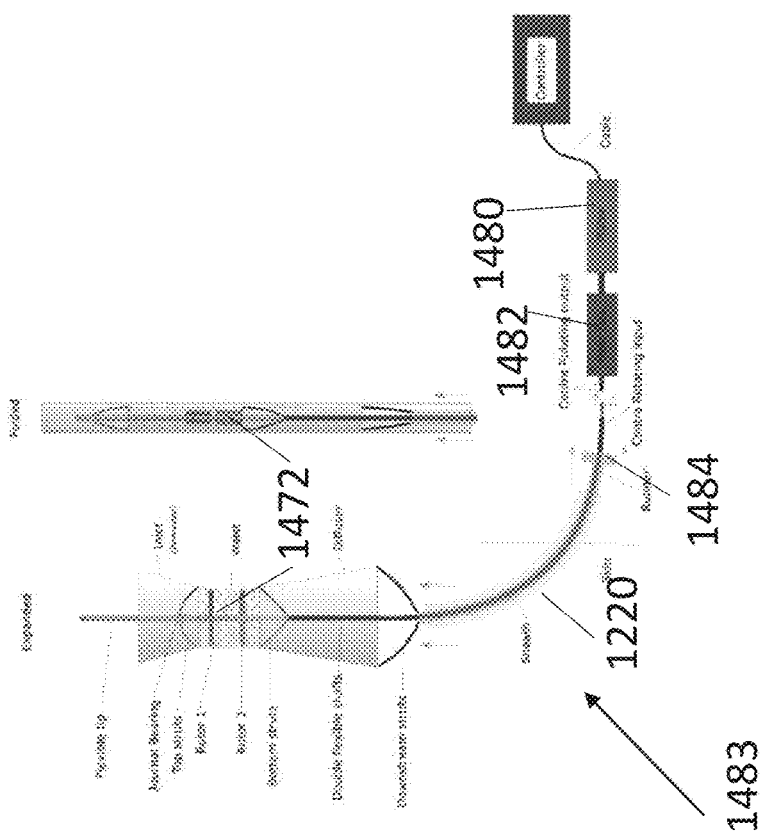

FIG. 149 depicts an embodiment of system 1481. In this embodiments the system is recoverable by sheath 1220 and runner 1484.

Figure 150:
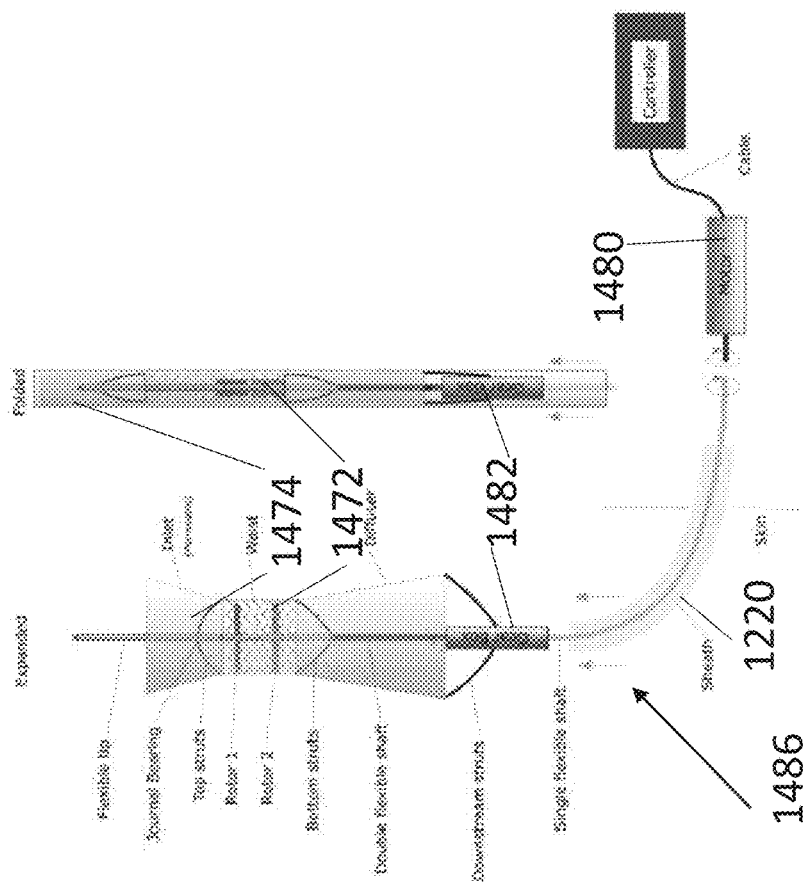

FIG. 150 depicts a system 1486. System 1486 is similar to system 1470 with various differences. In some embodiments the contra-rotating rotors 1472 are disposed inside the collapsed hourglass 1474. In some embodiments the, intra-corporeal gearbox is positioned just downstream of collapsed hourglass 1482. The motor 1480 is extra-corporeal. In some embodiments, this system is recoverable by sheath 1220.

Figure 151:
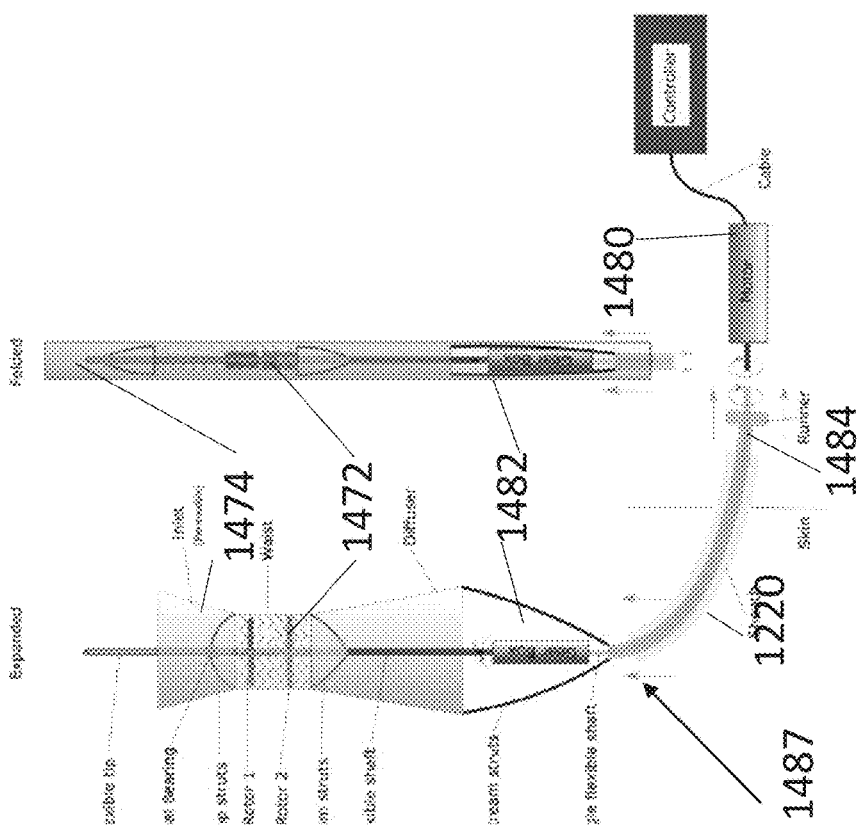

FIG. 151 depicts contra-rotating rotors 1472 inside the hourglass 1474. The intra-corporeal gearbox is located just downstream of collapsed hourglass 1474. The motor 1480 is extra-corporeal motor. In some embodiments, recoverable 1220 by sheath and runner 1484. The runner is in FIG. 151.

FIG. 152 illustrates this inlet-section porosity. There is just mesh located at the inlet. In some embodiments inlet-section porosity is achieved by having no biocompatible covering of the frame at the inlet.

Figure 153A:
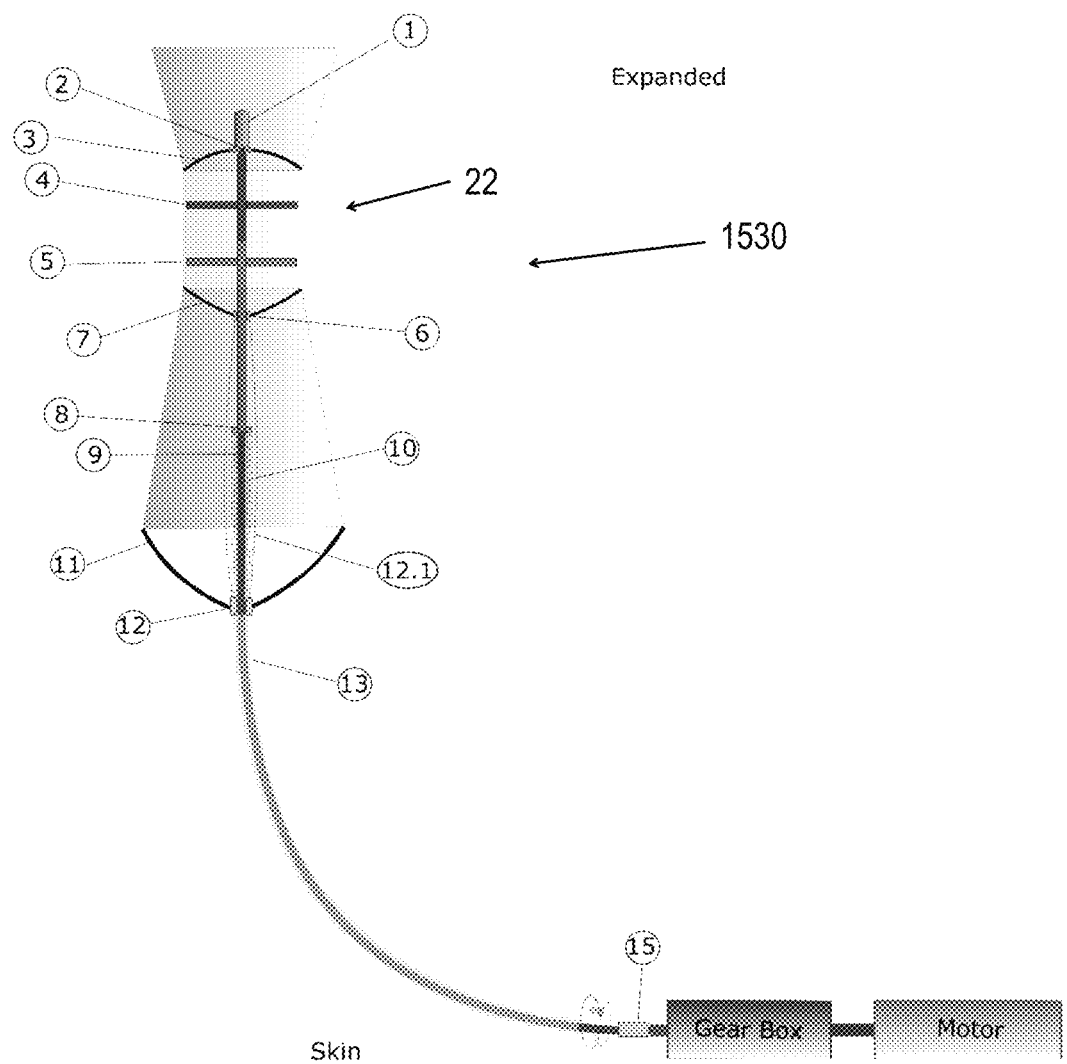

FIG. 153A illustrates another embodiment of a circulatory support device 1530 in an expanded configuration. A nose cone 1 is mounted on the top of the axial-radial bearing 2 at the end of an elongate member. The nose cone 1 can be relatively short, and stationary. An axial-radial bearing 2 can be configured to prevent rotor(s) from one or both of axial and radial displacement. Top centralizer struts 3 can extend radially outward from the elongate member and are configured to connect the bearing 2 to the housing 22, which can be a stent with a generally hourglass or other geometry as disclosed elsewhere herein. Top centralizer struts 3 thus centering the overall pump head. Any number of struts 3 can be present, such as two, three, four, five, or more or less struts, or ranges including any two of the foregoing values. First rotor 4 can include a shaped tip head configured to be attached to the bearing 2. Second rotor 5 can include a long rigid hub to allow the bearing 2 to slide freely during the retrieval phase. First radial locating ring (e.g., loose bearing) 6 can be configured to prevent rotors, such as second rotor 5 from radial displacement, while still allowing the second rotor 5 the freedom to travel axially. Bottom centralizing struts 7 are configured to extend radially outwardly from the elongate member, and are configured to connect the first radial locating ring 6 to the housing 22, thus centering the pump head. A slider 8 can connect a rotating hub (e.g., of rotor(s)) to a sleeve or sheath 13, part of which can include bi-flex shafts or bellows for example. A plurality, such as two or more contra-rotating shafts 9 can transmit the torque from an external power to first rotor 4 and second rotor 5. In some embodiments, part of the sheath 13 can include an extendable sleeve 10 (e.g., bellows made of PTFE or another material) which covers the shafts and connects one end to the slider, and another end to a third radial locating ring (e.g., loose bearing) 12. Cords 11 can connect the lower end of a diffuser to a third radial locating ring 12. A biocompatible stationary sleeve or sheath 13 can cover the contra-rotating shafts 9. In some configurations, the sheath 13 can also serve as a retrieving catheter. Slider 8, sleeve 10, and third radial locating ring 12 can be configured to slide inside of sleeve 13. A coupling mechanism 15 can be configured to transmit the contra-rotating motion from the gear box to the contra-rotating shafts.

Figure 153B:
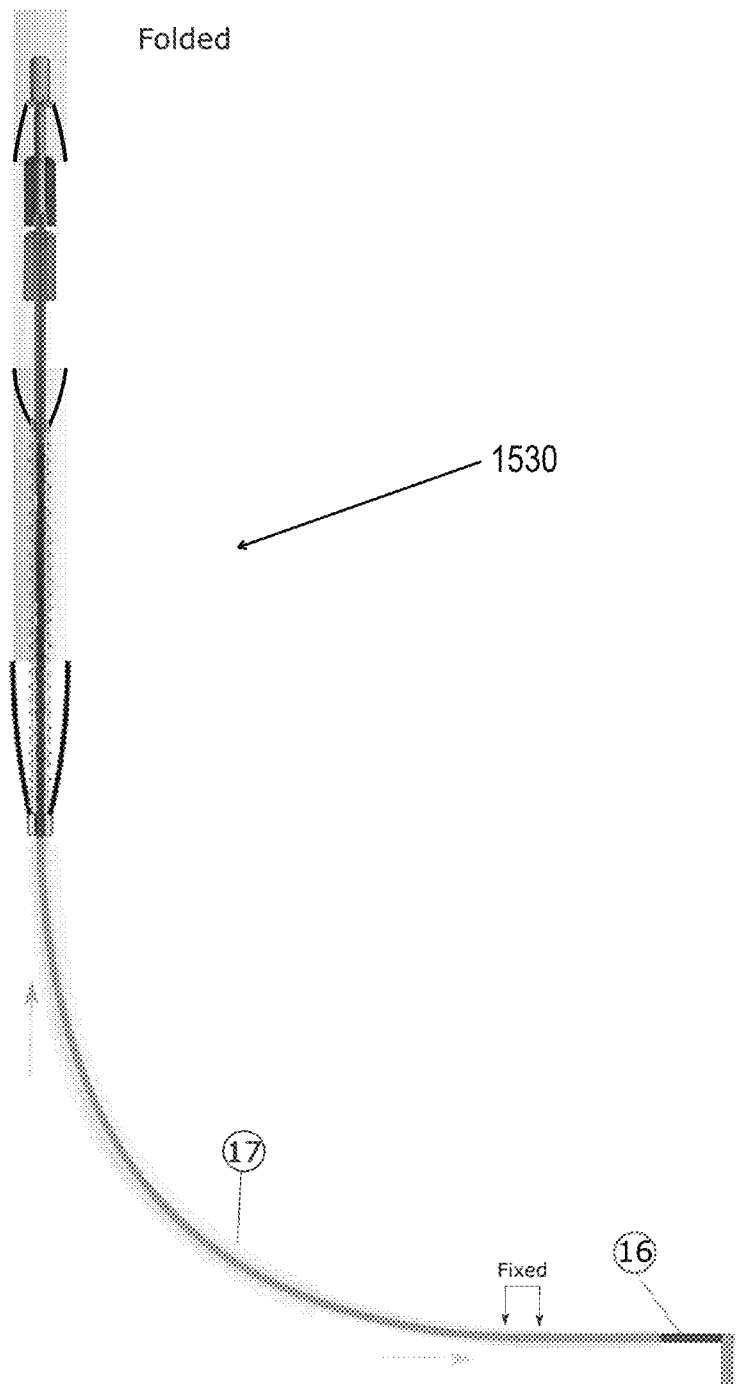

FIG. 153B illustrates the circulatory support device 1530 of FIG. 153A in a folded or radially compressed configuration for delivery and/or removal from the body. Also illustrated are placement and retrieving rods 16, which can include in some cases one for each shaft, used only during implantation and retrieval, to enable sheath 13 to go over the pump head and collapse it inside it, while holding the contra-rotating shafts in place. Sheath 17 can be utilized instead of sheath 13, and can be shorter than sheath 13 in some cases as extending only partially in between the distance between bearing 12 and coupling mechanism 15 and/or rods 16, such as less than about 90%, 80%, 70%, 60%, 50%, or less of the distance, or ranges including any two of the foregoing values.

In some embodiments, blades of a propeller or impeller can be made of flat plates of nitinol curved into a 3D twisted shape.

Figure 154A:
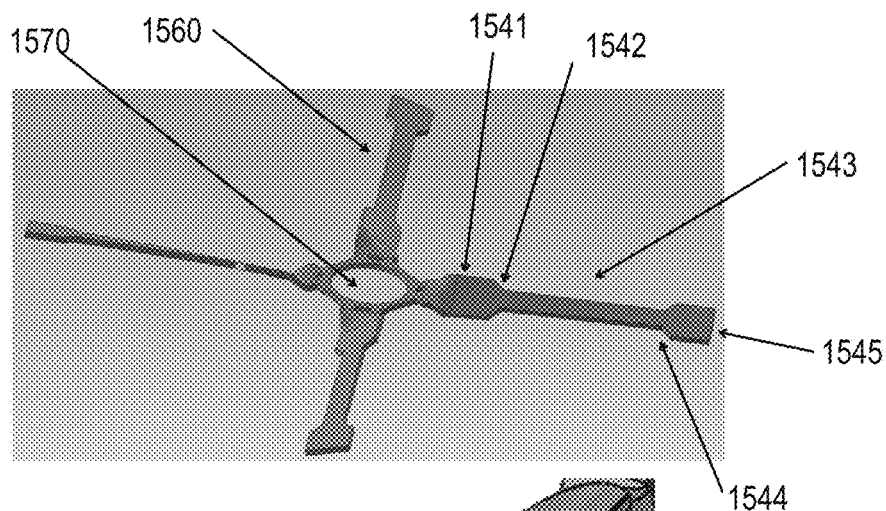
Figure 154B:
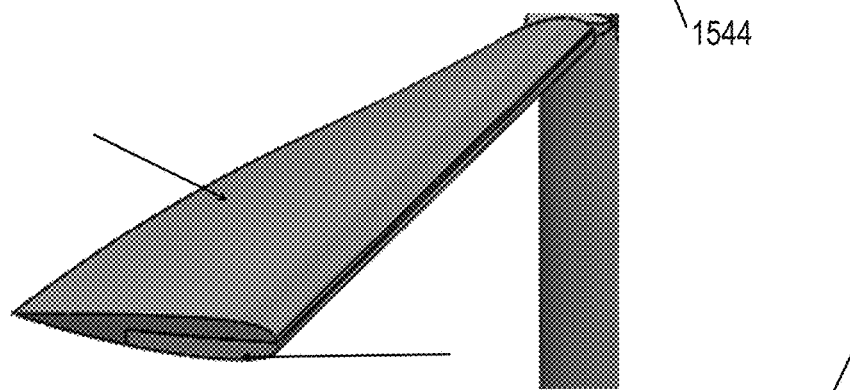
Figure 154:
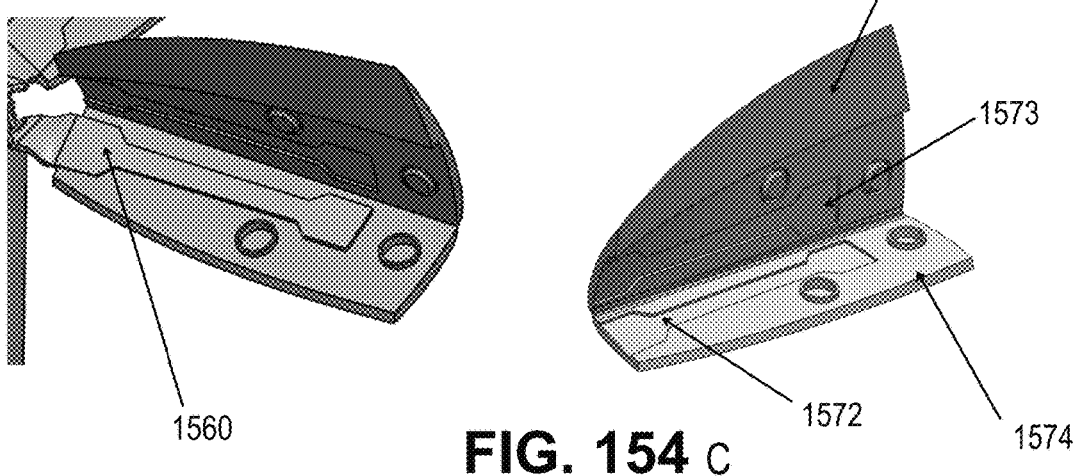

In some embodiments, blades can take on an airfoil geometry. In some embodiments, as illustrated in FIG. 154A-154C, the blades can include a base component 1560 with a "dogbone" like shape, with a first width at a first end 1541, a first transition zone 1542, wherein the width decreases (e.g., gradually decreases as shown), a central portion 1543 with a second width that is less than the first width, a second transition zone 1544, wherein the width increases (e.g., gradually increases as shown) to a third width at a second end 1545, wherein the first width can be equal to the third width, and the first width and the third width are greater than the second width. In some embodiments, the second width is about, between about, or no more than about 20%, 30%, 40%, 50%, 60%, 70%, 80%, or 90% of the first width (and the third width), or ranges including any two of the foregoing values. In some embodiments, the length of the central portion 1543 is about, between about, or no more than about 20%, 30%, 40%, 50%, 60%, 70%, 80%, or 90% of the length of the entire blade 1560 from the first end 1541 to the second end 1545, or ranges including any two of the foregoing values. The base component 1560 can be welded or otherwise attached to a shaft 1570, such as a cylindrical shaft as shown. Two or more outer blade elements 1571, 1572, which can include inner facing surfaces with cut outs with the geometry or substantially with the geometry of the base component 1560 in order to fit the base component 1560 within the elements 1571, 1572. The outer facing surfaces of outer blade elements 1571 can form an airfoil shape in some cases. The outer blade elements 1571, 1572 can be made of a biocompatible material such as a metal or plastic, and then fused or otherwise attached together.

Figure 154D:
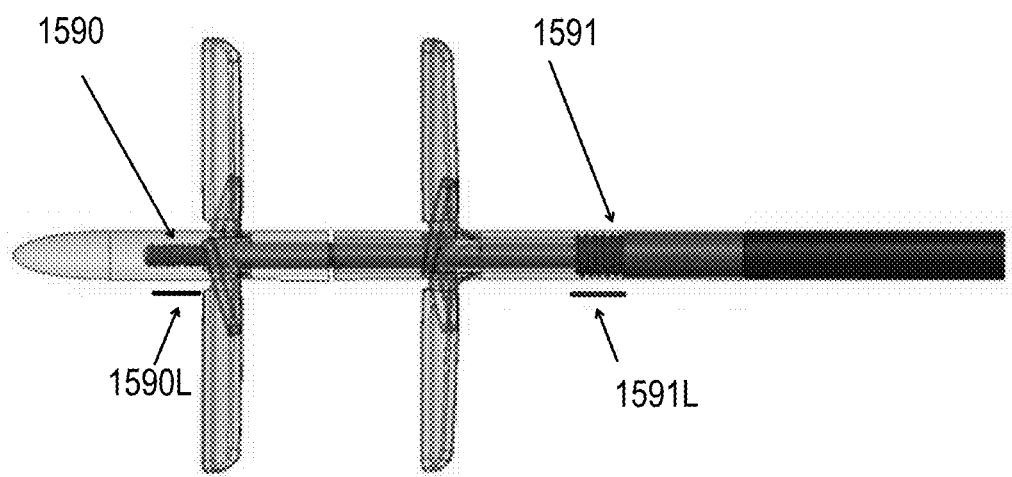

In some embodiments, as illustrated in FIG. 154D, threads 1590, 1591 having respective lengths 1590L, 1591L may be used to secure the hubs onto the bidirectional hubs. The threads 1590, 1591 can be in a rotation to screw in the shafts onto the hubs during pumping operation (and one or more, or only one of them will be reverse thread).

Figure 155:
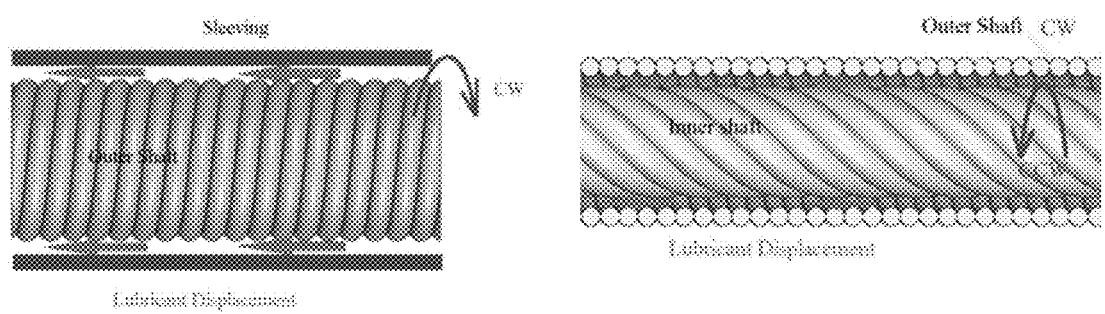

As illustrated in FIG. 155, a plurality of contra-rotating shafts can be made of coils arranged in a way so that the coils act as screw pumps between them, and between the outer coil and external sheath, so that it pumps lubricant in one direction. In an alternative configuration, the same action with unlubricated coils may be used to pump any material that is fretted away from the coil or sheath surfaces is pumped away from the internal pump head and towards the extra-corporeal gearbox.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims. It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The claims below are representative claims, and may be restructured and combined with other features described in the embodiments herein.

What is claimed is:

1. A mechanical circulatory support device, comprising:
a pump head comprising a pair of contra-rotating impellers positioned within a central waist section of an hourglass-shaped cage,
wherein an inlet of an inlet section of the hourglass-shaped cage and an outlet of an outlet section of the hourglass-shaped cage are configured to accommodate varying diameters, and wherein the inlet of the hourglass-shaped cage and the outlet of the hourglass-shaped cage are configured to be secured against an inside wall of blood vessels of various diameter sizes,
wherein the central waist section has a constant diameter when the inlet of the hourglass-shaped cage and the outlet of the hourglass-shaped cage are secured against the inside wall, thus the inlet and the outlet accommodate blood vessels of various diameter sizes with one size of the central waist section of the hourglass-shaped cage and the pump head comprising the pair of contra-rotating impellers.

2. The device of claim 1, wherein the central waist section of the hourglass-shaped cage comprises a memory-alloy frame covered with biocompatible material non-permeable to blood.

3. The device of claim 1, wherein the inlet section of the hourglass-shaped cage comprises perforations allowing blood permeability through the perforations and perfuse a region between the outside of the hourglass-shaped cage and the inside wall of the blood vessel, wherein the central waist section of the hourglass-shaped cage is non-permeable to blood.

4. The device of claim 1, wherein the pair of contra-rotating impellers of the pump head comprises collapsible blades installed in the central waist section of the hourglass-shaped cage.

5. The device of claim 1, wherein the pair of contra-rotating impellers of the pump head is driven by at least one extra-corporeal motor.

6. The device of claim 1, wherein the pair of contra-rotating impellers of the pump head is driven by at least one intra-corporeal motor.

7. The device of claim 1, wherein the pair of contra-rotating impellers of the pump head is powered by an intra-corporeal gearbox.

8. The device of claim 1, wherein the pair of contra-rotating impellers of the pump head is powered by an intra-corporeal gearbox and an extra-corporeal motor.

9. The device of claim 1, wherein the pair of contra-rotating impellers of the pump head is powered by an extra-corporeal gearbox and an extra-corporeal motor.

10. The device of claim 1, wherein no blood flow is permitted from the outlet to the inlet on the outside of the hourglass-shaped cage.

11. The device of claim 1, wherein the device prevents backflow and is configured to perfuse intercostal vessels.

12. The device of claim 1, wherein the inlet section of the hourglass-shaped cage is covered with biocompatible material non-permeable to blood.

13. The device of claim 1, wherein the inlet section of the hourglass-shaped cage is permeable to blood to perfuse the intercostal arteries.

14. The device of claim 1, wherein the collapsing of the pump head comprising the pair of contra-rotating impellers and the hourglass-shaped cage are achieved by a runner moving downstream and a sheath moving upstream.

15. A mechanical circulatory support device, comprising:
a pump head positioned within a central waist section of an hourglass-shaped cage,
wherein an inlet of an inlet section of the hourglass-shaped cage and an outlet of an outlet section of the hourglass-shaped cage are configured to accommodate varying diameters, and wherein the inlet of the hourglass-shaped cage and the outlet of the hourglass-shaped cage are configured to be secured within blood vessels of various diameter sizes,
wherein the central waist section has a constant diameter when the inlet of the hourglass-shaped cage and the outlet of the hourglass-shaped cage are secured, thus the device is configured to accommodate blood vessels of various diameters with one size of central waist section of the hourglass-shaped cage and the pump head, wherein the central waist section of the hourglass-shaped cage comprises a memory-alloy frame covered with biocompatible material non-permeable to blood, wherein the whole length of the hourglass-shaped cage is collapsible along its axis,
wherein the pump head comprises at least one pair of contra-rotating blade rows.

16. The device of claim 15, wherein the inlet section of the hourglass-shaped cage comprises perforations allowing blood permeability through the perforations and perfuse a region between the outside of the hourglass-shaped cage and the inside of a blood vessel.

17. The device of claim 15, wherein the pump head comprises collapsible blades installed in the central waist section of the hourglass-shaped cage.

18. The device of claim 15, wherein the pump head is driven by at least one extra-corporeal motor.

19. The device of claim 15, wherein the outlet section of the hourglass-shaped cage is non-permeable to blood.

20. The device of claim 1, wherein the central waist section and the outlet section of the hourglass-shaped cage are non-permeable to blood.

* * * * *